(12) United States Patent
Chen et al.

(10) Patent No.: US 7,776,875 B2
(45) Date of Patent: Aug. 17, 2010

(54) SPIROINDOLINONE DERIVATIVES

(75) Inventors: Li Chen, Shanghai (CN); Xingchun Han, Shanghai (CN); Yun He, Shanghai (CN); Song Yang, Shanghai (CN); Zhuming Zhang, Hillsborough, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/273,035

(22) Filed: Nov. 18, 2008

(65) Prior Publication Data

US 2009/0163512 A1  Jun. 25, 2009

Related U.S. Application Data

(60) Provisional application No. 61/107,381, filed on Oct. 22, 2008, provisional application No. 61/014,888, filed on Dec. 19, 2007.

(51) Int. Cl.
*A61K 31/438* (2006.01)
*C07D 471/10* (2006.01)

(52) U.S. Cl. .......... 514/278; 546/17; 544/242; 544/360; 514/253; 514/256

(58) Field of Classification Search ............... 514/278, 514/253, 256; 546/17; 544/242, 360
See application file for complete search history.

(56) References Cited

U.S. PATENT DOCUMENTS 7,495,007 B2 * 2/2009 Chen et al. ............... 514/278

| 2007/0213341 A1 | 9/2007 | Chen et al. |
| 2008/0009486 A1 | 1/2008 | Chen et al. |
| 2008/0114013 A1 | 5/2008 | Liu et al. |

OTHER PUBLICATIONS

J. Am Chem. Soc., 2005, 127, 10130.

* cited by examiner

*Primary Examiner*—Charanjit S Aulakh
(74) *Attorney, Agent, or Firm*—George W. Johnston; Patricia S. Rocha-Tramaloni

(57) ABSTRACT

There are provided compounds of the formula

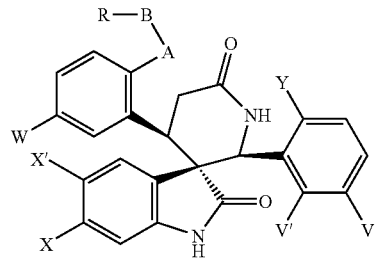

and pharmaceutically acceptable salts and esters and enantiomers thereof wherein W, X, X', Y, V, V', A, B and R are as described herein.

The compounds have utility as antiproliferative agents, especially, as anticancer agents.

12 Claims, No Drawings

SPIROINDOLINONE DERIVATIVES

PRIORITY TO RELATED APPLICATION(S)

This application claims the benefit of U.S. Provisional Application No. 61/107,381, filed Oct. 22, 2008, and U.S. Provisional Application No. 61/014,888, filed Dec. 19, 2007. The entire contents of the above-identified applications are hereby incorporated by reference.

SUMMARY OF THE INVENTION

The present invention relates to spiroindolinone derivatives of the formula

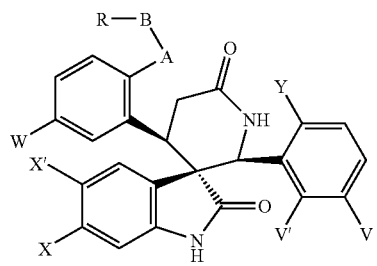

and its enantiomers and pharmaceutically acceptable salts and esters thereof wherein W, X, X', Y, V, V', A, B and R are as described herein.

The compounds have utility as antiproliferative agents, especially, as anticancer agents.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

A series of spiroindolinone as antagonists of MDM2 has previously been disclosed in J. Am Chem. Soc., 2005, 127, 10130 and also in US-2007-0213341-A1 published Sep. 13, 2007.

The present invention provides spiroindolinone derivatives which are small molecule inhibitors of the MDM2-p53 interaction. In cell-free and cell-based assays, compounds of the present invention are shown to inhibit the interaction of MDM2 protein with a p53-like peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

DETAILED DESCRIPTION OF THE INVENTION

The present invention relates to spiroindolinones of the formula

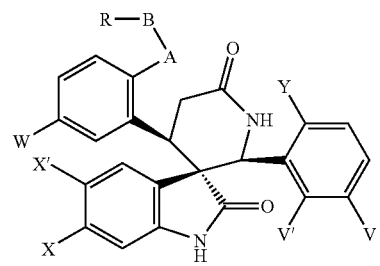

I wherein

X is Cl, F or Br,

X' is hydrogen or F

V is F, Cl or Br,

V' is hydrogen or F

Y is hydrogen, methyl, methoxy, F or Cl,

W is F, Cl, Br, I, ethynyl or isopropenyl,

A is O, NH, $CH_2$, C(=O), C(=O)NH, NHC(=O) or NHS$(=O)_2$,

B is a bond or $(CH_2)_m CR_1 R_2 (CH_2)_n$ m=0 or 1 n=0 or 1

$R_1$, $R_2$ are hydrogen or lower alkyl, and in the case of $R_1$ and $R_2$ they may independently link to form a cyclic structure selected from a substituted or unsubstituted cycloalkyl.

provided that if B is a bond, then R is selected from heterocyle, substituted heterocyle, heteroaryl, substituted heteroaryl, aryl, substituted aryl or substituted cycloalkyl, if B is not a bond, then R is selected from OR", NR'R", C(=O)NR'R", NHC(=O)R", NHS(=O)$_2$R", NHC(=O)NR'R" or C(=O)NR'S(=O)$_2$R", R', R" is independently selected from the group consisting of hydrogen, lower alkyl, aryl, lower alkenyl, substituted aryl, heteroaryl, substituted heteroaryl, heterocycle, substituted heterocycle, cycloalkyl and substituted cycloalkyl with the proviso that R" is not a hydrogen, and in the case of R' and R" they may independently link to form a cyclic structure selected from substituted or unsubstituted heteroaryl, substituted or unsubstituted cycloalkyl, substituted or unsubstituted cycloalkenyl or substituted or unsubstituted heterocycle and the pharmaceutically acceptable salts, esters and enantiomers thereof.

Preferred are compounds of formula I wherein X is Cl, X' is hydrogen or F, A is O, V is F or Cl, V' is hydrogen or F, Y is methyl, methoxyl Cl or F, W is Cl, F or Br, Most preferred compounds are those of the formula:

racemic (2'S,3S,4'R)-6-chloro-4'-{5-chloro-2-[1-methyl-1-(1-methyl-piperidin-4-ylcarbamoyl)-ethoxy]-phenyl}-2'-(5-fluoro-2-methyl-phenyl)spiro[3H-indole-3,3'-piperidine]-2,6'(1H)-dione racemic (2'S,3S,4'R)-6-chloro-4'-[5-chloro-2-(1-cyclobutylcarbamoyl-1-methyl-ethoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-{5-chloro-2-[1-(2-hydroxy-ethylcarbamoyl)-1-methyl-ethoxy]-phenyl}-2'-(5-fluoro-2-methyl-phenyl)-spiro[3H-indole-3,3'-piperidine]-2,6'(1H)-dione, racemic (2'S,3S,4'R)-4'-{2-[1-(2-acetylamino-ethylcarbamoyl)-1-methyl-ethoxy]-5-chloro-phenyl}-6-chloro-2'-(5-fluoro-2-methyl-phenyl)spiro[3H-indole-3,3'-piperidine]-2,6'(1H)-dione, (2'S,3S,4'R)-6-chloro-4'-{5-chloro-2-[1-(S-2,3-dihydroxypropyl carbamoyl)-1-methyl-ethoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-(2-methoxy-ethylcarbamoyl)-1-methyl-ethoxy]-phenyl}-2'-(5-fluoro-2-methyl-phenyl)-spiro[3H-indole-3,3'-piperidine]-2,6'(1H)-dione, racemic (2'S,3S,4'R)-6-chloro-4'-{5-chloro-2-[1-(3-dimethylamino-propylcarbamoyl)-1-methyl-ethoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-methyl-1-(2-piperidin-1-yl-ethylcarbamoyl)-ethoxy]-phenyl}-2'-(5-fluoro-2-methyl-phenyl)-spiro[3H-indole-3,3'-piperidine]-2,6'(1H)-dione, racemic (2'S,3S,4'R)-4'-[5-bromo-2-(2-methanesulfonylamino-1,1-dimethyl-2-oxo-ethoxy)-phenyl]-6-chloro-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-methanesulfonylaminocarbonyl-cyclobutoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-{5-chloro-2-[1-(4-fluorobenzenesulfonylaminocarbonyl)-cyclobutoxy]-phenyl}-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione, racemic (2'S,3S,4'R)-4'-[5-bromo-2-(3-methyl-oxetan-3-ylmethoxy)-phenyl]-6-chloro-2'-(5-chloro-2-methyl-phenyl)-spiro[3H-indole-3,3'-piperidine]-2,6'(1H)-dione, racemic (2'S,3S,4'R)-6-chloro-4'-[5-isopropenyl-2-(3-methyl-oxetan-3-ylmethoxy)-phenyl]-2'-(5-chloro-2-methyl-phenyl)-spiro[3H-indole-3,3'-piperidine]-2,6'(1H)-dione, racemic (2'S,3S,4'R)-6-chloro-2'-(5-chloro-2-methyl-phenyl)-4'-[5-ethynyl-2-(3-methyl-oxetan-3-ylmethoxy)-phenyl]-spiro[3H-indole-3,3'-piperidine]-2,6'(1H)-dione, racemic (2'S,3S,4'R)-4'-[2-(1-tert-butoxycarbonyl-piperidin-4-yloxy)-5-chloro-phenyl]-6-chloro-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(4-piperidinyloxy)-phenyl]-2'-(5-fluoro-2-methyl-phenyl)spiro[3H-indole-3,3'-piperidine]-2,6'(1H)-dione, racemic (2'S,3S,4'R)-4'-[2-(1-acetyl-4-piperidinyloxy)-5-chloro-phenyl]-6-chloro-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-methanesulfonyl-4-piperidinyloxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(pyrimidin-2-yloxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(2,2-dimethyl-3-oxo-3-pyrrolidin-1-yl-propoxy)-phenyl]-2'-(5-fluoro-2-methylphenyl)spiro[3H-indole-3,3'-piperidine]-2,6'(1H)-dione, racemic (2'S,3S,4'R)-6-chloro-4'-[5-chloro-2-(2-dimethylcarbamoyl-2-methyl-propoxy)-phenyl]-2'-(5-fluoro-2-methylphenyl)-spiro[3H-indole-3,3'-piperidine]-2,6'(1H)-dione, racemic (2'R,3S,4'R)-6-chloro-4'-[5-chloro-2-{[(2-hydroxyethyl)-methyl-carbamoyl]-methoxy}-phenyl]-2'-[2,5-difluorophenyl]spiro[3H-indole-3,3'-piperidine]-2,6'(1H)-dione, racemic (2'R,3S,4'R)-6-chloro-4'-[5-chloro-2-dimethylcarbamoylmethoxy-phenyl]-2'-(2,5-difluorophenyl)spiro[3H-indole-3,3'-piperidine]-2,6'(1H)-dione, racemic (2'R,3S,4'R)-6-chloro-4'-[5-chloro-2-(2-oxo-2-pyrrolidin-1-yl-ethoxy)-phenyl]-2'-(2,5-difluorophenyl)spiro[3H-indole-3,3'-piperidine]-2,6'(1H)-dione, racemic (2'S,3S,4'R)-6-chloro-4'-[5-bromo-2-(1-dimethylcarbamoyl-1-methyl-ethoxy)-phenyl]-2'-(5-chloro-2-methyl phenyl)spiro[3H-indole-3,3'-piperidine]-2,6'(1H)-dione, racemic (2'S,3S,4'R)-6-chloro-4'-[5-chloro-2-(1-dimethylcarbamoyl-1-methyl-ethoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(1-dimethylcarbamoyl-1-methyl-ethoxy)-phenyl]-2'-(5-fluoro-2-methylphenyl)spiro[3H-indole-3,3'-piperidine]-2,6'(1H)-dione, racemic (2'S,3S,4'R)-4'-{2-[2-(4-acetyl-piperazin-1-yl)-1,1-dimethyl-2-oxo-ethoxy]-5-chloro-phenyl}-6-chloro-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-methyl-1-(2,2,2-trifluoro-ethylcarbamoyl)-ethoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(3-methyl-oxetan-3-ylmethoxy)-phenyl]-2'-(5-fluoro-2-methyl-phenyl)-spiro[3H-indole-3,3'-piperidine]-2,6'(1H)-dione, racemic (2'R,3S,4'R)-6-chloro-4'-[5-chloro-2-(1-dimethylcarbamoyl-1-methyl-ethoxy)-phenyl]-2'-(2,5-difluoro-phenyl)spiro[3H-indole-3,3'-piperidine]-2,6'(1H)-dione, racemic (2'S,3S,4'R)-4'-[2-(2-amino-ethoxy) 5-chloro-phenyl]-6-chloro-2'-(5-fluoro-2-methyl phenyl)spiro[3H-indole-3,3'-piperidine]-2,6'(1H)-dione, racemic (2'S,3S,4'R)-6-chloro-4'-[5-chloro-2-(2-methanesulfonylamino-ethoxy)-phenyl]-2'-(5-fluoro-2-methyl phenyl)spiro[3H-indole-3,3'-piperidine]-2,6'(1H)-dione, racemic (2'S,3S,4'R)-6-chloro-4'-[5-chloro-2-[2-(3,3-dimethyl-ureido)-ethoxy]-phenyl]-2'-(5-fluoro-2-methyl phenyl)spiro[3H-indole-3,3'-piperidine]-2,6'(1H)-dione, racemic (2'R,3S,4'R)-6-chloro-4'-[5-chloro-2-(1-dimethylcarbamoyl-1-methyl-ethoxy)-phenyl]-2'-(2-fluoro-5chloro-phenyl)spiro[3H-indole-3,3'-piperidine]-2,6'(1H)-dione, racemic (2'S,3S,4'R)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione, racemic (2'S,3S,4'R)-2'-[5-bromo-2-(4-methoxycarbonyl-phenoxy)-phenyl]-6-chloro-4'-(3-fluorophenyl)spiro[3H-indole-3,3'-piperidine]-2,6'(1H)-dione, racemic (2'S,3S,4'R)-4'-[5-bromo-2-(1-tert-butoxycarbonyl-piperidin-4-yloxy)-phenyl]-6-chloro-2'-(3-fluorophenyl)spiro[3H-indole-3,3'-piperidine]-2,6'(1H)-dione, racemic (2'S,3S,4'R)-4'-[5-bromo-2-(4-piperidinyloxy)-phenyl]-6-chloro-2'-(5-fluorophenyl)spiro[3H-indole-3,3'-piperidine]-2,6'(1H)-dione, racemic (2'S,3S,4'R)-4'-[2-(1-acetyl-4-piperidinyloxy)-5-bromo-phenyl]-6-chloro-2'-(3-fluorophenyl)spiro[3H-indole-3,3'-piperidine]-2,6'(1H)-dione, racemic (2'S,3S,4'R)-4'-[5-bromo-2-(1-methyl-4-piperidinyloxy)-phenyl]-6-chloro-2'-(3-fluorophenyl)spiro[3H-indole-3,3'-piperidine]-2,6'(1H)-dione, racemic (2'S,3S,4'R)-4'-[5-bromo-2-(1-tert-butoxycarbonyl-piperidin-4-yloxy)-phenyl]-6-chloro-2'-(3-chlorophenyl)spiro[3H-indole-3,3'-piperidine]-2,6'(1H)-dione, racemic (2'S,3S,4'R)-4'-[5-bromo-2-(4-piperidinyloxy)-phenyl]-6-chloro-2'-(5-chlorophenyl)spiro[3H-indole-3,3'-piperidine]-2,6'(1H)-dione, racemic (2'S,3S,4'R)-4'-[2-(1-acetyl-4-piperidinyloxy)-5-bromo-phenyl]-6-chloro-2'-(3-chlorophenyl)spiro[3H-indole-3,3'-piperidine]-2,6'(1H)-dione, racemic (2'S,3S,4'R)-4'-[5-bromo-2-(1-methyl-4-piperidinyloxy)-phenyl]-6-chloro-2'-(3-chlorophenyl)spiro[3H-indole-3,3'-piperidine]-2,6'(1H)-dione, chiral (2'S,3S,4'R)-6-chloro-4'-[5-chloro-2-(2-methanesulfonylamino-ethoxy)-phenyl]-2'-(5-fluoro-2-methyl-phenyl)spiro[3H-indole-3,3'-piperidine]-2,6'(1H)-dione, racemic (2'R,3S,4'R)-6-chloro-2'-(2-chloro-5-fluoro-phenyl)-4'-[5-chloro-2-(2-methanesulfonylamino-1,1-dimethyl-2-oxo-ethoxy)-phenyl]spiro[3H-indole-3,3'-piperidine]-2,6'(1H)-dione, chiral (2'S,3S,4'R)-6-chloro-4'-[5-chloro-2-(2-methanesulfonylamino-1,1-dimethyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-methoxylcarbamoyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-cyanocarbamoyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-hydroxycarbamoyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-fluoro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(4-methoxyphenoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(2-tert-butoxycarbonylamino-ethoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(2-tert-butoxycarbonylamino-ethoxy)-phenyl]-2'-(5-fluoro-2-methyl phenyl)spiro[3H-indole-3,3'-piperidine]-2,6'(1H)-dione, racemic (2'S,3S,4'R)-6-chloro-4'-{5-chloro-2-[(2-cyclobutanecarbonyl-amino)-ethoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(2-cyano-2-cyclopropyl-methoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-cyano-cyclopentyl-methoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-cyanomethoxy-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-cyanomethoxy-phenyl]-2'-(5-fluoro-2-methyl-phenyl)spiro[3H-indole-3,3'-piperidine]-2,6'(1H)-dione, racemic (2'S,3S,4'R)-4'-[2-(4-tert-butoxycarbonyl-piperazin-1-yl)-5-chloro-phenyl]-6-chloro-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(piperazin-1-yl)-phenyl]-2'-(5-fluoro-2-methyl phenyl)spiro[3H-indole-3,3'-piperidine]-2,6'(1H)-dione, racemic (2'S,3S,4'R)-4'-[2-(4-acetyl-piperazin-1-yl)-5-chloro-phenyl]-6-chloro-2'-(5-fluoro-2-methyl phenyl)spiro[3H-indole-3,3'-piperidine]-2,6'(1H)-dione, racemic (2'S,3S,4'R)-6-chloro-4'-{5-chloro-2-[4-(2-hydroxy-ethyl)-piperazin-1-yl]-phenyl}-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(2-cyclopropanesulfonylamino-1,1-dimethyl-2-oxo-ethoxy)-phenyl]-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(2-trifluoromethanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione, racemic (2'R,3S,4'R)-4'-[5-chloro-2-(2-methanesulfonylamino-1,1-dimethyl-2-oxo-ethoxy)-phenyl]-6-chloro-2'-(2,3-difluoro-6-methyl-phenyl)spiro[3H-indole-3,3'-piperidine]-2,6'(1H)-dione, racemic (2'S,3S,4'R)-6-chloro-4'-[5-chloro-2-(2-methanesulfonylamino-2-oxo-ethoxy)-phenyl]-2'-(5-fluoro-2-methyl-phenyl)spiro[3H-indole-3,3'-piperidine]-2,6'(1H)-dione, racemic (2'S,3S,4'R)-4'-[5-chloro-2-(2-methanesulfonylamino-1,1-dimethyl-2-oxo-ethoxy)-phenyl]-6-chloro-2'-(5-chloro-2-methoxy-phenyl)-spiro[3H-indole-3,3'-piperidine]-2,6'(1H)-dione, racemic (2'S,3S,4'R)-6-chloro-4'-[5-chloro-2-(1-ethyl-1-hydroxycarbonyl-propoxy)-phenyl]-2'-(5-fluoro-2-methylphenyl)spiro[3H-indole-3,3'-piperidine]-2,6'(1H)-dione, racemic (2'S,3S,4'R)-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-{5-chloro-2-[1-ethyl-1-(2-hydroxy-ethylcarbamoyl)-propoxy]-phenyl}-2'-(5-fluoro-2-methyl-phenyl)spiro[3H-indole-3,3-piperidine]-2,6'(1H)-dione, racemic (2'S,3S,4'R)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)-spiro[3H-indole-3,3'-piperidine]-2,6'(1H)-dione, racemic (2'S,3S,4'R)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)-spiro[3H-indole-3,3'-piperidine]-2,6'(1H)-dione, racemic (2'S,3S,4'R)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione, chiral (2'S,3S,4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione, chiral (2'R,3R,4'S)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione, chiral (2'S,3S,4'R)-4'-[5-chloro-2-(2-ethanesulfonylamino-1,1-dimethyl-2-oxo-ethoxy)-phenyl]-6-chloro-2'-(5-fluoro-2-methyl-phenyl)spiro[3H-indole-3,3'-piperidine]-2,6'(1H)-dione, racemic (2'S,3S,4'R)-4'-[5-chloro-2-(2-methanesulfonylamino-1,1-dimethyl-2-oxo-ethoxy)-phenyl]-6-chloro-2'-(5-methyl-2-methoxy-phenyl)-spiro[3H-indole-3,3'-piperidine]-2,6'(1H)-dione, racemic (2'S,3S,4'R)-6-chloro-4'-[5-chloro-2-(3-methanesulfonylamino-2,2-dimethyl-3-oxo-propoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione, chiral (2'R,3R,4'S)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(2-methanesulfonylamino-1,1-dimethyl-2-oxo-ethoxy)-phenyl]-2'-(5-chloro-2-methyl-phenyl)-spiro[3H-indole-3,3'-piperidine]-2,6'(1H)-dione, chiral (2'S,3S,4'R)-6-chloro-4'-[5-chloro-2-(2-methanesulfonylamino-1,1-dimethyl-2-oxo-ethoxy)-phenyl]-2'-(5-chloro-2-methyl-phenyl)spiro[3H-indole-3,3'-piperidine]-2,6'(1H)-dione, chiral (2'S,3S,4'R)-6-chloro-4'-{5-chloro-2-[2-(2-methoxyethanesulfonylamino)-1,1-dimethyl-2-oxo-ethoxy]-phenyl}-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(1-methanesulfonylaminocarbonyl-1-propyl-butoxy)-phenyl]-2'-(5-chloro-2-methyl-phenyl)-spiro[3H-indole-3,3'-piperidine]-2,6'(1H)-dione, racemic (2'S,3S,4'R)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione, racemic (2'S,3S,4'R)-6-bromo-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-(5-chloro-2-methanesulfinylmethoxy-phenyl)-2'-(5-fluoro-2-methyl-phenyl)spiro[3H-indole-3,3'-piperidine]-2,6'(1H)-dione, racemic (2'S,3S,4'R)-[2-(tert-butylsulfamoyl-methoxy)-5-chloro-phenyl]-6-chloro-2'-(5-fluoro-2-methyl-phenyl)spiro[3H-indole-3,3'-piperidine]-2,6'(1H)-dione and racemic (2'S,3S,4'R)-6-chloro-4'-[5-chloro-2-(2-methanesulfonylamino-1,1-diethyl-2-oxo-ethoxy)-phenyl]-5-fluoro-2'-(5-fluoro-2-methyl-phenyl)-spiro[3H-indole-3,3'-piperidine]-2,6'(1H)-dione In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the aryl, heteroaryl and heterocycle rings are halogen, lower alkoxy, lower alkyl and amino.

If alkyl, alkenyl, alkynyl or similar groups are linked with both ends to the same moiety, cyclic structures may result, where two hydrogens of said moiety are being replaced by the two ends of the alkyl, alkenyl, alkynyl or similar group, thus creating cyclic structures, such as, tetralin, macrocycles or spiro compounds.

The term "alkyl" refers to straight- or branched-chain saturated hydrocarbon groups having from 1 to about 20 carbon atoms. In certain embodiments, alkyl substituents may be lower alkyl substituents. The term "lower alkyl" refers to alkyl groups having from 1 to 8 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 8, preferably 2 to 6 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, iodine or bromine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts have at least one asymmetric carbon atom and therefore may be present as racemic mixtures or different stereoisomers. The various isomers can be isolated by known separation methods, e.g., chromatography. The invention includes all stereoisomers.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II or III compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formula I having a carboxyl group or hydroxy group, which esters retain the biological effectiveness and properties of the compound of formula I and are cleaved in vivo (in the organism) to the corresponding active carboxylic acid or alcohol respectively.

Synthesis

Compounds of this invention in formula I can be synthesized according to the following general schemes. It will be readily apparent to those of ordinary skill in the art that compounds in formula I can be prepared by substitution of the reagents or agents in the general synthesis routes. Using purification by chiral chromatography, compounds in formula I can be obtained as an optically pure or enriched enantiomers.

Scheme 1

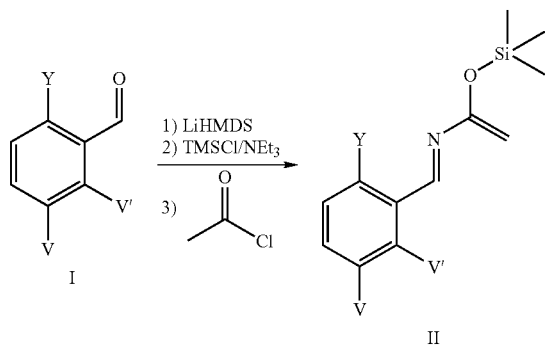

In general an appropriately selected aldehyde I can be reacted with lithium hexamethyldisilamide, chlorotrialkylsilane and acetyl chloride in a one-pot, multi-steps manner to generate 2-aza-1,3-butadiene II (Scheme I) and can be used as a crude product. Ghosez, L. and others have reported the preparation of 2-aza-1,3-butadienes and their use in aza Diels-Alder reaction to form heterocycle (Ref: *Tetrahedron* 1995, 11021; *J. Am. Chem. Soc.* 1999, 2617; and literatures cited therein). The appropriately selected aldehyde I are either commercially available or can be synthesized by well-established multiple literature methods.

Scheme 2

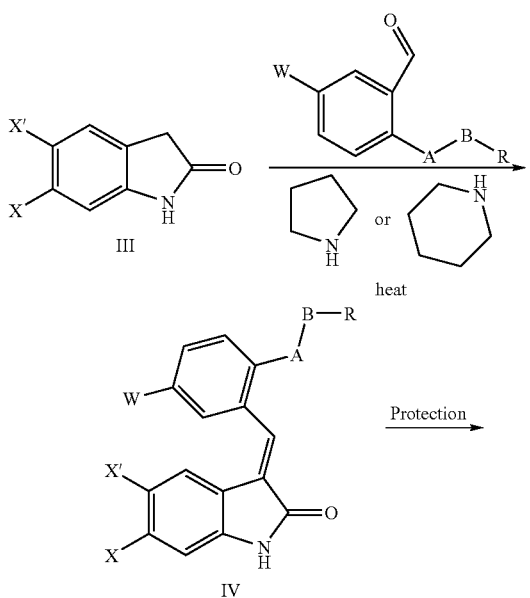

-continued

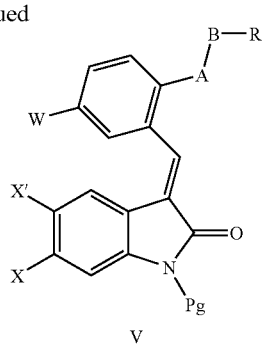

V

Oxindole III can be reacted with an appropriately substituted aldehyde in the presence of base under heated condition in either a protic like methanol, ethanol or an aprotic solvent like toluene, o-xylene to give intermediate IV. The commonly used base is either pyrrolidine or piperidine. Intermediate IV can be protected to give intermediate V. The protective group can be attached by using ethyl chloroformate, di-tert-butyl dicarbonate, SEM-Cl, benzyl bromide, and a base like 4-(dimethylamine)pyridine (DMAP), triethylamine, NaH, or LiH according to well established literature procedures. Examples of protective group formation and their deprotection have been described and reviewed comprehensively by Greene, T. W. et al in "Protective Groups in Organic Synthesis, $2^{nd}$ Edition. John Wiley & Sons Inc.

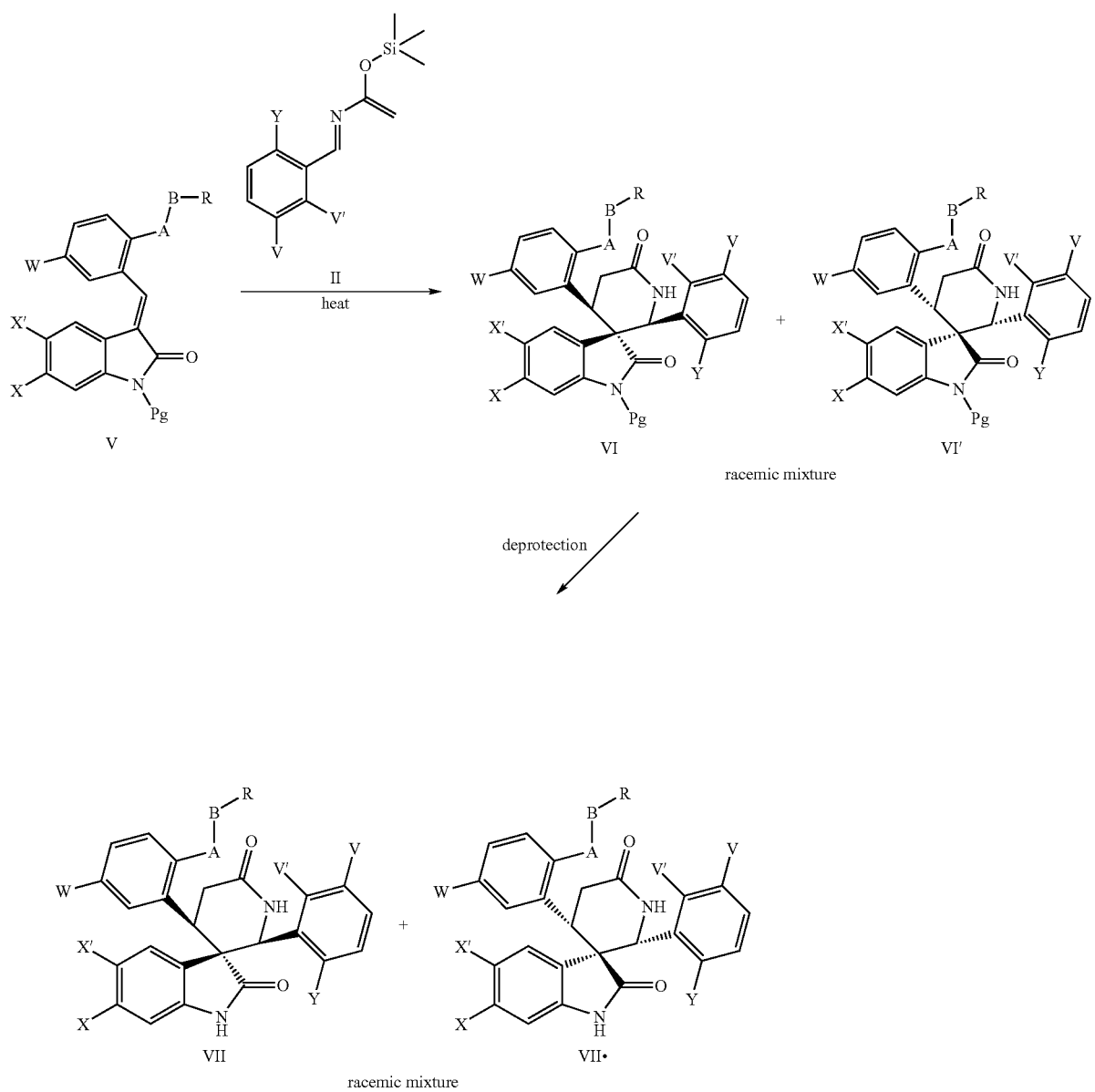

Intermediate V can be reacted with a selected 2-aza-butadiene II prepared in Scheme 1 in toluene or o-xylene under heating from 110° C. to 160° C. and anhydrous condition to form intermediate VI and VI' as the major products shown as a racemic mixture of two enantiomers. A subsequent reaction to remove protective group (Pg) leads to various R₂ derivatized compound VII and VII'. (Scheme 3). In the case Pg is Boc group, Boc group can be removed by either trifluoroacetic acid or prolonged heating at a temperature between 110 to 116° C. Racemic mixture of VI and VI' or VII and VII' can be readily resolved into two chiral enantiomers by chiral Super Fluid Chromatography (SFC) or chiral HPLC or chiral column chromatography.

Scheme 4

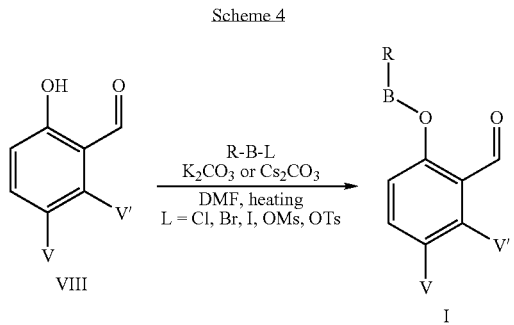

When A is O, B is selected from lower alkyl or lower cycloalkyl, intermediate I can be prepared by reaction of reagent VIII, and compound R—B-L, a base like K₂CO₃ or Cs₂CO₃ in anhydrous N,N-dimethylformamide or N,N-dimethylacetamide under heating conditions. L is a good leaving group like Cl, Br, I, OMs or OTs. Compound VIII is either commercially available or readily prepared according to well established literature procedure (Scheme 4).

Scheme 5

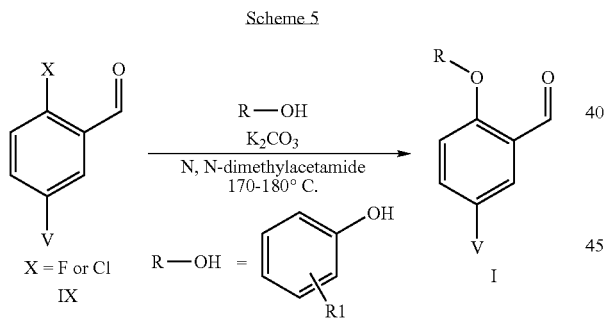

When A is O, B is a bond, and R is selected from aryl, substituted aryl, hetereoaryl, or substituted heteroaryl group in formular I, intermediate I can be prepared by Ullman reaction of compound XI and R—OH under heated conditions (Scheme 5).

When B is selected from lower alkyl or lower cycloalkyl in formula I, the analogues X-a are prepared first according to the methods in Scheme 1-3, followed by a hydrolysis reaction to give the corresponding acid, which is converted into analogues X-b by using well-known methods for carboxamide formation (Scheme 6).

Scheme 6

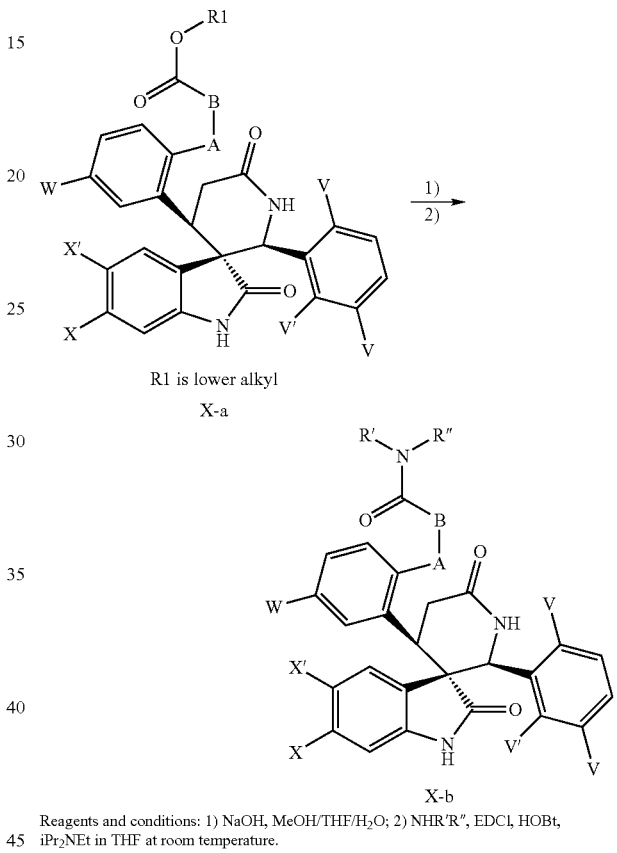

Reagents and conditions: 1) NaOH, MeOH/THF/H₂O; 2) NHR'R'', EDCl, HOBt, iPr₂NEt in THF at room temperature.

Analogues XI-a are prepared first according to the methods in Scheme 1-3, XI-a can be then converted into XI-b, XI-c, XI-d (Scheme 7).

Scheme 7

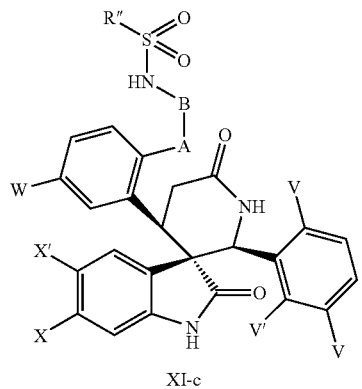

-continued

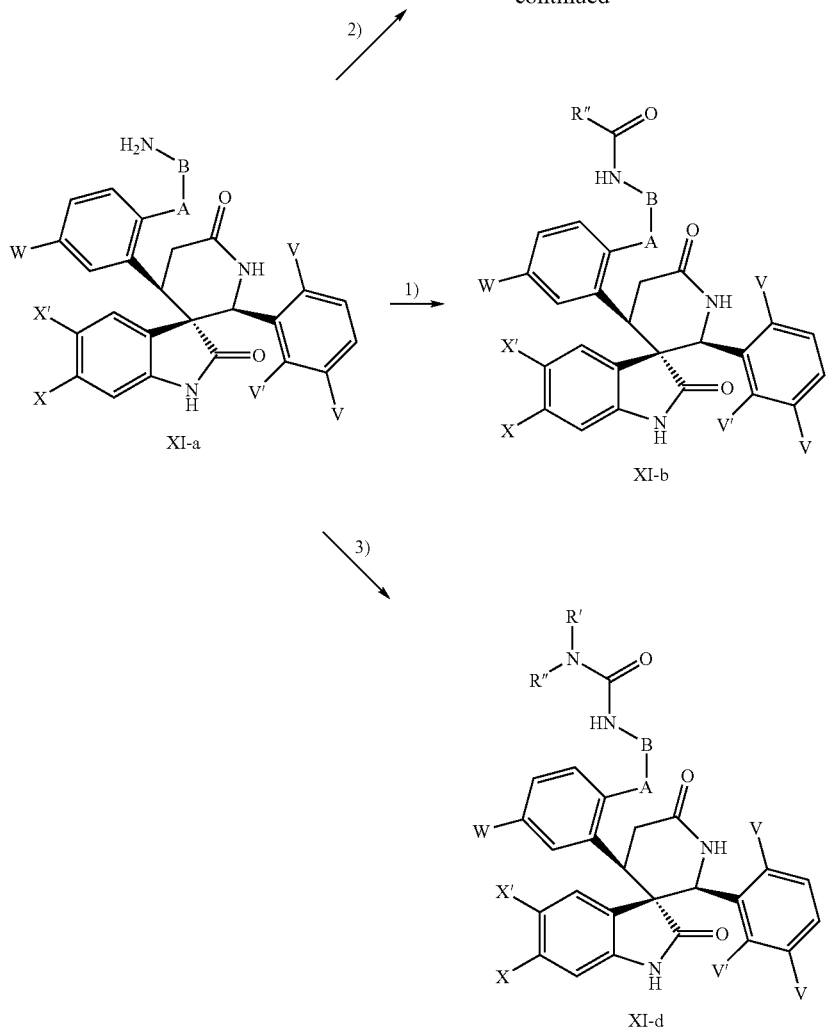

Reagents and conditions: 1) R'R"C(═O)Cl, pyridine, DCM, room temperarure 2) R"S(═O)$_2$Cl, NEt$_3$ in DMF, room temperature; 3) R'R"NC(═O)Cl, NEt$_3$ or R"NCO, room temperature;

The following examples and references are provided to aid the understanding of the present invention, the true scope of which is set forth in the appended claims.

Example 1a

Preparation of Intermediate 2-(4-chloro-2-formyl-phenoxy)-2-methyl-propionic acid ethyl ester

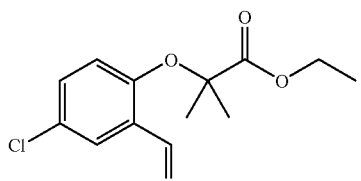

M.W. 270.72
C$_{13}$H$_{15}$ClO$_4$

5-Chloro-2-hydroxy-benzaldehyde (7 g, 45 mmol), 2-bromo-2-methyl-propionic acid ethyl ester (11.4 g, 58 mmol), K$_2$CO$_3$ (18.6 g, 135 mmol) and KI (0.97 g, 5.8 mmol) were mixed in DMF (20 mL). Then the reaction mixture was heated at 110° C. for 3 h. The mixture was filtered and the filtrate was concentrated. The residue was dissolved in ethyl acetate and washed with 1N NaOH. Then the organic layer was separated, dried over Na$_2$SO$_4$ and concentrated to give title compound (7 g)

Example 1b

Preparation of Intermediate E/Z-2-{4-Chloro-2-[6-chloro-2-oxo-1,2-dihydro-indol-ylidenemethyl]-phenoxy}-2-methyl-propionic acid ethyl ester

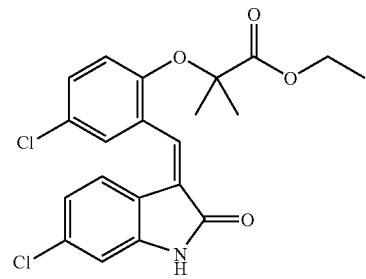

M.W. 420.30
C$_{21}$H$_{19}$Cl$_2$NO$_4$ 2-(4-chloro-2-formyl-phenoxy)-2-methyl-propionic acid ethyl ester (7 g, 26 mmol) and 6-chlorooxindole (3.6 g, 22 mmol) were mixed in anhydrous methanol (30 mL) at room temperature. Then pyrrolidine (1.85 g, 26 mmol) was added slowly. The reaction mixture was heated at 70° C. for 3 h. Then the mixture was cooled to room temperature and filtered. The precipitate was dried and collected to give E/Z-2-[4-chloro-2-(6-chloro-2-oxo-1,2-dihydro-indol-3-ylidenemethyl)-phenoxy]-2-methyl-propionic acid ethyl ester as a yellow solid (7.2 g).

Example 1c

Preparation of Intermediate E/Z 6-Chloro-3-[5-chloro-2-(1-ethoxycarbonyl-1-methyl-ethoxy)-benzylidene]-2-oxo-2,3-dihydro-indole-1-carboxylic acid tert-butyl ester

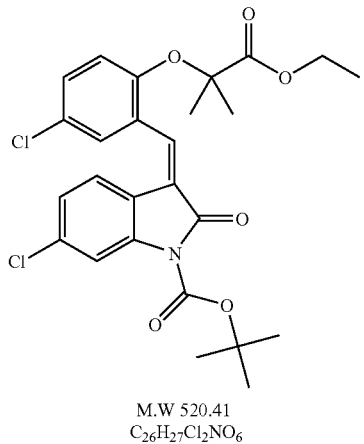

M.W 520.41
C$_{26}$H$_{27}$Cl$_2$NO$_6$

To a solution of E/Z 2-[4-chloro-2-(6-chloro-2-oxo-1,2-dihydro-indol-3-ylidenemethyl)-phenoxy]-2-methyl-propionic acid ethyl ester (7.2 g, 17.2 mmol) in dichloromethane (50 mL) at r.t was added di-tert-butyl-dicarbonate (4.5 g, 20.6 mmol), followed by the addition of 4-dimethylaminopyridine (0.2 g, 1.72 mmol). The reaction mixture was stirred at r.t. for 0.5 h, then the mixture was washed with 0.5N HCl aqueous solution. The organic layer was separated, dried and concentrated to give title compound as a yellow solid (8 g).

Example 1d

Preparation of Intermediate 1-(5-fluoro-2-methylphenyl)-3-trimethylsilyoxy-2-aza-1,3-butadiene

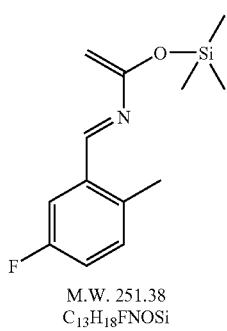

M.W. 251.38
C$_{13}$H$_{18}$FNOSi

To 1,1,1,3,3,3-hexamethyldisilazane (2.18 mL, 10.5 mmol) (Aldrich) under nitrogen at room temperature was added n-butyllithium (2.5 M, 4.2 mL, 10.5 mmol) (Aldrich). The reaction mixture was stirred at room temperature for 10 minutes. Then dry tetrahydrofuran (30 mL) was added, followed by the addition of 5-fluoro-2-methyl-benzaldehyde (1.38 g, 10 mmol) (Platte). After the mixture was stirred at room temperature for 0.5 h, trimethylsilyl chloride (1.33 mL, 10.5 mmol) (Aldrich) was added dropwise. Then the temperature of the mixture was lowered to 0° C. on a cooling ice bath. To this mixture was added triethylamine (1.9 mL, 13.6 mmol) in one portion, followed by the dropwise addition of a solution of acetyl chloride (0.97 mL, 13.6 mmol) in diethyl ether (50 mL). The cooling bath was removed, and the mixture was stirred at room temperature for 1 h. The mixture was quickly filtered on celite under nitrogen, and filtrate was concentrated under reduced pressure to give crude 1-(5-fluoro-2-methylphenyl)-3-trimethylsilyoxy-2-aza-1,3-butadiene as a yellow gum and used for the next step without further purification.

Example 1e

Preparation of Intermediate racemic (2'S,3S,4'R)-6-chloro-4'-[5-chloro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione

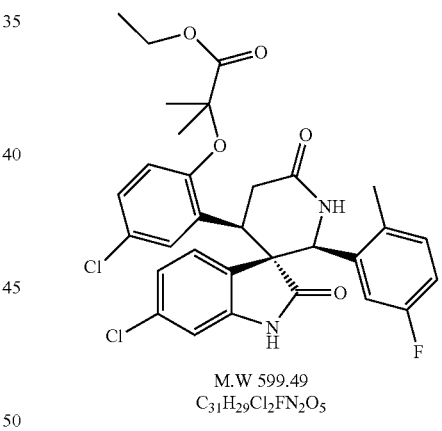

M.W 599.49
C$_{31}$H$_{29}$Cl$_2$FN$_2$O$_5$

To a toluene solution (50 mL) of 1-(5-fluoro-2-methylphenyl)-3-trimethylsilyoxy-2-aza-1,3-butadiene (77 mmol) was added E/Z 6-chloro-3-[5-chloro-2-(1-ethoxycarbonyl-1-methyl-ethoxy)-benzylidene]-2-oxo-2,3-dihydro-indole-1-carboxylic acid tert-butyl ester (8 g, 15.44 mmol). Then the reaction mixture were heated at 130° C. for 2. After the solution was cooled to room temperature, methanol was added, and then the mixture was concentrated. Then a mixture of trifluoroacetic acid (10 mL) and dichloromethane (30 mL) was added. The reaction mixture was stirred at room temperature for 10 min. The solution was concentrated and the residue was purified by Prep-HPLC to give title compound as a white solid (2.7 g).

m/z (M+H)$^+$: 599

Example 1f

Preparation of Intermediate racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione

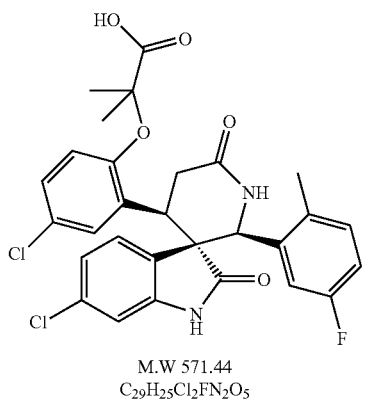

M.W 571.44
C29H25Cl2FN2O5

Racemic (2'S,3S,4'R)-6-chloro-4'-[5-chloro-2-(1-ethoxy-carbonyl-1-methyl-ethoxy)-phenyl]-2'-(5-fluoro-2-methyl phenyl)spiro[3H-indole-3,3'-piperidine]-2,6'(1H)-dione (2.7 g, 4.5 mmol) was dissolved in THF (20 mL). Then aqueous solution (10 mL) of KOH (0.5 g) was added. The mixture was refluxed for 1 h. After cooled to room temperature, the solution was concentrated and then the residue was acidified to "pH" 2-3 by addition of concentrated aqueous HCl solution. The white solid was collected by filtration to give title compound (1.6 g).
m/z (M+H)+: 571

Example 1g

Preparation of Racemic (2'S,3S,4'R)-6-chloro-4'-{5-chloro-2-[1-methyl-1-(1-methyl-piperidin-4-ylcarbamoyl)-ethoxy]-phenyl}-2'-(5-fluoro-2-methyl-phenyl)spiro[3H-indole-3,3'-piperidine]-2,6'(1H)-dione

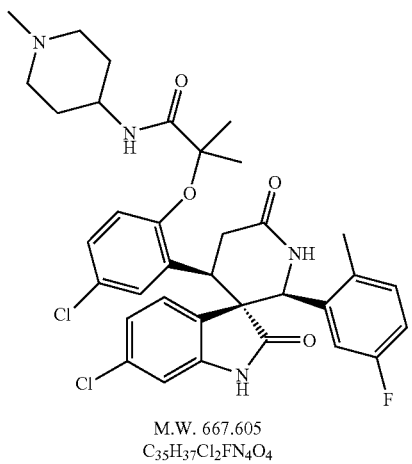

M.W. 667.605
C35H37Cl2FN4O4

To a mixture of racemic (2'S,3S,4'R)-6-chloro-4'-[5-chloro-2-(2-hydroxy-1,1-dimethyl-ethoxy)-phenyl]-2'-[5-fluoro-2-methylphenyl]-spiro[3H-indole-3,3'-piperidine]-2,6'(1H)-dione (35 mg, 0.06 mmol), EDCl (18 mg, 0.094 mmol), HOBt (14 mg, 0.094 mmol) and DIPEA (23 mg, 0.2 mmol) in THF (1 mL) was added 1-methyl-piperidin-4-ylamine (21 mg, 0.18 mmol). The mixture was stirred at room temperature overnight, purified by prep-HPLC to give the title compound as a white solid (7 mg).
m/z (M+H)+: 667

Example 2

Preparation of Racemic (2'S,3S,4'R)-6-chloro-4'-[5-chloro-2-(1-cyclobutylcarbamoyl-1-methyl-ethoxy)-phenyl]-2'-(5-fluoro-2-methyl-phenyl)spiro[3H-indole-3,3'-piperidine]-2,6'(1H)-dione

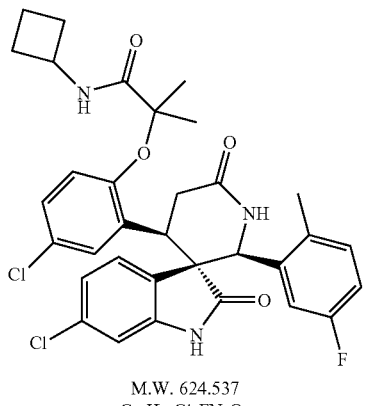

M.W. 624.537
C33H32Cl2FN3O4

To a mixture of racemic (2'S,3S,4'R)-6-chloro-4'-[5-chloro-2-(2-hydroxy-1,1-dimethyl-ethoxy)-phenyl]-2'-[5-fluoro-2-methylphenyl]-spiro[3H-indole-3,3'-piperidine]-2,6'(1H)-dione (35 mg, 0.06 mmol), EDCl (18 mg, 0.094 mmol), HOBt (14 mg, 0.094 mmol) and DIPEA (23 mg, 0.2 mmol) in THF (1 mL) was added cyclobutylamine (13 mg, 0.18 mmol). The mixture was stirred at room temperature overnight, purified by prep-HPLC to give the title compound as a white solid (16 mg).
m/z (M+H)+: 624

Example 3

Preparation of Racemic (2'S,3S,4'R)-6-chloro-4'-{5-chloro-2-[1-(2-hydroxy-ethylcarbamoyl)-1-methyl-ethoxy]-phenyl}-2'-(5-fluoro-2-methyl-phenyl)-spiro[3H-indole-3,3'-piperidine]-2,6'(1H)-dione

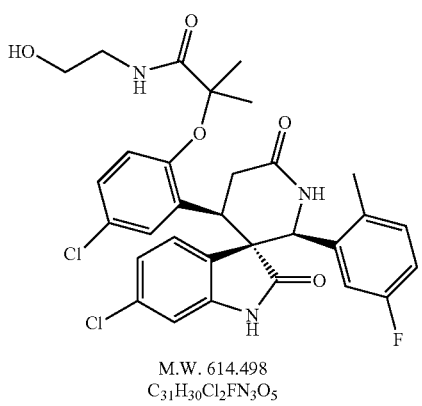

M.W. 614.498
C31H30Cl2FN3O5

To a mixture of racemic (2'S,3S,4'R)-6-chloro-4'-[5-chloro-2-(2-hydroxy-1,1-dimethyl-ethoxy)phenyl]-2'-[5-fluoro-2-methylphenyl]-spiro[3H-indole-3,3'-piperidine]-2,6'(1H)-dione (35 mg, 0.06 mmol), EDCl (18 mg, 0.094 mmol), HOBt (14 mg, 0.094 mmol) and DIPEA (23 mg, 0.2 mmol) in THF (1 mL) was added 2-amino-ethanol (11 mg, 0.18 mmol). The mixture was stirred at room temperature overnight, purified by prep-HPLC to give the title compound as a white solid (9 mg).

m/z (M+H)$^+$: 614

Example 4

Preparation of Racemic (2'S,3S,4'R)-4'-{2-[1-(2-acetylamino-ethylcarbamoyl)-1-methyl-ethoxy]-5-chloro-phenyl}-6-chloro-2'-(5-fluoro-2-methyl-phenyl)spiro[3H-indole-3,3'-piperidine]-2,6'(1H)-dione

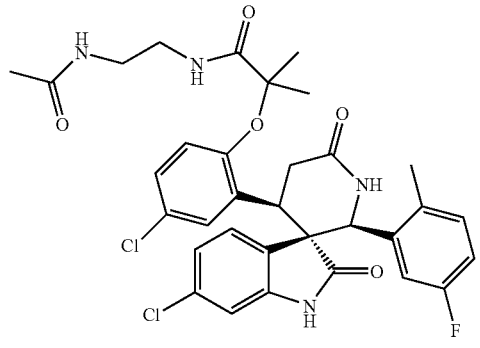

M.W. 655.551
$C_{33}H_{33}Cl_2FN_4O_5$

To a mixture of racemic (2'S,3S,4'R)-6-chloro-4'-[5-chloro-2-(2-hydroxy-1,1-dimethyl-ethoxy)-phenyl]-2'-[5-fluoro-2-methylphenyl]-spiro[3H-indole-3,3'-piperidine]-2,6'(1H)-dione (35 mg, 0.06 mmol), EDCl (18 mg, 0.094 mmol), HOBt (14 mg, 0.094 mmol) and DIPEA (23 mg, 0.2 mmol) in THF (2 mL) was added N-(2-amino-ethyl)-acetamide (19 mg, 0.18 mmol). The mixture was stirred at room temperature overnight, purified by prep-HPLC to give the title compound as a white solid (11 mg).

m/z (M+H)$^+$: 655

Example 5

Preparation of (2'S,3S,4'R)-6-chloro-4'-{5-chloro-2-[1-(S-2,3-dihydroxy-propyl carbamoyl)-1-methyl-ethoxy]-phenyl}-2'-(5-fluoro-2-methyl-phenyl)spiro[3H-indole-3,3'-piperidine]-2,6'(1H)-dione

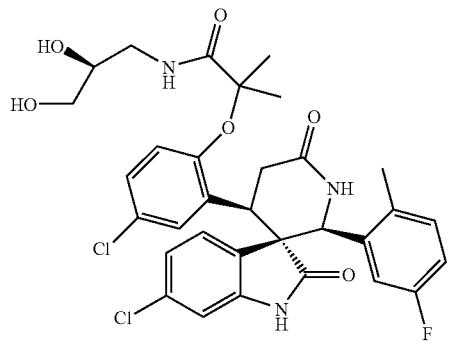

M.W. 644.524
$C_{32}H_{32}Cl_2FN_3O_6$

To a mixture of racemic (2'S,3S,4'R)-6-chloro-4'-[5-chloro-2-(2-hydroxy-1,1-dimethyl-ethoxy)-phenyl]-2'-[5-fluoro-2-methylphenyl]-spiro[3H-indole-3,3'-piperidine]-2,6'(1H)-dione (35 mg, 0.06 mmol), EDCl (18 mg, 0.094 mmol), HOBt (14 mg, 0.094 mmol) and DIPEA (23 mg, 0.2 mmol) in THF (2 mL) was added S-3-amino-1,2-propanediol (17 mg, 0.18 mmol). The mixture was stirred at room temperature overnight, purified by prep-HPLC to give the title compound as a white solid (7 mg).

m/z (M+H)$^+$: 644

Example 6

Preparation of Racemic (2'S,3S,4'R)-6-chloro-4'-{5-chloro-2-[1-(2-methoxy-ethylcarbamoyl)-1-methyl-ethoxy]-phenyl}-2'-(5-fluoro-2-methyl-phenyl)-spiro[3H-indole-3,3'-piperidine]-2,6'(1H)-dione

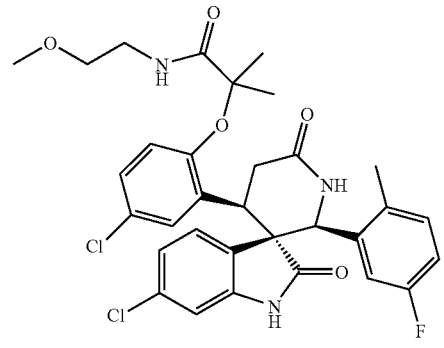

M.W. 628.525
$C_{32}H_{32}Cl_2FN_3O_5$

To a mixture of racemic (2'S,3S,4'R)-6-chloro-4'-[5-chloro-2-(2-hydroxy-1,1-dimethyl-ethoxy)-phenyl]-2'-[5-fluoro-2-methylphenyl]-spiro[3H-indole-3,3'-piperidine]-2,6'(1H)-dione (35 mg, 0.06 mmol), EDCl (18 mg, 0.094 mmol), HOBt (14 mg, 0.094 mmol) and DIPEA (23 mg, 0.2 mmol) in THF (2 mL) was added 2-methoxy-ethylamine (14 mg, 0.18 mmol). The mixture was stirred at room temperature overnight, purified by prep-HPLC to give the title compound as a white solid (10 mg).

m/z (M+H)$^+$: 628.

Example 7

Preparation of Racemic (2'S,3S,4'R)-6-chloro-4'-{5-chloro-2-[1-(3-dimethylamino-propylcarbamoyl)-1-methyl-ethoxy]-phenyl}-2'-(5-fluoro-2-methyl-phenyl)spiro[3H-indole-3,3'-piperidine]-2,6'(1H)-dione

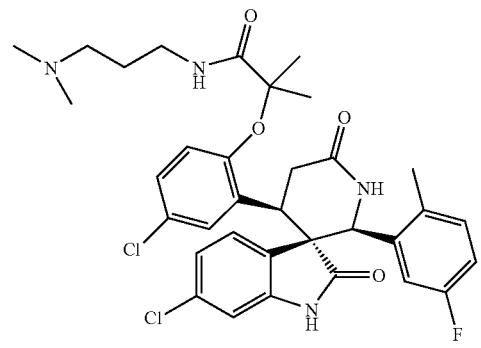

M.W. 655.594
$C_{34}H_{37}Cl_2FN_4O_4$

To a mixture of racemic (2'S,3S,4'R)-6-chloro-4'-[5-chloro-2-(2-hydroxy-1,1-dimethyl-ethoxy)-phenyl]-2'-[5-fluoro-2-methylphenyl]spiro[3H-indole-3,3'-piperidine]-2,6'(1H)-dione (35 mg, 0.06 mmol), EDCl (18 mg, 0.094 mmol), HOBt (14 mg, 0.094 mmol) and DIPEA (23 mg, 0.2 mmol) in THF (2 mL) was added N,N-dimethyl-propane-1,3-diamine (19 mg, 0.18 mmol). The mixture was stirred at room temperature overnight, purified by prep-HPLC to give the title compound as a white solid (7 mg).

m/z (M+H)⁺: 655

Example 8

Preparation of Racemic (2'S,3S,4'R)-6-chloro-4'-{5-chloro-2-[1-methyl-1-(2-piperidin-1-yl-ethylcarbamoyl)-ethoxy]-phenyl}-2'-(5-fluoro-2-methyl-phenyl)-spiro[3H-indole-3,3'-piperidine]-2,6'(1H)-dione

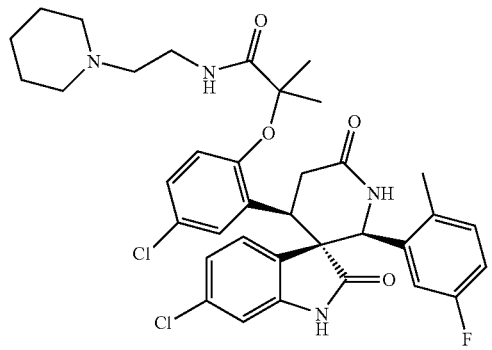

M.W. 681.632
$C_{36}H_{39}Cl_2FN_4O_4$

To a mixture of racemic (2'S,3S,4'R)-6-chloro-4'-[5-chloro-2-(2-hydroxy-1,1-dimethyl-ethoxy)-phenyl]-2'-[5-fluoro-2-methylphenyl]-spiro[3H-indole-3,3'-piperidine]-2,6'(1H)-dione (35 mg, 0.06 mmol), EDCl (18 mg, 0.094 mmol), HOBt (14 mg, 0.094 mmol) and DIPEA (23 mg, 0.2 mmol) in THF (2 mL) was added 2-piperidin-1-yl-ethylamine (24 mg, 0.18 mmol). The mixture was stirred at room temperature overnight, purified by prep-HPLC to give the title compound as a white solid (7 mg).

m/z (M+H)⁺: 681

Example 9a

Preparation of Intermediate 2-[4-bromo-2-(6-chloro-2-oxo-1,2-dihydro-indol-3-ylidenemethyl)-phenoxy]-2-methyl-propionic acid ethyl ester

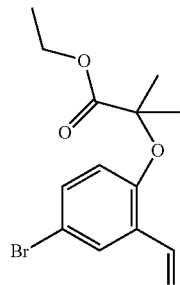

M.W. 315.17
$C_{13}H_{15}BrO_4$

5-Bromo-2-hydroxy-benzaldehyde (20 g, 100 mmol), 2-bromo-2-methyl-propionic acid ethyl ester (29 g, 150 mmol), $K_2CO_3$ (27.6 g, 200 mmol) and KI (3.2 g, 19 mmol) were mixed in DMF (100 mL). Then the reaction mixture was heated at 110° C. for 3 h. The mixture was filtered and the filtrate was concentrated. The residue was dissolved in ethyl acetate and washed with 1N NaOH. Then the organic layer was separated, dried over $Na_2SO_4$ and concentrated to give title compound (21 g)

Example 9b

Preparation of Intermediate E/Z-2-[4-bromo-2-(6-chloro-2-oxo-1,2-dihydro-indol-3-ylidenemethyl)-phenoxy]-2-methyl-propionic acid ethyl ester

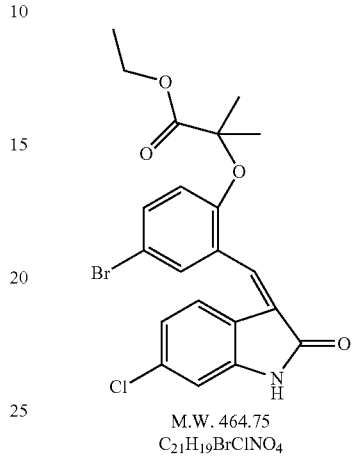

M.W. 464.75
$C_{21}H_{19}BrClNO_4$

To the mixture of 6-chlorooxindole (10.6 g, 63 mmol) and 2-(4-bromo-2-formyl-phenoxy)-2-methyl-propionic acid ethyl ester (20 g, 63 mmol) in methanol (150 mL) was added pyrrolidine (4.5 g, 63 mmol) dropwise. The mixture was then heated at 70° C. for 1 h. After cooled to 4° C., the mixture was filtered and the precipitate was collected, dried to give a mixture of E/Z-2-[4-bromo-2-(6-chloro-2-oxo-1,2-dihydro-indol-3-ylidenemethyl)-phenoxy]-2-methyl-propionic acid ethyl ester (18.5 g, 63%).

Example 9c

Preparation of Intermediate E/Z 3-[5-bromo-2-(1-ethoxycarbonyl-1-methyl-ethoxy)-benzylidene]-6-chloro-2-oxo-2,3-dihydro-indole-1-carboxylic acid tert-butyl ester

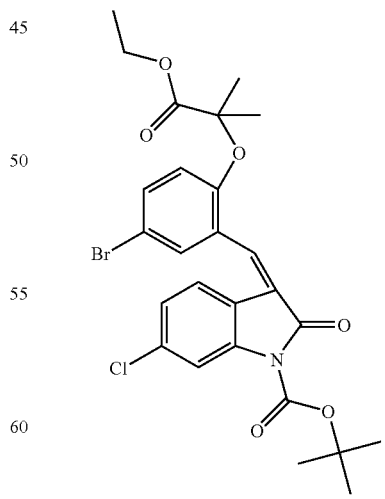

M.W. 564.87
$C_{26}H_{27}BrClNO_6$

To a solution of E/Z-2-[4-bromo-2-(6-chloro-2-oxo-1,2-dihydro-indol-3-ylidenemethyl)-phenoxy]-2-methyl-propionic acid ethyl ester (5 g, 11 mmol) in dichloromethane (50 mL) at r.t was added di-tert-butyl-dicarbonate (2.4 g, 11 mmol), followed by the addition of 4-dimethylaminopyridine (1 g, 8.2 mmol). The reaction mixture was stirred at r.t. for 2 h, washed with aqueous HCl solution (0.5M) and water. The organic layer was separated, dried over $Na_2SO_4$, concentrated to give E/Z 3-[5-bromo-2-(1-ethoxycarbonyl-1-methyl-ethoxy)-benzylidene]-6-chloro-2-oxo-2,3-dihydro-indole-1-carboxylic acid tert-butyl ester as a yellow oil (5.5 g, 88%).

Example 9d

Preparation of Intermediate racemic (2'S,3S,4'R)-4'-[5-bromo-2-(1-ethoxycarbonyl-1-methyl-ethoxy)-phenyl]-6-chloro-2'-(5-fluoro-2-methyl-phenyl)spiro[3H-indole-3,3'-piperidine]-2,6'(1H)-dione

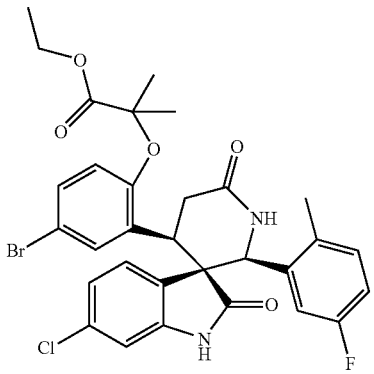

M.W. 643.94
$C_{31}H_{29}BrClFN_2O_5$

In a manner similar to the method described in Example 1 e, E/Z-3-[5-bromo-2-(1-ethoxycarbonyl-1-methyl-ethoxy)-benzylidene]-6-chloro-2-oxo-2,3-dihydro-indole-1-carboxylic acid tert-butyl ester (1.5 g, 2.6 mmol).) was reacted with 1-(5-fluoro-2-methyl-phenyl)-3-trimethylsilyoxy-2-aza-1,3-butadiene (2 M solution in toluene, 5 mL, 10 mmol) and then trifluoroacetic acid in dichloromethane to give the title compound (RO5233645-000) (700 mg). m/z (M+H)$^+$: 643

Example 9e

Preparation of Intermediate racemic (2'S,3S,4'R)-4'-[5-bromo-2-(1-hydroxycarbonyl-1-methyl-ethoxy)-phenyl]-6-chloro-2'-(5-fluoro-2-methyl-phenyl)spiro[3H-indole-3,3'-piperidine]-2,6'(1H)-dione

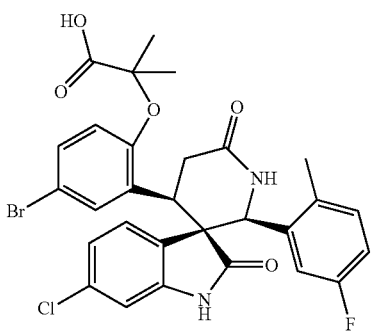

M.W. 615.89
$C_{29}H_{25}BrClFN_2O_5$

To a mixture of racemic (2'S,3S,4'R)-4'-[5-bromo-2-(1-ethoxycarbonyl-1-methyl-ethoxy)-phenyl]-6-chloro-2'-(5-fluoro-2-methyl-phenyl)spiro[3H-indole-3,3'-piperidine]-2,6'(1H)-dione (120 mg, 0.19 mmol) in methanol (4 mL) was added a solution of NaOH (24 mg, 0.6 mmol) in water (2 mL). The mixture was heated at 70° C. for 3 h, evaporated to remove most of methanol, cooled to room temperature, and acidified to "pH" 1 with aqueous HCl solution. The precipitate was collected and dried to give product as a white solid (75 mg). m/z (M+H)$^+$: 615

Example 9f

Preparation of Racemic (2'S,3S,4'R)-4'-[5-bromo-2-(2-methanesulfonylamino-1,1-dimethyl-2-oxo-ethoxy)-phenyl]-6-chloro-2'-(5-fluoro-2-methyl-phenyl)-spiro[3H-indole-3,3'-piperidine]-2,6'(1H)-dione

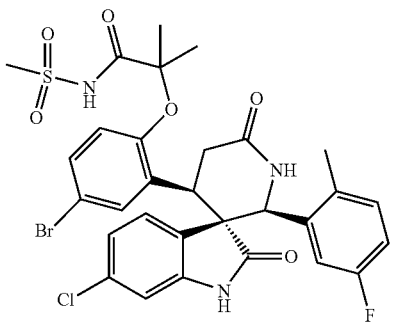

M.W. 692.987
$C_{30}H_{28}BrClFN_3O_6S$

A solution of racemic (2'S,3S,4'R)-4'-[5-bromo-2-(1-hydroxycarbonyl-1-methyl-ethoxy)-phenyl]-6-chloro-2'-(5-fluoro-2-methyl-phenyl)spiro[3H-indole-3,3'-piperidine]-2,6'(1H)-dione (20 mg, 0.032 mmol) and CDI (11 mg, 0.064 mmol) in DMF (0.2 mL) was heated at 60° C. for 30 min, then cooled to room temperature. To this solution was added a mixture of methanesulfonamide (19 mg, 0.2 mmol) and NaH (8 mg, 60%, 0.2 mmol) in DMF (0.2 mL). The resulting mixture was stirred at room temperature for 10 min, purified by prep-HPLC to give the title compound as a white solid (10 mg).

Example 10a

Preparation of Intermediate 1-(4-chloro-2-formyl-phenoxy)-cyclobutanecarboxylic acid methyl ester

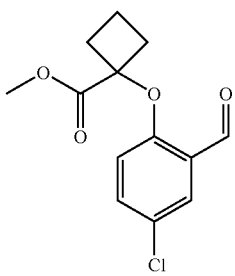

M.W. 268.70
$C_{13}H_{13}ClO_4$

To a mixture of 5-chloro-2-hydroxy-benzaldehyde (10 g, 64 mmol), KI (3 g) and $K_2CO_3$ (13 g, 94 mmol) in DMF (100 mL) was added 1-bromo-cyclobutanecarboxylic acid methyl ester (15 g, 77 mmol). The mixture was heated at 140° C. for 1.5 h. Then additional 1-bromo-cyclobutanecarboxylic acid methyl ester (0.5 g, 2.6 mmol) was added and the mixture was heated at 140° C. for additional 10 min, cooled to room temperature and partitioned between ethyl acetate and water. The organic layer was washed with water, dried over anhydrous Na$_2$SO$_4$, concentrated to give the title compound as dark oil (18 g).

Example 10b

Preparation of Intermediate E/Z-1-[4-chloro-2-(6-chloro-2-oxo-1,2-dihydro-indol-3-ylidenemethyl)-phenoxy]-cyclobutanecarboxylic acid methyl ester

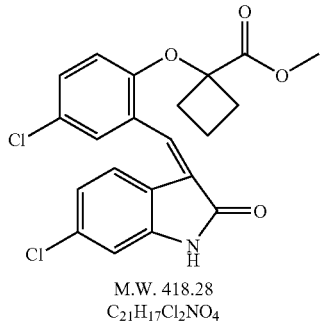

M.W. 418.28
C$_{21}$H$_{17}$Cl$_2$NO$_4$

To the mixture of 6-chlorooxindole (10 g, 60 mmol) and 1-(4-chloro-2-formyl-phenoxy)-cyclobutanecarboxylic acid methyl este (18 g, 67 mmol) in methanol (100 mL) was added pyrrolidine (4.5 mg, 63 mmol) dropwise. The mixture was then heated at 80° C. for 1 h. After cooled to room temperature, the mixture was filtered and the precipitate was collected, dried to give the title compound (6 g).

Example 10c

Preparation of Intermediate E/Z-6-chloro-3-[5-chloro-2-(1-methoxycarbonyl-cyclobutoxy)-benzylidene]-2-oxo-2,3-dihydro-indole-1-carboxylic acid tert-butyl ester

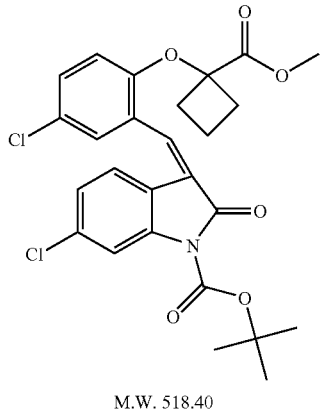

M.W. 518.40
C$_{26}$H$_{25}$Cl$_2$NO$_6$

To a solution of E/Z-1-[4-chloro-2-(6-chloro-2-oxo-1,2-dihydro-indol-3-ylidenemethyl)-phenoxy]-cyclobutanecarboxylic acid methyl ester (6 g, 14 mmol) in DCM (50 mL) at r.t was added diteret-butyl-dicarbonate (4.7 g, 21 mmol), followed by the addition of 4-dimethylaminopyridine (1 g, 8.2 mmol). The reaction mixture was stirred at r.t. for 2 h, washed with HCl aq. (0.5 M) and water, dried over anhydrous Na$_2$SO$_4$, concentrated to give the title compound as a yellow solid (5 g)

Example 10d

Preparation of Intermediate racemic (2'S,3S,4'R)-6-chloro-4'-[5-chloro-2-(1-methoxycarbonyl-cyclobutoxy)-phenyl]-2'-(5-fluoro-2-methyl-phenyl)-spiro [3H-indole-3,3'-piperidine]-2,6'(1H)-dione

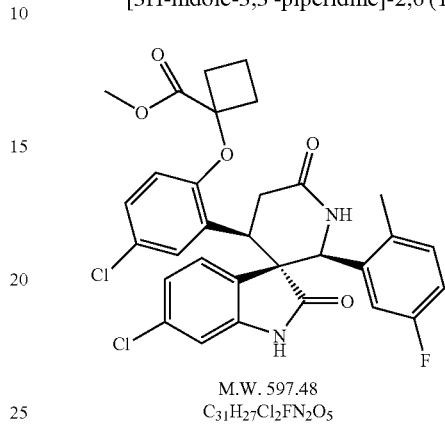

M.W. 597.48
C$_{31}$H$_{27}$Cl$_2$FN$_2$O$_5$

To a toluene solution of 1-(5-fluoro-2-methylphenyl)-3-trimethylsilyoxy-2-aza-1,3-butadiene in toluene (2 M, 5 mL, 10 mmol) was added E/Z 6-chloro-3-[5-chloro-2-(1-methoxycarbonyl-cyclobutoxy)-benzylidene]-2-oxo-2,3-dihydro-indole-1-carboxylic acid tert-butyl ester (1.5 g, 2.9 mmol). The reaction mixture was heated at 80° C. overnight under argon protection, then TFA (5 mL) was added, and the resulting mixture was stirred at room temperature for 20 min, evaporated in vacuo. The residue was partitioned between ethyl acetate and NaOH aq. (1 M). The organic layer was washed with water, dried over anhydrous Na$_2$SO$_4$, concentrated and purified by column chromatography to give the title compound as a white solid (340 mg).

Example 10e

Preparation of Intermediate racemic (2'S,3S,4'R)-6-chloro-4'-[5-chloro-2-(1-hydroxycarbonyl-cyclobutoxy)-phenyl]-2'-(5-fluoro-2-methyl-phenyl)spiro [3H-indole-3,3'-piperidine]-2,6'(1H)-dione

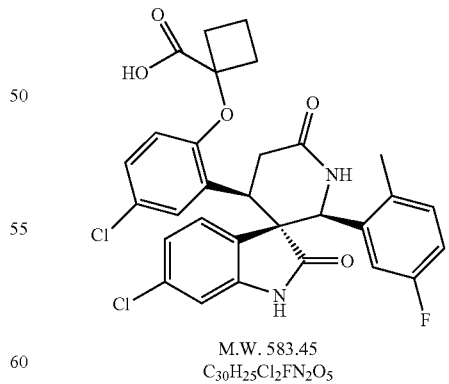

M.W. 583.45
C$_{30}$H$_{25}$Cl$_2$FN$_2$O$_5$

To a mixture of racemic (2'R,3R,4'S)-6-chloro-4'-[5-chloro-2-(1-methoxycarbonyl-cyclobutoxy)-phenyl]-2'-(5-fluoro-2-methyl-phenyl)-spiro[3H-indole-3,3'-piperidine]-2,6'(1H)-dione (200 mg, 0.33 mmol) in methanol (4 mL) was added a solution of NaOH (40 mg, 1 mmol) in water (2 mL). The mixture was heated at 70° C. for 2 h, evaporated to remove methanol, cooled to room temperature, and acidified to "pH" 1 with HCl aq. The precipitate was collected, washed with water and dried to give the title compound as a white solid (175 mg).

Example 10f

Preparation of Racemic (2'S,3S,4'R)-6-chloro-4'-[5-chloro-2-(1-methanesulfonylaminocarbonyl-cyclobutoxy)-phenyl]-2'-(5-fluoro-2-methyl-phenyl)-spiro[3H-indole-3,3'-piperidine]-2,6'(1H)-dione

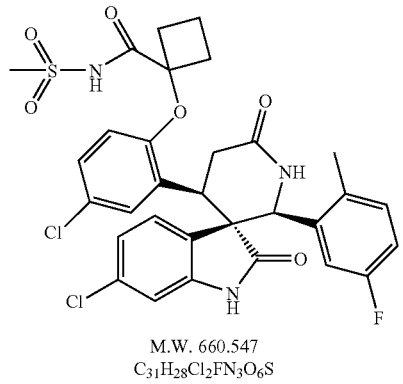

M.W. 660.547
$C_{31}H_{28}Cl_2FN_3O_6S$

A solution of racemic (2'S,3S,4'R)-6-chloro-4'-[5-chloro-2-(1-hydroxycarbonyl-cyclobutoxy)-phenyl]-2'-(5-fluoro-2-methyl-phenyl)spiro[3H-indole-3,3'-piperidine]-2,6'(1H)-dione (50 mg, 0.086 mmol) and CDI (28 mg, 0.17 mmol) in DMF (0.5 mL) was heated at 60° C. for 30 min, and then cooled to root temperature. To this solution was added a mixture of methanesulfonamide (95 mg, 1 mmol) and NaH (40 mg, 60%, 1 mmol) in DMF (1 mL). The resulting mixture was stirred at room temperature for 10 min, purified by prep-HPLC to give the title compound t as a white solid (20 mg).

Example 11

Preparation of Racemic (2'S,3S,4'R)-6-chloro-4'-{5-chloro-2-[1-(4-fluoro-benzenesulfonylaminocarbonyl)-cyclobutoxy]-phenyl}-2'-(5-fluoro-2-methyl-phenyl)-spiro[3H-indole-3,3'-piperidine]-2,6'(1H)-dione

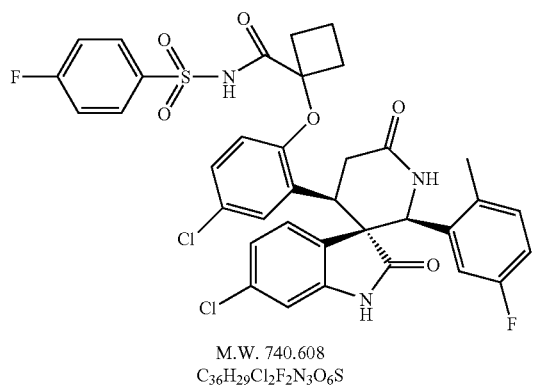

M.W. 740.608
$C_{36}H_{29}Cl_2F_2N_3O_6S$

A solution of racemic (2'S,3S,4'R)-6-chloro-4'-[5-chloro-2-(1-hydroxycarbonyl-cyclobutoxy)-phenyl]-2'-(5-fluoro-2-methyl-phenyl)spiro[3H-indole-3,3'-piperidine]-2,6'(1H)-dione (50 mg, 0.086 mmol) and CDI (28 mg, 0.17 mmol) in DMF (0.5 mL) was heated at 60° C. for 30 min, and then cooled to root temperature. To this solution was added a mixture of 4-fluoro-benzenesulfonamide (175 mg, 1 mmol) and NaH (40 mg, 60%, 1 mmol) in DMF (1 mL). The resulting mixture was stirred at room temperature for 10 min, purified by prep-HPLC to give the title compound as a white solid (20 mg).

Example 12a

Preparation of Intermediate chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione

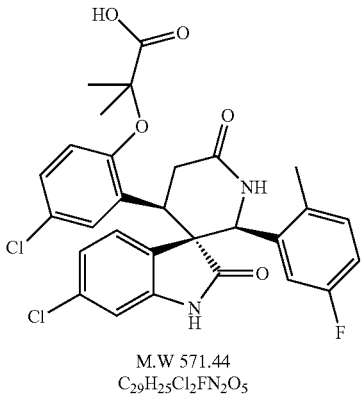

M.W 571.44
$C_{29}H_{25}Cl_2FN_2O_5$

Separation of the two enantiomers from racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione was conducted by chiral HPLC to provide chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione as a white solid (8 mg) (RO5221490-000) and chiral (2'R,3R,4'S)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione as a white solid (8 mg) (RO5221491-000).

m/z (M+H)⁺: 571

Example 12b

Preparation of Chiral (2'S,3S,4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione

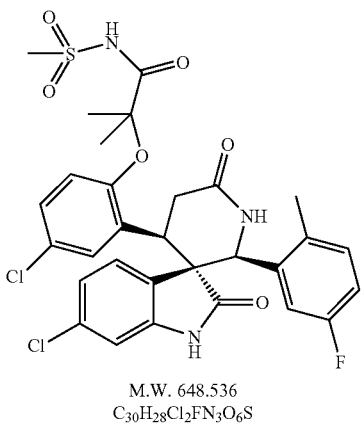

M.W. 648.536
$C_{30}H_{28}Cl_2FN_3O_6S$

A solution of chiral (2'S,3S,4'R)-6-chloro-4'-[5-chloro-2-(2-hydroxy-1,1-dimethyl-ethoxy)-phenyl]-2'-[5-fluoro-2-methylphenyl]spiro[3H-indole-3,3'-piperidine]-2,6'(1H)-dione (20 mg, 0.035 mmol) and CDI (11 mg, 0.068 mmol) in DMF (0.2 mL) was heated at 60° C. for 30 min, and then cooled to root temperature. To this solution was added a mixture of methanesulfonamide (19 mg, 0.2 mmol) and NaH (8 mg, 60%, 0.2 mmol) in DMF (0.2 mL). The resulting mixture was stirred at room temperature for 10 min, purified by prep-HPLC to give the title compound as a white solid (7 mg).

Example 13a

Preparation of Intermediate of 5-chloro-2-methyl-benzaldehyde

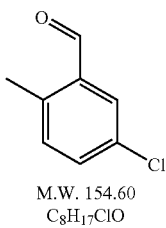

M.W. 154.60
$C_8H_{17}ClO$

A mixture of paraformaldehyde (11.5 g, 0.38 mol) and hydroxylamine hydrochloride (26.3 g, 0.38 mol) in water (170 mL) was heated until a clear solution was obtained. Then there was added hydrated sodium acetate (51 g, 0.38 mol), and the mixture was boiled gently under reflux for 15 minutes to give a 10% solution of formaldoxime. A mixture of 2-choro-4-methylaniline (35.5 g, 0.25 mol) and water (50 mL) was stirred, and concentrated hydrochloric acid (57 mL) was added slowly. The mixture was cooled to room temperature, 100 g of ice was added, and the temperature of the mixture was maintained at −5° C. to +5° C. by means of an ice-salt bath. To the stirred mixture there was added a solution of sodium nitrite (17.5 g, 0.25 mol) in water (25 mL). After completion of the addition, the stirring was continued for a period of 15 minutes. The stirred solution of the diazonium salt was made neutral to Congo red by the addition of a solution of hydrated sodium acetate in water (35 mL). The aqueous 10% formaldoxime was added hydrated cupric sulfate (6.5 g, 0.026 mol), sodium sulfite (1.0 g, 0.0079 mole), and a solution of hydrated sodium acetate (160 g) in water (180 mL). The solution was maintained at 10-15° C. by means of a cold-water bath and stirred vigorously. The neutral diazonium salt solution was slowly introduced below the surface of the formaldoxime. After the addition of the diazonium salt solution was complete, the stirring was continued for an additional hour and then the mixture was treated with concentrated hydrochloric acid (230 mL). The mixture was gently heated under reflux for 2 hours. The mixture was extracted with three portions of ether (150 mL), and the ethereal extracts were washed with a saturated NaCl solution, Then the organic layer was dried over anhydrous $Na_2SO_4$ and concentrated to obtain yellow solid (Yield: 21 g, 36%).

m/z $(M+H)^+$: 155

Example 13b

Preparation of Intermediate 1-(5-chloro-2-methylphenyl)-3-trimethylsilyoxy-2-aza-1,3-butadiene

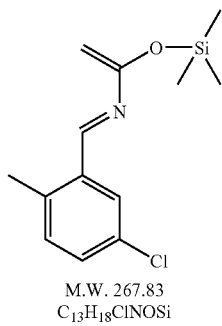

M.W. 267.83
$C_{13}H_{18}ClNOSi$

In a manner similar to the method described in example 1c, 5-chloro-2-methylbenzaldehyde (15 g, 97 mmol) was used as the starting to react with 1M THF solution of LiHMDS (97 mmol, 97 mL), trimethylsilyl chloride (10.3 g, 97 mmol), triethylamine (13.2 g, 126 mmol) and acetyl chloride (9.5 g, 126 mmol) to give crude 1-(5-chloro-2-methylphenyl)-3-trimethylsilyoxy-2-aza-1,3-butadiene as a yellow gum and used without further purification.

Example 13c

Preparation of Intermediate toluene-4-sulfonic acid 3-methyl-oxetan-3-ylmethyl ester

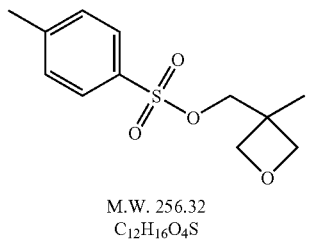

M.W. 256.32
$C_{12}H_{16}O_4S$

To a mixture of (3-methyl-oxetan-3-yl)-methanol (10.2 g, 0.1 mol) and DMAP (18.3 g, 0.15 mol) in DCM (100 mL) was added 4-methyl-benzenesulfonyl chloride (19 g, 0.1 mol). The mixture was stirred at room temperature for 1 h, then filtered. The filtrate was washed with HCl aq. (1 M) and water, dried over anhydrous $Na_2SO_4$ and concentrated to give the title compound (18 g).

Example 13d

Preparation of Intermediate 5-bromo-2-(3-methyl-oxetan-3-ylmethoxy)-benzaldehyde

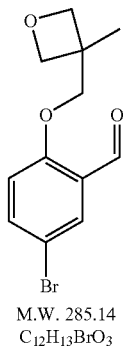

M.W. 285.14
$C_{12}H_{13}BrO_3$

To a mixture of 5-bromo-2-hydroxy-benzaldehyde (14 g, 70 mmol), KI (5 g) and K$_2$CO$_3$ (19 g, 140 mmol) in DMF (100 mL) was added toluene-4-sulfonic acid 3-methyl-oxetan-3-ylmethyl ester (18 g, 70 mmol). The mixture was heated at 140° C. for 2 h, and then cooled to room temperature, partitioned between water and ethyl acetate. The organic layer was washed with water for 3 times, dried over anhydrous Na$_2$SO$_4$ and concentrated. The residue was purified by column chromatography to give the title compound (10 g).

Example 13e

Preparation of Intermediate E/Z 3-[5-bromo-2-(3-methyl-oxetan-3-ylmethoxy)-benzylidene]-6-chloro-1,3-dihydro-indol-2-one

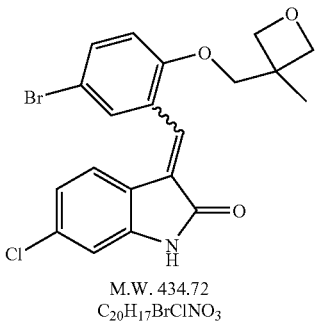

M.W. 434.72
C$_{20}$H$_{17}$BrClNO$_3$

To the mixture of 6-chlorooxindole (1.2 g, 7 mmol) and 4-Chloro-2-formyl-benzoic acid methyl ester (1.4 g, 7 mmol) in methanol (10 mL) was added pyrrolidine (490 mg, 7 mmol) dropwise. The mixture was then heated at 70° C. for 3 h. After cooled to 4° C., the mixture was filtered and the precipitate was collected, dried to give the title compound as a bright yellow solid (500 mg).

Example 13f

Preparation of Intermediate E/Z-3-[5-Bromo-2-(3-methyl-oxetan-3-ylmethoxy)-benzylidene]-6-chloro-2-oxo-2,3-dihydro-indole-1-carboxylic acid tert-butyl ester

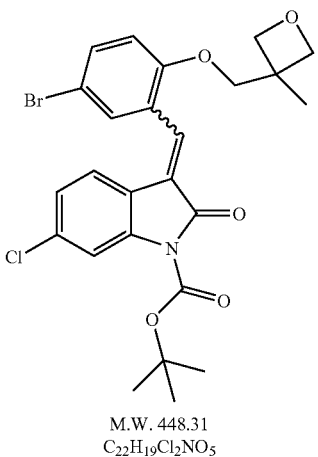

M.W. 448.31
C$_{22}$H$_{19}$Cl$_2$NO$_5$

To a solution E/Z-4-Chloro-2-(6-chloro-2-oxo-1,2-dihydro-indol-3-ylidenemethyl)-benzoic acid methyl ester (500 mg, 1.4 mmol) in DCM (10 mL) at rt was added diteret-butyl-dicarbonate (470 mg, 2.1 mmol), followed by the addition of 4-dimethylaminopyridine (100 mg, 0.82 mmol). The reaction mixture was stirred at r.t. for 2 h, then purified by column chromatography to give the title compound as a yellow solid (450 mg).

Example 13g

Preparation of Racemic (2'S,3S,4'R)-4'-[5-bromo-2-(3-methyl-oxetan-3-ylmethoxy)-phenyl]-6-chloro-2'-(5-chloro-2-methyl-phenyl)-spiro[3H-indole-3,3'-piperidine]-2,6'(1H)-dione

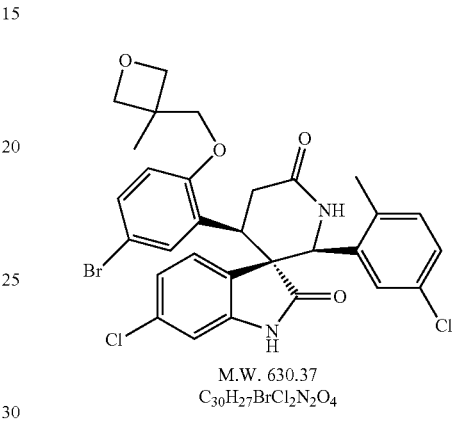

M.W. 630.37
C$_{30}$H$_{27}$BrCl$_2$N$_2$O$_4$

In a manner similar to the method described in example 1e, E/Z-6-chloro-3-(5-chloro-2-methoxycarbonyl-benzylidene)-2-oxo-2,3-dihydro-indole-1-carboxylic acid tert-butyl ester (450 mg, 1 mmol) was reacted with intermediate 1-(5-chloro-2-methylphenyl)-3-trimethylsilyoxy-2-aza-1,3-butadiene (1 M solution in toluene, 4 mL, 4 mmol) to give the title compound (60 mg).
m/z (M+H)$^+$: 459

Example 14

Preparation of Racemic (2'S,3S,4'R)-6-chloro-4'-[5-isopropenyl-2-(3-methyl-oxetan-3-ylmethoxy)-phenyl]-2'-(5-chloro-2-methyl-phenyl)-spiro[3H-indole-3,3'-piperidine]-2,6'(1H)-dione

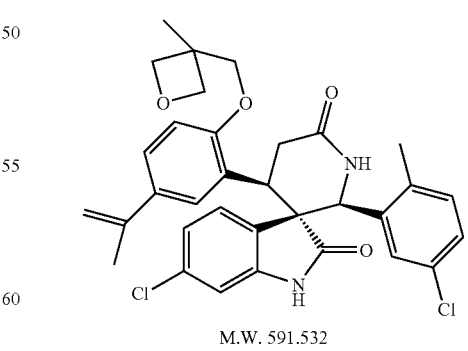

M.W. 591.532
C$_{33}$H$_{32}$BrCl$_2$N$_2$O$_4$

To a mixture of racemic (2'S,3S,4'R)-4'-[5-bromo-2-(3-methyl-oxetan-3-ylmethoxy)-phenyl]-6-chloro-2'-(5-chloro-2-methyl-phenyl)-spiro[3H-indole-3,3'-piperidine]-

2,6'(1H)-dione (50 mg, 0.08 mmol), isopropenylboronic acid pinacol ester (40 mg, 0.24 mmol) and K₃PO₄ (50 mg, 0.24 mmol) in THF was added Pd(PPh₃)₄ (15 mg). The mixture was heated at 80° C. for 8 h under an argon atmosphere, purified by prep-HPLC to give the title compound as a white solid (6 mg).

Example 15a

Preparation of Intermediate trimethylsilylacetylene boronic acid dimethyl ester

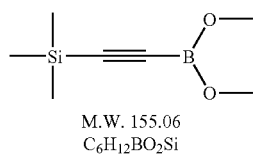

M.W. 155.06
C₆H₁₂BO₂Si

A solution of trimethylsilylacetylene (0.51 mL) in THF (4 mL) was cooled to −78° C. under argon, and then a solution of n-BuLi in n-hexane (1.6 M, 2.25 mL, 3.6 mmol) was added via syringe. The resulting mixture was stirred at the same temperature for 15 min, then trimethylborate (0.4 mL, 3.6 mmol) was added. The cooling bath was removed, and the mixture was stirred at room temperature for 15 min to give a solution of the title compound.

Example 15b

Preparation of Intermediate racemic (2'S,3S,4'R)-6-chloro-2'-(5-chloro-2-methyl-phenyl)-4'-[2-(3-methyl-oxetan-3-ylmethoxy)-5-trimethylsilanylethynyl-phenyl]spiro[3H-indole-3,3'-piperidine]-2,6'(1H)-dione

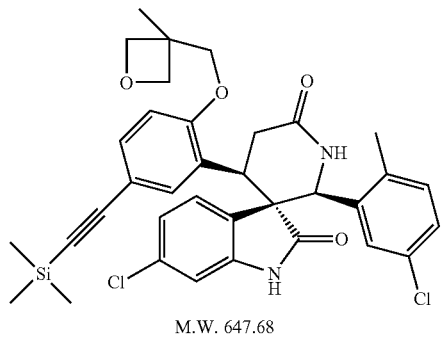

M.W. 647.68
C₃₅H₃₆Cl₂N₂O₄Si

To a mixture of racemic (2'S,3S,4'R)-4'-[5-bromo-2-(3-methyl-oxetan-3-ylmethoxy)-phenyl]-6-chloro-2'-(5-chloro-2-methyl-phenyl)-spiro[3H-indole-3,3'-piperidine]-2,6'(1H)-dione (50 mg, 0.08 mmol), trimethylsilylacetylene boronic acid dimethyl ester (0.7 M, 0.7 mL, 0.49 mmol) and K₃PO₄ (100 mg, 0.48 mmol) in THF was added Pd(PPh₃)₄ (15 mg) under argon. The reaction mixture was heated at 80° C. for 20 h, purified by prep-HPLC to give the title compound as a white solid.

Example 15c

Preparation of Racemic (2'S,3S,4'R)-6-chloro-2'-(5-chloro-2-methyl-phenyl)-4'-[5-ethynyl-2-(3-methyl-oxetan-3-ylmethoxy)-phenyl]-spiro[3H-indole-3,3'-piperidine]-2,6'(1H)-dione

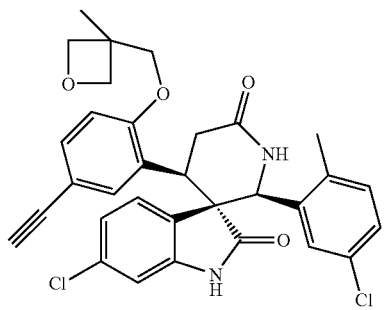

M.W. 575.489
C₃₂H₂₈Cl₂N₂O₄

To a solution of racemic (2'S,3S,4'R)-6-chloro-2'-(5-chloro-2-methyl-phenyl)-4'-[2-(3-methyl-oxetan-3-ylmethoxy)-5-trimethylsilanylethynyl-phenyl]spiro[3H-indole-3,3'-piperidine]-2,6'(1H)-dione in methanol (5 mL) was added K₂CO₃ (100 mg). The mixture was stirred at room temperature for 2 h, purified by prep-HPLC to give the title compound as a white solid (2.5 mg).

Example 16a

Preparation of Intermediate 4-methanesulfonyloxy-piperidine-1-caboxylic acid tert-butyl ester

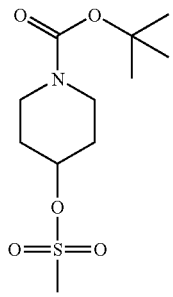

M.W. 279.36
C₁₁H₂₁NO₅S

To a solution of 4-hydroxy-piperidine-1-carboxylic acid tert-butyl ester (2 g, 20 mmol) and DMAP (3 g, 24 mmol) in DCM (50 mL) was dropped methanesulfonyl chloride (2.7 g, 24 mmol) in ice bath. The reaction mixture was stirred for 2 h at room temperature. Then the mixture was filtered and washed by 0.5N HCl (50 mL), 1N Na₂CO₃ (50 mL) and brine (50 mL), dried over anhydrous Na₂SO₄, concentrated to give title compound as a white solid (Yield: 5 g, 90%).

Example 16b

Preparation of Intermediate 4-(4-chloro-2-formyl-phenoxy)-piperidine-1-carboxylic acid tert-butyl ester

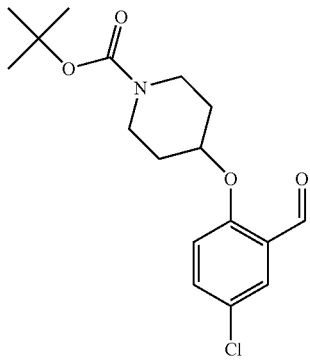

M.W. 339.82
$C_{17}H_{22}ClNO_4$

To a mixture of 5-chloro-2-hydroxy-benzaldehyde (3.15 g, 20 mmol), KI (0.1 g) and $K_2CO_3$ (8.28 g, 60 mmol) in DMF (100 mL) was added 4-methanesulfonyloxy-piperidine-1-caboxylic acid tert-butyl ester (7.26 g, 26 mmol). The mixture was heated at 100° C. for 2 h, then cooled to room temperature and partitioned between ethyl acetate and water. The organic layer was washed with 1N NaOH (30 mL), water, and dried over anhydrous $Na_2SO_4$, concentrated to give the title compound as white solid (Yield: 5.3 g, 78%).

Example 16c

Preparation of Intermediate E/Z-4-[4-chloro-2-(6-chloro-2-oxo-1,2-dihydro-indol-3-ylidenemethyl)-phenoxy]-piperidine-1-carboxylic acid tert-butyl ester

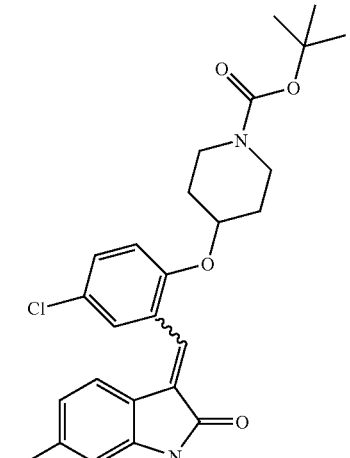

M.W. 489.40
$C_{25}H_{26}Cl_2N_2O_4$

To a mixture of 6-chlorooxindole (0.84 g, 5 mmol) and 4-(4-chloro-2-formyl-phenoxy)-piperidine-1-carboxylic acid tert-butyl ester (1.7 g, 5 mmol) in methanol (10 mL) was added pyrrolidine (0.4 mL, 5 mmol) dropwise. The mixture was then heated at 70° C. for 3 h. After cooled to 4° C., the mixture was filtered and the precipitate was collected, dried to give the title compound as a bright yellow solid (1 g).

Example 16d

Preparation of Intermediate E/Z-3-[2-(1-tert-Butoxy-carbonyl-piperidin-4-yloxy)-5-chloro-benzylidene]-6-chloro-2-oxo-2,3-dihydro-indole-1-carboxylic acid tert-butyl ester

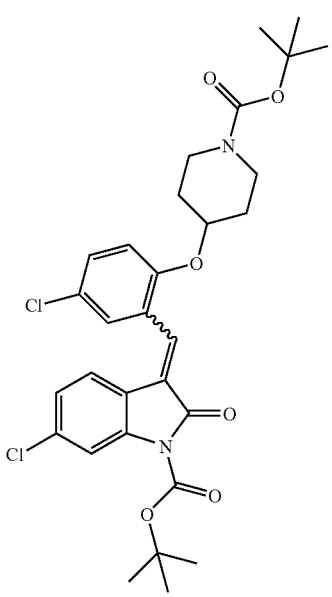

M.W. 589.52
$C_{30}H_{34}Cl_2N_2O_6$

To a solution of E/Z-4-[4-Chloro-2-(6-chloro-2-oxo-1,2-dihydro-indol-3-ylidenemethyl)-phenoxy]-piperidine-1-carboxylic acid tert-butyl ester (2.44 g, 5 mmol) in DCM (10 mL) at r.t. was added diteret-butyl-dicarbonate (1.6 g, 7.5 mmol), followed by the addition of 4-dimethylaminopyridine (0.06 g, 0.5 mmol). The reaction mixture was stirred for 2 h and washed with 0.5N hydrochloric acid, dried over anhydrous $Na_2SO_4$, then the solvent was removed to give title compound (Yield: 2.7 g, 92%).

Example 16e

Preparation of Racemic (2'S,3S,4'R)-4'-[2-(1-tert-butoxycarbonyl-piperidin-4-yloxy)-5-chloro-phenyl]-6-chloro-2'-(5-fluoro-2-methyl-phenyl)spiro[3H-indole-3,3'-piperidine]-2,6'(1H)-dione

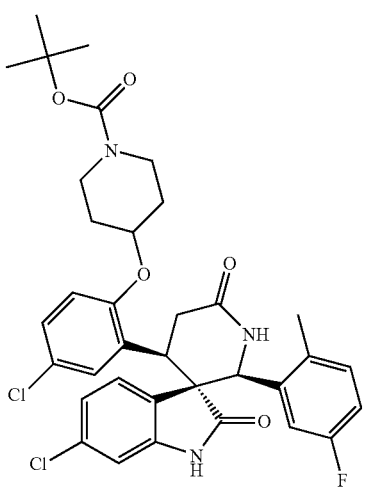

M.W. 668.60
$C_{35}H_{36}Cl_2FN_3O_5$

To a solution of 1-(5-fluoro-2-methyl-phenyl)-3-trimethylsilyoxy-2-aza-1,3-butadiene (15 mL, 30 mmol) in toluene (50 mL) was added E/Z-3-[2-(1-tert-Butoxycarbonyl-piperidin-4-yloxy)-5-chloro-benzylidene]-6-chloro-2-oxo-2,3-dihydro-indole-1-carboxylic acid tert-butyl ester (3.6 g, 6 mmol). The reaction mixture was stirred under argon at 65° C. for 3 h and then heated at 130° C. for 4 h. After cooled to room temperature, the mixture was concentrated. The residue was purified by chromatography to give the title compound as a white solid (Yield: 1 g).

m/z (M+H)$^+$: 669

Example 17a

Preparation of Racemic (2'S,3S,4'R)-6-chloro-4'-[5-chloro-2-(4-piperidinyloxy)-phenyl]-2'-(5-fluoro-2-methyl-phenyl)spiro[3H-indole-3,3'-piperidine]-2,6'(1H)-dione

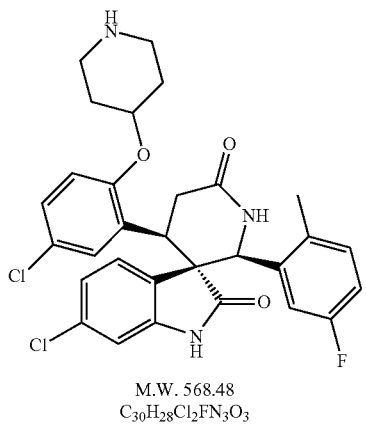

M.W. 568.48
$C_{30}H_{28}Cl_2FN_3O_3$

A solution of racemic (2'S,3S,4'R)-4'-[2-(1-tert-butoxycarbonyl-piperidin-4-yloxy)-5-chloro-phenyl]-6-chloro-2'-(5-fluoro-2-methyl-phenyl)spiro[3H-indole-3,3'-piperidine]-2,6'(1H)-dione (0.7 g, 1 mmol) in TFA (10 mL) was stirred at r.t. for 0.5 h. The solution was diluted with DCM, washed with 1N Na$_2$CO$_3$ aq. (50 mL) and brine (50 mL), dried over anhydrous Na$_2$SO$_4$, concentrated to give title compound as a yellow solid (Yield: 0.6 g).

Example 17b

Preparation of Racemic (2'S,3S,4'R)-4'-[2-(1-acetyl-4-piperidinyloxy)-5-chloro-phenyl]-6-chloro-2'-(5-fluoro-2-methyl-phenyl)spiro[3H-indole-3,3'-piperidine]-2,6'(1H)-dione

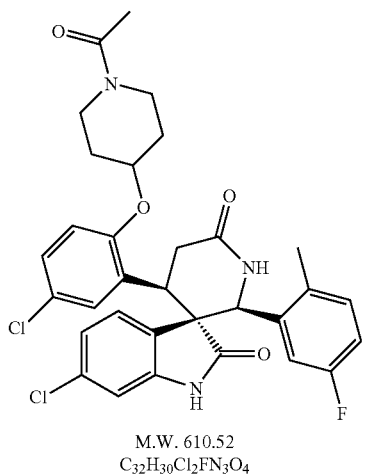

M.W. 610.52
$C_{32}H_{30}Cl_2FN_3O_4$

To a mixture of racemic (2'S,3S,4'R)-6-chloro-4'-[5-chloro-2-(4-piperidinyloxy)-phenyl]-2'-(5-fluoro-2-methyl-phenyl)spiro[3H-indole-3,3'-piperidine]-2,6'(1H)-dione (110 mg, 0.2 mmol), acetyl chloride (0.017 mL, 0.24 mmol) in DCM (5 mL) was added pyridine (23 mg, 0.3 mmol) at r.t. The reaction mixture was stirred for 4 h, then concentrated and partitioned between ethyl acetate and water. The organic layer was separated, and the aqueous layer was extracted with ethyl acetate. The combined organic layers were dried over MgSO$_4$ and concentrated. The residue was purified with Prep-HPLC to give the title compound as a white solid (Yield: 10 mg).

m/z (M+H)$^+$: 611

Example 18

Preparation of Racemic (2'S,3S,4'R)-6-chloro-4'-[5-chloro-2-(1-methanesulfonyl-4-piperidinyloxy)-phenyl]-2'-(5-fluoro-2-methyl-phenyl)spiro[3H-indole-3,3'-piperidine]-2,6'(1H)-dione

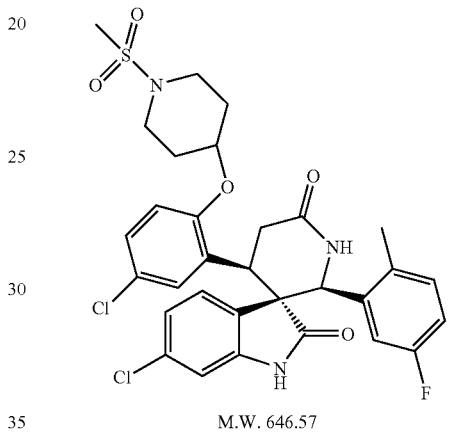

M.W. 646.57
$C_{31}H_{30}Cl_2FN_3O_5S$

To a mixture of racemic (2'S,3S,4'R)-6-chloro-4'-[5-chloro-2-(4-piperidinyloxy)-phenyl]-2'-(5-fluoro-2-methyl-phenyl)spiro[3H-indole-3,3'-piperidine]-2,6'(1H)-dione (110 mg, 0.2 mmol), methanesulfonyl chloride (0.0185 mL, 0.24 mmol) in DCM (5 mL) was added pyridine (23 mg, 0.3 mmol) at r.t. The reaction mixture was stirred for 4 h, then concentrated and partitioned between ethyl acetate and water. The organic layer was separated, and the aqueous layer was extracted with ethyl acetate. The combined organic layers were dried over MgSO$_4$ and concentrated. The residue was purified with Prep-HPLC to give the title compound as a white solid (Yield: 8 mg).

m/z (M+H)$^+$: 494

Example 19a

Preparation of Intermediate
5-chloro-2-(pyrimidin-2-yloxy)-benzaldehyde

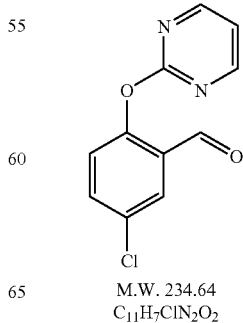

M.W. 234.64
$C_{11}H_7ClN_2O_2$

5-Chloro-2-hydroxy-benzaldehyde (4 g, 25.6 mmol), 2-chloro-pyrimidine (5.4 g, 48 mmol), t-BuOK (3.5 g, 29 mmol) were mixed in DMF (20 mL). Then the mixture was heated for 2 hour at 120° C. The mixture was filtered and the filtrate was concentrated. The residue was dissolved in ethyl acetate and washed with 1N NaOH. Then the organic layer was dried over anhydrous Na$_2$SO$_4$ and concentrated to give title compound as a white solid (Yield: 1.5 g, 25%).

Example 19b

Preparation of Intermediate E/Z-6-Chloro-3-[5-chloro-2-(pyrimidin-2-yloxy)-benzylidene]-1,3-dihydro-indol-2-one

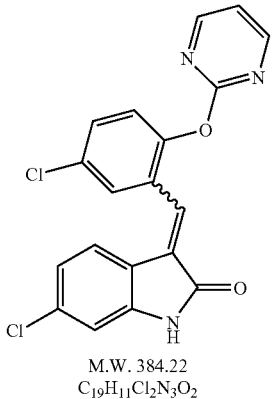

M.W. 384.22
C$_{19}$H$_{11}$Cl$_2$N$_3$O$_2$

To a mixture of 6-chlorooxindole (1.1 g, 6.4 mmol) and 5-chloro-2-(pyrimidin-2-yloxy)-benzaldehyde (1.5 g, 6.4 mmol) in methanol (10 mL) was added pyrrolidine (0.5 mL, 6.4 mmol) dropwise. The mixture was then heated at 70° C. for 3 h. After cooled to 4° C., the mixture was filtered and the precipitate was collected, dried to give the title compound as a bright yellow solid (1.3 g).

Example 19c

Preparation of Intermediate E/Z-6-Chloro-3-[5-chloro-2-(pyrimidin-2-yloxy)-benzylidene]-2-oxo-2,3-dihydro-indole-1-carboxylic acid tert-butyl ester

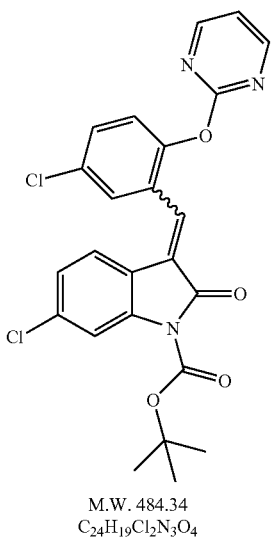

M.W. 484.34
C$_{24}$H$_{19}$Cl$_2$N$_3$O$_4$

To a solution of E/Z-6-Chloro-3-[5-chloro-2-(pyrimidin-2-yloxy)-benzylidene]-1,3-dihydro-indol-2-one (1.33 g, 3.5 mmol) in DCM (10 mL) was added diteret-butyl-dicarbonate (0.9 g, 4.2 mmol) at r.t., followed by the addition of 4-dimethylaminopyridine (0.04 g, 0.35 mmol). The reaction mixture was stirred for 2 h and washed with 0.5N hydrochloric acid, dried over anhydrous Na$_2$SO$_4$, then the solvent was removed to give title compound. (Yield: 1.4 g)

Example 19d

Preparation of Racemic (2'S,3S,4'R)-6-chloro-4'-[5-chloro-2-(pyrimidin-2-yloxy)-phenyl]-2'-(5-fluoro-2-methyl-phenyl)spiro[3H-indole-3,3'-piperidine]-2,6' (1H)-dione

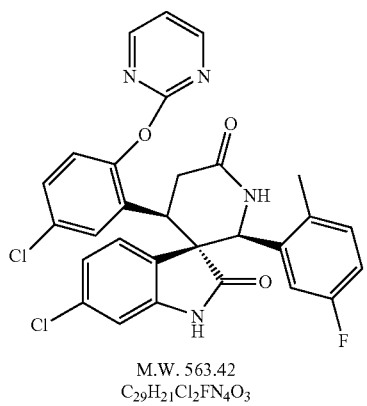

M.W. 563.42
C$_{29}$H$_{21}$Cl$_2$FN$_4$O$_3$

In a manner similar to the method described in example 1e, 6-chloro-3-[5-chloro-2-(pyrimidin-2-yloxy)-benzylidene]-2-oxo-2,3-dihydro-indole-1-carboxylic acid tert-butyl ester (1 g, 2 mmol) was reacted with 1-(5-fluoro-2-methylphenyl)-3-trimethylsilyoxy-2-aza-1,3-butadiene (10 mL, 20 mmol) in toluene to give title compound as a white solid (Yield: 40 mg).
m/z (M+H)$^+$: 563

Example 20a

Preparation of Intermediate 2,2-dimethyl-3-(toluene-4-sulfonyloxy)-propionic acid methyl ester

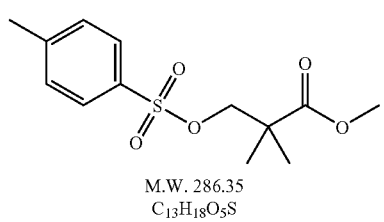

M.W. 286.35
C$_{13}$H$_{18}$O$_5$S

To a mixture of 3-hydroxy-2,2-dimethyl-propionic acid methyl ester (13.2 g, 0.1 mol), K$_2$CO$_3$ (20 g, 0.14 mol) and DMAP (6.2 g, 0.05 mol) in DCM (100 mL) was added p-toluenesulfonyl chloride (19 g, 0.1 mol). The mixture was stirred at room temperature overnight, then filtered. The filtrate was washed with HCl aq. (1 M) and water, dried over anhydrous Na$_2$SO$_4$ and concentrated to give the title compound (15 g).

Example 20b

Preparation of Intermediate 3-(4-chloro-2-formyl-phenoxy)-2,2-dimethyl-propionic acid methyl ester

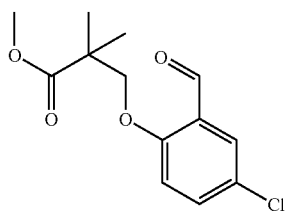

M.W. 270.72
$C_{13}H_{15}ClO_4$ 5-chloro-2-hydroxy-benzaldehyde (3.1 g, 2 mmol), 2,2-dimethyl-3-(toluene-4-sulfonyloxy)-propionic acid methyl ester (5.46 g, 24 mmol), $K_2CO_3$ (5.5 g, 40 mmol) and KI (0.1 g) were mixed in DMF (20 mL). Then the mixture was irradiated by microwave for an hour at 150° C. The mixture was filtered and the filtrate was concentrated. The residue was dissolved in ethyl acetate and washed with 1N NaOH. Then the organic layer was dried over anhydrous $Na_2SO_4$ and concentrated to give title compound (Yield: 5 g, 92.5%).

Example 20c

Preparation of Intermediate E/Z-3-[4-Chloro-2-(6-chloro-2-oxo-1,2-dihydro-indol-3-ylidenemethyl)-phenoxy]-2,2-dimethyl-propionic acid methyl ester

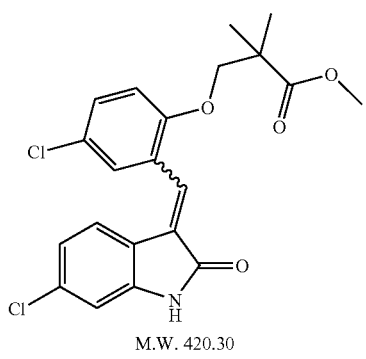

M.W. 420.30
$C_{21}H_{19}Cl_2NO_4$ 3-(4-chloro-2-formyl-phenoxy)-2,2-dimethyl-propionic acid methyl ester (6.7 g, 25 mmol) and 6-Chloro-1,3-dihydro-indol-2-one (4.35 g, 25 mmol) were mixed in 20 mL of anhydrous methanol. Then pyrrolidine (2 mL, 25 mmol) was added dropwise at r.t. The mixture was heated to 70° C. for 3 h and cooled to room temperature. The precipitate was collected by filtration and dried to give title compound as yellow solid (Yield: 7 g, 67%).

m/z (M+H)$^+$: 420

Example 20d

Preparation of Intermediate E/Z-6-Chloro-3-[5-chloro-2-(2-methoxycarbonyl-2-methyl-propoxy)-benzylidene]-2-oxo-2,3-dihydro-indole-1-carboxylic acid tert-butyl ester

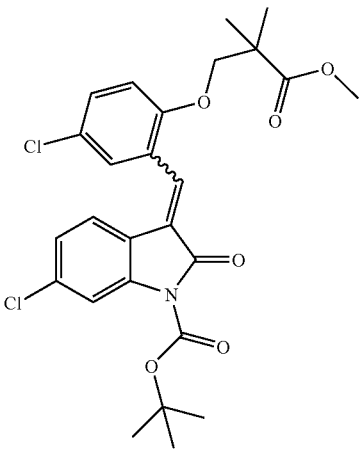

M.W. 520.41 $C_{26}H_{27}Cl_2NO_6$

To a solution of E/Z-3-[4-Chloro-2-(6-chloro-2-oxo-1,2-dihydro-indol-3-ylidenemethyl)-phenoxy]-2,2-dimethyl-propionic acid methyl ester (7 g, 16.7 mmol) in DCM (20 mL) at r.t. was added di-teret-butyl-dicarbonate (5.4 g, 25 mmol), followed by the addition of 4-dimethylaminopyridine (0.2 g, 1.7 mmol). The reaction mixture was stirred for 2 h and washed with 0.5 N hydrochloric acid, then the solvent was removed to give title compound (Yield: 8 g).

Example 20e

Preparation of Intermediate racemic (2'S,3S,4'R)-6-chloro-4'-[5-chloro-2-(2-methoxycarbonyl-2-methyl-propoxy)-phenyl]-2'-(5-fluoro-2-methylphenyl)spiro[3H-indole-3,3'-piperidine]-2,6'(1H)-dione

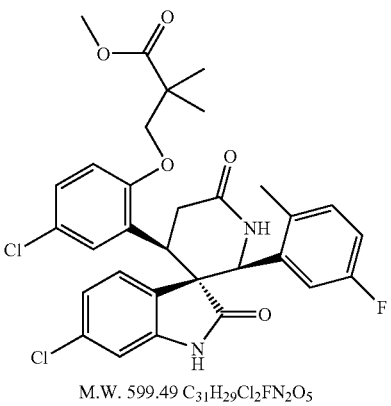

M.W. 599.49 $C_{31}H_{29}Cl_2FN_2O_5$

In a manner similar to the method described in Example 1e, E/Z-6-chloro-3-[5-chloro-2-(2-methoxycarbonyl-2-methyl-propoxy)-benzylidene]-2-oxo-2,3-dihydro-indole-1-carboxylic acid tert-butyl ester (4.5 g, 9 mmol) was reacted with 1-(5-Fluoro-2-methylphenyl)-3-trimethylsilyoxy-2-aza-1,3-butadiene (63 mmol) in toluene to give title compound as a white solid (Yield: 300 mg, 5.5%).

m/z (M+H)$^+$: 599

Example 20f

Preparation of Intermediate racemic (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione

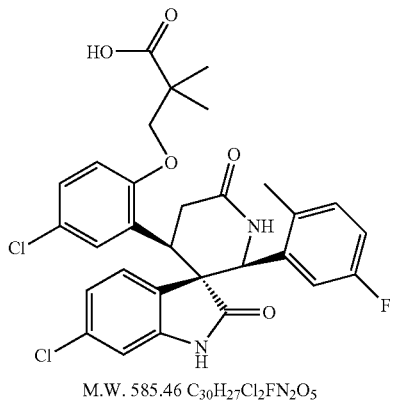

M.W. 585.46 C$_{30}$H$_{27}$Cl$_2$FN$_2$O$_5$

A mixture of 330 mg racemic (2'R,3R,4'S)-6-chloro-4'-[5-chloro-2-(2-methoxycarbonyl-2-methyl-propoxy)-phenyl]-2'-(5-fluoro-2-methylphenyl)spiro[3H-indole-3,3'-piperidine]-2,6'(1H)-dione (330 mg, 0.55 mmol), NaOH (80 mg, 2 mmol), H$_2$O (5 mL) and methanol (10 mL) was heated at 60° C. for 2 h. Then the methanol was removed in vacuum. The water solution was acidified by concentrated hydrochloric acid to "pH" 2. The white precipitate was collected by filtration to give title compound (Yield: 250 mg).

Example 20g

Preparation of Racemic (2'S,3S,4'R)-6-chloro-4'-[5-chloro-2-(2,2-dimethyl-3-oxo-3-pyrrolidin-1-yl-propoxy)-phenyl]-2'-(5-fluoro-2-methylphenyl)spiro[3H-indole-3,3'-piperidine]-2,6'(1H)-dione

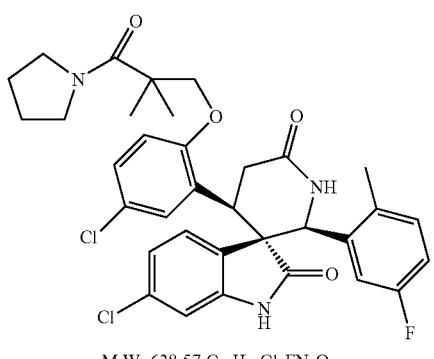

M.W. 638.57 C$_{34}$H$_{34}$Cl$_2$FN$_3$O$_4$

To a mixture of racemic (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione (40 mg, 0.07 mmol), pyrrolidine (0.0083 mL, 0.1 mmol), EDC.HCl (20 mg, 0.1 mmol), and HOBt (14 mg, 0.1 mmol) in THF (5 mL) was added DIPEA (0.018 mL, 0.2 mmol) at rt. The reaction mixture was stirred for 4 h, then concentrated and partitioned between ethyl acetate and water. The organic layer was separated, and the aqueous layer was extracted with ethyl acetate. The organic layers were dried over MgSO$_4$ and concentrated. The residue was purified with Prep-HPLC to give the title compound as a white solid (Yield: 8 mg).

m/z (M+H)$^+$: 638

Example 21

Preparation of Racemic (2'S,3S,4'R)-6-chloro-4'-[5-chloro-2-(2-dimethylcarbamoyl-2-methyl-propoxy)-phenyl]-2'-(5-fluoro-2-methylphenyl)-spiro[3H-indole-3,3'-piperidine]-2,6'(1H)-dione

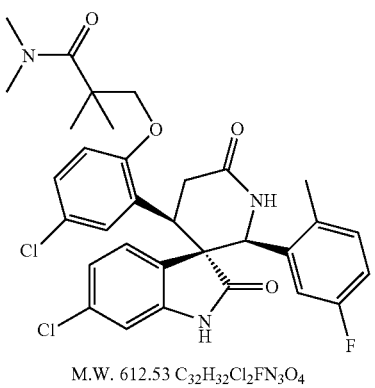

M.W. 612.53 C$_{32}$H$_{32}$Cl$_2$FN$_3$O$_4$

To a mixture of racemic (2'S,3S,4'R)-6-chloro-4'-[5-chloro-2-(2-hydroxycarbonyl-2-methyl-propoxy)-phenyl]-2'-(5-fluoro-2-methylphenyl)spiro[3H-indole-3,3'-piperidine]-2,6'(1H)-dione (40 mg, 0.07 mmol), dimethylamine hydrochloric salt (8.2 mg, 0.1 mmol), EDC.HCl (20 mg, 0.1 mmol), and HOBt (14 mg, 0.1 mmol) in THF (5 mL) was added DIPEA (0.018 mL, 0.2 mmol) at r.t. The reaction mixture was stirred for 4 h, then concentrated and partitioned between ethyl acetate and water. The organic layer was separated, and the aqueous layer was extracted with ethyl acetate. The organic layers were dried over MgSO$_4$ and concentrated. The residue was purified with Prep-HPLC to give the title compound as a white solid (Yield: 10 mg).

m/z (M+H)$^+$: 612

Example 22a

Preparation of Intermediate (4-chloro-2-formyl-phenoxy)-acetic acid methyl ester

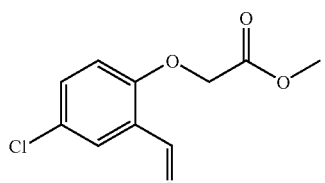

M.W. 228.63 C$_{10}$H$_9$ClO$_4$

5-Chloro-2-hydroxy-benzaldehyde (30 g, 192 mmol), bromo-acetic acid methyl ester (29.4 g, 192 mmol), K₂CO₃ (53 g, 384 mmol) and KI (9.6 g, 57 mmol) were mixed in acetone (100 mL). Then the mixture was heated at 80° C. for 30 min. The mixture was filtered and the filtrate was concentrated. The residue was dissolve in ethyl acetate and washed with base aqueous solution (1N NaOH). The organic layer was separated, dried and concentrated to give (4-chloro-2-formyl-phenoxy)-acetic acid methyl ester yellow solid. (44 g)

Example 22b

Preparation of Intermediate E/Z-[4-Chloro-2-(6-chloro-2-oxo-1,2-dihydro-indol-3-ylidenemethyl)-phenoxy]-acetic acid methyl ester

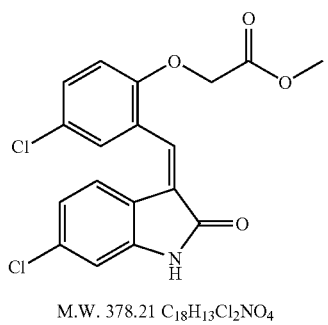

M.W. 378.21 C₁₈H₁₃Cl₂NO₄

In a manner similar to the method described in Example 227b, (4-chloro-2-formyl-phenoxy)-acetic acid methyl ester (34 g, 149 mmol) was reacted with 6-chlorooxindole (20.7 g, 124 mmol) and pyrrolidine (10.58 g, 149 mmol) in methanol to give title compound as a yellow solid (35 g).

Example 22c

Preparation of Intermediate E/Z-6-chloro-3-(5-chloro-2-methoxycarbonylmethoxy-benzylidene)-2-oxo-2,3-dihydro-indole-1-carboxylic acid tert-butyl ester

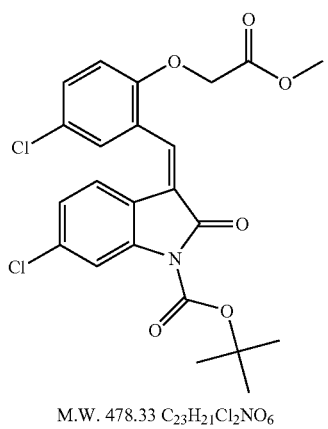

M.W. 478.33 C₂₃H₂₁Cl₂NO₆

In a manner similar to the method described in Example 227c, E/Z-[4-Chloro-2-(6-chloro-2-oxo-1,2-dihydro-indol-3-ylidenemethyl)-phenoxy]-acetic acid methyl ester (35 g, 92.8 mmol) was reacted with diteret-butyl-dicarbonate (22.3 g, 102 mmol) and DMAP (2.3 g, 18.6 mmol) in CH₂Cl₂ to give title compound as yellow oil (30 g).

Example 22d

Preparation of Intermediate 1-(2,5-difluoro-phenyl)-3-trimethylsilyoxy-2-aza-1,3-butadiene

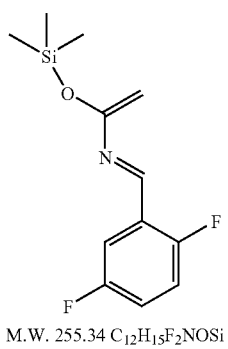

M.W. 255.34 C₁₂H₁₅F₂NOSi

To dry tetrahydrofuran (100 mL) was added 1M THF solution of LiHMDS (105 mmol, 105 mL) under nitrogen at room temperature, followed by the addition of 2,5-difluorobenzaldehyde (14.9 g, 105 mmol). After the mixture was stirred at room temperature for 1 h, trimethylsilyl chloride (13.3 mL, 105 mmol) was added dropwise. Then the temperature of the mixture was lowered to 0° C. on a cooling ice bath. To this mixture was added triethylamine (19 mL, 136 mmol) in one portion, followed by the dropwise addition of a solution of acetyl chloride (3.88 mL, 54.4 mmol) in diethyl ether (300 ml). The cooling bath was removed, and the mixture was stirred at room temperature overnight. The mixture was quickly filtered on celite under nitrogen, and filtrate was concentrated under reduced pressure to give 1-(2,5-difluoro-phenyl)-3-trimethylsilyoxy-2-aza-1,3-butadiene as a yellow gum and used for the next step without further purification.

Example 22e

Preparation of Intermediate racemic (2'R,3S,4'R)-6-chloro-4'-[5-chloro-2-(2-methoxycarbonyl-methoxy)-phenyl]-2'-[2,5-difluorophenyl]spiro[3H-indole-3,3'-piperidine]-2,6'(1H)-dione

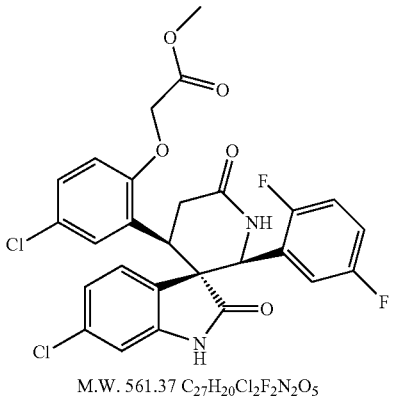

M.W. 561.37 C₂₇H₂₀Cl₂F₂N₂O₅

In a manner similar to the method described in Example 1e, E/Z-6-Chloro-3-(5-chloro-2-methoxycarbonylmethoxy-benzylidene)-2-oxo-2,3-dihydro-indole-1-carboxylic acid tert-butyl ester (9.5 g, 20 mmol) was reacted with 1-(2,5- difluoro-phenyl)-3-trimethylsilyoxy-2-aza-1,3-butadiene (60 mmol) in toluene to give title compound as a white solid (Yield: 1.5 g).

m/z (M+H)$^+$: 561

Example 22f

Preparation of Intermediate racemic (2'R,3S,4'R)-6-chloro-4'-[5-chloro-2-(2-hydroxycarbonyl-methoxy)-phenyl]-2'-[2,5-difluorophenyl]spiro[3H-indole-3,3'-piperidine]-2,6'(1H)-dione

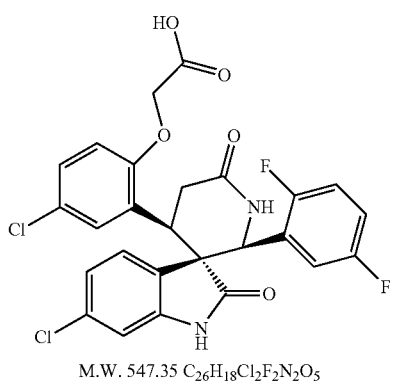

M.W. 547.35 $C_{26}H_{18}Cl_2F_2N_2O_5$

A mixture of (2'R,3S,4'R)-6-chloro-4'-[5-chloro-2-(2-methoxycarbonyl-methoxy)-phenyl]-2'-[2,5-difluorophenyl]spiro[3H-indole-3,3'-piperidine]-2,6'(1H)-dione (600 mg, 1.07 mmol), NaOH (120 mg, 3 mmol), H$_2$O (5 mL) and methanol (5 mL) was heated at 60° C. for 2 h. Then the methanol was removed in vacuum. The water solution was acidified by concentrated hydrochloric acid (1.5 mL) to "pH" 2. The white precipitate was collected by filtration to give title (Yield: 500 mg).

m/z (M+H)$^+$: 547

Example 22g

Preparation of Racemic (2'R,3S,4'R)-6-chloro-4'-[5-chloro-2-{[(2-hydroxy-ethyl)-methyl-carbamoyl]-methoxy}-phenyl]-2'-[2,5-difluorophenyl]spiro[3H-indole-3,3'-piperidine]-2,6'(1H)-dione

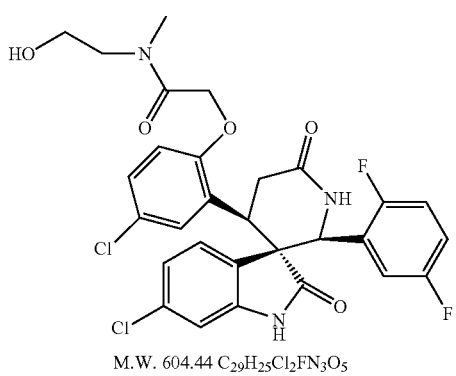

M.W. 604.44 $C_{29}H_{25}Cl_2FN_3O_5$

To a mixture of racemic (2'R,3S,4'R)-6-chloro-4'-[5-chloro-2-(2-hydroxycarbonyl-methoxy)-phenyl]-2'-[2,5-difluorophenyl]spiro[3H-indole-3,3'-piperidine]-2,6'(1H)-dione (76 mg, 0.14 mmol), 2-methylamino-ethanol (0.018 mL, 0.21 mmol), EDC.HCl (40 mg, 0.21 mmol), and HOBt (28 mg, 0.21 mmol) in THF (5 mL) was added DIPEA (0.036 mL, 0.4 mmol) at r.t. The reaction mixture was stirred for 4 h, then concentrated and partitioned between ethyl acetate and water. The organic layer was separated, and the aqueous layer was extracted with ethyl acetate. The organic layers were dried over MgSO$_4$ and concentrated. The residue was purified with Prep-HPLC to give the title compound as a white solid (Yield: 36 mg).

m/z (M+H)$^+$: 604

Example 23

Preparation of Racemic (2'R,3S,4'R)-6-chloro-4'-[5-chloro-2-dimethylcarbamoylmethoxy-phenyl]-2'-(2,5-difluorophenyl)spiro[3H-indole-3,3'-piperidine]-2,6'(1H)-dione

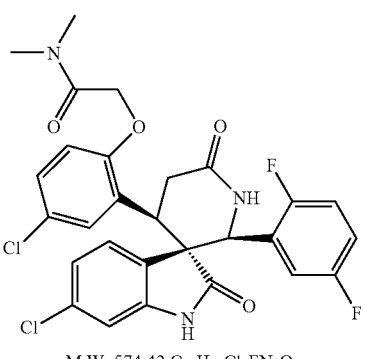

M.W. 574.42 $C_{28}H_{23}Cl_2FN_3O_4$

To a mixture of racemic (2'R,3S,4'R)-6-chloro-4'-[5-chloro-2-(2-hydroxycarbonyl-methoxy)-phenyl]-2'-[2,5-difluorophenyl]spiro[3H-indole-3,3'-piperidine]-2,6'(1H)-dione (76 mg, 0.14 mmol), dimethylamine hydrochloric salt (17 mg, 0.21 mmol), EDC.HCl (40 mg, 0.21 mmol), and HOBt (28 mg, 0.21 mmol) in THF (5 mL) was added DIPEA (0.036 mL, 0.4 mmol) at rt. The reaction mixture was stirred for 4 h, then concentrated and partitioned between ethyl acetate and water. The organic layer was separated, and the aqueous layer was extracted with ethyl acetate. The organic layers were dried over MgSO$_4$ and concentrated. The residue was purified with Prep-HPLC to give the title compound as a white solid (Yield: 10 mg).

m/z (M+H)$^+$: 574

Example 24

Preparation of Racemic (2'R,3S,4'R)-6-chloro-4'-[5-chloro-2-(2-oxo-2-pyrrolidin-1-yl-ethoxy)-phenyl]-2'-(2,5-difluorophenyl)spiro[3H-indole-3,3'-piperidine]-2,6'(1H)-dione

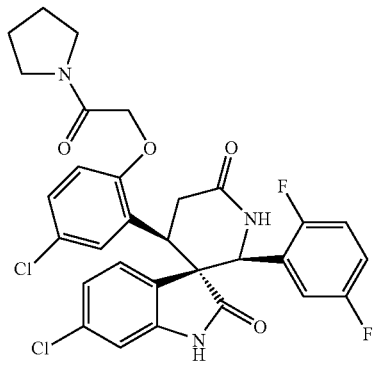

M.W. 600.45 C$_{30}$H$_{25}$Cl$_2$F$_2$N$_3$O$_4$

To a mixture of racemic (2'R,3S,4'R)-6-chloro-4'-[5-chloro-2-(2-hydroxycarbonyl-methoxy)-phenyl]-2'-[2,5-difluorophenyl]spiro[3H-indole-3,3'-piperidine]-2,6'(1H)-dione (76 mg, 0.14 mmol), pyrrolidine (0.017 mL, 0.21 mmol), EDC.HCl (40 mg, 0.21 mmol), and HOBt (28 mg, 0.21 mmol) in THF (5 mL) was added DIPEA (0.036 mL, 0.4 mmol) at rt. The reaction mixture was stirred for 4 h, then concentrated and partitioned between ethyl acetate and water. The organic layer was separated, and the aqueous layer was extracted with ethyl acetate. The organic layers were dried over MgSO$_4$ and concentrated. The residue was purified with Prep-HPLC to give the title compound as a white solid (Yield: 33 mg).

m/z (M+H)$^+$: 600

Example 25a

Preparation of Intermediate racemic (2'S,3S,4'R)-4'-[5-bromo-2-(2-ethoxycarbonyl-2-methyl-ethoxy)-phenyl]-6-chloro-2'-(5-chloro-2-methyl phenyl)spiro[3H-indole-3,3'-piperidine]-2,6'(1H)-dione

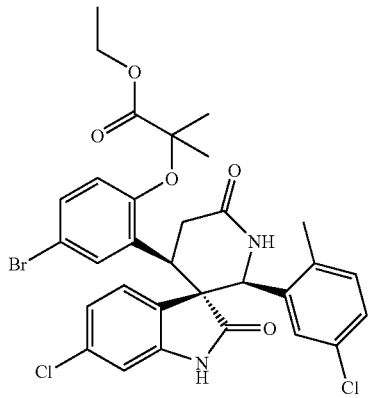

M.W. 660.40 C$_{31}$H$_{29}$BrCl$_2$N$_2$O$_5$

In a manner similar to the method described in Example 1e, 3-[5-bromo-2-(1-ethoxycarbonyl-1-methyl-ethoxy)-benzylidene]-6-chloro-2-oxo-2,3-dihydro-indole-1-carboxylic acid tert-butyl ester (3.9 g, 8 mmol) was reacted with 1-(5-chloro-2-methylphenyl)-3-trimethylsilyoxy-2-aza-1,3-butadiene (21 mmol) in toluene to give the title compound as a white solid (Yield: 600 mg).

Example 25b

Preparation of Intermediate racemic (2'S,3S,4'R)-4'-[5-bromo-2-(2-hydroxycarbonyl-2-methyl-ethoxy)-phenyl]-6-chloro-2'-(5-chloro-2-methyl phenyl)spiro[3H-indole-3,3'-piperidine]-2,6'(1H)-dione

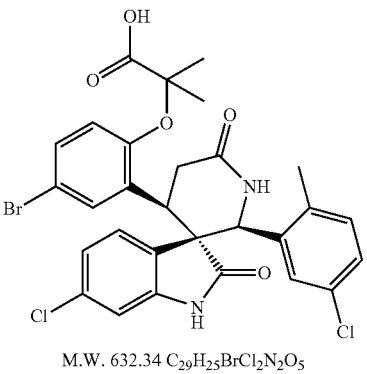

M.W. 632.34 C$_{29}$H$_{25}$BrCl$_2$N$_2$O$_5$

A mixture of racemic (2'S,3S,4'R)-4'-[5-bromo-2-(2-ethoxycarbonyl-2-methyl-ethoxy)-phenyl]-6-chloro-2'-(5-chloro-2-methyl phenyl)spiro[3H-indole-3,3'-piperidine]-2,6'(1H)-dione (200 mg, 0.3 mmol), NaOH (40 mg, 1 mmol), H$_2$O (5 mL) and THF (5 mL) was heated at 80° C. for 2 h. Then THF was removed in vacuum. The water solution was acidified by concentrated hydrochloric acid (1.5 mL) to "pH" 2. The white precipitate was collected by filtration to give the title compound as a white solid (Yield: 100 mg).

m/z (M+H)$^+$: 631

Example 25c

Preparation of Racemic (2'S,3S,4'R)-6-chloro-4'-[5-bromo-2-(1-dimethylcarbamoyl-1-methyl-ethoxy)-phenyl]-2'-(5-chloro-2-methyl phenyl)spiro[3H-indole-3,3'-piperidine]-2,6'(1H)-dione

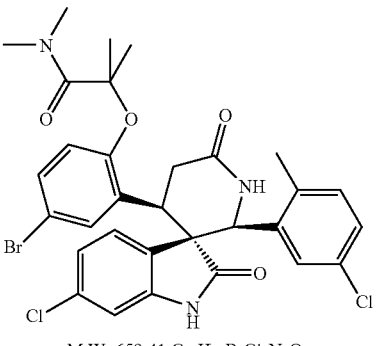

M.W. 659.41 C$_{31}$H$_{30}$BrCl$_2$N$_3$O$_4$

To a mixture of racemic (2'S,3S,4'R)-4'-[5-bromo-2-(2-hydroxycarbonyl-2-methyl-ethoxy)-phenyl]-6-chloro-2'-(5-chloro-2-methyl phenyl)spiro[3H-indole-3,3'-piperidine]-2,6'(1H)-dione (44 mg, 0.07 mmol), dimethylamine hydrochloric salt (17 mg, 0.21 mmol), EDC.HCl (20 mg, 0.1 mmol), and HOBt (14 mg, 0.1 mmol) in THF (5 mL) was added DIPEA (0.018 mL, 0.2 mmol) at r.t. The reaction mixture was stirred for 4 h, then concentrated and partitioned between ethyl acetate and water. The organic layer was separated, and the aqueous layer was extracted with ethyl acetate. The organic layers were dried over MgSO$_4$ and concentrated. The residue was purified with Prep-HPLC to give the title compound as a white solid (Yield: 14 mg).

m/z (M+H)$^+$: 659

Example 26a

Preparation of Racemic (2'S,3S,4'R)-6-chloro-4'-[5-chloro-2-(1-dimethylcarbamoyl-1-methyl-ethoxy)-phenyl]-2'-(5-fluoro-2-methyl-phenyl)spiro[3H-indole-3,3'-piperidine]-2,6'(1H)-dione

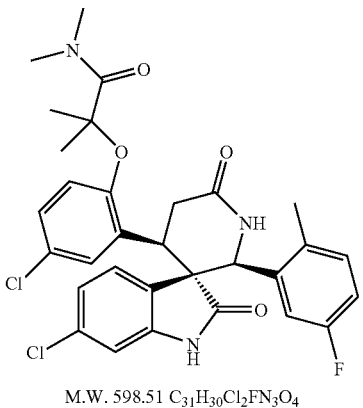

M.W. 598.51 C$_{31}$H$_{30}$Cl$_2$FN$_3$O$_4$

A mixture of racemic (2'S,3S,4'R)-6-chloro-4'-[5-chloro-2-(2-hydroxycarbonyl-2-methyl-ethoxy)-phenyl]-2'-(5-fluoro-2-methyl-phenyl)spiro[3H-indole-3,3'-piperidine]-2,6'(1H)-dione in Example 1f (150 mg, 0.263 mmol), dimethylamine hydrochloride (43 mg, 0.526 mmol), EDC.HCl (100 mg, 0.526 mmol), HOBt (71 mg, 0.526 mmol) and DIPEA (204 mg, 1.579 mmol) in anhydrous THF (3 mL) was stirred at room temperature overnight. Then the mixture was filtered and the filtrate was concentrated. The residue was purified by Prep-HPLC to give title compound as a white solid (50 mg).

m/z (M+H)$^+$: 598

Example 26b

Preparation of Chiral (2'S,3S,4'R)-6-chloro-4'-[5-chloro-2-(1-dimethylcarbamoyl-1-methyl-ethoxy)-phenyl]-2'-(5-fluoro-2-methyl-phenyl)spiro[3H-indole-3,3'-piperidine]-2,6'(1H)-dione

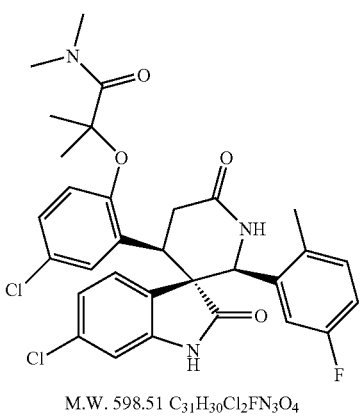

M.W. 598.51 C$_{31}$H$_{30}$Cl$_2$FN$_3$O$_4$

Separation of the two enantiomers from racemic (2'S,3S,4'R)-6-chloro-4'-[5-chloro-2-(1-dimethylcarbamoyl-1-methyl-ethoxy)-phenyl]-2'-(5-fluoro-2-methyl-phenyl)spiro[3H-indole-3,3'-piperidine]-2,6'(1H)-dione (RO5215923-000, 10 mg) was conducted by chiral column to provide chiral (2'S,3S,4'R)-6-chloro-4'-[5-chloro-2-(1-dimethylcarbamoyl-1-methyl-ethoxy)-phenyl]-2'-(5-fluoro-2-methyl-phenyl)spiro[3H-indole-3,3'-piperidine]-2,6'(1H)-dione as a white solid (1.4 mg) (RO5217765-000) and chiral (2'R,3R,4'S)-6-chloro-4'-[5-chloro-2-(1-dimethylcarbamoyl-1-methyl-ethoxy)-phenyl]-2'-(5-fluoro-2-methyl-phenyl)spiro[3H-indole-3,3'-piperidine]-2,6'(1H)-dione as a white solid (2 mg) (RO5217766-000).

m/z (M+H)$^+$: 598

Example 27

Preparation of Racemic (2'S,3S,4'R)-4'-{2-[2-(4-acetyl-piperazin-1-yl)-1,1-dimethyl-2-oxo-ethoxy]-5-chloro-phenyl}-6-chloro-2'-(5-fluoro-2-methyl-phenyl)spiro[3H-indole-3,3'-piperidine]-2,6'(1H)-dione

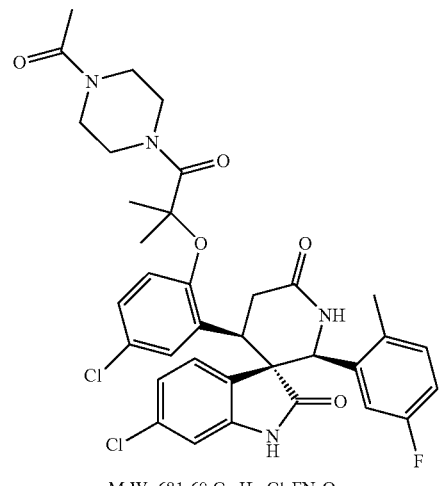

M.W. 681.60 C$_{35}$H$_{35}$Cl$_2$FN$_4$O$_5$

A mixture of racemic (2'S,3S,4'R)-6-chloro-4'-[5-chloro-2-(2-hydroxycarbonyl-2-methyl-ethoxy)-phenyl]-2'-(5-fluoro-2-methyl-phenyl)spiro[3H-indole-3,3'-piperidine]-2,6'(1H)-dione (150 mg, 0.263 mmol), N-acetylpiperazine (67 mg, 0.526 mmol), EDC.HCl (100 mg, 0.526 mmol), HOBt (71 mg, 0.526 mmol) and DIPEA (204 mg, 1.579 mmol) in anhydrous THF (3 mL) was stirred at room temperature overnight. Then the mixture was filtered and the filtrate was concentrated. The residue was purified by Prep-HPLC to give title compound as a white solid (40 mg).

m/z (M+H)$^+$: 681

Example 28

Preparation of Racemic (2'S,3S,4'R)-6-chloro-4'-{5-chloro-2-[1-methyl-1-(2,2,2-trifluoro-ethylcarbamoyl)-ethoxy]-phenyl}-2'-(5-fluoro-2-methyl-phenyl)spiro[3H-indole-3,3'-piperidine]-2,6'(1H)-dione

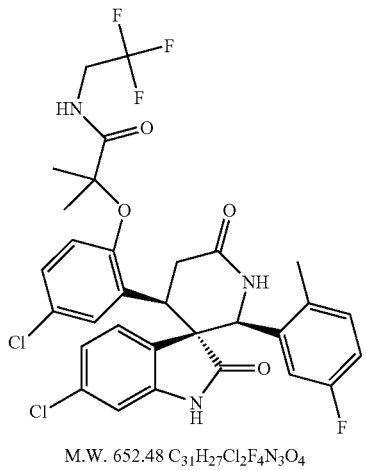

M.W. 652.48 $C_{31}H_{27}Cl_2F_4N_3O_4$

In a manner similar to the method described in Example 27, racemic (2'S,3S,4'R)-6-chloro-4'-[5-chloro-2-(2-hydroxycarbonyl-2-methyl-ethoxy)-phenyl]-2'-(5-fluoro-2-methyl-phenyl)spiro[3H-indole-3,3'-piperidine]-2,6'(1H)-dione (150 mg, 0.263 mmol) was reacted with 2,2,2-trifluoroethylamine hydrochloride (71 mg, 0.526 mmol), EDC.HCl (100 mg, 0.526 mmol), HOBt (71 mg, 0.526 mmol) and DIPEA (204 mg, 1.579 mmol) in anhydrous THF (3 mL) to give title compound as a white solid (50 mg).
m/z (M+H)$^+$: 652

Example 29a

Preparation of Racemic (2'S,3S,4'R)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione

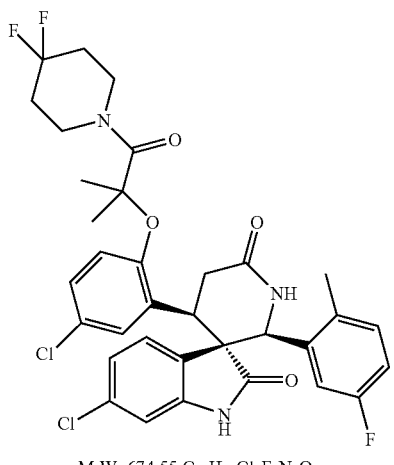

M.W. 674.55 $C_{34}H_{32}Cl_2F_3N_3O_4$

In a manner similar to the method described in Example 27, racemic (2'S,3S,4'R)-6-chloro-4'-[5-chloro-2-(2-hydroxycarbonyl-2-methyl-ethoxy)-phenyl]-2'-(5-fluoro-2-methyl-phenyl)spiro[3H-indole-3,3'-piperidine]-2,6'(1H)-dione (150 mg, 0.263 mmol) was reacted with 4,4-difluoropiperidine hydrochloride (83 mg, 0.526 mmol), EDC.HCl (100 mg, 0.526 mmol), HOBt (71 mg, 0.526 mmol) and DIPEA (204 mg, 1.579 mmol) in anhydrous THF (3 mL) to give title compound as a white solid (40 mg).
m/z (M+H)$^+$: 674

Example 29b

Preparation of Chiral (2'S,3S,4'R)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione

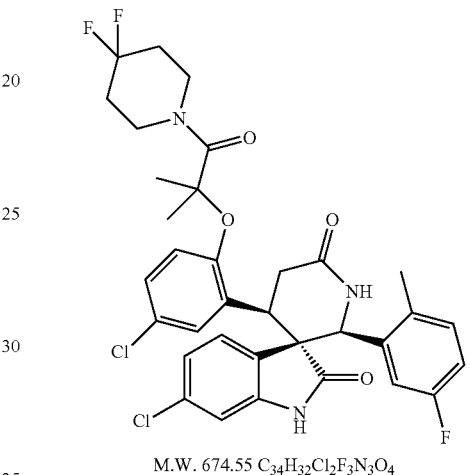

M.W. 674.55 $C_{34}H_{32}Cl_2F_3N_3O_4$

Separation of the two enantiomers from racemic (2'S,3S,4'R)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione (RO5215926-000, 30 mg) was conducted by chiral column to provide chiral (2'S,3S,4'R)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione as a white solid (9 mg) (RO5217767-000) and chiral (2'R,3R,4'S)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione as a white solid (8 mg). m/z (M+H)$^+$: 674

Example 30a

Preparation of Intermediate 5-chloro-2-(3-methyl-oxetan-3-ylmethoxy)-benzaldehyde

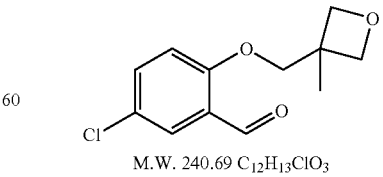

M.W. 240.69 $C_{12}H_{13}ClO_3$

A mixture of 5-chloro-2-hydroxy-benzaldehyde (4.5 g, 29 mmol), toluene-4-sulfonic acid 3-methyl-oxetan-3-ylmethyl ester in Example 13c (6.4 g, 25 mmol) and $K_2CO_3$ (8 g, 58 mmol) in anhydrous N,N-dimethylformamide (40 mL) was heated at 100° C. for 1 h. Then the mixture was filtered and the filtrate was concentrated. The residue was dissolve in EtOAc (50 mL). The solution was washed with water, dried and concentrated to give title compound as a yellow oil (5.2 g).

Example 30b

Preparation of Intermediate E/Z-6-Chloro-3-[5-chloro-2-(3-methyl-oxetan-3-ylmethoxy)-benzylidene]-1,3-dihydro-indol-2-one

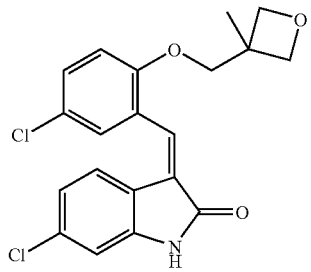

M.W. 390.27 $C_{20}H_{17}Cl_2NO_3$

To the mixture of 5-chloro-2-(3-methyl-oxetan-3-ylmethoxy)-benzaldehyde (2 g, 8.3 mmol) and 6-Chloro-1,3-dihydro-indol-2-one (1.27 g, 7.6 mmol) in methanol (20 mL) was added pyrrolidine (0.6 g, 9.1 mmol) dropwise. The mixture was then heated at 70° C. for 2 h. After cooled to room temperature, the mixture was filtered and resulting precipitate was collected, dried to give title compound as a yellow solid (2.3 g).

Example 30c

Preparation of Intermediate E/Z-6-Chloro-3-[5-chloro-2-(3-methyl-oxetan-3-ylmethoxy)-benzylidene]-2-oxo-2,3-dihydro-indole-1-carboxylic acid tert-butyl ester

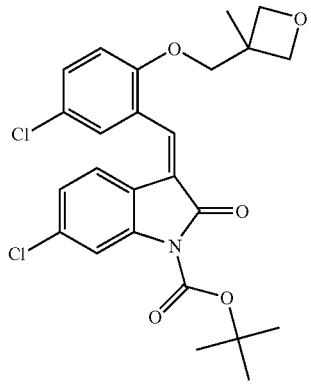

M.W. 490.39 $C_{25}H_{25}Cl_2NO_5$

At room temperature, to a solution of E/Z-6-Chloro-3-[5-chloro-2-(3-methyl-oxetan-3-ylmethoxy)-benzylidene]-1,3-dihydro-indol-2-one (2.3 g) in DCM (30 mL) was added Di-tert-butyl-dicarbonate (1.5 g), followed by the addition of 4-dimethylaminopyridine (0.072 g). After stirring for 0.5 h at room temperature, the solution was washed with 0.5N HCl aqueous solution twice, dried over anhydrous $Na_2SO_4$ and concentrated to give title compound as a yellow oil (2.5 g).

Example 30d

Preparation of Racemic (2'S,3S,4'R)-6-chloro-4'-[5-chloro-2-(3-methyl-oxetan-3-ylmethoxy)-phenyl]-2'-(5-fluoro-2-methyl-phenyl)-spiro[3H-indole-3,3'-piperidine]-2,6'(1H)-dione

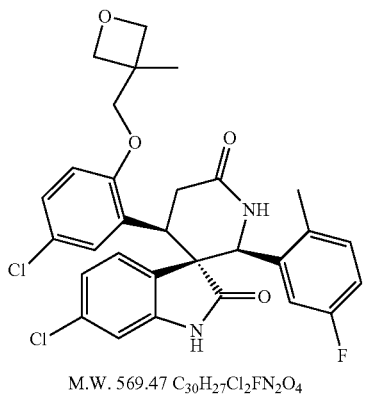

M.W. 569.47 $C_{30}H_{27}Cl_2FN_2O_4$

To a solution of 1-(5-fluoro-2-methyl-phenyl)-3-trimethylsilyoxy-2-aza-1,3-butadiene (7.1 mmol) in anhydrous toluene (7 mL) was added E/Z-6-Chloro-3-[5-chloro-2-(3-methyl-oxetan-3-ylmethoxy)-benzylidene]-2-oxo-2,3-dihydro-indole-1-carboxylic acid tert-butyl ester (0.7 g, 1.4 mmol). The solution was stirred under Ar in a sealed tube at 140° C. for 3 h. After the solution was cooled to room temperature and concentrated, the residue was purified by chromatography (DCM:$CH_3OH$=50:1) to give crude product. The crude product was purified again by Prep-HPLC to give title compound as a white solid (12 mg).

m/z (M+H)$^+$: 569

Example 31a

Preparation of Intermediate racemic (2'R,3S,4'R)-6-chloro-4'-[5-chloro-2-(2-ethoxycarbonyl-2-methyl-ethoxy)-phenyl]-2'-(2,5-difluoro-phenyl)spiro[3H-indole-3,3'-piperidine]-2,6'(1H)-dione

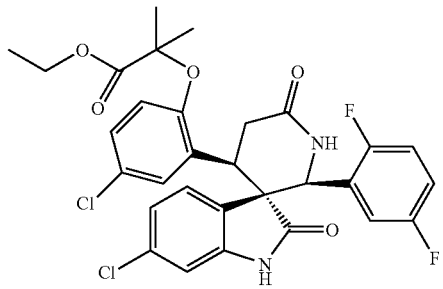

M.W. 603.45 $C_{30}H_{26}Cl_2F_2N_2O_5$

To a solution of 1-(2,5-difluoro-phenyl)-3-trimethylsilyoxy-2-aza-1,3-butadiene in Example 22d (30.8 mmol) in anhydrous toluene (30 mL) was added E/Z 6-Chloro-3-[5-chloro-2-(1-ethoxycarbonyl-1-methyl-ethoxy)-benzylidene]-2-oxo-2,3-dihydro-indole-1-carboxylic acid tert-butyl ester in Example 1c (8 g, 15.4 mmol). The solution was heated to 80° C. for 5 h under Ar. After the solution was cooled to room temperature and concentrated, the residue was purified by chromatography (DCM:CH₃OH=50:1) to give title compound as a white solid (1.7 g).
m/z (M+H)⁺: 603

Example 31b

Preparation of Intermediate racemic (2'R,3S,4'R)-6-chloro-4'-[5-chloro-2-(2-hydroxycarbonyl-2-methyl-ethoxy)-phenyl]-2'-(2,5-difluoro phenyl)spiro[3H-indole-3,3'-piperidine]-2,6'(1H)-dione

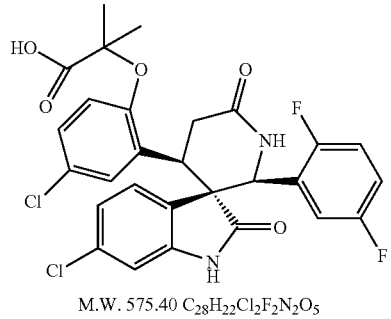

M.W. 575.40 C₂₈H₂₂Cl₂F₂N₂O₅

A mixture of racemic (2'R,3R,4'S)-6-chloro-4'-[5-chloro-2-(2-ethoxycarbonyl-2-methyl-ethoxy)-phenyl]-2'-(2,5-difluoro phenyl)spiro[3H-indole-3,3'-piperidine]-2,6'(1H)-dione (400 mg), NaOH (111 mg), H₂O (5 mL) and THF (10 mL) was heated at 80° C. for 1 h. Then THF was removed by vacuum. The water solution was acidified by concentrated hydrochloric acid to "pH" 1. The white precipitate was collected by filtration to give title compound as a white solid (300 mg).
m/z (M+H)⁺: 575

Example 31c

Preparation of Racemic (2'R,3S,4'R)-6-chloro-4'-[5-chloro-2-(1-dimethylcarbamoyl-1-methyl-ethoxy)-phenyl]-2'-(2,5-difluoro-phenyl)spiro[3H-indole-3,3'-piperidine]-2,6'(1H)-dione

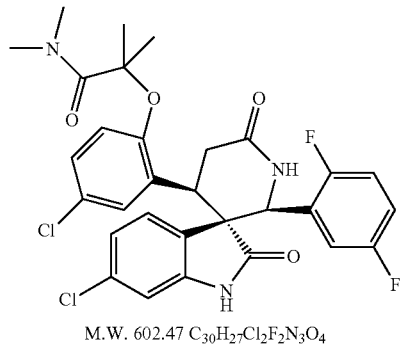

M.W. 602.47 C₃₀H₂₇Cl₂F₂N₃O₄

A mixture of racemic (2'S,3S,4'R)-6-chloro-4'-[5-chloro-2-(2-hydroxycarbonyl-2-methyl-ethoxy)-phenyl]-2'-(2,5-difluoro phenyl)spiro[3H-indole-3,3'-piperidine]-2,6'(1H)-dione (100 mg, 0.174 mmol), dimethylamine hydrochloride (28 mg, 0.348 mmol), EDC.HCl (66 mg, 0.348 mmol), HOBt (47 mg, 0.348 mmol) and DIPEA (135 mg, 1.044 mmol) in anhydrous DMF (3 mL) was stirred at room temperature overnight. Then the mixture was filtered and the filtrate was concentrated. The residue was purified by Prep-HPLC to give the title compound as a white solid (50 mg).
m/z (M+H)⁺: 602

Example 32a

Preparation of Intermediate (2-Bromo-ethyl)-carbamic acid tert-butyl ester

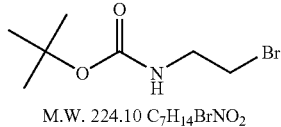

M.W. 224.10 C₇H₁₄BrNO₂

At room temperature, to a mixture of Di-tert-butyl-dicarbonate (17.8 g) and DIPEA (11.6 g) in EtOH (200 mL) was added 2-aminoethylbromide hydrobromide (20 g). After stirring for 3 h, the solution was concentrated and the residue was dissolved in EtOAc. The organic layer was washed with water for 3 times, dried over anhydrous a₂SO₄ and concentrated to give title compound as a light yellow oil (15 g).

Example 32b

Preparation of Intermediate [2-(4-chloro-2-formyl-phenoxy)-ethyl]-carbamic acid tert-butyl ester

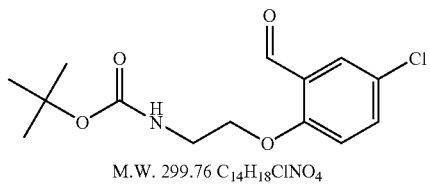

M.W. 299.76 C₁₄H₁₈ClNO₄

In a manner similar to the method described in Example 1a, (2-bromo-ethyl)-carbamic acid tert-butyl ester (10 g, 44.8 mmol) was reacted with 5-chloro-2-hydroxy-benzaldehyde (7 g, 44.8 mmol), K₂CO₃ (18.6 g, 134 mmol) and KI (1.48 g, 8.96 mmol) to give title compound as a oil (9.56 g)

Example 32c

Preparation of Intermediate E/Z-{2-[4-Chloro-2-(6-chloro-2-oxo-1,2-dihydro-indol-3-ylidenemethyl)-phenoxy]-ethyl}-carbamic acid tert-butyl ester

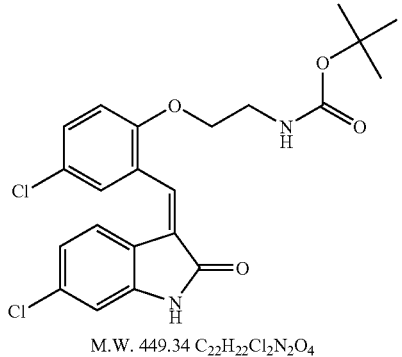

M.W. 449.34 C₂₂H₂₂Cl₂N₂O₄

In a manner similar to the method described in Example 1b, [2-(4-Chloro-2-formyl-phenoxy)-ethyl]-carbamic acid tert-butyl ester (8 g, 27 mmol) was reacted with 6-chloro-1,3-dihydro-indol-2-one (4.5 g, 27 mmol) and pyrrolidine (2.1 g, 30 mmol) in methanol (70 mL) to give title compound as a yellow solid (16 g).

Example 32d

Preparation of Intermediate E/Z-3-[2-(2-tert-butoxy-carbonylamino-ethoxy)-5-chloro-benzylidene]-6-chloro-2-oxo-2,3-dihydro-indole-1-carboxylic acid tert-butyl ester

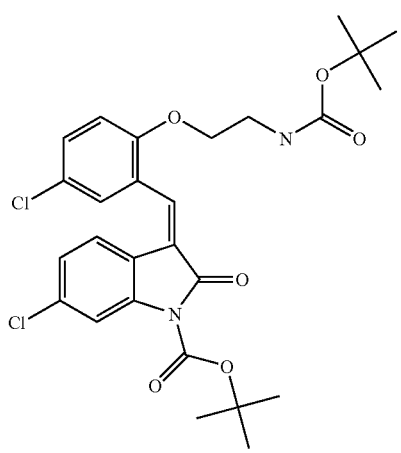

M.W. 549.46 $C_{27}H_{30}Cl_2N_2O_6$

In a manner similar to the method described in Example 1c, E/Z-{2-[4-chloro-2-(6-chloro-2-oxo-1,2-dihydro-indol-3-ylidenemethyl)-phenoxy]-ethyl}-carbamic acid tert-butyl ester (12 g, 30, 27 mmol) was reacted with di-tert-butyl-dicarbonate (5.8 g, 27 mmol) and DMAP (0.66 g, 5.4 mmol) in $CH_2Cl_2$ (150 mL) to give title compound as a yellow solid (12.4 g)

Example 32e

Preparation of Racemic (2'S,3S,4'R)-4'-[2-(2-amino-ethoxy)5-chloro-phenyl]-6-chloro-2'-(5-fluoro-2-methyl phenyl)spiro[3H-indole-3,3'-piperidine]-2,6'(1H)-dione

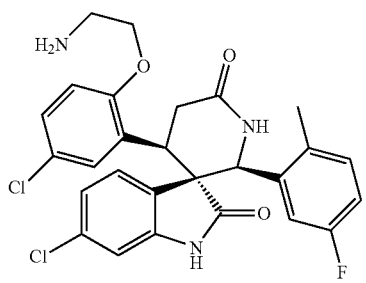

M.W. 528.42 $C_{27}H_{24}Cl_2FN_3O_3$

In a manner similar to the method described in Example 1e, E/Z-3-[2-(2-tert-butoxycarbonylamino-ethoxy)-5-chloro-benzylidene]-6-chloro-2-oxo-2,3-dihydro-indole-1-carboxylic acid tert-butyl ester (4 g, 7.3 mmol) was reacted with 1-(5-fluoro-2-methyl-phenyl)-3-trimethylsilyoxy-2-aza-1,3-butadiene (29 mmol) in toluene and then trifluoroacetic acid (20 mL) in dichloromethane (30 mL) to give title compound as a white solid (130 mg).

m/z (M+H)$^+$: 528

Example 32f

Preparation of Racemic (2'S,3S,4'R)-6-chloro-4'-[5-chloro-2-(2-methanesulfonylamino-ethoxy)-phenyl]-2'-(5-fluoro-2-methyl phenyl)spiro[3H-indole-3,3'-piperidine]-2,6'(1H)-dione

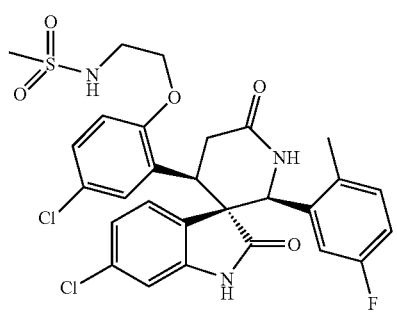

M.W. 606.50 $C_{28}H_{26}Cl_2FN_3O_5S$

At 0° C., to a mixture of racemic (2'S,3S,4'R)-4'-[2-(2-amino-ethoxy)5-chloro-phenyl]-6-chloro-2'-(5-fluoro-2-methyl phenyl)spiro[3H-indole-3,3'-piperidine]-2,6'(1H)-dione (40 mg, 0.076 mmol) and methanesulfonyl chloride (85 mg, 0.76 mmol) in DMF (1 mL) was added triethylamine slowly (75 mg, 0.76 mmol). After stirring for 0.5 h, the mixture was filtered, concentrated and the residue was purified by Prep-HPLC to give title compound as a white solid (20 mg).

m/z (M+H)$^+$: 606

Example 32g

Preparation of Chiral (2'S,3S,4'R)-6-chloro-4'-[5-chloro-2-(2-methanesulfonylamino-ethoxy)-phenyl]-2'-(5-fluoro-2-methyl-phenyl)spiro[3H-indole-3,3'-piperidine]-2,6'(1H)-dione

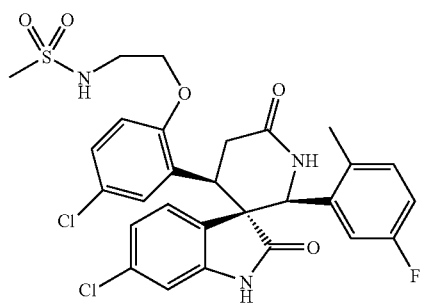

M.W. 606.50 $C_{28}H_{26}Cl_2FN_3O_5S$

Separation of the two enantiomers from racemic (2'S,3S, 4'R)-6-chloro-4'-[5-chloro-2-(2-methanesulfonylamino-ethoxy)-phenyl]-2'-(5-fluoro-2-methyl-phenyl)spiro[3H-indole-3,3'-piperidine]-2,6'(1H)-dione was conducted by chiral SFC to provide chiral (2'S,3S,4'R)-6-chloro-4'-[5-chloro-2-(2-methanesulfonylamino-ethoxy)-phenyl]-2'-(5-fluoro-2-methyl-phenyl)spiro[3H-indole-3,3'-piperidine]-2,6'(1H)-dione as a white solid (5 mg) (RO5253420-000) and chiral (2'R,3R,4'S)-6-chloro-4'-[5-chloro-2-(2-methanesulfonylamino-ethoxy)-phenyl]-2'-(5-fluoro-2-methyl-phenyl)spiro[3H-indole-3,3'-piperidine]-2,6'(1H)-dione as a white solid (5 mg).

m/z (M+H)$^+$: 606

Example 33

Preparation of Racemic (2'S,3S,4'R)-6-chloro-4'-[5-chloro-2-[2-(3,3-dimethyl-ureido)-ethoxy]-phenyl]-2'-(5-fluoro-2-methyl phenyl)spiro[3H-indole-3,3'-piperidine]-2,6'(1H)-dione

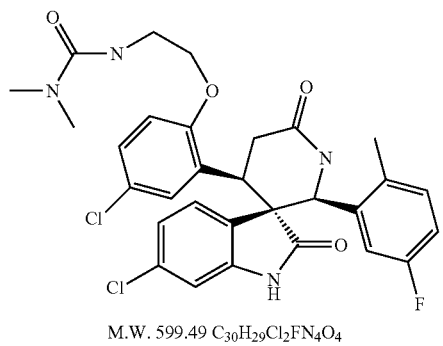

M.W. 599.49 C$_{30}$H$_{29}$Cl$_2$FN$_4$O$_4$

At room temperature, a mixture of racemic (2'S,3S,4'R)-4'-[2-(2-amino-ethoxy)5-chloro-phenyl]-6-chloro-2'-(5-fluoro-2-methyl phenyl)spiro[3H-indole-3,3'-piperidine]-2,6'(1H)-dione (40 mg, 0.076 mmol), dimethylcarbamoyl chloride (41 mg, 0.379 mmol) and triethylamine (38 mg, 0.379 mmol) was stirred 0.5 h. Then the mixture was filtered, concentrated and the residue was purified by Prep-HPLC to give the title compound as a white solid (10 mg).

m/z (M+H)$^+$: 599

Example 34a

Preparation of Intermediate 1-(5-chloro-2-fluoro-phenyl)-3-trimethylsilyoxy-2-aza-1,3-butadiene

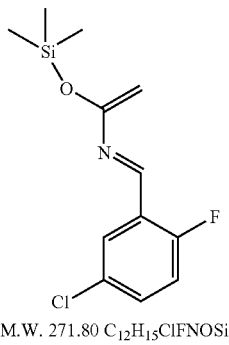

M.W. 271.80 C$_{12}$H$_{15}$ClFNOSi

In a manner similar to the method described in Example 1d, 2-fluoro-5-chloro benzaldehyde (3 g, 19 mmol) was reacted with LiHMDS (1M solution in THF, 19 mL, 19 mmol), trimethylsilyl chloride (2.4 mL, 19 mmol), triethylamine (3.44 mL, 24.6 mmol) and acetyl chloride (1.75 mL, 24.6 mmol) to give title compound and used for the next step without further purification.

Example 34b

Preparation of Intermediate racemic (2'R,3S,4'R)-6-chloro-4'-[5-chloro-2-(1-ethoxycarbonyl-1-methyl-ethoxy)-phenyl]-2'-(5-chloro-2-fluoro-phenyl)spiro[3H-indole-3,3'-piperidine]-2,6'(1H)-dione

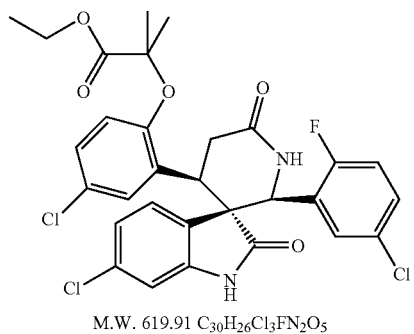

M.W. 619.91 C$_{30}$H$_{26}$Cl$_3$FN$_2$O$_5$

In a manner similar to the method described in Example 1e, E/Z-6-chloro-3-[5-chloro-2-(1-ethoxycarbonyl-1-methyl-ethoxy)-benzylidene]-2-oxo-2,3-dihydro-indole-1-carboxylic acid tert-butyl ester prepared in Example 1c (1.04 g, 2 mmol) was reacted with 1-(2-fluoro-5-chlorophenyl)-3-trimethylsilyoxy-2-aza-1,3-butadiene (10 mmol) in toluene and then trifluoroacetic acid in dichloromethane to give title compound as a white solid (0.48 g).

m/z (M+H)$^+$: 619

Example 34c

Preparation of Intermediate racemic (2'R,3S,4'R)-6-chloro-4'-[5-chloro-2-(1-hydroxycarbonyl-1-methyl-ethoxy)-phenyl]-2'-(5-chloro-2-fluoro-phenyl)spiro[3H-indole-3,3'-piperidine]-2,6'(1H)-dione

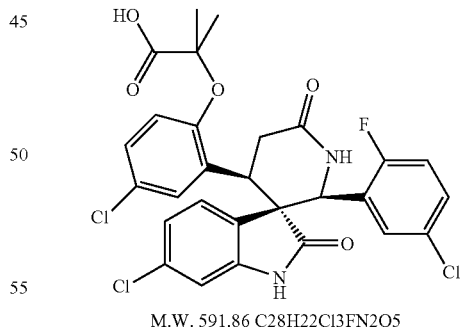

M.W. 591.86 C$_{28}$H$_{22}$Cl$_3$FN$_2$O$_5$

A mixture of racemic (2'R,3S,4'R)-6-chloro-4'-[5-chloro-2-(1-ethoxycarbonyl-1-methyl-ethoxy)-phenyl]-2'-(5-chloro-2-fluoro-phenyl)spiro[3H-indole-3,3'-piperidine]-2,6'(1H)-dione (185 mg), NaOH (120 mg), H$_2$O (15 mL) and methanol (5 mL) was heated at 80° C. for 2 h. Then the mixture was concentrated. The remaining aqueous solution was acidified to "pH" 1 by concentrated aqueous HCl solution. The white precipitate was collected by filtration to give title compound as a white solid (150 mg).

m/z (M+H)$^+$: 591

Example 34d

Preparation of Racemic (2'R,3S,4'R)-6-chloro-4'-[5-chloro-2-(1-dimethylcarbamoyl-1-methyl-ethoxy)-phenyl]-2'-(2-fluoro-5chloro-phenyl)spiro[3H-indole-3,3'-piperidine]-2,6'(1H)-dione

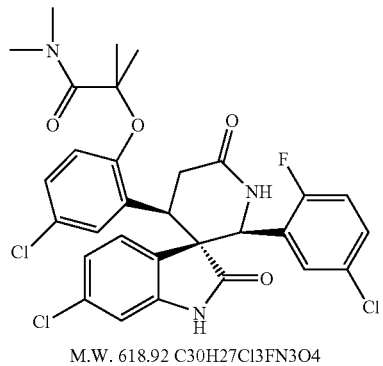

M.W. 618.92 C30H27Cl3FN3O4

A mixture of racemic (2'R,3S,4'R)-6-chloro-4'-[5-chloro-2-(1-hydroxycarbonyl-1-methyl-ethoxy)-phenyl]-2'-(5-chloro-2-fluoro-phenyl)spiro[3H-indole-3,3'-piperidine]-2,6'(1H)-dione (30 mg), dimethylamine hydrochloride (8.5 mg), 4-dimethylamino pyridine (18 mg), EDCl (21 mg) and DIPEA (129 mg) in THF (4 mL) was stirred at room temperature overnight. Then the solvent was removed and the residue was separated by preparative HPLC to give title compound as white solid (7 mg).

m/z (M+H)+: 618.

Example 35a

Preparation of Intermediate 4-(4-bromo-2-formyl-phenoxy)-benzoic acid methyl ester

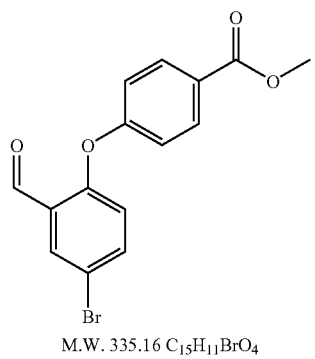

M.W. 335.16 C15H11BrO4

To a solution of 5-bromo-2-fluorobenzaldehyde (4.04 g, 20 mmol) (Alfa) in N,N-dimethylacetamide (30 mL) was added anhydrous K2CO3 (2.76 g, 20 mmol), and methyl 4-hydroxybenzoate (3.1 g, 20 mmol, Aldrich). The reaction mixture was heated at 170° C. for 1 h. The mixture was cooled to room temperature, diluted with ethyl acetate, washed with water, brine. The organic layer was separated, aqueous layer was extracted with ethyl acetate. The combined organic layers were washed with water, dried over MgSO4, concentrated. The residue was purified by chromatography (EtOAc:hexanes=1:8 then 1:4) to give 4-(4-bromo-2-formyl-phenoxy)-benzoic acid methyl ester as a white solid (Yield 6.4 g, 95%).

Similar transformations have been described by Marsh, G. et al in *Eur. J. Org. Chem.* 2003, 2566-2576. The procedures were used with little modification.

Example 35b

Preparation of Intermediate E/Z-4-[4-bromo-2-(6-chloro-2-oxo-1,2-dihydro-indol-3-ylidenemethyl)-phenoxy]-benzoic acid methyl ester

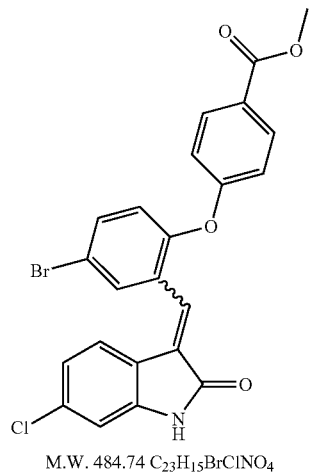

M.W. 484.74 C23H15BrClNO4

In a manner similar to the method described in Example 1a, 6-chlorooxindole (1.6 g, 9.2 mmol) (Crescent) was reacted with 4-(4-bromo-2-formyl-phenoxy)-benzoic acid methyl ester (2.8 g, 8.4 mmol) and pyrrolidine in methanol at 90° C. for 2 h to give E/Z-4-[4-bromo-2-(6-chloro-2-oxo-1,2-dihydro-indol-3-ylidenemethyl)-phenoxy]-benzoic acid methyl ester as a bright yellow solid (Yield 3 g, 81%).

Example 35c

Preparation of Intermediate E/Z-3-[5-bromo-2-(4-methoxycarbonyl-phenoxy)-benzylidene]-6-chloro-2-oxo-2,3-dihydro-indole-1-carboxylic acidtert-butyl ester

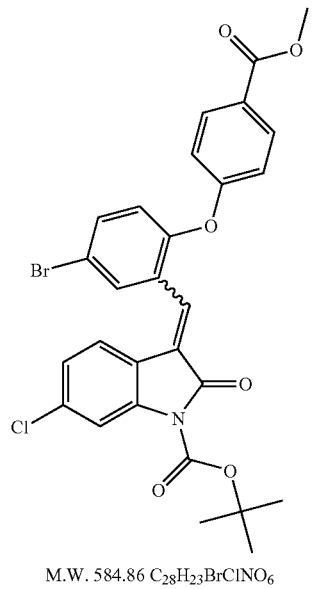

M.W. 584.86 C28H23BrClNO6

In a manner similar to the method described in Example 1b, E/Z-4-[4-bromo-2-(6-chloro-2-oxo-1,2-dihydro-indol-3-ylidenemethyl)-phenoxy]-benzoic acid methyl ester (3 g, 6.1 mmol) was reacted with di-tert-butyl-dicarbonate (1.9 g, 8.7 mmol) (Aldrich) and 4-dimethylaminopyridine to give E/Z-3-[5-bromo-2-(4-methoxycarbonyl-phenoxy)-benzylidene]-

6-chloro-2-oxo-2,3-dihydro-indole-1-carboxylic acid tert-butyl ester as an orange solid (Yield 3.2 g, 88%).

Example 35d

Preparation of Intermediate 1-(3-chlorophenyl)-3-trimethylsilyoxy-2-aza-1,3-butadiene

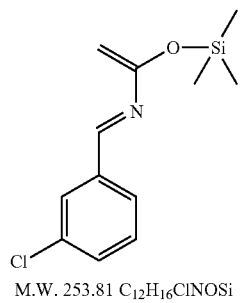

M.W. 253.81 C$_{12}$H$_{16}$ClNOSi

To 1,1,1,3,3,3-hexamethyldisilazane (2.18 mL, 10.5 mmol) (Aldrich) under nitrogen at room temperature was added n-butyllithium (2.5 M, 4.2 mL, 10.5 mmol) (Aldrich). The reaction mixture was stirred at room temperature for 10 minutes. Then dry tetrahydrofuran (30 mL) was added, followed by the addition of 3-chloro-benzaldehyde (1.19 mL, 10.5 mmol) (Aldrich). After the mixture was stirred at room temperature for 0.5 h, trimethylsilyl chloride (1.33 mL, 10.5 mmol) (Aldrich) was added dropwise. Then the temperature of the mixture was lowered to 0° C. on a cooling ice bath. To this mixture was added triethylamine (1.9 mL, 13.6 mmol) in one portion, followed by the dropwise addition of a solution of acetyl chloride (0.97 mL, 13.6 mmol) in diethyl ether (50 mL). The cooling bath was removed, and the mixture was stirred at room temperature for 1 h. The mixture was quickly filtered on celite under nitrogen, and filtrate was concentrated under reduced pressure to give crude 1-(3-chlorophenyl)-3-trimethylsilyoxy-2-aza-1,3-butadiene as a yellow gum and used for the next step without further purification.

Example 35e

Preparation of Racemic (2'S,3S,4'R)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione

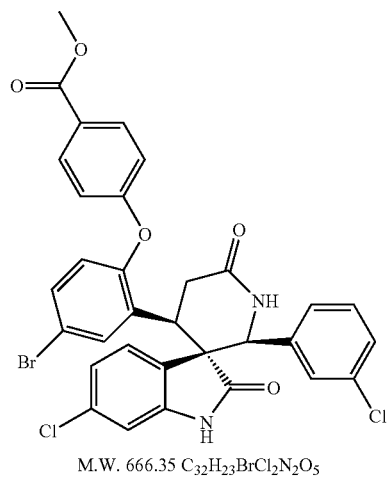

M.W. 666.35 C$_{32}$H$_{23}$BrCl$_2$N$_2$O$_5$

In a manner similar to the method described in Example 1e, E/Z-6-chloro-3-[5-bromo-2-(4-methoxycarbonyl-phenoxy)-benzylidene]-2-oxo-2,3-dihydro-indole-1-carboxylic acid tert-butyl ester (1.2 g, 2 mmol) was reacted with 1-(3-chlorophenyl)-3-trimethylsilyoxy-2-aza-1,3-butadiene (15 mmol) in toluene and then trifluoroacetic acid in dichloromethane to give title compound as a off white solid (0.6 g, 45%).

HRMS(ES$^+$) m/z Calcd for C$_{32}$H$_{23}$BrCl$_2$N$_2$O$_5$+H [(M+H)$^+$]: 665.0240. Found: 665.0235

Example 36a

Preparation of Intermediate 1-(3-fluorophenyl)-3-trimethylsilyoxy-2-aza-1,3-butadiene

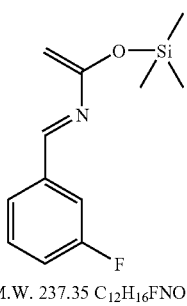

M.W. 237.35 C$_{12}$H$_{16}$FNOSi

In a manner similar to the method described in example 35d, 3-fluoro-benzaldehyde (1.11 mL, 10.5 mmol) (Fluka) was used as the starting material in place of 3-chloro-benzaldehyde to react with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.9 mL, 13.6 mmol) and acetyl chloride (0.97 mL, 13.6 mmol) to give 1-(3-fluorophenyl)-3-trimethylsilyoxy-2-aza-1,3-butadiene as a yellow gum and used for the next step without further purification.

Example 36b

Preparation of Racemic (2'S,3S,4'R)-2'-[5-bromo-2-(4-methoxycarbonyl-phenoxy)-phenyl]-6-chloro-4'-(3-fluorophenyl)spiro[3H-indole-3,3'-piperidine]-2,6'(1H)-dione

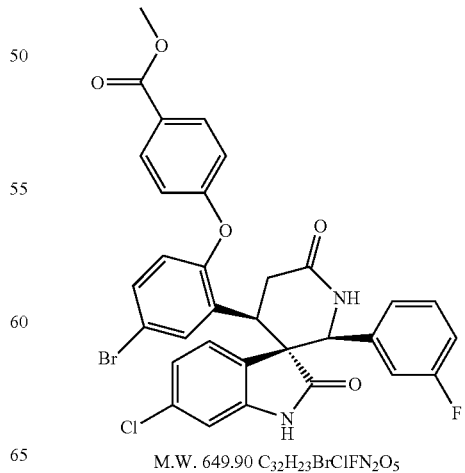

M.W. 649.90 C$_{32}$H$_{23}$BrClFN$_2$O$_5$

In a manner similar to the method described in Example 1e, E/Z-6-chloro-3-[5-bromo-2-(4-methoxycarbonyl-phenoxy)-benzylidene]-2-oxo-2,3-dihydro-indole-1-carboxylic acid tert-butyl ester (1 g, 1.7 mmol) was reacted with 1-(3-fluorophenyl)-3-trimethylsilyoxy-2-aza-1,3-butadiene (10.5 mmol) in toluene and then trifluoroacetic acid in dichloromethane to give title compound as a off white solid (0.68 g, 58%).

HRMS(ES$^+$) m/z Calcd for $C_{32}H_{23}BrClFN_2O_5$+H [(M+H)$^+$]: 649.0536. Found: 649.0538.

Example 37a

Preparation of Intermediate 4-(4-bromo-2-formyl-phenoxy)-piperidine-1-carboxylic acid tert-butyl ester

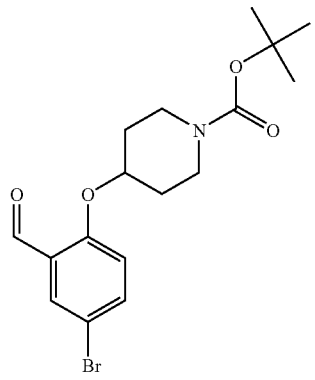

M.W. 384.27 $C_{17}H_{22}BrNO_4$

In a manner similar to the method described in example 4a, 5-bromosalicylaldehyde (5.65 g, 28 mmol) (Aldrich) reacted with 4-(toluene-4-sulfonyloxy)-piperidine-1-carboxylic acid tert-butyl ester (5 g, 14 mmol, ASTATECH) and $K_2CO_3$ in N,N-dimethylformamide to give 4-(4-bromo-2-formyl-phenoxy)-piperidine-1-carboxylic acid tert-butyl ester as a yellow gum (Yield 5.15 g, 51%).

Example 37a

Preparation of Intermediate E/Z-4-[4-bromo-2-(6-chloro-2-oxo-1,2-dihydro-indol-3-ylidenemethyl)-phenoxy]-piperidine-1-carboxylic acid tert-butyl ester

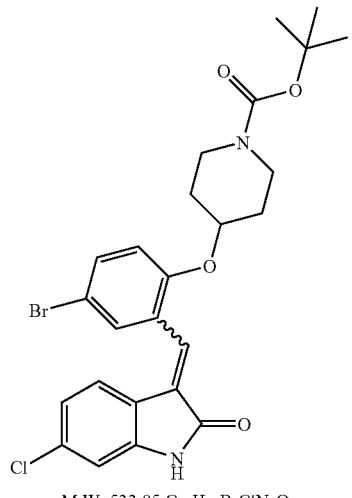

M.W. 533.85 $C_{25}H_{26}BrClN_2O_4$

To a mixture of 6-chlorooxindole (4.58 g, 20 mmol) and 4-(4-bromo-2-formyl-phenoxy)-piperidine-1-carboxylic acid tert-butyl ester (10 g, 26 mmol) in methanol (50 mL) was added piperidine (2.56 mL, 26 mmol) dropwise. The mixture was then heated at 100° C. for 3 h. After cooled to 4° C., the mixture was filtered and the precipitate was collected, dried to give the title compound as a bright yellow solid (12.4 g, 90%).

Example 37c

Preparation of Intermediate E/Z-3-[5-bromo-2-(1-tert-butoxycarbonyl-piperidin-4-yloxy)-benzylidene]-6-chloro-2-oxo-2,3-dihydro-indole-1-carboxylic acid tert-butyl ester

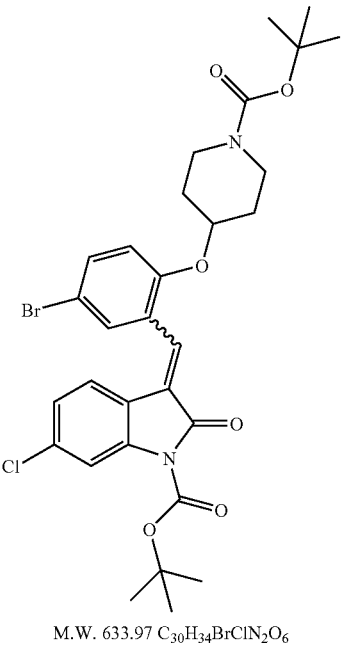

M.W. 633.97 $C_{30}H_{34}BrClN_2O_6$

To a solution of E/Z-4-[4-bromo-2-(6-chloro-2-oxo-1,2-dihydro-indol-3-ylidenemethyl)-phenoxy]-piperidine-1-carboxylic acid tert-butyl ester (12.4 g, 23 mmol) in DCM (200 mL) at r.t. was added di-tert-butyl-dicarbonate (9.27 g, 42.4 mmol), followed by the addition of 4-dimethylaminopyridine (0.13 g) and triethylamine (16 mL, 114 mmol). The reaction mixture was stirred at 0° C. for 0.5 h and washed with 0.5N hydrochloric acid, dried over anhydrous $Na_2SO_4$, then the solvent was removed. The residue was purified by chromatography (20% EtOAc:hexanes) to give title compound as a yellow solid (Yield: 10.8 g, 74%).

Example 37d

Preparation of Racemic (2'S,3S,4'R)-4'-[5-bromo-2-(1-tert-butoxycarbonyl-piperidin-4-yloxy)-phenyl]-6-chloro-2'-(3-fluorophenyl)spiro[3H-indole-3,3'-piperidine]-2,6'(1H)-dione

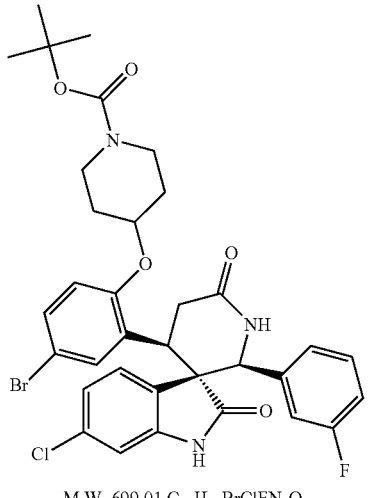

M.W. 699.01 C$_{34}$H$_{34}$BrClFN$_3$O$_5$

To a solution of 1-(3-fluoro-phenyl)-3-trimethylsilyoxy-2-aza-1,3-butadiene in example 36a (24 mmol) in toluene (100 mL) was added E/Z-3-[5-bromo-2-(1-tert-butoxycarbonyl-piperidin-4-yloxy)-benzylidene]-6-chloro-2-oxo-2,3-dihydro-indole-1-carboxylic acid tert-butyl ester (3.85 g, 6 mmol). The reaction mixture was stirred under argon at 140° C. for 5 h. After cooled to room temperature, the mixture was concentrated. The residue was purified by chromatography (20%-30% EtOAc:DCM) to give the title compound as a off white solid (Yield: 0.38 g).

HRMS(ES$^+$) m/z Calcd for C$_{34}$H$_{34}$BrClFN$_3$O$_5$+H [(M+H)$^+$]: 698.1427. Found: 698.1423.

Example 38a

Preparation of Racemic (2'S,3S,4'R)-4'-[5-bromo-2-(4-piperidinyloxy)-phenyl]-6-chloro-2'-(5-fluorophenyl)spiro[3H-indole-3,3'-piperidine]-2,6'(1H)-dione

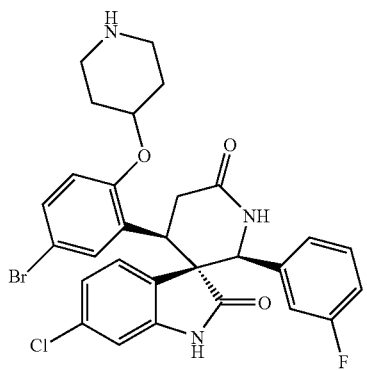

M.W. 598.90 C$_{29}$H$_{26}$BrClFN$_3$O$_3$

A solution of racemic (2'S,3S,4'R)-4'-[5-bromo-2-(1-tert-butoxycarbonyl-piperidin-4-yloxy)-phenyl]-6-chloro-2'-(3-fluorophenyl)spiro[3H-indole-3,3'-piperidine]-2,6'(1H)-dione (0.35 g, 0.5 mmol) in TFA (2 mL) and dichloromethane (2 mL) was stirred at r.t. for 0.5 h. The solution was diluted with DCM, washed with 1N Na$_2$CO$_3$ aq. (50 mL) and brine (50 mL), dried over anhydrous Na$_2$SO$_4$, concentrated to give title compound as a yellow solid (Yield: 0.21 g, 70%).

Example 38b

Preparation of Racemic (2'S,3S,4'R)-4'-[2-(1-acetyl-4-piperidinyloxy)-5-bromo-phenyl]-6-chloro-2'-(3-fluorophenyl)spiro[3H-indole-3,3'-piperidine]-2,6'(1H)-dione

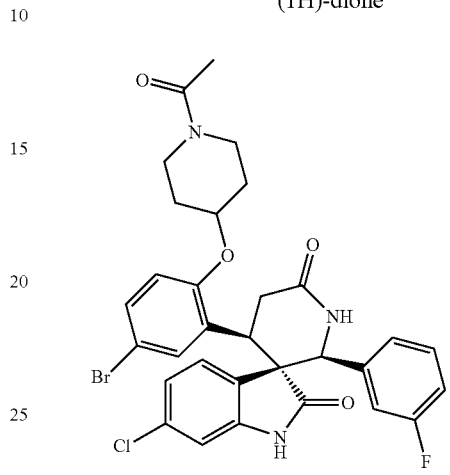

M.W. 640.93 C$_{31}$H$_{28}$BrClFN$_3$O$_4$

To a mixture of racemic (2'S,3S,4'R)-4'-[5-bromo-2-(4-piperidinyloxy)-phenyl]-6-chloro-2'-(3-fluorophenyl)spiro[3H-indole-3,3'-piperidine]-2,6'(1H)-dione (60 mg, 0.1 mmol), acetyl chloride (9.4 mg, 0.12 mmol) in tetrahydrofuran (2 mL) was added triethylamine (0.027 mL, 0.2 mmol) at r.t. The reaction mixture was stirred for 4 h, then concentrated and partitioned between ethyl acetate and water. The organic layer was separated, and the aqueous layer was extracted with ethyl acetate. The combined organic layers were dried over MgSO$_4$ and concentrated. The residue was triturated in dichloromethane and hexanes to give the title compound as a off white solid (Yield: 43 mg).

HRMS(ES$^+$) m/z Calcd for C$_{31}$H$_{28}$BrClFN$_3$O$_4$+H [(M+H)$^+$]: 640.1009. Found: 640.1007

Example 39

Preparation of Racemic (2'S,3S,4'R)-4'-[5-bromo-2-(1-methyl-4-piperidinyloxy)-phenyl]-6-chloro-2'-(3-fluorophenyl)spiro[3H-indole-3,3'-piperidine]-2,6'(1H)-dione

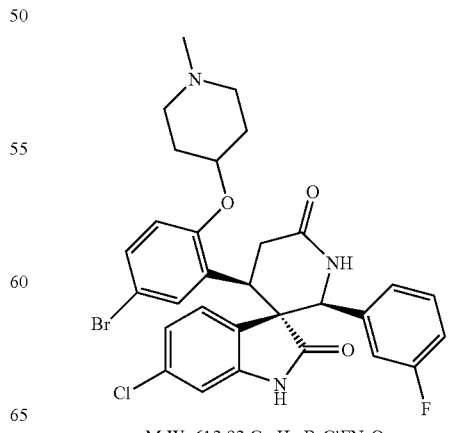

M.W. 612.92 C$_{30}$H$_{28}$BrClFN$_3$O$_3$

To a mixture of racemic (2'S,3S,4'R)-4'-[5-bromo-2-(4-piperidinyloxy)-phenyl]-6-chloro-2'-(3-fluorophenyl)spiro[3H-indole-3,3'-piperidine]-2,6'(1H)-dione (150 mg, 0.25 mmol) in methanol (10 mL) was added an aqueous solution (37 wt %, Aldrich) of formaldehyde (0.03 mL, 0.38 mmol) and NaCNBH$_3$ (25 mg, 0.38 mmol). The reaction mixture was stirred at room temperature for 1 h, then concentrated. The residue was partitioned between ethyl acetate and water. The organic layer was separated, and the aqueous layer was extracted with ethyl acetate. The organic layers were combined, washed with brine, dried over MgSO$_4$, and concentrated. The residue was purified by chromatography (MeOH:EtOAc:triethylamine=12:88:5) to give racemic (2'S,3S,4'R)-4'-[5-bromo-2-(1-methyl-4-piperidinyloxy)-phenyl]-6-chloro-2'-(3-fluorophenyl)spiro[3H-indole-3,3'-piperidine]-2,6'(1H)-dione as a white solid (Yield 100 mg, 65%).

HRMS(ES$^+$) m/z Calcd for $C_{30}H_{28}BrClFN_3O_3$+H [(M+H)$^+$]: 612.1060. Found: 612.1059.

Example 40

Preparation of Racemic (2'S,3S,4'R)-4'-[5-bromo-2-(1-tert-butoxycarbonyl-piperidin-4-yloxy)-phenyl]-6-chloro-2'-(3-chlorophenyl)spiro[3H-indole-3,3'-piperidine]-2,6'(1H)-dione

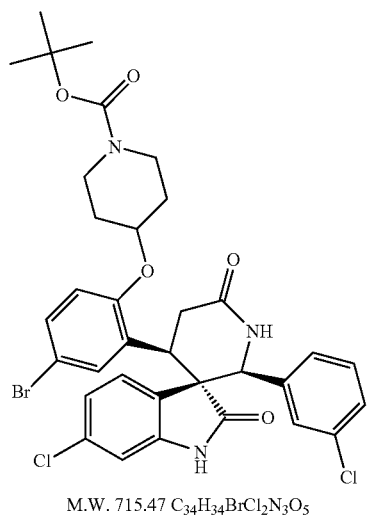

M.W. 715.47 $C_{34}H_{34}BrCl_2N_3O_5$

In a manner similar to the method described in Example 37d, 1-(3-chloro-phenyl)-3-trimethylsilyoxy-2-aza-1,3-butadiene in example 35d (43 mmol) in was reacted with E/Z-3-[5-bromo-2-(1-tert-butoxycarbonyl-piperidin-4-yloxy)-benzylidene]-6-chloro-2-oxo-2,3-dihydro-indole-1-carboxylic acid tert-butyl ester in example 37c (10.8 g, 17 mmol) in toluene at 140° C. for 5 h to give the title compound as a yellow solid (Yield: 1.5 g).

HRMS(ES$^+$) m/z Calcd for $C_{34}H_{34}BrCl_2N_3O_5$+H [(M+H)$^+$]: 714.1132. Found: 714.1128

Example 41a

Preparation of Racemic (2'S,3S,4'R)-4'-[5-bromo-2-(4-piperidinyloxy)-phenyl]-6-chloro-2'-(5-chlorophenyl)spiro[3H-indole-3,3'-piperidine]-2,6'(1H)-dione

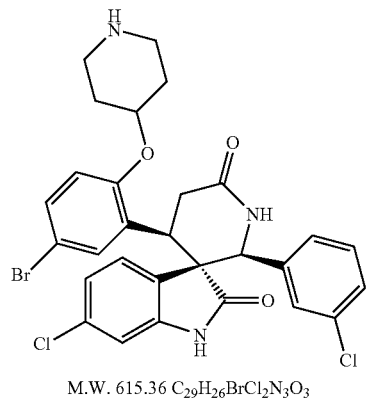

M.W. 615.36 $C_{29}H_{26}BrCl_2N_3O_3$

In a manner similar to the method described in Example 38a, racemic (2'S,3S,4'R)-4'-[5-bromo-2-(1-tert-butoxycarbonyl-piperidin-4-yloxy)-phenyl]-6-chloro-2'-(3-chlorophenyl)spiro[3H-indole-3,3'-piperidine]-2,6'(1H)-dione (0.75 g, 1 mmol) was reacted with trifluoroacetic acid in dichloromethane to give title compound as a yellow solid (Yield: 0.6 g, 93%).

Example 41b

Preparation of Racemic (2'S,3S,4'R)-4'-[2-(1-acetyl-4-piperidinyloxy)-5-bromo-phenyl]-6-chloro-2'-(3-chlorophenyl)spiro[3H-indole-3,3'-piperidine]-2,6'(1H)-dione

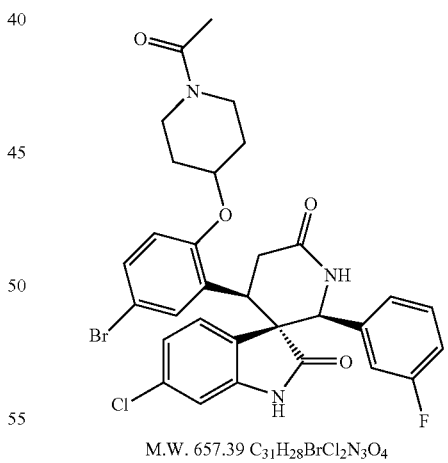

M.W. 657.39 $C_{31}H_{28}BrCl_2N_3O_4$

In a manner similar to the method described in Example 38b, racemic (2'S,3S,4'R)-4'-[5-bromo-2-(4-piperidinyloxy)-phenyl]-6-chloro-2'-(3-chlorophenyl)spiro[3H-indole-3,3'-piperidine]-2,6'(1H)-dione (85 mg, 0.14 mmol) was reacted with acetyl chloride (13 mg, 0.17 mmol), triethylamine in tetrahydrofuran to give the title compound as a white solid (Yield: 43 mg).

HRMS(ES$^+$) m/z Calcd for $C_{31}H_{28}BrCl_2N_3O_4$+H [(M+H)$^+$]: 656.0713. Found: 656.0708

Example 42

Preparation of Racemic (2'S,3S,4'R)-4'-[5-bromo-2-(1-methyl-4-piperidinyloxy)-phenyl]-6-chloro-2'-(3-chlorophenyl)spiro[3H-indole-3,3'-piperidine]-2,6'(1H)-dione

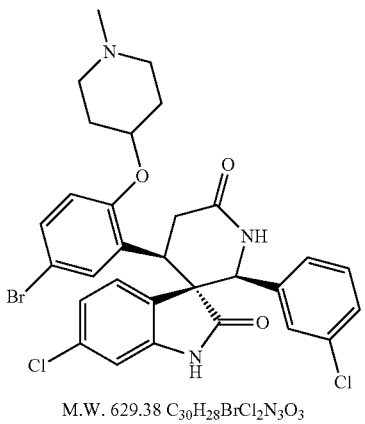

M.W. 629.38 C₃₀H₂₈BrCl₂N₃O₃

In a manner similar to the method described in Example 39, racemic (2'S,3S,4'R)-4'-[5-bromo-2-(4-piperidinyloxy)-phenyl]-6-chloro-2'-(chlorophenyl)spiro[3H-indole-3,3'-piperidine]-2,6'(1H)-dione (100 mg, 0.16 mmol) in methanol (10 mL) was reacted with aqueous solution (37 wt %, Aldrich) of formaldehyde (0.02 mL, 0.24 mmol) and NaCNBH₃ (15 mg, 0.24 mmol) in methanol to give the title compound as a white solid (Yield 57 mg, 57%).

HRMS(ES⁺) m/z Calcd for C₃₀H₂₈BrCl₂N₃O₃+H [(M+H)⁺]: 628.0764. Found: 628.0765.

Example 43a

Preparation of Intermediate 1-(2-chloro-5-fluoro-phenyl)-3-trimethylsilyoxy-2-aza-1,3-butadiene

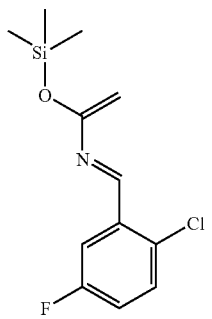

M.W. 271.80 C₁₂H₁₅ClFNOSi

To dry tetrahydrofuran (200 mL) was added 1M THF solution of LiHMDS (210 mL, 210 mmol) under Ar protection at room temperature, followed by the addition of 2-chloro-5-fluoro-benzaldehyde (33 g, 210 mmol). After the mixture was stirred at room temperature for 1 h, trimethylsilyl chloride (26.6 mL, 210 mmol) was added dropwise. Then the temperature of the mixture was lowered to 0° C. on a cooling ice bath. To this mixture was added triethylamine (38 mL, 273 mmol) in one portion, followed by the dropwise addition of a solution of acetyl chloride (20 mL, 273 mmol) in diethyl ether (500 mL). The cooling bath was removed, and the mixture was stirred at room temperature for 4 h. The mixture was quickly filtered on celite under nitrogen, and filtrate was concentrated under reduced pressure to give crude 1-(2-chloro-5-fluoro-phenyl)-3-trimethylsilyoxy-2-aza-1,3-butadiene as a yellow gum and used for the next step without further purification.

Example 43b

Preparation of Intermediate racemic (2'R,3S,4'R)-6-chloro-4'-[5-chloro-2-(1-ethoxycarbonyl-1-methyl-ethoxy)-phenyl]-2'-(2-chloro-5-fluoro-phenyl)spiro[3H-indole-3,3'-piperidine]-2,6'(1H)-dione

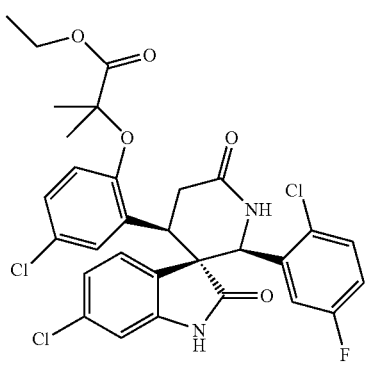

M.W. 619.91 C₃₀H₂₆Cl₃FN₂O₅

In a manner similar to the method described in Example 1e, E/Z-6-chloro-3-[5-chloro-2-(1-ethoxycarbonyl-1-methyl-ethoxy)-benzylidene]-2-oxo-2,3-dihydro-indole-1-carboxylic acid tert-butyl ester (3 g, 5.76 mmol) was reacted with 1-(2-chloro-5-fluoro-phenyl)-3-trimethylsilyoxy-2-aza-1,3-butadiene (23 mmol) in toluene to give the title compound as a white solid (400 mg).

m/z (M+H)⁺: 619

Example 43c

Preparation of Intermediate racemic (2'R,3S,4'R)-6-chloro-2'-(2-chloro-5-fluoro-phenyl)-4'-[5-chloro-2-(1-hydroxycarbonyl-1-methyl-ethoxy)-phenyl]spiro[3H-indole-3,3'-piperidine]-2,6'(1H)-dione

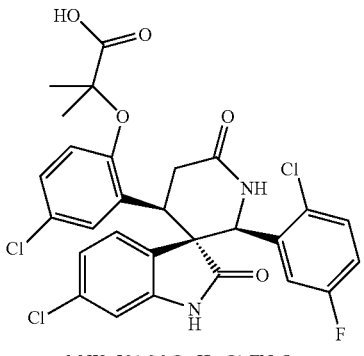

M.W. 591.86 C₂₈H₂₂Cl₃FN₂O₅

A mixture of racemic (2'R,3S,4'R)-6-chloro-4'-[5-chloro-2-(1-ethoxycarbonyl-1-methyl-ethoxy)-phenyl]-2'-(2-chloro-5-fluoro-phenyl)spiro[3H-indole-3,3'-piperidine]-2,6'(1H)-dione (150 mg, 0.24 mmol), NaOH (70 mg, 1.75 mmol), H₂O (2 mL) and THF (6 mL) was heated at 70° C. for 1 h. After cooled to room temperature, the solution was concentrated and the residue was acidified to "pH" 2-3 by addition of concentrated aqueous HCl. The white solid was collected by filtration to give the title compound which was used for next step reaction without further purification.

m/z (M+H)⁺: 591

Example 43d

Preparation of Racemic (2'R,3S,4'R)-6-chloro-2'-(2-chloro-5-fluoro-phenyl)-4'-[5-chloro-2-(2-methanesulfonylamino-1,1-dimethyl-2-oxo-ethoxy)-phenyl]spiro[3H-indole-3,3'-piperidine]-2,6'(1H)-dione

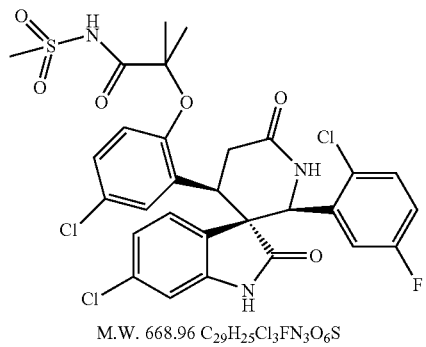

M.W. 668.96 C₂₉H₂₅Cl₃FN₃O₆S

A solution of racemic (2'R,3S,4'R)-6-chloro-2'-(2-chloro-5-fluoro-phenyl)-4'-[5-chloro-2-(1-hydroxycarbonyl-1-methyl-ethoxy)-phenyl]spiro[3H-indole-3,3'-piperidine]-2,6'(1H)-dione (143 mg, 0.24 mmol) and CDI (78 mg, 0.48 mmol) in DMF (5 mL) was stirred at room temperature for 30 min. Then to this solution was added a mixture of methanesulfonamide (475 mg, 5 mmol) and NaH (200 mg, 60%, 5 mmol) in DMF (5 mL), which had been stirred for 1 h at room temperature. After the resulting mixture was heated at 60° C. for 1 h, it was poured into water (5 mL) and the mixture was acidified by concentrated aqueous HCl, extracted with EtOAc twice. The combined extracts were dried over anhydrous Na₂SO₄, concentrated and the residue was purified by flash column to give the title compound as a white solid (100 mg).

m/z (M+H)⁺: 668

Example 44

Preparation of Chiral (2'S,3S,4'R)-6-chloro-4'-[5-chloro-2-(2-methanesulfonylamino-1,1-dimethyl-ethoxy)-phenyl]-2'-(5-fluoro-2-methyl-phenyl)spiro[3H-indole-3,3'-piperidine]-2,6'(1H)-dione

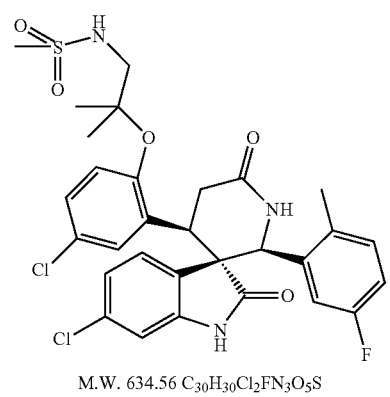

M.W. 634.56 C₃₀H₃₀Cl₂FN₃O₅S

At 0° C., to a solution of chiral (2'S,3S,4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione (20 mg, 0.03 mmol) prepared in Example 12b in THF (1 mL) was added a toluene solution (1 M) of DIBALH (0.18 mL, 0.18 mmol) in one portion. After stirred for 0.5 h, the mixture was quenched with water. Then the mixture was filtered and the filtrate was concentrated. The residue was purified by Prep-HPLC to give the title compound as a white solid (9 mg).

m/z (M+H)⁺: 634

Example 45

Preparation of Racemic (2'S,3S,4'R)-6-chloro-4'-[5-chloro-2-(1-methoxylcarbamoyl-1-methyl-ethoxy)-phenyl]-2'-(5-fluoro-2-methyl-phenyl)spiro[3H-indole-3,3'-piperidine]-2,6'(1H)-dione

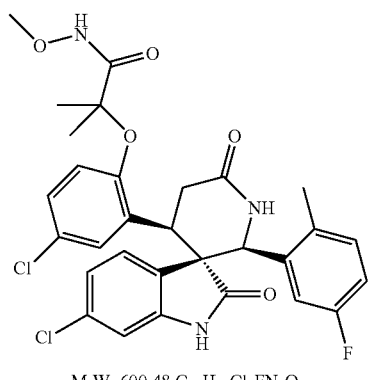

M.W. 600.48 C₃₀H₂₈Cl₂FN₃O₅

To a mixture of racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (30 mg, 0.05 mmol) prepared in Example 1f, EDCl (20 mg, 0.1 mmol), HOBt (16 mg, 0.1 mmol) and DIPEA (40 mg, 0.3 mmol) in THF (1 mL) was added o-methylhydroxylamine hydrochloride (22 mg, 0.25 mmol). The mixture was stirred at room temperature overnight and purified by prep-HPLC to give the title compound as a white solid (11 mg).
m/z (M+H)$^+$: 600

Example 46

Preparation of Racemic (2'S,3S,4'R)-6-chloro-4'-[5-chloro-2-(1-cyanocarbamoyl-1-methyl-ethoxy)-phenyl]-2'-(5-fluoro-2-methyl-phenyl)spiro[3H-indole-3,3'-piperidine]-2,6'(1H)-dione

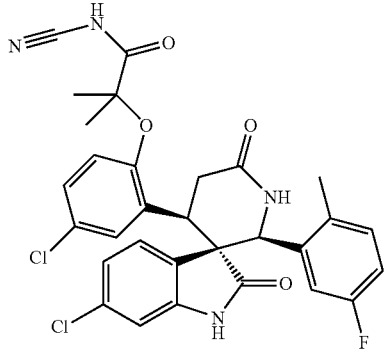

M.W. 595.46 C$_{30}$H$_{25}$Cl$_2$FN$_4$O$_4$

To a mixture of racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (30 mg, 0.05 mmol) prepared in Example 1f, EDCl (20 mg, 0.1 mmol), HOBt (16 mg, 0.1 mmol) and DIPEA (20 mg, 0.15 mmol) in THF (1 mL) was added cyanamide (50% in H$_2$O) (20 mg, 0.24 mmol). The mixture was stirred at room temperature overnight and purified by prep-HPLC to give the title compound as a white solid (14 mg).
m/z (M+H)$^+$: 595

Example 47

Preparation of Racemic (2'S,3S,4'R)-6-chloro-4'-[5-chloro-2-(1-hydroxycarbamoyl-1-methyl-ethoxy)-phenyl]-2'-(5-fluoro-2-methyl-phenyl)spiro[3H-indole-3,3'-piperidine]-2,6'(1H)-dione

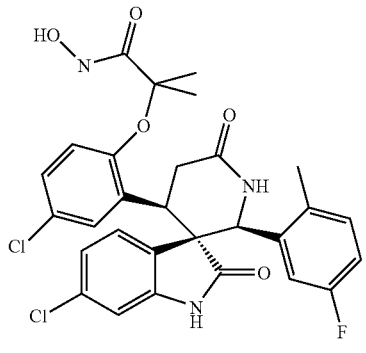

M.W. 586.45 C$_{29}$H$_{26}$Cl$_2$FN$_3$O$_5$

To a mixture of racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (30 mg, 0.053 mmol) prepared in Example 1f, EDCl (20 mg, 0.1 mmol), HOBt (16 mg, 0.1 mmol) and DIPEA (40 mg, 0.3 mmol) in THF (1 mL) was added hydroxylamine hydrochloride ((18 mg, 0.26 mmol). The mixture was stirred at room temperature overnight and purified by prep-HPLC to give the title compound as a white solid (14 mg).
m/z (M+H)$^+$: 586

Example 48a

Preparation of Intermediate E/Z-2-[2-(6-chloro-2-oxo-1,2-dihydro-indol-3-ylidenemethyl)-4-fluoro-phenoxy]-2-methyl-propionic acid ethyl ester

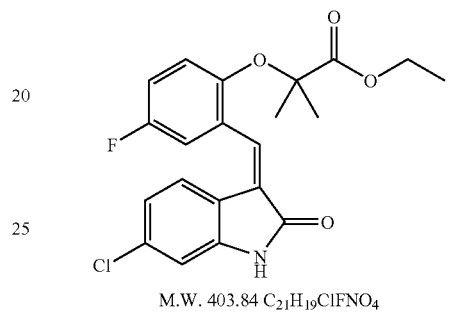

M.W. 403.84 C$_{21}$H$_{19}$ClFNO$_4$

To the mixture of 6-chlorooxindole (5.3 g, 31.7 mmol) and 2-(4-fluoro-2-formyl-phenoxy)-2-methyl-propionic acid ethyl ester (8 g, 31.7 mmol) in methanol (30 mL) was added pyrrolidine (2.6 mL, 31.7 mmol) dropwise. Then the mixture was heated at 70° C. for 3 h. After cooled to room temperature, the mixture was filtered and the precipitate was collected, dried to give the title compound as a yellow solid (10 g).

Example 48b

Preparation of Intermediate E/Z-6-chloro-3-[2-(1-ethoxycarbonyl-1-methyl-ethoxy)-5-fluoro-benzylidene]-2-oxo-2,3-dihydro-indole-1-carboxylic acid tert-butyl ester

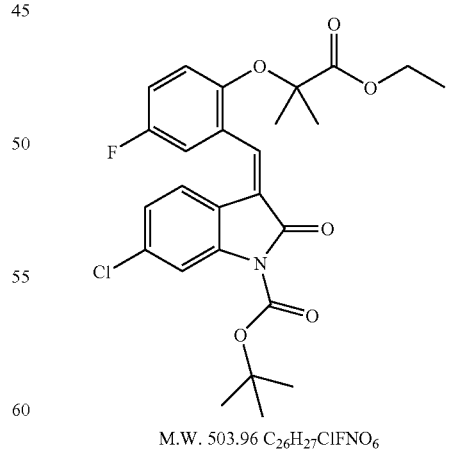

M.W. 503.96 C$_{26}$H$_{27}$ClFNO$_6$

To a solution of E/Z-2-[2-(6-chloro-2-oxo-1,2-dihydro-indol-3-ylidenemethyl)-4-fluoro-phenoxy]-2-methyl-propionic acid ethyl ester (5 g, 12 mmol) in dichloromethane (50 mL) at room temperature was added di-tert-butyl-dicarbonate (3.1 g, 14 mmol), followed by the addition of 4-dimethylaminopyridine (0.15 g, 1.2 mmol). After the reaction mixture was stirred at room temperature for 2 h, the solution was washed with HCl aq. (1 M) and brine twice, dried over anhydrous Na$_2$SO$_4$ and concentrated to give the title compound as a yellow solid (6.5 g).

Example 48c

Preparation of Intermediate racemic (2'S,3S,4'R)-6-chloro-4'-[5-fluoro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione

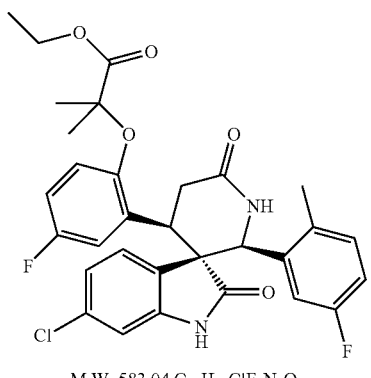

M.W. 583.04 C$_{31}$H$_{29}$ClF$_2$N$_2$O$_5$

In a manner similar to the method described in Example 1e, E/Z-6-Chloro-3-[2-(1-ethoxycarbonyl-1-methyl-ethoxy)-5-fluoro-benzylidene]-2-oxo-2,3-dihydro-indole-1-carboxylic acid tert-butyl ester (5 g, 10 mmol) was reacted with 1-(5-fluoro-2-methyl-phenyl)-3-trimethylsilyoxy-2-aza-1,3-butadiene (40 mmol) in toluene to give the title compound as a white solid (800 mg).

m/z (M+H)$^+$: 583

Example 48d

Preparation of Intermediate racemic (2'S,3S,4'R)-6-chloro-4'-[5-fluoro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione

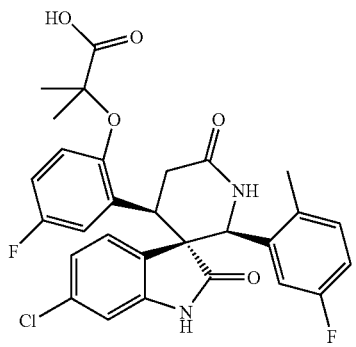

M.W. 554.98 C$_{29}$H$_{25}$ClF$_2$N$_2$O$_5$

A mixture of racemic (2'S,3S,4'R)-6-chloro-4'-[5-fluoro-2-(1-ethoxycarbonyl-1-methyl-ethoxy)-phenyl]-2'-(5-fluoro-2-methyl-phenyl)spiro[3H-indole-3,3'-piperidine]-2,6'(1H)-dione (300 mg, 0.52 mmol), NaOH (41 mg, 1.03 mmol), H$_2$O (1 mL) and THF (10 mL) was heated at 65° C. for 1 h. After cooled to room temperature, the solution was concentrated and the residue was acidified to "pH" 2-3 by addition of concentrated aqueous HCl. The white solid was collected by filtration, dried to give the title compound (200 mg).

m/z (M+H)$^+$: 555

Example 48e

Preparation of Racemic (2'S,3S,4'R)-6-chloro-4'-[5-fluoro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione

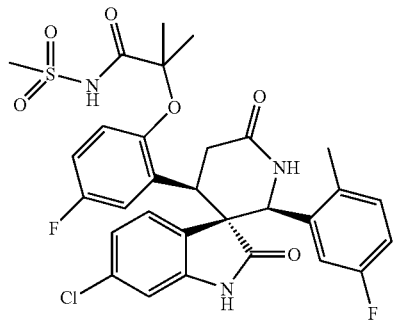

M.W. 632.09 C$_{30}$H$_{28}$ClF$_2$N$_3$O$_6$S

A solution of racemic (2'S,3S,4'R)-6-chloro-4'-[5-fluoro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (100 mg, 0.18 mmol) and CDI (58 mg, 0.36 mmol) in DMF (5 mL) was heated at 60° C. for 0.5 h. Then to this solution was added a mixture of methanesulfonamide (475 mg, 5 mmol) and NaH (200 mg, 60%, 5 mmol) in DMF (5 mL), which had been stirred for 1 h at room temperature. After the resulting mixture was stirred at room temperature for 0.5 h, it was poured into water (5 mL) and the aqueous solution was acidified to "pH" 2-3 by concentrated aqueous hydrochloride. After the aqueous phase was extracted with EtOAc twice, the combined organic phases were dried over anhydrous Na$_2$SO$_4$, concentrated and the residue was purified by flash column to give the title compound as a white solid (80 mg).

m/z (M+H)$^+$: 632

Example 49a

Preparation of Intermediate 5-chloro-2-(4-methoxy-phenoxy)-benzaldehyde

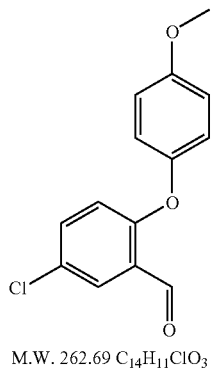

M.W. 262.69 C$_{14}$H$_{11}$ClO$_3$

At the room temperature, anhydrous Na$_2$CO$_3$ (16 g, 0.15 mol) was added into a mixture of 4-methoxy-phenol (14.8 g, 0.12 mol) and 5-chloro-2-fluoro-benzaldehyde (16 g, 0.10 mol) in N,N-Dimethylacetamide (100 mL). After the mixture was refluxed for 3 h, it was cooled to room temperature. Then DCM and water were added. The organic phase was separated, washed with aqueous NaOH (1 N) and brine, dried over anhydrous $Na_2SO_4$ and concentrated to give the title compound (16 g).

Example 49b

Preparation of Intermediate E/Z-6-chloro-3-[5-chloro-2-(4-methoxy-phenoxy)-benzylidene]-1,3-dihydro-indol-2-one

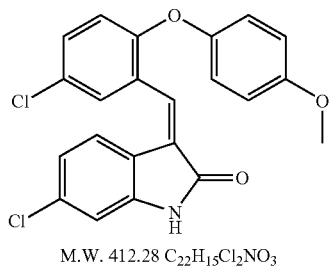

M.W. 412.28 $C_{22}H_{15}Cl_2NO_3$

To the mixture of 6-chlorooxindole (8.3 g, 49.7 mmol) and 5-chloro-2-(4-methoxy-phenoxy)-benzaldehyde (13 g, 49.7 mmol) in methanol (100 mL) was added pyrrolidine (4.1 mL, 49.5 mmol) dropwise. The mixture was then heated at 70° C. for 3 h. After cooled to room temperature, the mixture was filtered and the precipitate was collected, dried to give the title compound as a yellow solid (15.5 g).

Example 49c

Preparation of Intermediate E/Z-6-Chloro-3-[5-chloro-2-(4-methoxy-phenoxy)-benzylidene]-2-oxo-2,3-dihydro-indole-1-carboxylic acid tert-butyl ester

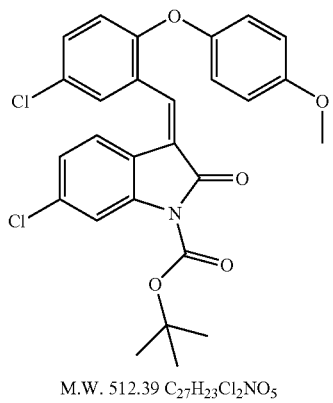

M.W. 512.39 $C_{27}H_{23}Cl_2NO_5$

To a solution of E/Z-6-chloro-3-[5-chloro-2-(4-methoxy-phenoxy)-benzylidene]-1,3-dihydro-indol-2-one (15.5 g, 38 mmol) in dichloromethane (100 mL) at room temperature was added di-tert-butyl-dicarbonate (12.3 g, 56 mmol), followed by the addition of 4-dimethylaminopyridine (0.46 g, 3.8 mmol). After the reaction mixture was stirred at room temperature for 2 h, the solution was washed with 1M HCl solution and brine twice, dried over anhydrous $Na_2SO_4$ and concentrated to give the title compound as a yellow solid (16.5 g).

Example 49d

Preparation of Racemic (2'S,3S,4'R)-6-chloro-4'-[5-chloro-2-(4-methoxy-phenoxy)-phenyl]-2'-(5-fluoro-2-methyl-phenyl)spiro[3H-indole-3,3'-piperidine]-2,6'(1H)-dione

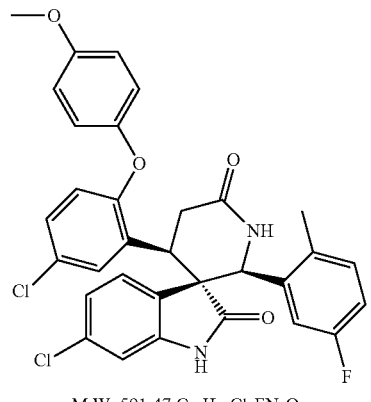

M.W. 591.47 $C_{32}H_{25}Cl_2FN_2O_4$

In a manner similar to the method described in Example 1e, E/Z-6-chloro-3-[5-chloro-2-(4-methoxy-phenoxy)-benzylidene]-2-oxo-2,3-dihydro-indole-1-carboxylic acid tert-butyl ester (5 g, 10 mmol) was reacted with 1-(5-fluoro-2-methyl-phenyl)-3-trimethylsilyoxy-2-aza-1,3-butadiene (50 mmol) in toluene to give the title compound as a white solid (160 mg).

m/z (M+H)$^+$: 591

Example 50a

Preparation of Racemic (2'S,3S,4'R)-6-chloro-4'-[5-chloro-2-(2-tert-butoxycarbonylamino-ethoxy)-phenyl]-2'-(5-fluoro-2-methyl-phenyl)spiro[3H-indole-3,3'-piperidine]-2,6'(1H)-dione

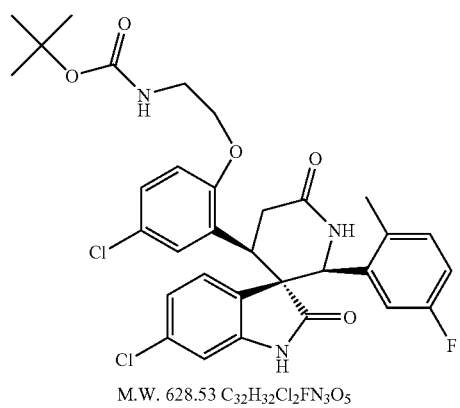

M.W. 628.53 $C_{32}H_{32}Cl_2FN_3O_5$

In a manner similar to the method described in Example 1e, E/Z-3-[2-(2-tert-butoxycarbonylamino-ethoxy)-5-chlorobenzylidene]-6-chloro-2-oxo-2,3-dihydro-indole-1-carboxylic acid tert-butyl ester (8 g, 14.6 mmol) prepared in Example 32d was reacted with 1-(5-fluoro-2-methyl-phenyl)-3-trimethylsilyoxy-2-aza-1,3-butadiene (43.8 mmol) in toluene (22 mL) to give the title compound as a white solid (830 mg).

m/z (M+H)+: 628

Example 50b

Preparation of Chiral (2'S,3S,4'R)-6-chloro-4'-[5-chloro-2-(2-tert-butoxycarbonylamino-ethoxy)-phenyl]-2'-(5-fluoro-2-methyl phenyl)spiro[3H-indole-3,3'-piperidine]-2,6'(1H)-dione

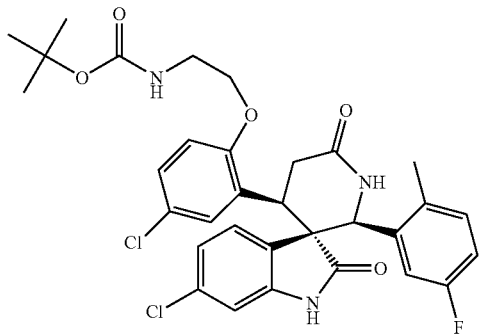

M.W. 628.53 C32H32Cl2FN3O5

Separation of the two enantiomers from racemic (2'S,3S,4'R)-6-chloro-4'-[5-chloro-2-(2-tert-butoxycarbonylamino-ethoxy)-phenyl]-2'-(5-fluoro-2-methyl phenyl)spiro[3H-indole-3,3'-piperidine]-2,6'(1H)-dione (40 mg), was conducted by chiral SFC to provide chiral (2'S,3S,4'R)-6-chloro-4'-[5-chloro-2-(2-tert-butoxycarbonylamino-ethoxy)-phenyl]-2'-(5-fluoro-2-methyl phenyl)spiro[3H-indole-3,3'-piperidine]-2,6'(1H)-dione as a white solid (RO5252565-000, 13 mg) and chiral (2'R,3R,4'S)-6-chloro-4'-[5-chloro-2-(2-tert-butoxycarbonylamino-ethoxy)-phenyl]-2'-(5-fluoro-2-methyl phenyl)spiro[3H-indole-3,3'-piperidine]-2,6'(1H)-dione as a white solid (RO5252566-000, 10 mg).

m/z (M+H)+: 628

Example 51

Preparation of Racemic (2'S,3S,4'R)-6-chloro-4'-{5-chloro-2-[(2-cyclobutanecarbonyl-amino)-ethoxy]-phenyl}-2'-(5-fluoro-2-methyl-phenyl)spiro[3H-indole-3,3'-piperidine]-2,6'(1H)-dione

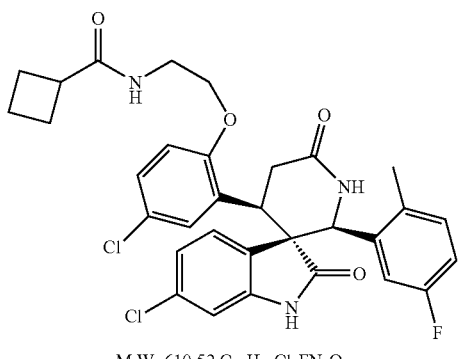

M.W. 610.52 C32H30Cl2FN3O4

At room temperature, a mixture of racemic (2'S,3S,4'R)-4'-[2-(2-amino-ethoxy)5-chloro-phenyl]-6-chloro-2'-(5-fluoro-2-methyl phenyl)spiro[3H-indole-3,3'-piperidine]-2,6'(1H)-dione (100 mg, 0.189 mmol) prepared in Example 32e, cyclobutanecarboxylic acid (98 mg, 0.948 mmol), EDC.HCl (181 mg, 0.948 mmol), HOBt (128 mg, 0.948 mmol) and DIPEA (245 mg, 1.897 mmol) in anhydrous DMF (4 mL) was stirred overnight. Then the mixture was filtered and the filtrate was concentrated. The residue was purified by Prep-HPLC to give the title compound as a white solid (19 mg).

m/z (M+H)+: 610

Example 52a

Preparation of Intermediate toluene-4-sulfonic acid 1-cyano-cyclopropylmethyl ester

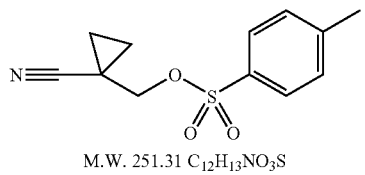

M.W. 251.31 C12H13NO3S

At 0° C., to a solution of 1-hydroxymethyl-cyclopropanecarbonitrile (3.7 g, 38 mmol) in CH2Cl2 (40 mL) was added pyridine (3.62 g, 45.8 mmol) and p-toluenesulfonyl chloride (7.27 g, 38 mmol). After stirred for 3 h, the solution was concentrated and the residue was used for next step reaction without further purification.

Example 52b

Preparation of Intermediate 1-(4-chloro-2-formyl-phenoxymethyl)-cyclopropanecarbonitrile

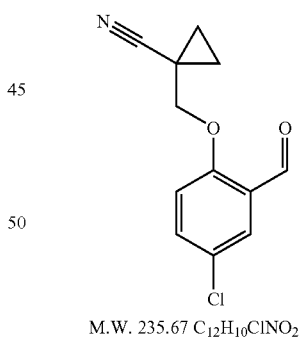

M.W. 235.67 C12H10ClNO2

To a solution of the crude toluene-4-sulfonic acid 1-cyano-cyclopropylmethyl ester in DMF (30 mL) was added 5-chloro-2-hydroxy-benzaldehyde (5.9 g, 38 mmol) and K2CO3 (10.5 g, 76 mmol) slowly. The reaction mixture was placed in a sealed tube and irradiated by microwave reactor at 75° C. for 30 min. After cooled to room temperature, the mixture was poured into water. The solution was diluted with EtOAc (200 mL), washed with water, dried and concentrated to give the title compound as a black oil (4.76 g). The oil was used for next step reaction directly without further purification.

Example 52c

Preparation of Intermediate E/Z-1-[4-Chloro-2-(6-chloro-2-oxo-1,2-dihydro-indol-3-ylidenemethyl)-phenoxymethyl]-cyclopropanecarbonitrile

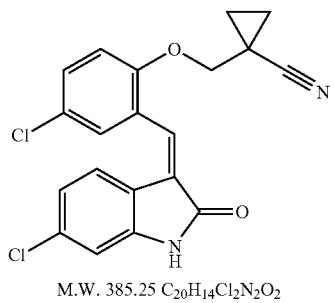

M.W. 385.25 $C_{20}H_{14}Cl_2N_2O_2$

In a manner similar to the method described in Example 1b, 1-(4-chloro-2-formyl-phenoxymethyl)-cyclopentanecarbonitrile (4.7 g, 20 mmol) was reacted with 6-chlorooxindole (2.78 g, 16.67 mmol) and pyrrolidine (1.54 g, 21.67 mmol) in methanol to give the title compound as a yellow solid (3.43 g).

Example 52d

Preparation of Intermediate E/Z-6-chloro-3-[5-chloro-2-(1-cyano-cyclopropylmethoxy)-benzylidene]-2-oxo-2,3-dihydro-indole-1-carboxylic acid tert-butyl ester

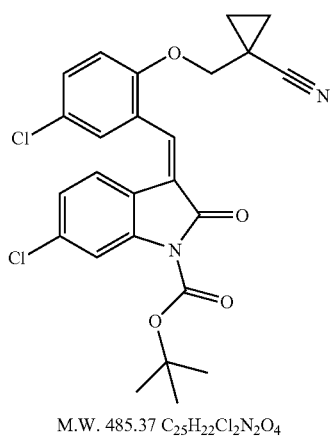

M.W. 485.37 $C_{25}H_{22}Cl_2N_2O_4$

In a manner similar to the method described in Example 1c, E/Z-1-[4-chloro-2-(6-chloro-2-oxo-1,2-dihydro-indol-3-ylidenemethyl)-phenoxymethyl]-cyclopropanecarbonitrile (3.43 g, 8.93 mmol) was reacted with di-tert-butyl-dicarbonate (4.68 g, 21.44 mmol) and 4-dimethylaminopyridine (0.109 g, 0.893 mmol) in $CH_2Cl_2$ to give the title compound as a red oil (4 g).

Example 52e

Preparation of Intermediate racemic (2'S,3S,4'R)-6-chloro-4'-[5-chloro-2-(2-cyano-2-cyclopropyl-methoxy)-phenyl]-2'-(5-fluoro-2-methyl-phenyl)spiro[3H-indole-3,3'-piperidine]-2,6'(1H)-dione

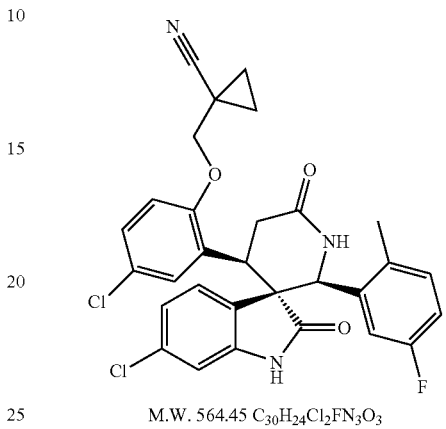

M.W. 564.45 $C_{30}H_{24}Cl_2FN_3O_3$

In a manner similar to the method described in Example 1e, E/Z-6-chloro-3-[5-chloro-2-(1-cyano-cyclopropyl-methoxy)-benzylidene]-2-oxo-2,3-dihydro-indole-1-carboxylic acid tert-butyl ester (4 g, 8.25 mmol) was reacted with 1-(5-fluoro-2-methyl-phenyl)-3-trimethylsilyoxy-2-aza-1,3-butadiene (40 mmol) in toluene (40 mL) and then trifluoroacetic acid (10 mL) in dichloromethane (30 mL) to give the title compound as a white solid (60 mg).

m/z (M+H)$^+$: 564

Example 52f

Preparation of Chiral (2'S,3S,4'R)-6-chloro-4'-[5-chloro-2-(2-cyano-2-cyclopropyl-methoxy)-phenyl]-2'-(5-fluoro-2-methyl-phenyl)spiro[3H-indole-3,3'-piperidine]-2,6'(1H)-dione

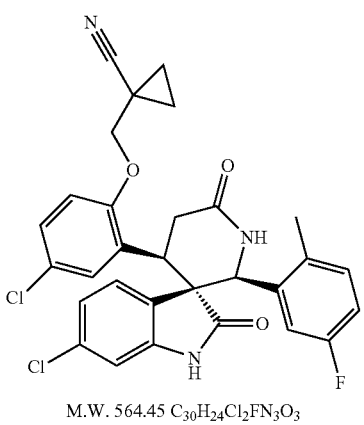

M.W. 564.45 $C_{30}H_{24}Cl_2FN_3O_3$

Separation of the two enantiomers from racemic (2'S,3S,4'R)-6-chloro-4'-[5-chloro-2-(2-cyano-2-cyclopropyl-methoxy)-phenyl]-2'-(5-fluoro-2-methyl-phenyl)spiro[3H-indole-3,3'-piperidine]-2,6'(1H)-dione (40 mg) was conducted by chiral SFC to provide chiral (2'S,3S,4'R)-6-chloro-4'-[5-chloro-2-(2-cyano-2-cyclopropyl-methoxy)-phenyl]-2'-(5-fluoro-2-methyl-phenyl)spiro[3H-indole-3,3'-piperidine]-2,6'(1H)-dione as a white solid (9 mg) (RO5259160-000) and chiral (2'R,3R,4'S)-6-chloro-4'-[5-chloro-2-(2-cyano-2-cyclopropyl-methoxy)-phenyl]-2'-(5-fluoro-2-methyl-phenyl)spiro[3H-indole-3,3'-piperidine]-2,6'(1H)-dione as a white solid (5 mg).

m/z (M+H)$^+$: 564

Example 53a

Preparation of Intermediate toluene-4-sulfonic acid 1-cyano-cyclopentylmethyl ester

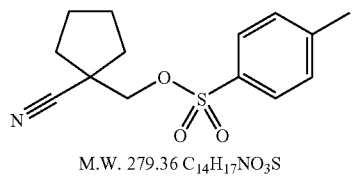

M.W. 279.36 C$_{14}$H$_{17}$NO$_3$S

At 0° C., to a solution of 1-hydroxymethyl-cyclopentanecarbonitrile (10 g, 79.9 mmol) in CH$_2$Cl$_2$ (100 mL) was added pyridine (6.3 g, 79.9 mmol) and p-toluenesulfonyl chloride (12.18 g, 63.9 mmol). After stirred for 3 h, the solution was concentrated and the residue was used for next step reaction without further purification.

Example 53b

Preparation of Intermediate 1-(4-chloro-2-formyl-phenoxymethyl)-cyclopentanecarbonitrile

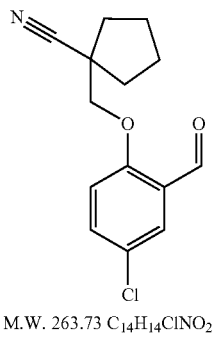

M.W. 263.73 C$_{14}$H$_{14}$ClNO$_2$

To a solution of the crude toluene-4-sulfonic acid 1-cyano-cyclopentylmethyl ester in DMF (70 mL) was added 5-chloro-2-hydroxy-benzaldehyde (12.48 g, 80 mmol) and K$_2$CO$_3$ (13.25 g, 96 mmol). After heated at 100° C. for 3 h, the reaction mixture was poured into water. The solution was diluted with EtOAc (200 mL), washed with water, dried and concentrated to give the title compound as a yellow oil (17.4 g). The oil was used for next step reaction directly without further purification.

Example 53c

Preparation of E/Z-1-[4-chloro-2-(6-chloro-2-oxo-1,2-dihydro-indol-3-ylidenemethyl)-phenoxymethyl]-cyclopentanecarbonitrile

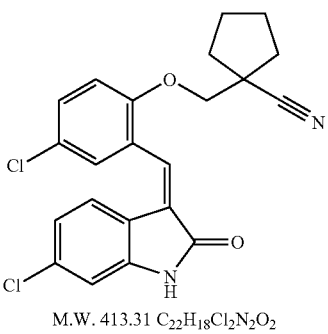

M.W. 413.31 C$_{22}$H$_{18}$Cl$_2$N$_2$O$_2$

In a manner similar to the method described in Example 1b, 1-(4-chloro-2-formyl-phenoxymethyl)-cyclopentanecarbonitrile (17.4 g, 66 mmol) was reacted with 6-chlorooxindole (8.5 g, 51 mmol) and pyrrolidine (4.69 g, 66 mmol) in methanol to give the title compound as a yellow solid (19 g).

Example 53d

Preparation of Intermediate E/Z-6-chloro-3-[5-chloro-2-(1-cyano-cyclopentylmethoxy)-benzylidene]-2-oxo-2,3-dihydro-indole-1-carboxylic acid tert-butyl ester

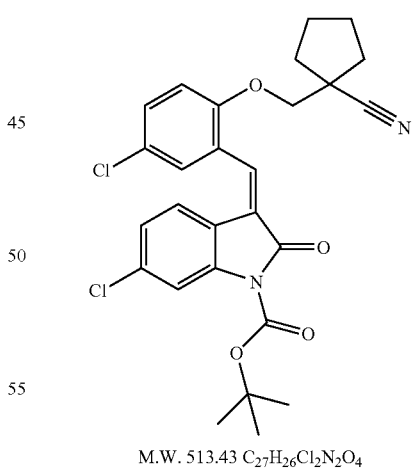

M.W. 513.43 C$_{27}$H$_{26}$Cl$_2$N$_2$O$_4$

In a manner similar to the method described in Example 1c, E/Z-1-[4-chloro-2-(6-chloro-2-oxo-1,2-dihydro-indol-3-ylidenemethyl)-phenoxymethyl]-cyclopentanecarbonitrile (19 g, 46 mmol) was reacted with di-tert-butyl-dicarbonate (15 g, 69 mmol) and 4-dimethylaminopyridine (0.56 g, 4.6 mmol) in CH$_2$Cl$_2$ to give the title compound as a yellow oil (14 g).

Example 53e

Preparation of Intermediate racemic (2'S,3S,4'R)-6-chloro-4'-[5-chloro-2-(1-cyano-cyclopentyl-methoxy)-phenyl]-2'-(5-fluoro-2-methyl-phenyl)-2,3-dihydro-2,6'-dioxo spiro[indole-3,3'-piperidine]-1-carboxylic acid tert-butyl ester

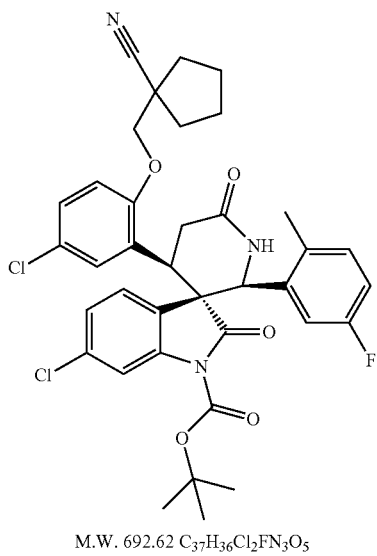

M.W. 692.62 $C_{37}H_{36}Cl_2FN_3O_5$

To a solution of 1-(5-fluoro-2-methyl-phenyl)-3-trimethylsilyoxy-2-aza-1,3-butadiene (30 mmol) in toluene (30 mL) was added E/Z-6-Chloro-3-[5-chloro-2-(1-cyano-cyclopentylmethoxy)-benzylidene]-2-oxo-2,3-dihydro-indole-1-carboxylic acid tert-butyl ester (6 g, 11.7 mmol). Then the reaction mixture were heated at 70° C. overnight. After the solution was cooled to room temperature, methanol was added. The solution was concentrated and the residue was purified by flash column to give the title compound as a white solid (500 mg).

m/z (M+H)$^+$: 692

Example 53f

Preparation of Racemic (2'S,3S,4'R)-6-chloro-4'-[5-chloro-2-(1-cyano-cyclopentyl-methoxy)-phenyl]-2'-(5-fluoro-2-methyl-phenyl)spiro[3H-indole-3,3'-piperidine]-2,6'(1H)-dione

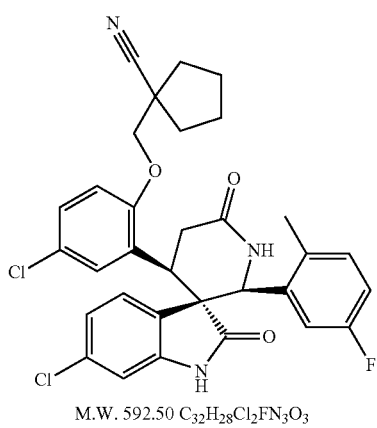

M.W. 592.50 $C_{32}H_{28}Cl_2FN_3O_3$ racemic (2'S,3S,4'R)-6-chloro-4'-[5-chloro-2-(1-cyano-cyclopentyl-methoxy)-phenyl]-2'-(5-fluoro-2-methyl-phenyl)-2,3-dihydro-2,6'-dioxo spiro[indole-3,3'-piperidine]-1-carboxylic acid tert-butyl ester (100 mg) was dissolved in trifluoroacetic acid (5 mL). After stirred at room temperature for 0.5 h, the reaction mixture was concentrated and the residue was purified by recrystallization to give the title compound as a yellow solid (38 mg).

m/z (M+H)$^+$: 592

Example 54a

Preparation of Intermediate 4-Chloro-2-[1,3]dioxolan-2-yl-phenol

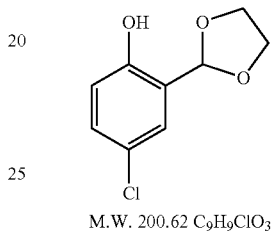

M.W. 200.62 $C_9H_9ClO_3$

A mixture of 5-chloro-2-hydroxybenzaldehyde (20.0 g, 0.128 mol), ethane-1,2-diol (40.0 g, 0.644 mol) and p-toluenesulfonic acid monohydrate (0.44 g, 2.56 mmol) dissolved in toluene (200 mL) was refluxed for 40 h with a dean-stark to remove water. After the reaction mixture was cooled to room temperature, EtOAc (200 mL) was added. Then the organic phase was washed with saturated NaHCO$_3$ solution, dried over anhydrous Na$_2$SO$_4$ and concentrated to give the title compound as a light-yellow solid (24.6 g).

Example 54b

Preparation of Intermediate (4-Chloro-2-[1,3]dioxolan-2-yl-phenoxy)-acetonitrile

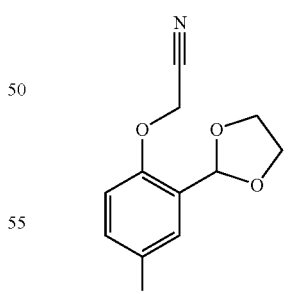

M.W. 239.66 $C_{11}H_{10}ClNO_3$

At room temperature, 2-chloroacetonitrile (12 g, 0.16 mol) was added into a mixture of 4-chloro-2-[1,3]dioxolan-2-yl-phenol (24.6 g, 0.123 mol) and K$_2$CO$_3$ (34 g, 0.246 mol) in DMF (150 mL). After the reaction mixture was heated at 100° C. for 3 h and cooled to room temperature, water was added. The aqueous phase was extracted with EtOAc twice, washed with saturated K₂CO₃ solution, water, and dried over anhydrous Na₂SO₄ to give crude (4-Chloro-2-[1,3]dioxolan-2-yl-phenoxy)-acetonitrile. The crude product was used for next step without further purification.

Example 54c

Preparation of Intermediate (4-chloro-2-formyl-phenoxy)-acetonitrile

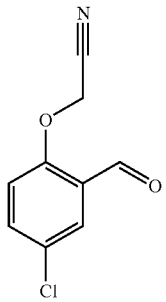

M.W. 195.61 C₉H₆ClNO₂.

At room temperature, a mixture of (4-chloro-2-[1,3]dioxolan-2-yl-phenoxy)-acetonitrile (28.68 g, 0.12 mol) and trifluoroacetic acid (41.04 g, 0.36 mol) in EtOAc (500 mL) was stirred overnight. Then the solution was washed with water, saturated NaHCO₃ solution twice, dried over anhydrous Na₂SO₄, and concentrated to give crude product (22 g). The crude product was directly used for next step without further purification.

Example 54d

Preparation of Intermediate E/Z-[4-chloro-2-(6-chloro-2-oxo-1,2-dihydro-indol-3-ylidenemethyl)-phenoxy]-acetonitrile

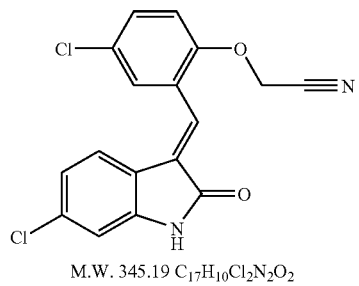

M.W. 345.19 C₁₇H₁₀Cl₂N₂O₂

To the mixture of 6-chlorooxindole (18.4 g, 0.110 mol) and (4-chloro-2-formyl-phenoxy)-acetonitrile (21.5 g, 0.110 mol) in methanol (200 mL) was added pyrrolidine (8.60 g, 0.121 mol) dropwise. Then the mixture was heated at 70° C. for 2 h. After cooled to room temperature, the mixture was filtered. The precipitate was collected and dried to give the title compound as a yellow solid (8.5 g).

Example 54e

Preparation of Intermediate E/Z-6-chloro-3-(5-chloro-2-cyanomethoxy-benzylidene)-2-oxo-2,3-dihydro-indole-1-carboxylic acid tert-butyl ester

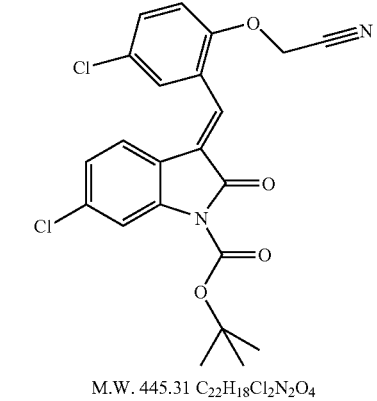

M.W. 445.31 C₂₂H₁₈Cl₂N₂O₄

To a solution of E/Z-[4-Chloro-2-(6-chloro-2-oxo-1,2-dihydro-indol-3-ylidenemethyl)-phenoxy]-acetonitrile (8.10 g, 23.46 mmol) in dichloromethane (100 mL) at room temperature was added di-tert-butyl-dicarbonate (6.15 g, 28.16 mmol), followed by the addition of 4-dimethylaminopyridine (0.86 g, 7.037 mmol). After the reaction mixture was stirred at room temperature for 2 h, the solution was washed with HCl aq. (0.5 M) and brine twice, dried over anhydrous Na₂SO₄ and concentrated to give the title compound as a red solid (8.70 g).

Example 54f

Preparation of Racemic (2'S,3S,4'R)-6-chloro-4'-[5-chloro-2-cyanomethoxy-phenyl]-2'-(5-fluoro-2-methyl-phenyl)spiro[3H-indole-3,3'-piperidine]-2,6' (1H)-dione

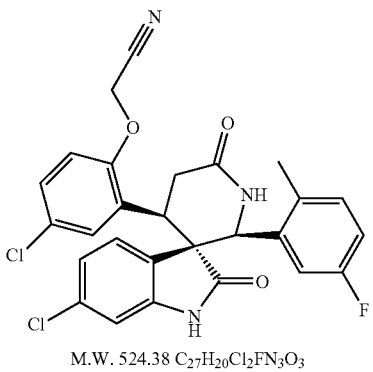

M.W. 524.38 C₂₇H₂₀Cl₂FN₃O₃

In a manner similar to the method described in Example 10d, E/Z-6-chloro-3-(5-chloro-2-cyanomethoxy-benzylidene)-2-oxo-2,3-dihydro-indole-1-carboxylic acid tert-butyl ester (5 g, 11 mmol) was reacted with 1-(5-fluoro-2-methyl-phenyl)-3-trimethylsilyoxy-2-aza-1,3-butadiene (44 mmol) in toluene to give the title compound as a white solid (100 mg).

m/z (M+H)⁺: 524

Example 54g

Preparation of Chiral (2'S,3S,4'R)-6-chloro-4'-[5-chloro-2-cyanomethoxy-phenyl]-2'-(5-fluoro-2-methyl-phenyl)spiro[3H-indole-3,3'-piperidine]-2,6'(1H)-dione

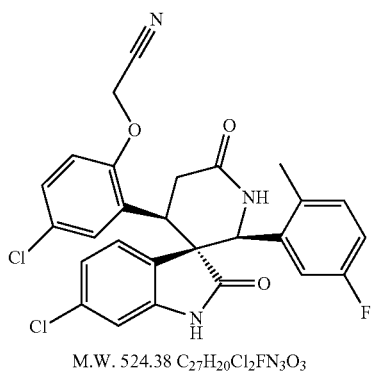

M.W. 524.38 C$_{27}$H$_{20}$Cl$_2$FN$_3$O$_3$

Separation of the two enantiomers from racemic (2'S,3S,4'R)-6-chloro-4'-[5-chloro-2-cyanomethoxy-phenyl]-2'-(5-fluoro-2-methyl-phenyl)spiro[3H-indole-3,3'-piperidine]-2,6'(1H)-dione (70 mg), was conducted by chiral SFC to provide chiral (2'S,3S,4'R)-6-chloro-4'-[5-chloro-2-cyanomethoxy-phenyl]-2'-(5-fluoro-2-methyl-phenyl)spiro[3H-indole-3,3'-piperidine]-2,6'(1H)-dione as a white solid (18 mg) (RO5259573-000) and chiral (2'R,3R,4'S)-6-chloro-4'-[5-chloro-2-cyanomethoxy-phenyl]-2'-(5-fluoro-2-methyl-phenyl)spiro[3H-indole-3,3'-piperidine]-2,6'(1H)-dione as a white solid (30 mg) (RO5259574-000)
m/z (M+H)$^+$: 524

Example 55a

Preparation of Intermediate 4-(4-chloro-2-formyl-phenyl)-piperazine-1-carboxylic acid tert-butyl ester

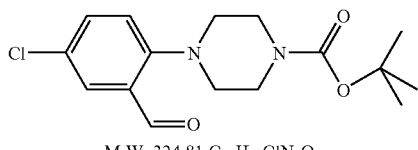

M.W. 324.81 C$_{16}$H$_{21}$ClN$_2$O$_3$

A mixture of 5-chloro-2-fluoro-benzaldehyde (10 g, 63 mmol), Piperazine-1-carboxylic acid tert-butyl ester (12 g, 63 mmol), K$_2$CO$_3$ (17 g, 123 mmol) in DMF (60 mL) was heated at 150° C. for 2 h. After cooled to room temperature, the mixture was poured into water (300 mL) and partitioned between diethyl ether and water. The combined organic phases were washed with water, dried over anhydrous Na$_2$SO$_4$ and concentrated. The residue was purified by flash column to give the title compound as a yellow solid (9 g).

Example 55b

Preparation of Intermediate E/Z-4-[4-chloro-2-(6-chloro-2-oxo-1,2-dihydro-indol-3-ylidenemethyl)-phenyl]-piperazine-1-carboxylic acid tert-butyl ester

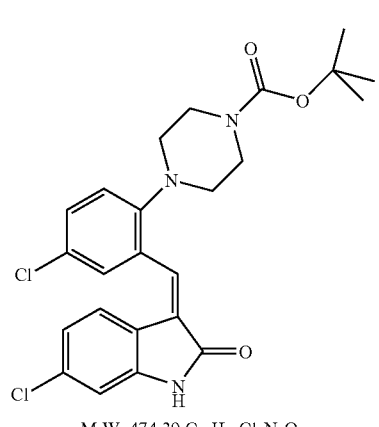

M.W. 474.39 C$_{24}$H$_{25}$Cl$_2$N$_3$O$_3$

In a manner similar to the method described in Example 1b, 4-(4-chloro-2-formyl-phenyl)-piperazine-1-carboxylic acid tert-butyl ester (8 g, 25 mmol) was reacted with 6-chlorooxindole (4.1 g, 25 mmol) and pyrrolidine (1.8 g, 25 mmol) in methanol (50 mL) to give the title compound as a yellow solid (11 g).

Example 55c

Preparation of Intermediate E/Z-3-[2-(4-tert-butoxy-carbonyl-piperazin-1-yl)-5-chloro-benzylidene]-6-chloro-2-oxo-2,3-dihydro-indole-1-carboxylic acid tert-butyl ester

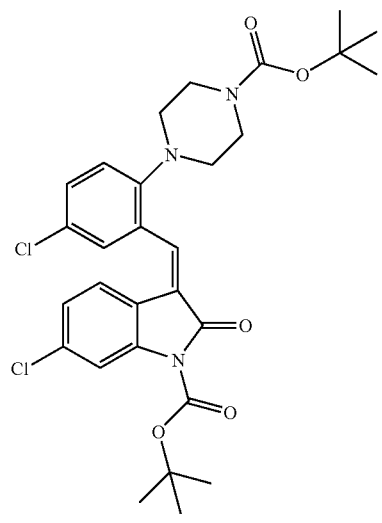

M.W. 574.51 C$_{29}$H$_{33}$Cl$_2$N$_3$O$_5$

At room temperature, to a solution of E/Z-4-[4-chloro-2-(6-chloro-2-oxo-1,2-dihydro-indol-3-ylidenemethyl)-phenyl]-piperazine-1-carboxylic acid tert-butyl ester (11 g, 23 mmol) in dichloromethane (100 mL) added di-tert-butyl-dicarbonate (5.6 g, 25 mmol), followed by the addition of 4-dimethylaminopyridine (2 g, 16 mmol). After stirred for 1 h, the mixture was washed by 1 N HCl solution twice, dried over anhydrous $Na_2SO_4$ and concentrated. The residue was purified by flash column to give the title compound as a yellow solid (8 g).

Example 55d

Preparation of Racemic (2'S,3S,4'R)-4'-[2-(4-tert-butoxycarbonyl-piperazin-1-yl)-5-chloro-phenyl]-6-chloro-2'-(5-fluoro-2-methyl-phenyl)spiro[3H-indole-3,3'-piperidine]-2,6'(1H)-dione

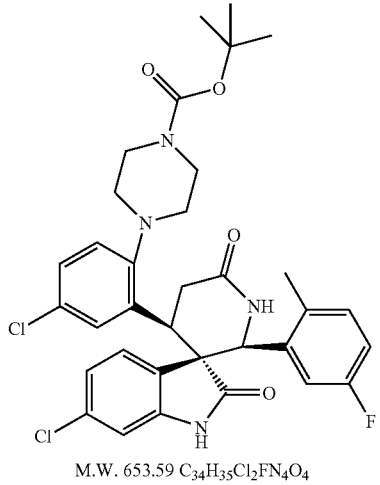

M.W. 653.59 $C_{34}H_{35}Cl_2FN_4O_4$

In a manner similar to the method described in Example 1e, E/Z-3-[2-(4-tert-butoxycarbonyl-piperazin-1-yl)-5-chloro-benzylidene]-6-chloro-2-oxo-2,3-dihydro-indole-1-carboxylic acid tert-butyl ester (3 g, 5.2 mmol) was reacted with 1-(5-fluoro-2-methyl-phenyl)-3-trimethylsilyoxy-2-aza-1,3-butadiene (14 mmol) in toluene to give the title compound as a white solid (600 mg).
m/z $(M+H)^+$: 653

Example 55e

Preparation of Racemic (2'S,3S,4'R)-6-chloro-4'-[5-chloro-2-(piperazin-1-yl)-phenyl]-2'-(5-fluoro-2-methyl phenyl)spiro[3H-indole-3,3'-piperidine]-2,6'(1H)-dione

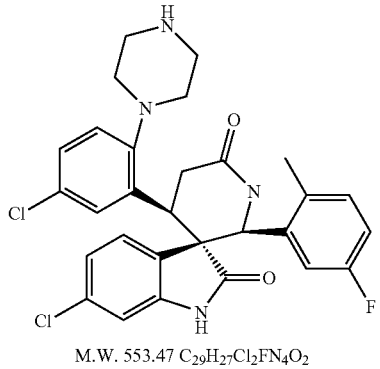

M.W. 553.47 $C_{29}H_{27}Cl_2FN_4O_2$

At room temperature, trifluoroacetic acid (2 mL) was added into a solution of racemic (2'S,3S,4'R)-4'-[2-(4-tert-butoxycarbonyl-piperazin-1-yl)-5-chloro-phenyl]-6-chloro-2'-(5-fluoro-2-methyl-phenyl)spiro[3H-indole-3,3'-piperidine]-2,6'(1H)-dione (280 mg, 0.43 mmol) in DCM (10 mL). After stirred for 2 h, the mixture was concentrated. The residue was dissolved in EtOAc, washed with 1 N NaOH and water, dried over anhydrous $Na_2SO_4$ and concentrated to give the title compound as a light yellow solid (230 mg).

Example 55f

Preparation of Racemic (2'S,3S,4'R)-4'-[2-(4-acetyl-piperazin-1-yl)-5-chloro-phenyl]-6-chloro-2'-(5-fluoro-2-methyl phenyl)spiro[3H-indole-3,3'-piperidine]-2,6'(1H)-dione

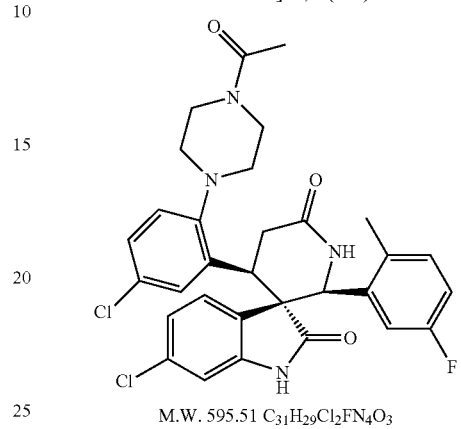

M.W. 595.51 $C_{31}H_{29}Cl_2FN_4O_3$

At room temperature, to a solution of racemic (2'S,3S,4'R)-6-chloro-4'-[5-chloro-2-(piperazin-1-yl)-phenyl]-2'-(5-fluoro-2-methyl phenyl)spiro[3H-indole-3,3'-piperidine]-2,6'(1H)-dione (30 mg, 0.054 mmol) in THF was added acetic anhydride (6 mg, 0.06 mmol). After stirred for 1 h, the mixture was concentrated and the residue was purified by Prep-HPLC to give the title compound as a white solid (10 mg).
m/z $(M+H)^+$: 595

Example 56

Preparation of Racemic (2'S,3S,4'R)-6-chloro-4'-{5-chloro-2-[4-(2-hydroxy-ethyl)-piperazin-1-yl]-phenyl}-2'-(5-fluoro-2-methyl-phenyl)spiro[3H-indole-3,3'-piperidine]-2,6'(1H)-dione

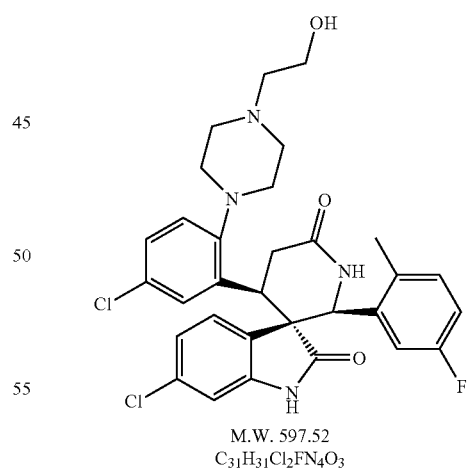

M.W. 597.52
$C_{31}H_{31}Cl_2FN_4O_3$

A mixture of racemic (2'S,3S,4'R)-6-chloro-4'-[5-chloro-2-(piperazin-1-yl)-phenyl]-2'-(5-fluoro-2-methyl-phenyl)spiro[3H-indole-3,3'-piperidine]-2,6'(1H)-dione (50 mg, 0.09 mmol), 2-Iodo-ethanol (155 mg, 0.9 mmol) and $Et_3N$ (18 mg, 0.18 mmol) in acetone (1 mL) was heated at 80° C. for 1 h. Then the mixture was concentrated and the residue was purified by Prep-HPLC to give the title compound as a white solid (26 mg).
m/z $(M+H)^+$: 597

Example 57

Preparation of Chiral (2'S,3S,4'R)-6-chloro-4'-[5-chloro-2-(2-cyclopropanesulfonylamino-1,1-dimethyl-2-oxo-ethoxy)-phenyl]-2'-(5-fluoro-2-methyl-phenyl)-spiro[3H-indole-3,3'-piperidine]-2,6'(1H)-dione

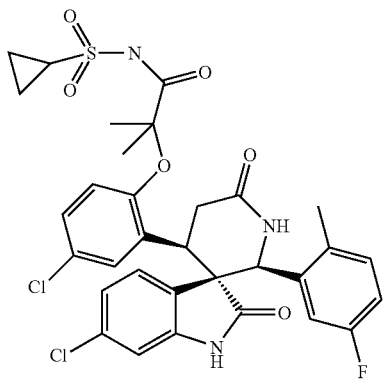

M.W 674.58
$C_{32}H_{30}Cl_2FN_3O_6S$

A solution of chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (45 mg, 0.079 mmol) prepared in Example 12a and CDI (26 mg, 0.16 mmol) in DMF (0.5 mL) was heated at 60° C. for 2 h. Then to this solution was added a mixture of cyclopropanesulfonamide (48 mg, 0.4 mmol) and NaH (13 mg, 60%, 0.3 mmol) in DMF (1 mL), which had been stirred for 1 h at room temperature. After the resulting mixture was stirred at room temperature for 1 h, it was poured into water (5 mL) and the aqueous solution was acidified to "PH" 2-3 by addition of concentrated hydrochloride solution. After the aqueous phase was extracted with EtOAc twice, the combined extracts were dried over anhydrous $Na_2SO_4$, concentrated and the residue was purified by flash column to give the title compound as a white solid (38 mg).

m/z (M+H)$^+$: 674

Example 58

Preparation of Chiral (2'S,3S,4'R)-6-chloro-4'-[5-chloro-2-(2-trifluoro-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione

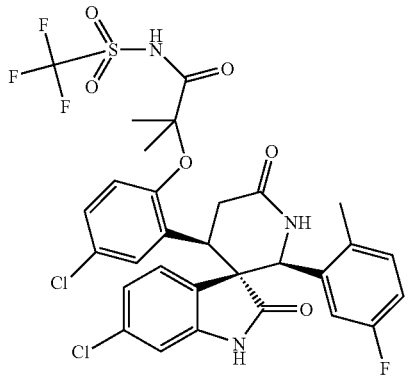

M.W 702.51
$C_{30}H_{25}Cl_2F_4N_3O_6S$

A solution of chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (120 mg, 0.21 mmol) prepared in Example 12a and CDI (68 mg, 0.42 mmol) in DMF (5 mL) was heated at 65° C. for 2 h. Then to this solution was added a mixture of trifluoromethanesulfonamide (314 mg, 2.10 mmol) and NaH (84 mg, 60%, 2.10 mmol) in DMF (5 mL), which had been stirred for 2 h at room temperature. After the resulting mixture was stirred at room temperature for 2 h, it was poured into water and the aqueous phase was acidified to "PH" 2-3 by addition of concentrated hydrochloric acid. After the aqueous phase was extracted with EtOAc twice, the combined organic phases were dried over anhydrous $Na_2SO_4$, concentrated and the residue was purified by Prep-HPLC to give the title compound as a yellow solid (14 mg).

m/z (M+H)$^+$: 702

Example 59a

Preparation of Intermediate 1-(2,3-difluoro-6-methyl-phenyl)-3-trimethylsilyoxy-2-aza-1,3-butadiene

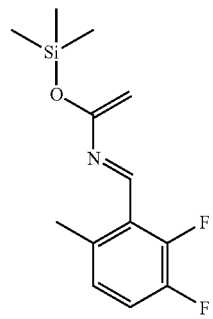

M.W. 269.37
$C_{13}H_{17}F_2NOSi$

To dry tetrahydrofuran (15 mL) was added 1M THF solution of LiHMDS (24.7 mmol, 24.7 mL) under Ar protection at room temperature, followed by the addition of 5,6-Difluoro-2-methyl-benzaldehyde (3.86 g, 24.7 mmol). After the mixture was stirred at room temperature for 1 h, trimethylsilyl chloride (3.1 mL, 24.7 mmol) was added dropwise. Then the temperature of the mixture was lowered to 0° C. on a cooling ice bath. To this mixture was added triethylamine (4.47 mL, 32 mmol) in one portion, followed by the dropwise addition of a solution of acetyl chloride (2.35 mL, 32 mmol) in diethyl ether (30 mL). The cooling bath was removed, and the mixture was stirred at room temperature for 4 h. The mixture was quickly filtered on celite under nitrogen, and filtrate was concentrated under reduced pressure to give crude 1-(2,3-difluoro-6-methyl-phenyl)-3-trimethylsilyoxy-2-aza-1,3-butadiene as a yellow gum and used for the next step without further purification.

Example 59b

Preparation of Intermediate racemic (2'R,3S,4'R)-6-chloro-4'-[5-chloro-2-(1-methoxycarbonyl-1-methyl-ethoxy)-phenyl]-2'-(2,3-difluoro-6-methyl-phenyl)spiro[3H-indole-3,3'-piperidine]-2,6'(1H)-dione

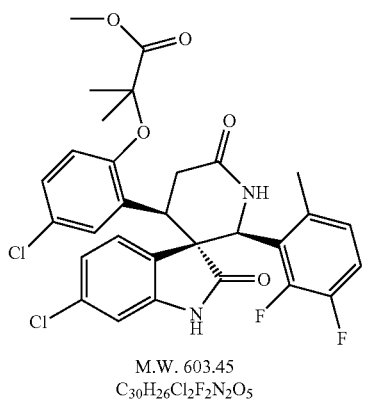

M.W. 603.45
$C_{30}H_{26}Cl_2F_2N_2O_5$

In a manner similar to the method described in Example 1e, E/Z-6-chloro-3-[5-chloro-2-(1-methoxycarbonyl-1-methyl-ethoxy)-benzylidene]-2-oxo-2,3-dihydro-indole-1-carboxylic acid tert-butyl ester (3 g, 5.94 mmol) was reacted with 1-(2,3-difluoro-6-methyl-phenyl)-3-trimethylsilyoxy-2-aza-1,3-butadiene (18 mmol) in toluene to give the title compound as a white solid (510 mg).

m/z (M+H)$^+$: 603

Example 59c

Preparation of Intermediate racemic (2'R,3S,4'R)-6-chloro-4'-[5-chloro-2-(1-hydroxycarbonyl-1-methyl-ethoxy)-phenyl]-2'-(2,3-difluoro-6-methyl-phenyl)spiro[3H-indole-3,3'-piperidine]-2,6'(1H)-dione

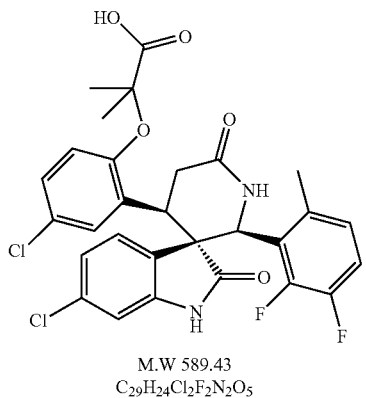

M.W 589.43
$C_{29}H_{24}Cl_2F_2N_2O_5$

A mixture of racemic (2'R,3S,4'R)-6-chloro-4'-[5-chloro-2-(1-methoxycarbonyl-1-methyl-ethoxy)-phenyl]-2'-(2,3-difluoro-6-methyl-phenyl)spiro[3H-indole-3,3'-piperidine]-2,6'(1H)-dione (110 mg, 0.18 mmol), NaOH (15 mg, 0.375 mmol), H$_2$O (2 mL) and methanol (5 mL) was heated at 80° C. for 2 h. After cooled to room temperature, the solution was acidified to "pH" 1-2 by addition of concentrated aqueous HCl solution. The aqueous phase was extracted with EtOAc. The organic layer was separated, washed with water, dried over anhydrous Na$_2$SO$_4$ and concentrated to give the crude product. The crude product was washed with ether twice to give the title compound as a white solid (10 mg).

m/z (M+H)$^+$: 589

Example 59d

Preparation of Racemic (2'R,3S,4'R)-4'-[5-chloro-2-(2-methanesulfonylamino-1,1-dimethyl-2-oxo-ethoxy)-phenyl]-6-chloro-2'-(2,3-difluoro-6-methyl-phenyl)spiro[3H-indole-3,3'-piperidine]-2,6'(1H)-dione

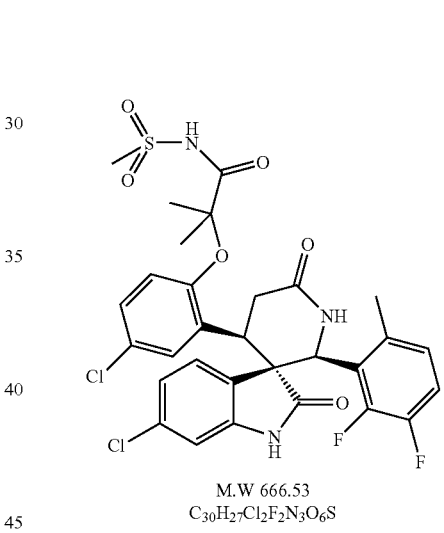

M.W 666.53
$C_{30}H_{27}Cl_2F_2N_3O_6S$

A solution of racemic (2'R,3S,4'R)-6-chloro-4'-[5-chloro-2-(1-hydroxycarbonyl-1-methyl-ethoxy)-phenyl]-2'-(2,3-difluoro-6-methyl-phenyl)spiro[3H-indole-3,3'-piperidine]-2,6'(1H)-dione (30 mg, 0.05 mmol) and CDI (16.2 mg, 0.1 mmol) in DMF (1 mL) was heated at 60° C. for 2 h. Then to this solution was added a mixture of methanesulfonamide (28.5 mg, 0.3 mmol) and NaH (10 mg, 60%, 0.25 mmol) in DMF (0.5 mL), which had been stirred for 2 h at room temperature. After the resulting mixture was stirred at room temperature for 2 h, it was poured into water and the aqueous solution was acidified to "PH" 1-2 by addition of concentrated hydrochloric acid. After the aqueous phase was extracted with EtOAc twice, the combined organic phases were dried over anhydrous Na$_2$SO$_4$, concentrated and the residue was purified by Prep-HPLC to give the title compound (25 mg).

m/z (M+H)$^+$: 666

Example 60a

Preparation of Intermediate racemic (2'S,3S,4'R)-6-chloro-4'-[5-chloro-2-(2-methoxycarbonyl-methoxy)-phenyl]-2'-[5-difluoro-2-methyl-phenyl]spiro[3H-indole-3,3'-piperidine]-2,6'(1H)-dione

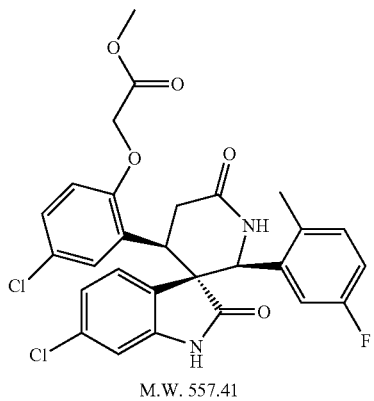

M.W. 557.41
$C_{28}H_{23}Cl_2FN_2O_5$

In a manner similar to the method described in Example 10d, E/Z-6-chloro-3-(5-chloro-2-methoxycarbonylmethoxy-benzylidene)-2-oxo-2,3-dihydro-indole-1-carboxylic acid tert-butyl ester (3 g, 6.2 mmol) was reacted with 1-(5-fluoro-2-methyl-phenyl)-3-trimethylsilyoxy-2-aza-1,3-butadiene (18 mmol) in toluene to give the title compound as a white solid (700 mg).

m/z (M+H)$^+$: 557

Example 60b

Preparation of Intermediate racemic (2'S,3S,4'R)-6-chloro-4'-[5-chloro-2-(2-hydroxycarbonyl-methoxy)-phenyl]-2'-[5-fluoro-2-methyl-phenyl]spiro[3H-indole-3,3'-piperidine]-2,6'(1H)-dione

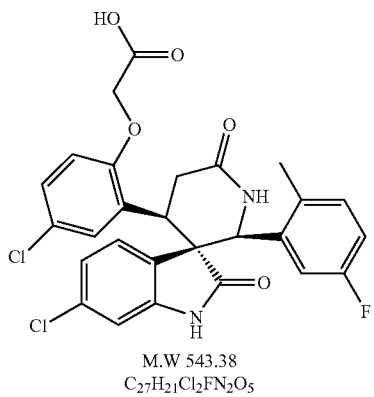

M.W 543.38
$C_{27}H_{21}Cl_2FN_2O_5$

A mixture of racemic (2'S,3S,4'R)-6-chloro-4'-[5-chloro-2-(2-methoxycarbonyl-methoxy)-phenyl]-2'-[5-difluoro-2-methyl-phenyl]spiro[3H-indole-3,3'-piperidine]-2,6'(1H)-dione (300 mg, 0.54 mmol), NaOH (43 mg, 1.07 mmol), H$_2$O (5 mL) and methanol (10 mL) was heated at 80° C. for 2 h. After cooled to room temperature, the solution was acidified to "pH" 1-2 by addition of concentrated HCl solution. The water phase was extracted with EtOAc, washed with water, dried over anhydrous Na$_2$SO$_4$ and concentrated to give the title compound as a white solid (280 mg).

m/z (M+H)$^+$: 543

Example 60c

Preparation of Racemic (2'S,3S,4'R)-6-chloro-4'-[5-chloro-2-(2-methanesulfonylamino-2-oxo-ethoxy)-phenyl]-2'-(5-fluoro-2-methyl-phenyl)spiro[3H-indole-3,3'-piperidine]-2,6'(1H)-dione

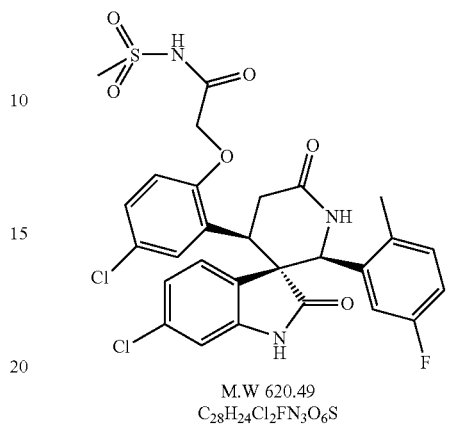

M.W 620.49
$C_{28}H_{24}Cl_2FN_3O_6S$

A solution of racemic (2'S,3S,4'R)-6-chloro-4'-[5-chloro-2-(2-hydroxycarbonyl-methoxy)-phenyl]-2'-[5-fluoro-2-methyl-phenyl]spiro[3H-indole-3,3'-piperidine]-2,6'(1H)-dione (300 mg, 0.55 mmol) and CDI (178 mg, 1.1 mmol) in DMF (5 mL) was heated at 70° C. for 1 h. Then to this solution was added a mixture of methanesulfonamide (313 mg, 3.3 mmol) and NaH (110 mg, 60%, 2.75 mmol) in DMF (3 mL), which had been stirred for 1 h at room temperature. After the resulting mixture was stirred at room temperature for 10 min, it was poured into water and the aqueous solution was acidified to "PH" 2 by addition of concentrated hydrochloric acid. After the aqueous phase was extracted with EtOAc twice, the combined organic extracts were dried over anhydrous Na$_2$SO$_4$, concentrated and the residue was purified by flash column to give the title compound as a white solid (50 mg).

m/z (M+H)$^+$: 620

Example 61a

Preparation of Intermediate 1-(5-chloro-2-methoxy-phenyl)-3-trimethylsilyoxy-2-aza-1,3-butadiene

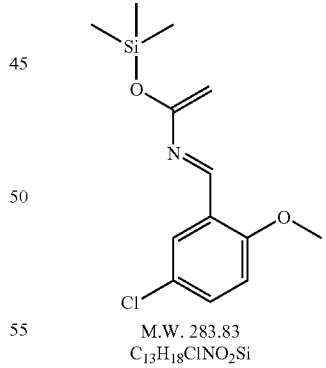

M.W. 283.83
$C_{13}H_{18}ClNO_2Si$

To dry tetrahydrofuran (50 mL) was added 1M THF solution of LiHMDS (45 mmol, 45 mL) under Ar protection at room temperature, followed by the addition of 5-chloro-2-methoxy-benzaldehyde (7.65 g, 45 mmol). After the mixture was stirred at room temperature for 1 h, trimethylsilyl chloride (5.6 mL, 45 mmol) was added dropwise. Then the temperature of the mixture was lowered to 0° C. on a cooling ice bath. To this mixture was added triethylamine (8.1 mL, 58.5 mmol) in one portion, followed by the dropwise addition of a solution of acetyl chloride (4.17 mL, 58.5 mmol) in diethyl ether (200 mL). The cooling bath was removed, and the mixture was stirred at room temperature for 4 h. The mixture was quickly filtered on celite under nitrogen, and filtrate was concentrated under reduced pressure to give crude 1-(5-chloro-2-methoxy-phenyl)-3-trimethylsilyoxy-2-aza-1,3-butadiene as a yellow gum and used for the next step without further purification.

Example 61b

Preparation of Intermediate racemic (2'S,3S,4'R)-6-chloro-4'-[5-chloro-2-(1-ethoxycarbonyl-1-methyl-ethoxy)-phenyl]-2'-(5-chloro-2-methoxy-phenyl) spiro[3H-indole-3,3'-piperidine]-2,6'(1H)-dione

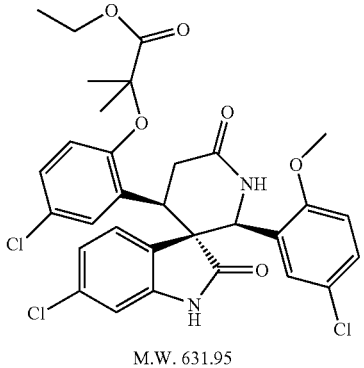

M.W. 631.95
$C_{31}H_{29}Cl_3N_2O_6$

In a manner similar to the method described in Example 10d, E/Z-6-chloro-3-[5-chloro-2-(1-ethoxycarbonyl-1-methyl-ethoxy)-benzylidene]-2-oxo-2,3-dihydro-indole-1-carboxylic acid tert-butyl ester (7 g, 13.5 mmol) was reacted with 1-(5-chloro-2-methoxy-phenyl)-3-trimethylsilyoxy-2-aza-1,3-butadiene (45 mmol) in toluene to give title compound as a white solid (850 mg).
m/z (M+H)⁺: 631

Example 61c

Preparation of Intermediate racemic (2'S,3S,4'R)-6-chloro-4'-[5-chloro-2-(1-hydroxycarbonyl-1-methyl-ethoxy)-phenyl]-2'-(5-chloro-2-methoxy-phenyl) spiro[3H-indole-3,3'-piperidine]-2,6'(1H)-dione

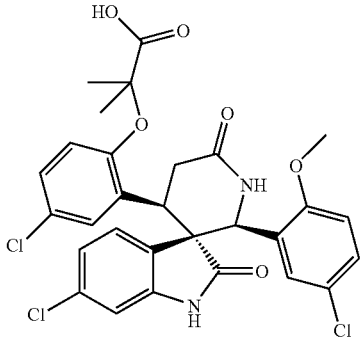

M.W 603.89
$C_{29}H_{25}Cl_3N_2O_6$

A mixture of racemic (2'S,3S,4'R)-6-chloro-4'-[5-chloro-2-(1-ethoxycarbonyl-1-methyl-ethoxy)-phenyl]-2'-(5-chloro-2-methoxy-phenyl)spiro[3H-indole-3,3'-piperidine]-2,6'(1H)-dione (150 mg, 0.24 mmol), NaOH (20 mg, 0.48 mmol), H₂O (3 mL) and THF (10 mL) was heated at 65° C. for 2 h. After cooled to room temperature, the solution was concentrated and the residue was acidified to "pH" 2-3 by addition of concentrated HCl solution. The precipitate was collected and dried to give the title compound as a white solid (100 mg).
m/z (M+H)⁺: 603

Example 61d

Preparation of Racemic (2'S,3S,4'R)-4'-[5-chloro-2-(2-methanesulfonylamino-1,1-dimethyl-2-oxo-ethoxy)-phenyl]-6-chloro-2'-(5-chloro-2-methoxy-phenyl)-spiro[3H-indole-3,3'-piperidine]-2,6'(1H)-dione

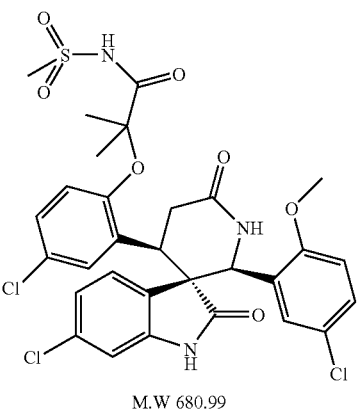

M.W 680.99
$C_{30}H_{28}Cl_3N_3O_7S$

A solution of racemic (2'S,3S,4'R)-6-chloro-4'-[5-chloro-2-(1-hydroxycarbonyl-1-methyl-ethoxy)-phenyl]-2'-(5-chloro-2-methoxy-phenyl)spiro[3H-indole-3,3'-piperidine]-2,6'(1H)-dione (122 mg, 0.2 mmol) and CDI (65 mg, 0.4 mmol) in DMF (5 mL) was heated at 60° C. for 2 h. Then to this solution was added a mixture of methanesulfonamide (144 mg, 1.2 mmol) and NaH (48 mg, 60%, 1.2 mmol) in DMF (5 mL), which had been stirred for 3 h at room temperature. After the resulting mixture was stirred at room temperature for 1 h, it was poured into water (5 mL) and the aqueous solution was acidified to "PH" 2-3 by addition of concentrated hydrochloride acid. After the aqueous phase was extracted with EtOAc twice, the combined organic extracts were dried over anhydrous Na₂SO₄, concentrated and the residue was purified by flash column to give the title compound as a white solid (11 mg).
m/z (M+H)⁺: 680

Example 62a

Preparation of Intermediate 2-(4-chloro-2-formyl-phenoxy)-butyric acid methyl ester

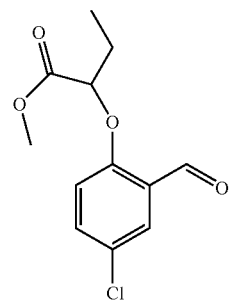

M.W 256.69
$C_{12}H_{13}ClO_4$

A mixture of 5-chloro-2-hydroxy-benzaldehyde (156 g, 1 mol), 2-bromo-butyric acid methyl ester (271 g, 1.5 mol), KI (2 g, 0.012 mol) and K₂CO₃ (276 g, 2 mol) in DMF (500 mL)

was heated at 130° C. for 2 h. After cooled to room temperature, the mixture was concentrated. The residue was partitioned between EtOAc and water. The organic layer was washed with water, brine, dried over anhydrous Na$_2$SO$_4$ and concentrated to give the title compound (240 g).

Example 62b

Preparation of Intermediate of 2-(4-chloro-2-[1,3]dioxolan-2-yl-phenoxy)-butyric acid methyl ester

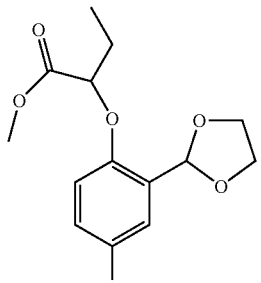

M.W. 300.74 C$_{14}$H$_{17}$ClO$_5$

A mixture of 2-(4-chloro-2-formyl-phenoxy)-butyric acid methyl ester (50 g, 0.195 mol), ethylene glycol (89 mL, 1.56 mol) and p-toluenesulfonic acid (2.8 g, 16.5 mmol) in toluene (400 mL) was refluxed with a Dean-Stark trap attached to remove the water. After 3 h, the reaction was cooled and washed with water, saturated NaHCO$_3$ and water, dried over anhydrous Na$_2$SO$_4$ and concentrated to give the title compound as a light yellow oil (40 g).

Example 62c

Preparation of Intermediate of 2-(4-chloro-2-[1,3] dioxolan-2-yl-phenoxy)-2-ethyl-butyric acid methyl ester

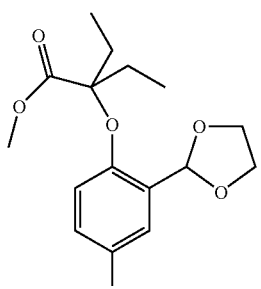

M.W. 328.80 C$_{16}$H$_{21}$ClO$_5$

Lithium bis(trimethylsilyl)amide (60 mL, 60 mmol, 1 M in THF) was slowly added to a solution of 2-(4-chloro-2-[1,3] dioxolan-2-yl-phenoxy)-butyric acid methyl ester (15 g, 50 mmol) in anhydrous THF (150 mL) at −78° C. After the mixture was stirred for 15 min, iodoethane (9.3 g, 60 mmol) was added. The mixture was allowed to warm to room temperature and stirred for 2 h. Then the mixture was diluted with ethyl acetate, washed with a saturated aqueous solution of NH$_4$Cl, dried over anhydrous Na$_2$SO$_4$ and concentrated to give the crude product as a oil (16 g).

Example 62d

Preparation of Intermediate of 2-(4-chloro-2-formyl-phenoxy)-2-ethyl-butyric acid methyl ester

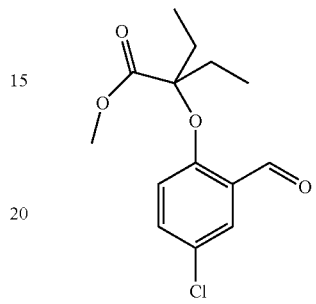

M.W. 284.74 C$_{14}$H$_{17}$ClO$_4$

A solution of 2-(4-chloro-2-[1,3]dioxolan-2-yl-phenoxy)-2-ethyl-butyric acid methyl ester (16 g, 48.8 mmol) in trifluoroacetic acid (20 mL) was stirred at room temperature for 3 h. Then the mixture was concentrated and the residue was partitioned between EtOAc and water. The organic layer was washed with 1N NaOH solution, water, dried over anhydrous Na$_2$SO$_4$ and concentrated to give the title compound (13 g).

Example 62e

Preparation of Intermediate of E/Z-2-[4-chloro-2-(6-chloro-2-oxo-1,2-dihydro-indol-3-ylidenemethyl)-phenoxy]-2-ethyl-butyric acid methyl ester

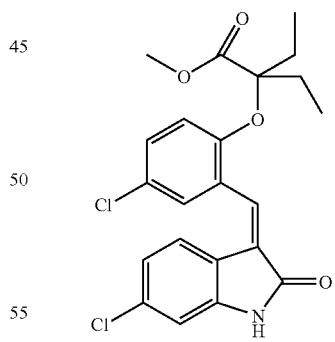

M.W. 434.32 C$_{22}$H$_{21}$Cl$_2$NO$_4$

To the mixture of 6-chlorooxindole (8.3 g, 49.7 mmol) and 2-(4-chloro-2-formyl-phenoxy)-2-ethyl-butyric acid methyl ester (13 g, 45.8 mmol) in methanol (200 mL) was added pyrrolidine (4.1 mL, 49.7 mmol) dropwise. The mixture was then heated at 70° C. for 2 h. After cooled to room temperature, the mixture was filtered and the precipitate was collected, dried to give the title compound as a yellow solid (15.5 g).

Example 62f

Preparation of Intermediate E/Z-3-[5-chloro-2-(1-ethyl-1-methoxycarbonyl-propoxy)-benzylidene]-6-chloro-2-oxo-2,3-dihydro-indole-1-carboxylic acid tert-butyl ester

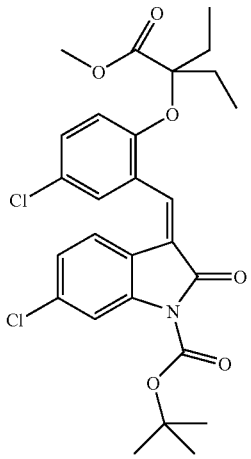

M.W. 534.44 C$_{27}$H$_{29}$Cl$_2$NO$_6$

To a solution of E/Z-2-[4-chloro-2-(6-chloro-2-oxo-1,2-dihydro-indol-3-ylidenemethyl)-phenoxy]-2-ethyl-butyric acid methyl ester (15.5 g, 36 mmol) in dichloromethane (200 mL) at room temperature was added di-tert-butyl-dicarbonate (8.6 g, 39 mmol), followed by the addition of 4-dimethylaminopyridine (0.4 g, 3.3 mmol). After the reaction mixture was stirred at room temperature for 1 h, the solution was washed with 1 M HCl and brine twice, dried over anhydrous Na$_2$SO$_4$ and concentrated to give the title compound as a yellow solid (15 g).

Example 62g

Preparation of Intermediate racemic (2'S,3S,4'R)-6-chloro-4'-[5-chloro-2-(1-ethyl-1-methoxycarbonyl-propoxy)-phenyl]-2'-(5-fluoro-2-methyl-phenyl)spiro[3H-indole-3,3'-piperidine]-2,6'(1H)-dione

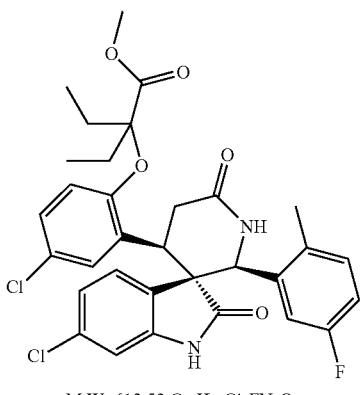

M.W. 613.52 C$_{32}$H$_{31}$Cl$_2$FN$_2$O$_5$

In a manner similar to the method described in Example 10d, E/Z-3-[5-chloro-2-(1-methoxycarbonyl-1-ethyl-propoxy)-benzylidene]-6-chloro-2-oxo-2,3-dihydro-indole-1-carboxylic acid tert-butyl ester (7.6 g, 15 mmol) was reacted with 1-(5-fluoro-2-methyl-phenyl)-3-trimethylsilyoxy-2-aza-1,3-butadiene (60 mmol) in toluene to give the title compound as a white solid (2.2 g).

m/z (M+H)$^+$: 613

Example 62h

Preparation of Racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione

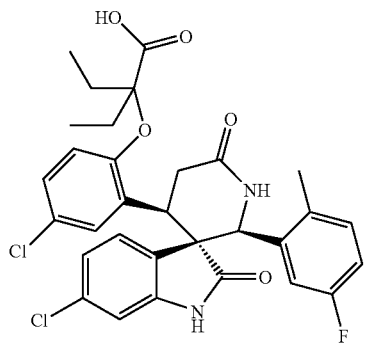

M.W. 599.49 C$_{31}$H$_{29}$Cl$_2$FN$_2$O$_5$

A mixture of racemic (2'S,3S,4'R)-6-chloro-4'-[5-chloro-2-(1-ethyl-1-methoxycarbonyl-propoxy)-phenyl]-2'-(5-fluoro-2-methyl-phenyl)spiro[3H-indole-3,3'-piperidine]-2,6'(1H)-dione (200 mg, 0.33 mmol), LiOH.H$_2$O (69 mg, 1.16 mmol), H$_2$O (2 mL) and methanol (20 mL) was refluxed for 2 h. After cooled to room temperature, the solution was concentrated and the residue was acidified to "pH" 2-3 by addition of concentrated HCl solution. The precipitate was collected by filtration to give the title compound as a white solid (57 mg).

m/z (M+H)$^+$: 599

Example 62i

Preparation of Racemic (2'S,3S,4'R)-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione

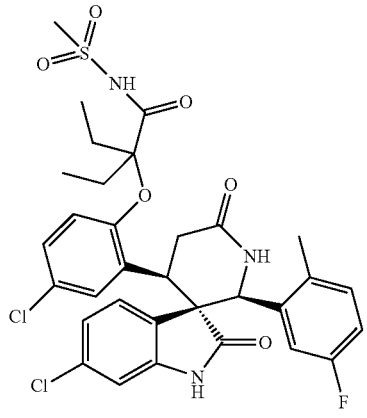

M.W. 676.60 C$_{32}$H$_{32}$Cl$_2$FN$_3$O$_6$S

A solution of racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione (30 mg, 0.05 mmol) and CDI (20 mg, 0.12 mmol) in DMF (1 mL) was heated at 60° C. for 2 h. Then to this solution was added a mixture of methanesulfonamide (28 mg, 0.3 mmol) and NaH (12 mg, 60%, 0.3 mmol) in DMF (1 mL), which had been stirred for 2 h at room temperature. After the resulting mixture was stirred at room temperature for 1 h, it was poured into water and the aqueous solution was acidified to "PH" 1-2 by addition of concentrated HCl solution. The aqueous phase was extracted with EtOAc twice, The combined organic phases were dried over anhydrous $Na_2SO_4$, concentrated and the residue was purified by flash column to give the title compound as a white solid (10 mg).

m/z (M+H)$^+$: 676

Example 62j

Preparation of Chiral (2'S,3S,4'R)-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione

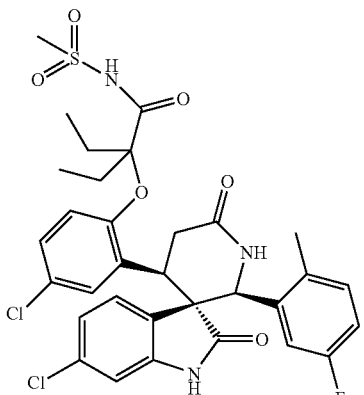

M.W. 676.60 $C_{32}H_{32}Cl_2FN_3O_6S$

Separation of the two enantiomers from racemic (2'S,3S,4'R)-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione (400 mg) was conducted by chiral SFC to provide chiral (2'S,3S,4'R)-6-chloro-4'-[5-chloro-2-(1-ethyl-1-methane-sulfonylaminocarbonyl-propoxy)-phenyl]-2'-(5-fluoro-2-methyl-phenyl)-spiro[3H-indole-3,3'-piperidine]-2,6'(1H)-dione as a white solid (130 mg) (RO5306899-000) and chiral (2'R,3R,4'S)-6-chloro-4'-[5-chloro-2-(1-ethyl-1-methane-sulfonylaminocarbonyl-propoxy)-phenyl]-2'-(5-fluoro-2-methyl-phenyl)-spiro[3H-indole-3,3'-piperidine]-2,6'(1H)-dione as a white solid (110 mg).

m/z (M+H)$^+$: 676

Example 63a

Preparation of Racemic (2'S,3S,4'R)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione

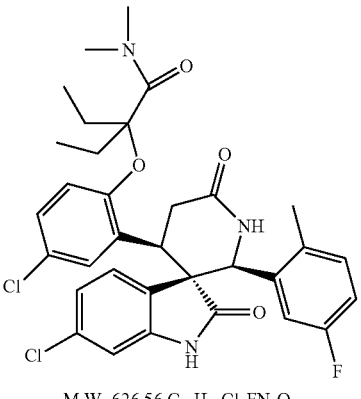

M.W. 626.56 $C_{33}H_{34}Cl_2FN_3O_4$

At room temperature, a mixture of racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione (50 mg, 0.084 mmol) prepared in Example 62h, dimethylamine hydrochloride (13.5 mg, 0.17 mmol), HATU (63.5 mg, 0.17 mmol) and DMAP (40.8 mg, 0.33 mmol) in DMF (2 mL) was stirred for 5 h. Then the mixture was poured into water and extracted with EtOAc thrice. The combined organic phases were washed with brine twice, dried over anhydrous $Na_2SO_4$ and concentrated. The residue was purified by flash column to give the title compound as a white solid (40 mg).

m/z (M+H)$^+$: 626

Example 63b

Preparation of Chiral (2'S,3S,4'R)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione

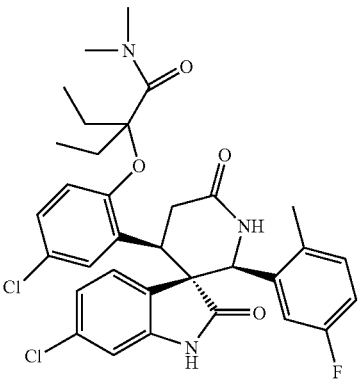

M.W. 626.56 $C_{33}H_{34}Cl_2FN_3O_4$

Separation of the two enantiomers from racemic (2'S,3S,4'R)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione (30 mg), was conducted by chiral SFC to provide chiral (2'S,3S,4'R)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione as a white solid (11 mg) (RO5314967-000) and chiral (2'R,3R,4'S)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione as a white solid (10 mg) m/z (M+H)⁺: 626

Example 64

Preparation of Racemic (2'S,3S,4'R)-6-chloro-4'-{5-chloro-2-[1-ethyl-1-(2-hydroxy-ethylcarbamoyl)-propoxy]-phenyl}-2'-(5-fluoro-2-methyl-phenyl)spiro[3H-indole-3,3-piperidine]-2,6'(1H)-dione

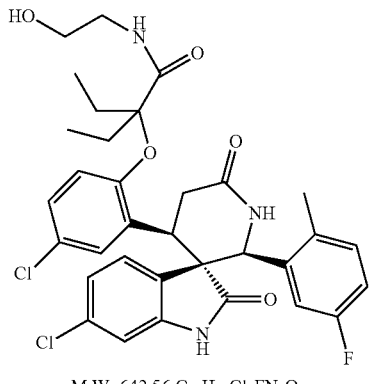

M.W. 642.56 C$_{33}$H$_{34}$Cl$_2$FN$_3$O$_5$

At room temperature, a mixture of racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione (50 mg, 0.084 mmol), ethanol amine (10 mg, 0.17 mmol), HATU (63.5 mg, 0.17 mmol) and DMAP (40.8 mg, 0.33 mmol) in DMF (2 mL) was stirred for 5 h. Then the mixture was poured into water and extracted with EtOAc thrice. The combined organic layers were washed with saturated brine twice, dried over anhydrous Na$_2$SO$_4$ and concentrated. The residue was purified by flash column to give the title compound as a white solid (10 mg).

m/z (M+H)⁺: 642

Example 65a

Preparation of Racemic (2'S,3S,4'R)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)spiro[3H-indole-3,3'-piperidine]-2,6'(1H)-dione

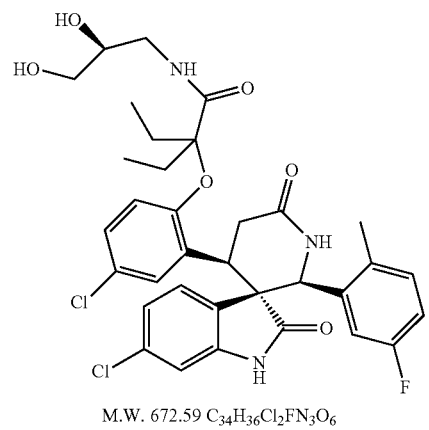

M.W. 672.59 C$_{34}$H$_{36}$Cl$_2$FN$_3$O$_6$

At room temperature, a mixture of racemic (2'S,3S,4'R)-6-chloro-4'-[1-ethyl-5-chloro-2-(1-hydroxycarbonyl-propoxy)-phenyl]-2'-(5-fluoro-2-methyl-phenyl)spiro[3H-indole-3,3'-piperidine]-2,6'(1H)-dione (50 mg, 0.084 mmol), (S)-3-amino-1,2-propanediol (27 mg, 0.3 mmol), HATU (114 mg, 0.30 mmol) and DMAP (72 mg, 0.59 mmol) in DMF (2 mL) was stirred for 5 h. Then the mixture was poured into water and extracted with EtOAc thrice. The combined organic phase was washed with saturated NaCl solution twice, dried over anhydrous Na$_2$SO$_4$ and concentrated. The residue was purified by flash column to give the title compound as a white solid (40 mg).

m/z (M+H)⁺: 672

Example 65b

Preparation of Chiral (2'S,3S,4'R)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)spiro[3H-indole-3,3'-piperidine]-2,6'(1H)-dione

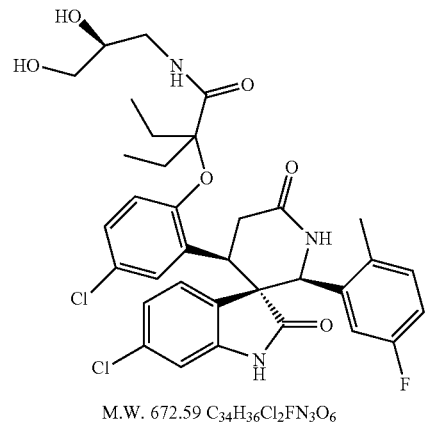

M.W. 672.59 C$_{34}$H$_{36}$Cl$_2$FN$_3$O$_6$

Separation of the two enantiomers from racemic (2'S,3S, 4'R)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)spiro[3H-indole-3,3'-piperidine]-2,6'(1H)-dione (30 mg), was conducted by chiral SFC to provide chiral (2'S,3S,4'R)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)spiro[3H-indole-3,3'-piperidine]-2,6'(1H)-dione as a white solid (10 mg) (RO5314969-000) and chiral (2'R,3R,4'S)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)spiro[3H-indole-3,3'-piperidine]-2,6'(1H)-dione as a white solid (13 mg) (RO5314970-000).

Example 66a

Preparation of Racemic (2'S,3S,4'R)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione

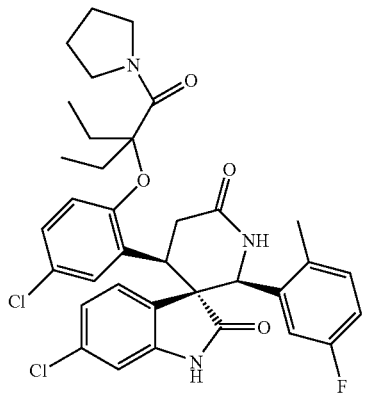

M.W. 652.60 C$_{35}$H$_{36}$Cl$_{2}$FN$_{3}$O$_{4}$

At room temperature, a mixture of racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione (50 mg, 0.084 mmol), pyrrolidine (12 mg, 0.17 mmol), HATU (63.5 mg, 0.17 mmol) and DMAP (40.8 mg, 0.33 mmol) in DMF (2 mL) was stirred for 5 h. Then the mixture was poured into water and extracted with EtOAc thrice. The combined organic layers were washed with saturated NaCl solution twice, dried over anhydrous Na$_{2}$SO$_{4}$ and concentrated. The residue was purified by flash column to give the title compound as a white solid (30 mg).

m/z (M+H)$^{+}$: 652

Example 66b

Preparation of Chiral (2'S,3S,4'R)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione

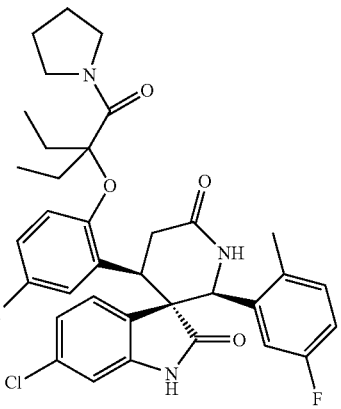

M.W. 652.60 C$_{35}$H$_{36}$Cl$_{2}$FN$_{3}$O$_{4}$

Separation of the two enantiomers from racemic (2'S,3S, 4'R)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione (30 mg), was conducted by chiral SFC to provide chiral (2'S,3S,4'R)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione as a white solid (10 mg) and chiral (2'R,3R,4'S)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione as a white solid (10 mg).

m/z (M+H)$^{+}$: 652

Example 67a

Preparation of Racemic (2'S,3S,4'R)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione

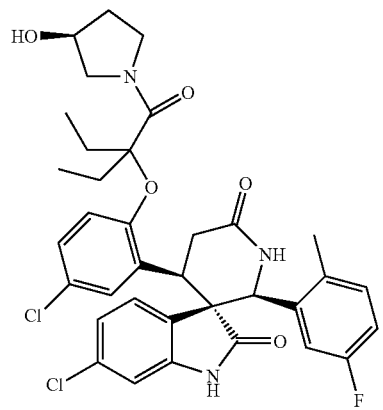

M.W. 668.60 C$_{35}$H$_{36}$Cl$_{2}$FN$_{3}$O$_{5}$

At room temperature, a mixture of racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione (120 mg, 0.2 mmol), (S)-3-hydroxypyrrolidine (35 mg, 0.4 mmol), HATU (152 mg, 0.4 mmol) and DMAP (73 mg, 0.6 mmol) in DMF (2 mL) was stirred for 4 h. Then the mixture was poured into water and extracted with EtOAc thrice. The combined organic phases were washed with saturated NaCl solution twice, dried over anhydrous $Na_2SO_4$ and concentrated. The residue was purified by flash column to give the title compound as a white solid (50 mg).

m/z $(M+H)^+$: 668

Example 67b

Preparation of Chiral (2'S,3S,4'R)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione

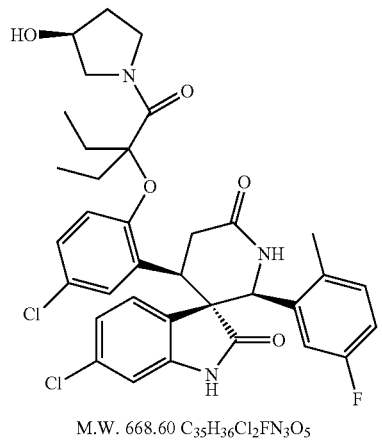

M.W. 668.60 $C_{35}H_{36}Cl_2FN_3O_5$

Separation of the two enantiomers from racemic (2'S,3S, 4'R)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione (30 mg), was conducted by chiral SFC to provide chiral (2'S,3S,4'R)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)spiro[3H-indole-3,3'-piperidine]-2, 6'(1H)-dione as a white solid (10 mg) and chiral (2'R,3R,4'S)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione as a white solid (10 mg).

m/z $(M+H)^+$: 668

Example 68a

Preparation of Racemic (2'S,3S,4'R)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione

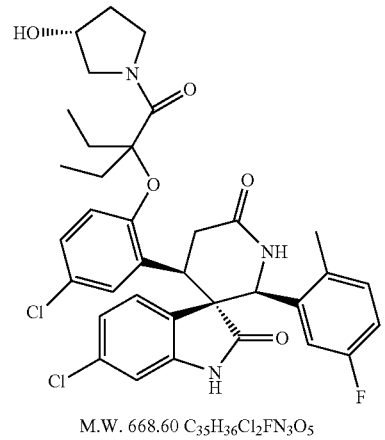

M.W. 668.60 $C_{35}H_{36}Cl_2FN_3O_5$

At room temperature, a mixture of racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione (120 mg, 0.2 mmol), R-3-hydroxypyrrolidine (35 mg, 0.4 mmol), HATU (152 mg, 0.4 mmol) and DMAP (73 mg, 0.6 mmol) in DMF (2 mL) was stirred for 4 h. Then the mixture was poured into water and extracted with EtOAc thrice. The combined organic phase was washed with saturated NaCl aqueous solution twice, dried over anhydrous $Na_2SO_4$ and concentrated. The residue was purified by flash column to give the title compound as a white solid (50 mg).

m/z $(M+H)^+$: 668

Example 68b

Preparation of Chiral (2'S,3S,4'R)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione

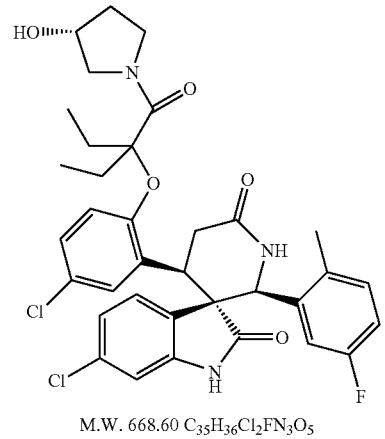

M.W. 668.60 $C_{35}H_{36}Cl_2FN_3O_5$

Separation of the two enantiomers from racemic (2'S,3S,4'R)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione (30 mg), was conducted by chiral SFC to provide chiral (2'S,3S,4'R)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione as a white solid (10 mg) and chiral (2'R,3R,4'S)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione as a white solid (10 mg).

m/z (M+H)$^+$: 668

Example 69a

Preparation of Racemic (2'S,3S,4'R)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione

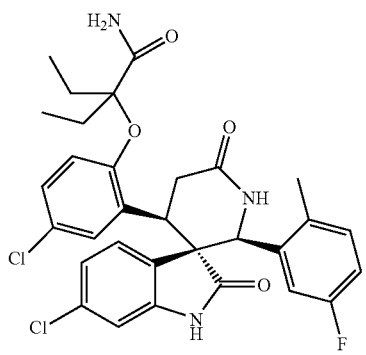

M.W. 598.51 C$_{31}$H$_{30}$Cl$_2$FN$_3$O$_4$

At the room temperature, a mixture of racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione (100 mg, 0.167 mmol), NH$_3$ in THF (8.5 mg, 0.5 mmol), HATU (100 mg, 0.25 mmol) and DMAP (60 mg, 0.50 mmol) in DMF (3 mL) was stirred for 4 h. Then the mixture was poured into water and extracted with EtOAc thrice. The combined organic phase was washed with saturated NaCl solution twice, dried over anhydrous Na$_2$SO$_4$ and concentrated. The residue was purified by flash column to give the title compound as a white solid (70 mg).

m/z (M+H)$^+$: 598

Example 69b

Preparation of Chiral (2'S,3S,4'R)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione

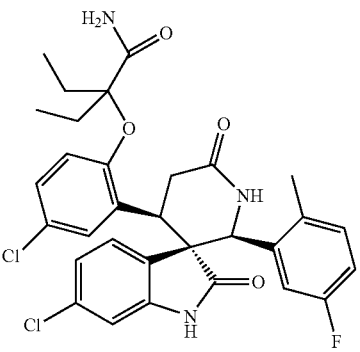

M.W. 598.51 C$_{31}$H$_{30}$Cl$_2$FN$_3$O$_4$

Separation of the two enantiomers from racemic (2'S,3S,4'R)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione (50 mg), was conducted by chiral SFC to provide chiral (2'S,3S,4'R)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione as a white solid (15 mg) and chiral (2'R,3R,4'S)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione as a white solid (15 mg).

m/z (M+H)$^+$: 598

Example 70a

Preparation of Intermediate racemic (2'S,3S,4'R)-6-chloro-4'-[5-chloro-2-(1-ethyl-1-methoxycarbonyl-propoxy)-phenyl]-2'-(5-chloro-2-methyl-phenyl)spiro[3H-indole-3,3'-piperidine]-2,6'(1H)-dione

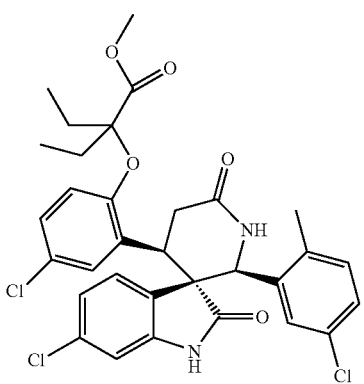

M.W. 629.97 C$_{32}$H$_{31}$Cl$_3$N$_2$O$_5$

In a manner similar to the method described in Example 10d, E/Z-3-[5-chloro-2-(1-methoxycarbonyl-1-ethyl-propoxy)-benzylidene]-6-chloro-2-oxo-2,3-dihydro-indole-1-carboxylic acid tert-butyl ester (2.63 g, 4.9 mmol) prepared in Example 62f was reacted with 1-(5-chloro-2-methyl-phenyl)-3-trimethylsilyoxy-2-aza-1,3-butadiene (20 mmol) prepared in Example 13b in toluene (20 mL) to give the title compound as a white solid (600 mg).

m/z (M+H)+: 629

Example 70b

Preparation of Intermediate racemic (2'S,3S,4'R)-6-chloro-4'-[5-chloro-2-(1-ethyl-1-hydroxycarbonyl-propoxy)-phenyl]-2'-(5-chloro-2-methyl-phenyl)spiro[3H-indole-3,3'-piperidine]-2,6'(1H)-dione

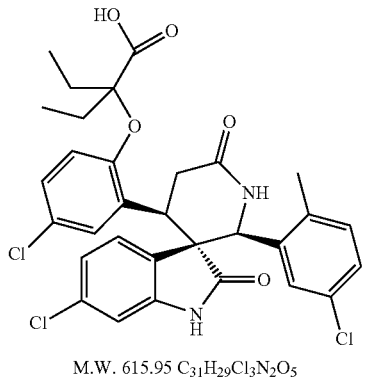

M.W. 615.95 C$_{31}$H$_{29}$Cl$_3$N$_2$O$_5$

A mixture of racemic (2'S,3S,4'R)-4'-[5-chloro-2-(1-ethyl-1-methoxycarbonyl-propoxy)-phenyl]-6-chloro-2'-(5-chloro-2-methyl-phenyl)spiro[3H-indole-3,3'-piperidine]-2,6'(1H)-dione (100 mg, 0.159 mmol), LiOH (19.87 mg, 0.8 mmol), H$_2$O (2 mL) and methanol (3 mL) was heated at 40° C. for 4 h. Then methanol was removed by vacuum. The aqueous solution was acidified to "PH" 1-2 by addition of concentrated hydrochloride acid. The precipitate was collected by filtration and purified by Prep-HPLC to give the title compound as a white solid (50 mg).

m/z (M+H)+: 615

Example 70c

Preparation of Racemic (2'S,3S,4'R)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

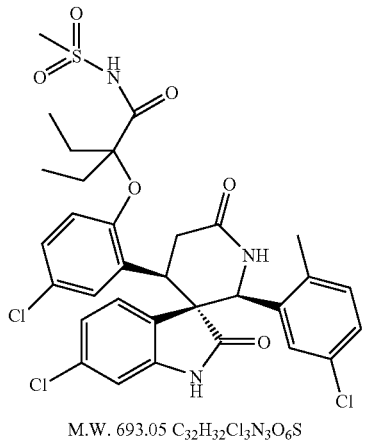

M.W. 693.05 C$_{32}$H$_{32}$Cl$_3$N$_3$O$_6$S

A solution of racemic (2'S,3S,4'R)-6-chloro-4'-[5-chloro-2-(1-ethyl-1-hydroxycarbonyl-propoxy)-phenyl]-2'-(5-chloro-2-methyl-phenyl)spiro[3H-indole-3,3'-piperidine]-2,6'(1H)-dione (150 mg, 0.244 mmol) and CDI (80 mg, 0.49 mmol) in DMF (2 mL) was heated at 60° C. for 2 h, then cooled to room temperature. In a separate flask a mixture of methanesulfonamide (231 mg, 2.44 mmol) and NaH (78 mg, 60%, 1.95 mmol) was stirred in DMF (3 mL) at room temperature for 2 h, then the resulting mixture was added into the above solution. The reaction mixture was stirred at room temperature for 1 h, then poured into water and "pH" was acidified to 2-3 by addition of concentrated HCl solution. The mixture was extracted with EtOAc twice, the combined extracts were dried over anhydrous Na$_2$SO$_4$, concentrated and the residue was purified by flash column to give the title compound as a white solid (10 mg).

m/z (M+H)+: 692

Example 71a

Preparation of Intermediate racemic (2'S,3S,4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

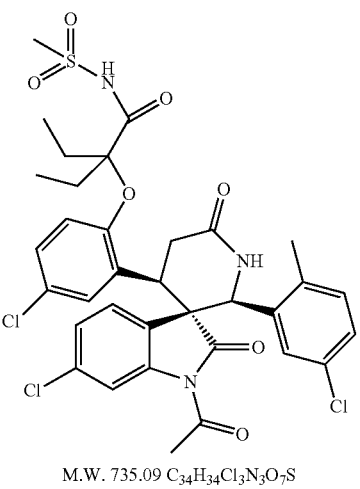

M.W. 735.09 C$_{34}$H$_{34}$Cl$_3$N$_3$O$_7$S

At room temperature, to a mixture of racemic (2'S,3S,4'R)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione (400 mg, 0.58 mmol) and acetic anhydride (71 mg, 0.69 mmol) in DCM (20 mL) was added DMAP (7 mg, 0.06 mmol) slowly. After the mixture was stirred for 2 h, the solution was washed by 0.5N HCl solution twice, dried over anhydrous Na$_2$SO$_4$ and concentrated. The residue was purified by Prep-HPLC to give the title compound as a white solid (100 mg).

Example 71b

Preparation of Intermediate chiral (2'S,3S,4'R)-1-acetyl-6-chloro-4'-[5-chloro-2-(1-ethyl-1-1-methanesulfonylaminocarbonyl-propoxy)-phenyl]-2'-(5-chloro-2-methyl-phenyl)-spiro[3H-indole-3,3'-piperidine]-2,6'(1H)-dione

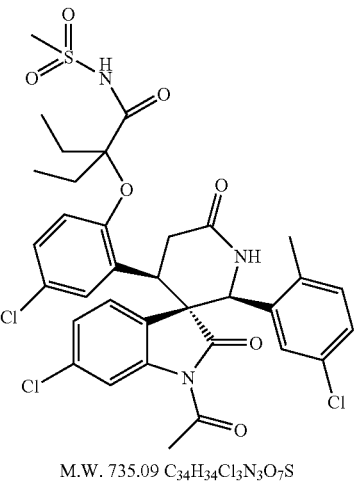

M.W. 735.09 C$_{34}$H$_{34}$Cl$_3$N$_3$O$_7$S

Separation of the two enantiomers from racemic (2'S,3S,4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione (50 mg), was conducted by chiral SFC to provide chiral (2'S,3S,4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione as a white solid (15 mg) m/z (M+H)$^+$: 734

Example 71c

Preparation of Chiral (2'S,3S,4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

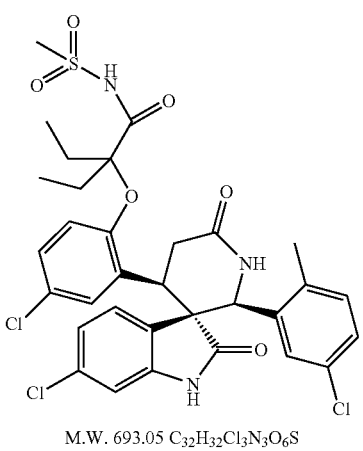

M.W. 693.05 C$_{32}$H$_{32}$Cl$_3$N$_3$O$_6$S

At room temperature, a mixture of chiral (2'S,3S,4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione (20 mg, 0.027 mmol) (RO5319795-000), NaOH (2 mg, 0.05 mmol), H$_2$O (0.5 mL) and methanol (2 mL) was stirred overnight. Then methanol was removed by vacuum. The aqueous solution was acidified by addition of concentrated HCl to "pH" 1-2 and extracted with EtOAc twice. The combined organic layers were dried over anhydrous Na$_2$SO$_4$ and concentrated to give the title compound as a white solid (10 mg).

m/z (M+H)$^+$: 692

Example 72a

Preparation of Intermediate chiral (2'R,3R,4'S)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

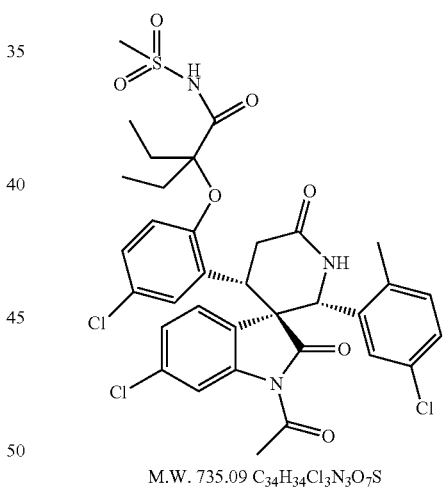

M.W. 735.09 C$_{34}$H$_{34}$Cl$_3$N$_3$O$_7$S

In the separation of the two enantiomers from racemic (2'S,3S,4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione (50 mg) by chiral SFC in Example 71b, chiral (2'R,3R,4'S)-1-acetyl-6-chloro-4'-[5-chloro-2-(1-ethyl-methanesulfonylaminocarbonyl-propoxy)-phenyl]-2'-(5-chloro-2-methyl-phenyl)-spiro[3H-indole-3,3'-piperidine]-2,6'(1H)-dione was obtained as the second product: a white solid (15 mg).

m/z (M+H)$^+$: 734

Example 72b

Preparation of Chiral (2'R,3R,4'S)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione

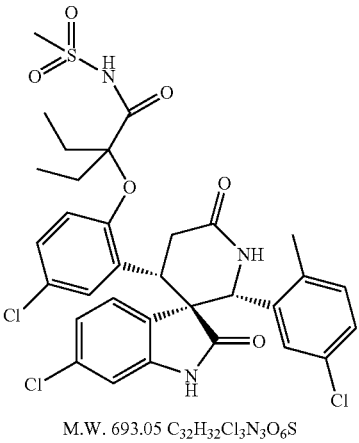

M.W. 693.05 C$_{32}$H$_{32}$Cl$_3$N$_3$O$_6$S

At room temperature, a mixture of chiral (2'R,3R,4'S)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione (20 mg, 0.027 mmol) (RO5319796-000), NaOH (2 mg, 0.05 mmol), H$_2$O (0.5 mL) and methanol (2 mL) was stirred overnight. Then methanol was removed by vacuum. The aqueous solution was acidified by addition of concentrated HCl to "pH" 1-2 and extracted with EtOAc twice. The combined organic layers were dried over anhydrous Na$_2$SO$_4$ and concentrated to give the title compound as a white solid (10 mg).
m/z (M+H)$^+$: 692

Example 73

Preparation of Chiral (2'S,3S,4'R)-4'-[5-chloro-2-(2-ethanesulfonylamino-1,1-dimethyl-2-oxo-ethoxy)-phenyl]-6-chloro-2'-(5-fluoro-2-methyl-phenyl)spiro[3H-indole-3,3'-piperidine]-2,6'(1H)-dione

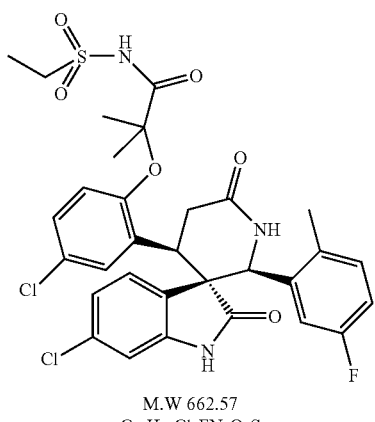

M.W 662.57
C$_{31}$H$_{30}$Cl$_2$FN$_3$O$_6$S

A solution of chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (57 mg, 0.1 mmol) prepared in Example 12a and CDI (32 mg, 0.2 mmol) in DMF (1 mL) was heated at 60° C. for 2 h. Then to this solution was added a mixture of ethanesulfonamide (66 mg, 0.6 mmol) and NaH (24 mg, 60%, 0.6 mmol) in DMF (1 mL), which had been stirred for 2 h at room temperature. After the resulting mixture was stirred at room temperature for 1 h, it was poured into water and the aqueous solution was acidified to "pH" 1-2 by addition of concentrated HCl. After the aqueous phase was extracted with EtOAc twice, the combined organic layers were dried over anhydrous Na$_2$SO$_4$, concentrated and the residue was purified by flash column to give the title compound as a white solid (10 mg).
m/z (M+H)$^+$: 662

Example 74a

Preparation of Intermediate 1-(5-methyl-2-methoxy-phenyl)-3-trimethylsilyoxy-2-aza-1,3-butadiene

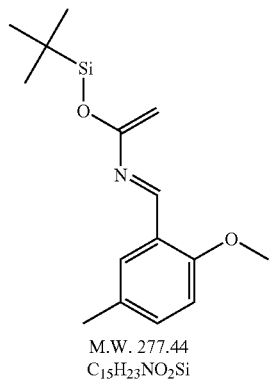

M.W. 277.44
C$_{15}$H$_{23}$NO$_2$Si

To dry tetrahydrofuran (60 mL) was added 1M THF solution of LiHMDS (51 mmol, 51 mL) under Ar at room temperature, followed by the addition of 2-Methoxy-5-methyl-benzaldehyde (7.65 g, 51 mmol). After the mixture was stirred at room temperature for 1 h, trimethylsilyl chloride (6.3 mL, 51 mmol) was added dropwise. Then the temperature of the mixture was lowered to 0° C. on a cooling ice bath. To this mixture was added triethylamine (9.3 mL, 66 mmol) in one portion, followed by the dropwise addition of a solution of acetyl chloride (4.71 mL, 66 mmol) in diethyl ether (300 mL). The cooling bath was removed, and the mixture was stirred at room temperature overnight. The mixture was quickly filtered on celite under nitrogen, and filtrate was concentrated under reduced pressure to give crude 1-(5-methyl-2-methoxy-phenyl)-3-trimethylsilyoxy-2-aza-1,3-butadiene as a yellow gum and used for the next step without further purification

Example 74b

Preparation of Intermediate racemic (2'S,3S,4'R)-6-chloro-4'-[5-chloro-2-(1-methoxycarbonyl-1-methyl-ethoxy)-phenyl]-2'-(5-methyl-2-methoxy-phenyl)spiro[3H-indole-3,3'-piperidine]-2,6'(1H)-dione

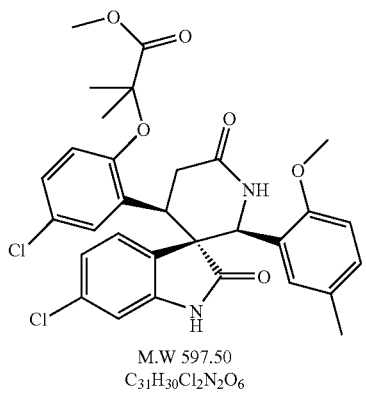

M.W 597.50
$C_{31}H_{30}Cl_2N_2O_6$

In a manner similar to the method described in Example 10d, E/Z-6-chloro-3-[5-chloro-2-(1-methoxycarbonyl-1-methyl-ethoxy)-benzylidene]-2-oxo-2,3-dihydro-indole-1-carboxylic acid tert-butyl ester (5 g, 10.31 mmol) prepared in Example 1c was reacted with 1-(5-methyl-2-methoxy-phenyl)-3-trimethylsilyoxy-2-aza-1,3-butadiene (51 mmol) in toluene to give the title compound as a white solid (143 mg).
m/z (M+H)$^+$: 597

Example 74c

Preparation of Intermediate racemic (2'S,3S,4'R)-6-chloro-4'-[5-chloro-2-(1-hydroxycarbonyl-1-methyl-ethoxy)-phenyl]-2'-(5-methyl-2-methoxy-phenyl)spiro[3H-indole-3,3'-piperidine]-2,6'(1H)-dione

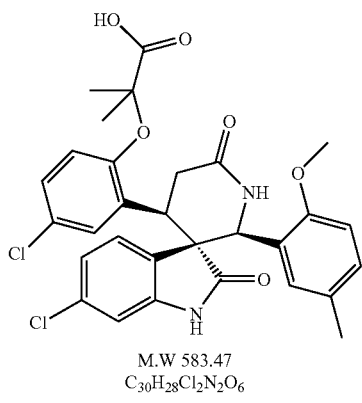

M.W 583.47
$C_{30}H_{28}Cl_2N_2O_6$

A mixture of racemic (2'S,3S,4'R)-6-chloro-4'-[5-chloro-2-(1-methoxycarbonyl-1-methyl-ethoxy)-phenyl]-2'-(5-methyl-2-methoxy-phenyl)spiro[3H-indole-3,3'-piperidine]-2,6'(1H)-dione (100 mg, 0.167 mmol), NaOH (33.5 mg, 0.837 mmol), H$_2$O (2 mL) and methanol (3 mL) was heated at 70° C. for 1 h. Then methanol was removed by vacuum and the aqueous solution was acidified to "pH" 1-2 by addition of concentrated HCl aqueous solution. The precipitate was collected by filtration and washed with CH$_2$Cl$_2$ twice to give the title compound as a white solid (21 mg).
m/z (M+H)$^+$: 583

Example 74d

Preparation of Racemic (2'S,3S,4'R)-4'-[5-chloro-2-(2-methanesulfonylamino-1,1-dimethyl-2-oxo-ethoxy)-phenyl]-6-chloro-2'-(5-methyl-2-methoxy-phenyl)-spiro[3H-indole-3,3'-piperidine]-2,6'(1H)-dione

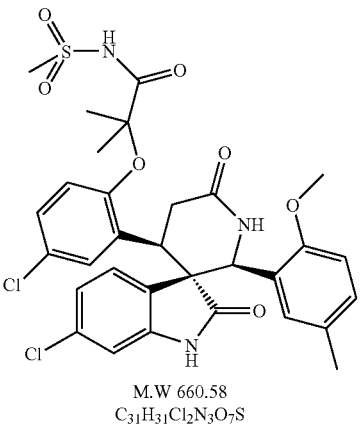

M.W 660.58
$C_{31}H_{31}Cl_2N_3O_7S$

A mixture of racemic (2'S,3S,4'R)-6-chloro-4'-[5-chloro-2-(1-hydroxycarbonyl-1-methyl-ethoxy)-phenyl]-2'-(5-methyl-2-methoxy-phenyl)spiro[3H-indole-3,3'-piperidine]-2,6'(1H)-dione (70 mg, 0.12 mmol) and CDI (39 mg, 0.24 mmol) in dry DMF (2 mL) was heated at 65° C. for 2 h. In a separate flask a mixture of methanesulfonamide (91 mg, 0.962 mmol) and NaH (60% in mineral oil) (38 mg, 0.95 mmol) (Aldrich) in DMF (3 mL), was stirred at room temperature for 2 h, then was added slowly to the above solution. The reaction mixture was stirred at room temperature for 2 h, then poured into water (3 mL) and the aqueous phase was acidified to "pH" 1-2 by addition of concentrated HCl. The mixture was extracted with EtOAc (20 mL) twice. The combined organic layers were dried over anhydrous Na$_2$SO$_4$, concentrated in vacuo and the residue was purified by Prep-HPLC to give the title compound as a white solid (8.5 mg).

Example 75

Preparation of Racemic (2'S,3S,4'R)-6-chloro-4'-[5-chloro-2-(3-methanesulfonylamino-2,2-dimethyl-3-oxo-propoxy)-phenyl]-2'-(5-fluoro-2-methyl-phenyl)spiro[3H-indole-3,3'-piperidine]-2,6'(1H)-dione

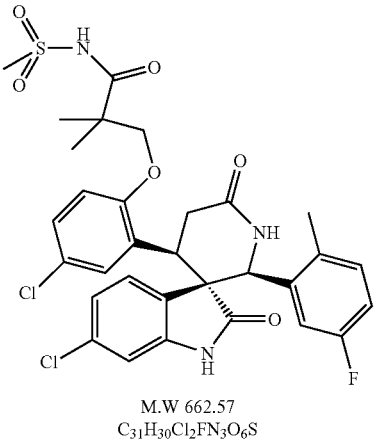

M.W 662.57
$C_{31}H_{30}Cl_2FN_3O_6S$

A solution of racemic (2'S,3S,4'R)-6-chloro-4'-[5-chloro-2-(2-hydroxycarbonyl-2-methyl-propoxy)-phenyl]-2'-(5-fluoro-2-methyl-phenyl)spiro[3H-indole-3,3'-piperidine]-2,6'(1H)-dione (300 mg, 0.5 mmol) prepared in Example 20f and CDI (160 mg, 1 mmol) in DMF (2 mL) was heated at 60° C. for 2 h. Then to this solution was added a mixture of methanesulfonamide (285 mg, 3 mmol) and NaH (120 mg, 60%, 3 mmol) in DMF (1 mL), which had been mixed and stirred at room temperature for 2 h. After the resulting mixture was stirred at room temperature for 1 h, it was poured into water and the aqueous solution was acidified to "pH" 1-2 by addition of concentrated HCl. After the aqueous phase was extracted with EtOAc twice, the combined organic layers were dried over anhydrous $Na_2SO_4$, concentrated and the residue was purified by flash column to give the title compound as a white solid (70 mg).

m/z (M+H)$^+$: 662

Example 76a

Preparation of Racemic (2'S,3S,4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione

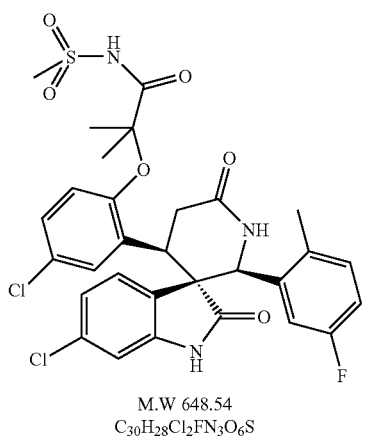

M.W 648.54
$C_{30}H_{28}Cl_2FN_3O_6S$

A solution of racemic (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (16 g, 0.028 mol) prepared in Example 1f and CDI (9 g, 0.056 mol) in DMF (70 mL) was heated at 65° C. for 2 h. Then to this solution was added a mixture of methanesulfonamide (16 g, 0.168 mol) and NaH (5.6 g, 60%, 0.14 mol) in DMF (100 mL), which had been mixed and stirred at room temperature for 2 h. After the resulting mixture was stirred at room temperature for 2 h, it was poured into water and the aqueous solution was acidified to "pH" 1-2 by addition of concentrated HCl. After the aqueous phase was extracted with EtOAc twice, the combined organic layers were dried over anhydrous $Na_2SO_4$, concentrated and the residue was purified by recrystallized to give the title compound (11.4 g).

m/z (M+H)$^+$: 648

Example 76b

Preparation of Chiral (2'R,3R,4'S)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione

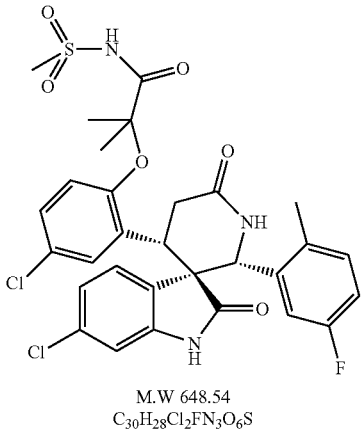

M.W 648.54
$C_{30}H_{28}Cl_2FN_3O_6S$

Separation of the two enantiomers from racemic (2'S,3S,4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione (50 mg), was conducted by chiral SFC to provide chiral (2'R,3R,4'S)-4'-[5-chloro-2-(2-methanesulfonylamino-1,1-dimethyl-2-oxo-ethoxy)-phenyl]-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione as a white solid (RO5302327-000, 15 mg) and chiral (2'S, 3S, 4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione as a white solid (RO5248115-000, 10 mg).

m/z (M+H)$^+$: 648

Example 77a

Preparation of Intermediate racemic (2'S,3S,4'R)-6-chloro-4'-[5-chloro-2-(1-methoxycarbonyl-1-methyl-ethoxy)-phenyl]-2'-(5-chloro-2-methyl-phenyl)spiro[3H-indole-3,3'-piperidine]-2,6'(1H)-dione

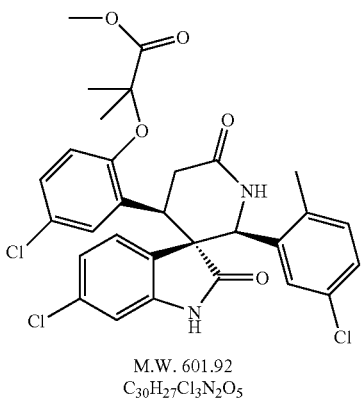

M.W. 601.92
$C_{30}H_{27}Cl_3N_2O_5$

In a manner similar to the method described in Example 10d, E/Z-6-chloro-3-[5-chloro-2-(1-methoxycarbonyl-1-methyl-ethoxy)-benzylidene]-2-oxo-2,3-dihydro-indole-1-carboxylic acid tert-butyl ester (7 g, 14 mmol) prepared in Example 1c was reacted with 1-(5-chloro-2-methyl-phenyl)-

3-trimethylsilyoxy-2-aza-1,3-butadiene (42 mmol) prepared in Example 13b in toluene and then trifluoroacetic acid in dichloromethane to give the title compound (1.8 g).

m/z (M+H)$^+$: 601

Example 77b

Preparation of Intermediate racemic (2'S,3S,4'R)-6-chloro-4'-[5-chloro-2-(1-hydroxycarbonyl-1-methyl-ethoxy)-phenyl]-2'-(5-chloro-2-methyl-phenyl)spiro[3H-indole-3,3'-piperidine]-2,6'(1H)-dione

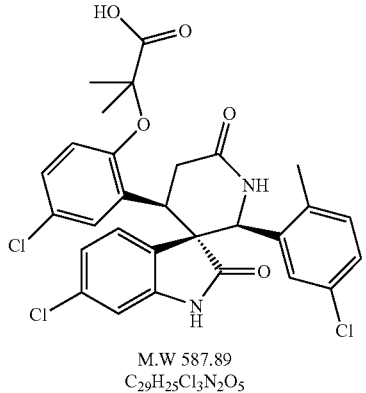

M.W 587.89
$C_{29}H_{25}Cl_3N_2O_5$

A mixture of racemic (2'S,3S,4'R)-6-chloro-4'-[5-chloro-2-(1-methoxycarbonyl-1-methyl-ethoxy)-phenyl]-2'-(5-chloro-2-methyl-phenyl)spiro[3H-indole-3,3'-piperidine]-2,6'(1H)-dione (600 mg, 1 mmol), NaOH (80 mg, 2 mmol), H$_2$O (3 mL) and methanol (10 mL) was heated at 70° C. for 2 h. After cooled to room temperature, the solution was concentrated and then the residue was acidified to "pH" 2-3 by addition of concentrated HCl. The white solid was collected by filtration to give the title compound as a white solid (50 mg).

m/z (M+H)$^+$: 587

Example 77c

Preparation of Racemic (2'S,3S,4'R)-6-chloro-4'-[5-chloro-2-(2-methanesulfonylamino-1,1-dimethyl-2-oxo-ethoxy)-phenyl]-2'-(5-chloro-2-methyl-phenyl)-spiro[3H-indole-3,3'-piperidine]-2,6'(1H)-dione

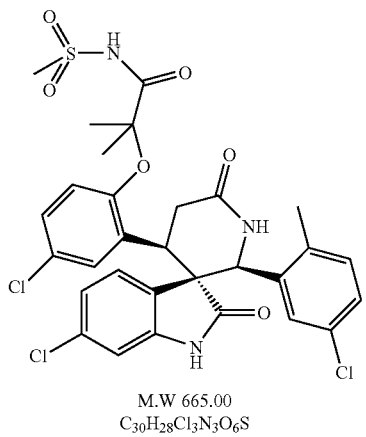

M.W 665.00
$C_{30}H_{28}Cl_3N_3O_6S$

A solution of racemic (2'S,3S,4'R)-6-chloro-4'-[5-chloro-2-(1-hydroxycarbonyl-1-methyl-ethoxy)-phenyl]-2'-(5-chloro-2-methyl-phenyl)spiro[3H-indole-3,3'-piperidine]-2,6'(1H)-dione (300 mg, 0.5 mmol) and CDI (160 mg, 1 mmol) in DMF (2 mL) was heated at 60° C. for 2 h. Then to this solution was added a mixture of methanesulfonamide (285 mg, 3 mmol) and NaH (120 mg, 60%, 3 mmol) in DMF (5 mL), which had been stirred at room temperature for 3 h. After the resulting mixture was stirred at room temperature for 1 h, it was poured into water and the aqueous solution was acidified to "pH" 1-2 by addition of concentrated HCl. After the aqueous phase was extracted with EtOAc twice, the combined organic layers were dried over anhydrous Na$_2$SO$_4$, concentrated and the residue was purified by flash column to give the title compound as a white solid (100 mg).

m/z (M+H)$^+$: 664

Example 77d

Preparation of Chiral (2'S,3S,4'R)-6-chloro-4'-[5-chloro-2-(2-methanesulfonylamino-1,1-dimethyl-2-oxo-ethoxy)-phenyl]-2'-(5-chloro-2-methyl-phenyl)-spiro[3H-indole-3,3'-piperidine]-2,6'(1H)-dione

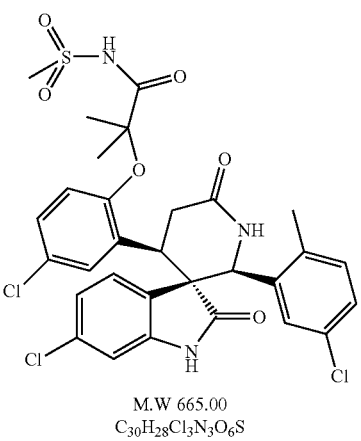

M.W 665.00
$C_{30}H_{28}Cl_3N_3O_6S$

Separation of the two enantiomers from racemic (2'S,3S,4'R)-6-chloro-4'-[5-chloro-2-(2-methanesulfonylamino-1,1-dimethyl-2-oxo-ethoxy)-phenyl]-2'-(5-chloro-2-methyl-phenyl)-spiro[3H-indole-3,3'-piperidine]-2,6'(1H)-dione (50 mg), was conducted by chiral SFC to provide chiral (2'S,3S,4'R)-6-chloro-4'-[5-chloro-2-(2-methanesulfonylamino-1,1-dimethyl-2-oxo-ethoxy)-phenyl]-2'-(5-chloro-2-methyl-phenyl)-spiro[3H-indole-3,3'-piperidine]-2,6'(1H)-dione as a white solid (RO5305963-000, 13 mg) and chiral (2'R,3R,4'S)-6-chloro-4'-[5-chloro-2-(2-methanesulfonylamino-1,1-dimethyl-2-oxo-ethoxy)-phenyl]-2'-(5-chloro-2-methyl-phenyl)-spiro[3H-indole-3,3'-piperidine]-2,6'(1H)-dione as a white solid, 11 mg.

m/z (M+H)$^+$: 664

Example 78

Preparation of Chiral (2'S,3S,4'R)-6-chloro-4'-{5-chloro-2-[2-(2-methoxy-ethanesulfonylamino)-1,1-dimethyl-2-oxo-ethoxy]-phenyl}-2'-(5-fluoro-2-methyl-phenyl)-spiro[3H-indole-3,3'-piperidine]-2,6'(1H)-dione

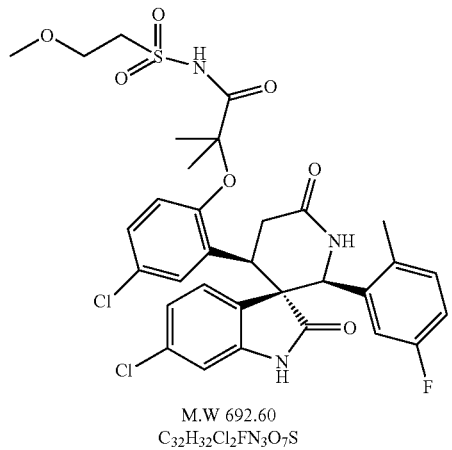

M.W 692.60
C$_{32}$H$_{32}$Cl$_2$FN$_3$O$_7$S

A solution of chiral (2'S,3S,4'R)-6-chloro-4'-[5-chloro-2-(1-hydroxycarbonyl-1-methyl-ethoxy)-phenyl]-2'-(5-fluoro-2-methyl-phenyl)spiro[3H-indole-3,3'-piperidine]-2,6'(1H)-dione (50 mg, 0.09 mmol) prepared in Example 12a and CDI (32 mg, 0.2 mmol) in DMF (2 mL) was heated at 60° C. for 2 h. Then to this solution was added a mixture of 2-methoxy-ethanesulfonic acid amide (139 mg, 1 mmol) and NaH (35 mg, 60%, 0.9 mmol) in DMF (2 mL), which had been stirred at room temperature for 3 h. After the resulting mixture was stirred at room temperature for 1 h, it was poured into water and the aqueous solution was acidified to "pH" 1-2 by addition of concentrated HCl. After the aqueous phase was extracted with EtOAc twice, the combined organic phases were dried over anhydrous Na$_2$SO$_4$, concentrated and the residue was purified by flash column to give the title compound as a white solid (10 mg).
m/z (M+H)$^+$: 692

Example 79a

Preparation of Intermediate 2-(4-chloro-2-formyl-phenoxy)-pentanoic acid ethyl ester

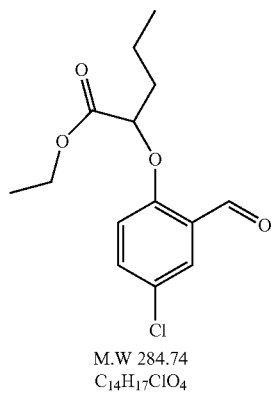

M.W 284.74
C$_{14}$H$_{17}$ClO$_4$

A mixture of 5-chloro-2-hydroxy-benzaldehyde (15 g, 0.1 mol), 2-bromo-pentanoic acid ethyl ester (27 g, 0.13 mol) and K$_2$CO$_3$ (27 g, 0.2 mol) in DMF (100 mL) was heated at 140° C. for 1 h. After cooled to room temperature, the mixture was poured into water and the water phase was extracted with EtOAc thrice. The combined organic layers were washed with water and brine, dried over anhydrous Na$_2$SO$_4$ and concentrated. The residue was purified by flash column to give the title compound as a colorless oil (24 g).

Example 79b

Preparation of Intermediate 2-(4-chloro-2-[1,3]dioxolan-2-yl-phenoxy)-pentanoic acid ethyl ester

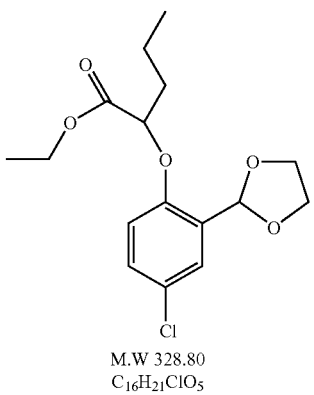

M.W 328.80
C$_{16}$H$_{21}$ClO$_5$

A mixture of 2-(4-chloro-2-formyl-phenoxy)-pentanoic acid ethyl ester (15 g, 53 mmol), ethylene glycol (25 mL, 440 mmol) and p-toluenesulfonic acid (0.8 g, 4.65 mmol) in toluene (150 mL) was refluxed with a Dean-Stark trap attached. After 3 h, the reaction was cooled and washed with water, saturated NaHCO$_3$ solution and water, and the organic layer was dried over anhydrous Na$_2$SO$_4$ and concentrated to give the title compound as a light yellow oil (16 g).

Example 79c

Preparation of Intermediate 2-(4-chloro-2-[1,3]dioxolan-2-yl-phenoxy)-2-propyl pentanoic acid ethyl ester M.W 370.88
C$_{19}$H$_{27}$ClO$_5$ Lithium bis(trimethylsilyl)amide (26 mL, 26 mmol, 1 M in THF) was slowly added to a solution of 2-(4-Chloro-2-[1,3]dioxolan-2-yl-phenoxy)-pentanoic acid ethyl ester (6.6 g, 20 mmol) in anhydrous THF (60 mL) at −78° C. After the mixture was stirred for 30 min at −78° C., 1-iodopropane (4 mL, 40 mmol) was added. The mixture was allowed to warm to room temperature and stirred for 2 h. Then the mixture was diluted with ethyl acetate, washed with a saturated aqueous solution of NH$_4$Cl, and the organic layer was separated, dried over anhydrous Na$_2$SO$_4$ and concentrated to give the title compound as a yellow oil (5 g).

Example 79d

Preparation of Intermediate 2-(4-chloro-2-formyl-phenoxy)-2-propyl-pentanoic acid ethyl ester

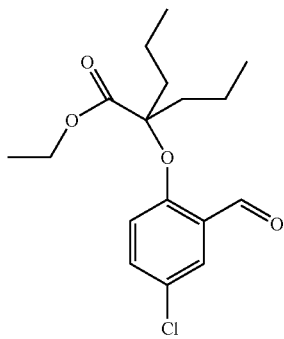

M.W 326.82
C$_{17}$H$_{23}$ClO$_4$

A solution of 2-(4-chloro-2-[1,3]dioxolan-2-yl-phenoxy)-2-propyl-pentanoic acid ethyl ester (15 g, 42 mmol) in TFA (30 mL) was stirred at room temperature overnight. Then the mixture was concentrated and the residue was partitioned between EtOAc and water. The organic layer was washed with NaOH solution (1 N), water, dried over anhydrous Na$_2$SO$_4$ and concentrated to give the title compound (14 g).

Example 79e

Preparation of Intermediate E/Z-2-[4-Chloro-2-(6-chloro-2-oxo-1,2-dihydro-indol-3-ylidenemethyl)-phenoxy]-2-propyl-pentanoic acid ethyl ester

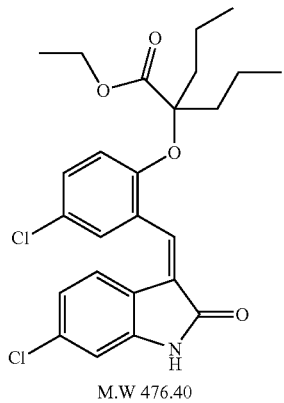

M.W 476.40
C$_{25}$H$_{27}$Cl$_2$NO$_4$

To the mixture of 6-chlorooxindole (9.3 g, 55.7 mmol) and 2-(4-chloro-2-formyl-phenoxy)-2-propyl-pentanoic acid ethyl ester (14 g, 42.9 mmol) in methanol (100 mL) was added pyrrolidine (3.3 g, 47.2 mmol) dropwise. The mixture was then heated at 80° C. for 2 h. After cooled to room temperature, the mixture was concentrated. The residue was purified by flash column to give the title compound (4.2 g).

Example 79f

Preparation of Intermediate E/Z-6-chloro-3-[5-chloro-2-(1-ethoxycarbonyl-1-propyl-butoxy)-benzylidene]-2-oxo-2,3-dihydro-indole-1-carboxylic acid tert-butyl ester

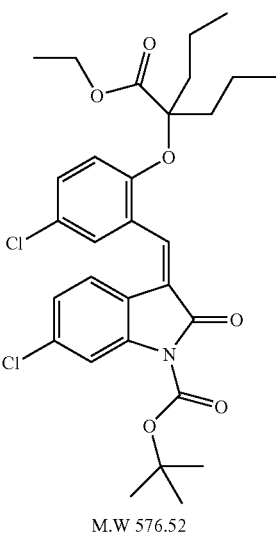

M.W 576.52
C$_{30}$H$_{35}$Cl$_2$NO$_6$

To a solution of E/Z-2-[4-chloro-2-(6-chloro-2-oxo-1,2-dihydro-indol-3-ylidenemethyl)-phenoxy]-2-propyl-pentanoic acid ethyl ester (4.2 g, 8.8 mmol) in dichloromethane (100 mL) at room temperature was added di-tert-butyl-dicarbonate (2.2 g, 9.68 mmol), followed by the addition of 4-dimethylaminopyridine (0.5 g, 4.1 mmol). After the reaction mixture was stirred at room temperature for 1 h, the solution was concentrated. The residue was purified by flash column to give the title compound as a yellow solid (2.6 g).

Example 79g

Preparation of Intermediate racemic (2'S,3S,4'R)-6-chloro-4'-[5-chloro-2-(1-ethoxycarbonyl-1-propyl-butoxy)-phenyl]-2'-(5-chloro-2-methyl-phenyl)spiro[3H-indole-3,3'-piperidine]-2,6'(1H)-dione

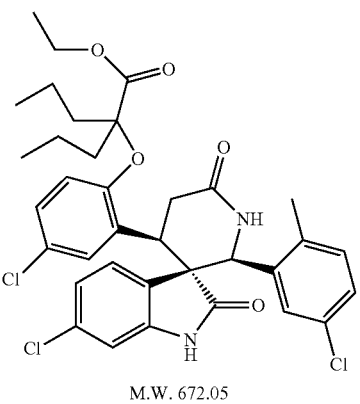

M.W. 672.05
C$_{35}$H$_{37}$Cl$_3$N$_2$O$_5$

In a manner similar to the method described in Example 10d, E/Z-6-chloro-3-[5-chloro-2-(1-ethoxycarbonyl-1-propyl-butoxy)-benzylidene]-2-oxo-2,3-dihydro-indole-1-carboxylic acid tert-butyl ester (1.3 g, 2.3 mmol) was reacted with 1-(5-chloro-2-methyl-phenyl)-3-trimethylsilyoxy-2-aza-1,3-butadiene (10 mmol) prepared in Example 13b in toluene to give the title compound as a white solid (310 mg).
m/z (M+H)$^+$: 671

Example 79h

Preparation of Intermediate racemic (2'S,3S,4'R)-6-chloro-4'-[5-chloro-2-(1-hydroxycarbonyl-1-propyl-butoxy)-phenyl]-2'-(5-chloro-2-methyl-phenyl)spiro[3H-indole-3,3'-piperidine]-2,6'(1H)-dione

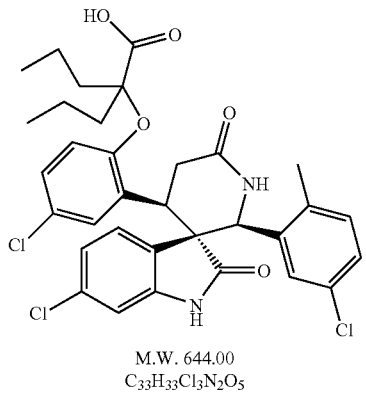

M.W. 644.00
$C_{33}H_{33}Cl_3N_2O_5$

A mixture of racemic (2'S,3S,4'R)-6-chloro-4'-[5-chloro-2-(1-ethoxycarbonyl-1-propyl-butoxy)-phenyl]-2'-(5-chloro-2-methyl-phenyl)spiro[3H-indole-3,3'-piperidine]-2,6'(1H)-dione (280 mg, 0.41 mmol), LiOH.H$_2$O (1 g, 24.6 mmol), H$_2$O (12 mL) and methanol (38 mL) was refluxed for 2 h. After cooled to room temperature, the solution was concentrated and then the mixture was acidified to "pH" 1-2 by addition of concentrated HCl solution and then extracted with EtOAc. The combined organic layers were washed with water and brine, dried over anhydrous Na$_2$SO$_4$ and concentrated to give the title compound as a light yellow solid (220 mg).
m/z (M+H)$^+$: 643

Example 79i

Preparation of Racemic (2'S,3S,4'R)-6-chloro-4'-[5-chloro-2-(1-methanesulfonylaminocarbonyl-1-propyl-butoxy)-phenyl]-2'-(5-chloro-2-methyl-phenyl)-spiro[3H-indole-3,3'-piperidine]-2,6'(1H)-dione

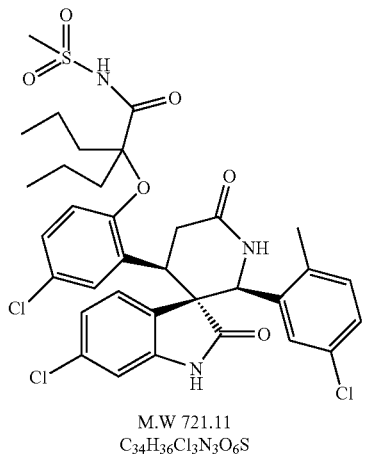

M.W 721.11
$C_{34}H_{36}Cl_3N_3O_6S$

A solution of racemic (2'S,3S,4'R)-6-chloro-4'-[5-chloro-2-(1-hydroxycarbonyl-1-propyl-butoxy)-phenyl]-2'-(5-chloro-2-methyl-phenyl)spiro[3H-indole-3,3'-piperidine]-2,6'(1H)-dione (140 mg, 0.22 mmol) and CDI (70 mg, 0.44 mmol) in DMF (2 mL) was heated at 60° C. for 2 h. Then to this solution was added a mixture of methanesulfonamide (207 mg, 2.2 mmol) and NaH (78 mg, 60%, 2 mmol) in DMF (2 mL), which had been stirred at room temperature for 2 h. After the resulting mixture was stirred at room temperature for 1 h, it was poured into water and the mixture was acidified to "pH" 1-2 by addition of concentrated HCl solution. After the aqueous phase was extracted with EtOAc twice, the combined organic layers were dried over anhydrous Na$_2$SO$_4$, concentrated and the residue was purified by flash column to give the title compound as a white solid (100 mg).
m/z (M+H)$^+$: 720

Example 79j

Preparation of Chiral (2'S,3S,4'R)-6-chloro-4'-[5-chloro-2-(1-methanesulfonylaminocarbonyl-1-propyl-butoxy)-phenyl]-2'-(5-chloro-2-methyl-phenyl)-spiro[3H-indole-3,3'-piperidine]-2,6'(1H)-dione

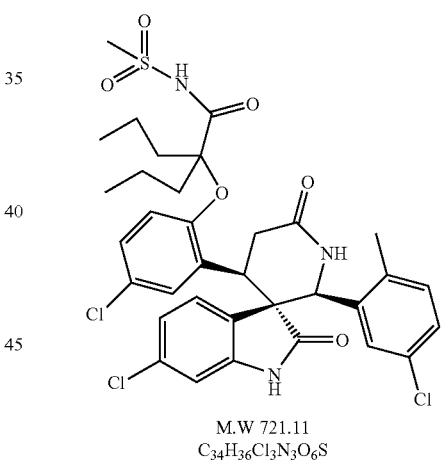

M.W 721.11
$C_{34}H_{36}Cl_3N_3O_6S$

Separation of the two enantiomers from racemic (2'S,3S,4'R)-6-chloro-4'-[5-chloro-2-(1-methanesulfonylaminocarbonyl-1-propyl-butoxy)-phenyl]-2'-(5-chloro-2-methyl-phenyl)-spiro[3H-indole-3,3'-piperidine]-2,6'(1H)-dione (50 mg), was conducted by chiral SFC to provide chiral (2'S,3S,4'R)-6-chloro-4'-[5-chloro-2-(1-methanesulfonylaminocarbonyl-1-propyl-butoxy)-phenyl]-2'-(5-chloro-2-methyl-phenyl)-spiro[3H-indole-3,3'-piperidine]-2,6'(1H)-dione as a white solid (25 mg) and chiral (2'R, 3R, 4'S)-6-chloro-4'-[5-chloro-2-(1-methanesulfonylaminocarbonyl-1-propyl-butoxy)-phenyl]-2'-(5-chloro-2-methyl-phenyl)-spiro[3H-indole-3,3'-piperidine]-2,6'(1H)-dione as a white solid (11 mg).
m/z (M+H)$^+$: 720

Example 80a

Preparation of Intermediate racemic (2'S,3S,4'R)-4'-[5-chloro-2-(1-ethoxycarbonyl-1-propyl-butoxy)-phenyl]-6-chloro-2'-(5-fluoro-2-methyl-phenyl)spiro[3H-indole-3,3'-piperidine]-2,6'(1H)-dione

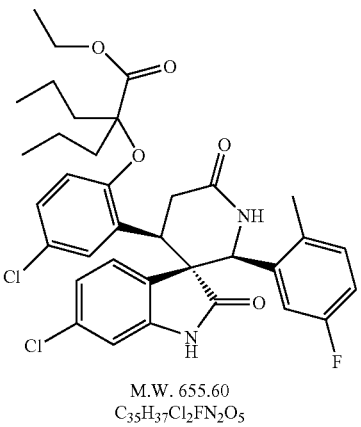

M.W. 655.60
$C_{35}H_{37}Cl_2FN_2O_5$

In a manner similar to the method described in Example 10d, E/Z-6-chloro-3-[5-chloro-2-(1-ethoxycarbonyl-1-propyl-butoxy)-benzylidene]-2-oxo-2,3-dihydro-indole-1-carboxylic acid tert-butyl ester (1.3 g, 2.3 mmol) was reacted with 1-(5-fluoro-2-methyl-phenyl)-3-trimethylsilyoxy-2-aza-1,3-butadiene (10 mmol) prepared in Example 1d in toluene to give the title compound as a white solid (150 mg).

m/z (M+H)$^+$: 655

Example 80b

Preparation of Intermediate racemic (2'S,3S,4'R)-6-chloro-4'-[5-chloro-2-(1-hydroxycarbonyl-1-propyl-butoxy)-phenyl]-2'-(5-fluoro-2-methyl-phenyl)spiro[3H-indole-3,3'-piperidine]-2,6'(1H)-dione

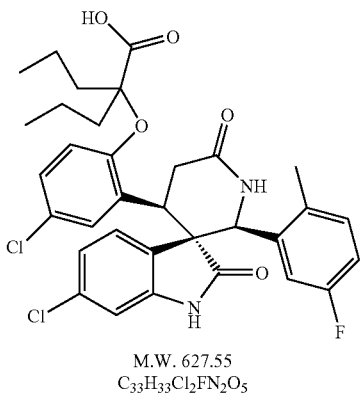

M.W. 627.55
$C_{33}H_{33}Cl_2FN_2O_5$

A mixture of racemic (2'S,3S,4'R)-6-chloro-4'-[5-chloro-2-(1-ethoxycarbonyl-1-propyl-butoxy)-phenyl]-2'-(5-fluoro-2-methyl-phenyl)spiro[3H-indole-3,3'-piperidine]-2,6'(1H)-dione (130 mg, 0.198 mmol), LiOH.H$_2$O (1 g, 24.6 mmol), H$_2$O (5 mL) and methanol (15 mL) was refluxed for 2 h. After cooled to room temperature, the solution was concentrated and then the water phase was acidified to "pH" 1-2 by addition of concentrated HCl solution and then extracted with EtOAc. The combined organic layers were washed with water and brine, dried over anhydrous Na$_2$SO$_4$ and concentrated to give the title compound as a light yellow solid (115 mg).

m/z (M+H)$^+$: 627

Example 80c

Preparation of Racemic (2'S,3S,4'R)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione

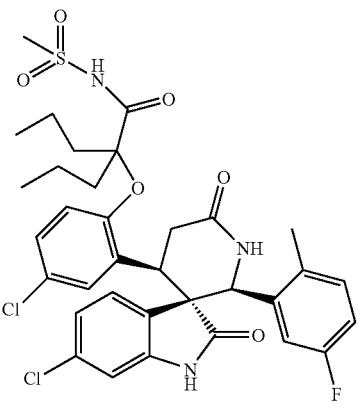

M.W 704.65
$C_{34}H_{36}Cl_2FN_3O_6S$

A solution of racemic (2'S,3S,4'R)-6-chloro-4'-[5-chloro-2-(1-hydroxycarbonyl-1-propyl-butoxy)-phenyl]-2'-(5-fluoro-2-methyl-phenyl)spiro[3H-indole-3,3'-piperidine]-2,6'(1H)-dione (80 mg, 0.13 mmol) and CDI (40 mg, 0.25 mmol) in DMF (2 mL) was heated at 60° C. for 2 h. Then to this solution was added a mixture of methanesulfonamide (123 mg, 1.3 mmol) and NaH (52 mg, 60%, 1.3 mmol) in DMF (2 mL), which had been stirred at room temperature for 2 h. After the resulting mixture was stirred at room temperature for 1 h, it was poured into water and the aqueous solution was acidified by concentrated HCl solution. After the aqueous phase was extracted with EtOAc twice, the combined organic layers were dried over anhydrous Na$_2$SO$_4$, concentrated and the residue was purified by flash column to give the title compound as a white solid (60 mg).

m/z (M+H)$^+$: 704

Example 80d

Preparation of Chiral (2'S,3S,4'R)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione

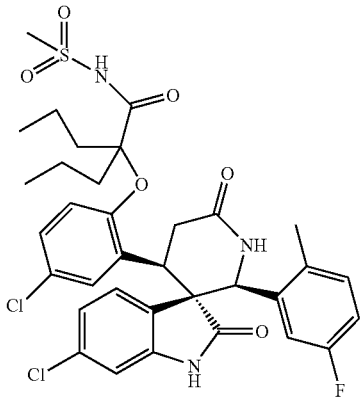

M.W 704.65
$C_{34}H_{36}Cl_2FN_3O_6S$

Separation of the two enantiomers from racemic (2'S,3S,4'R)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione (50 mg), was conducted by chiral SFC to provide chiral (2'S,3S,4'R)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione as a white solid (13 mg) (RO5315395-000) and chiral (2'R,3R,4'S)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione as a white solid (11 mg) (RO5315396-000).

m/z (M+H)$^+$: 704

Example 81a

Preparation of Intermediate E/Z-2-{2-[6-bromo-2-oxo-1,2-dihydro-indol-(3E)-ylidenemethyl]-4-chloro-phenoxy}-2-ethyl-butyric acid methyl ester

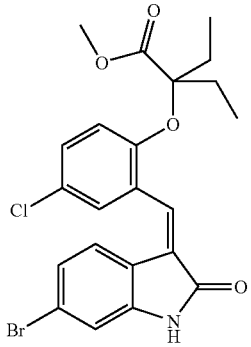

M.W 478.77
$C_{22}H_{21}BrClNO_4$

To the mixture of 6-bromooxindole (10.5 g, 49.7 mmol) and 2-(4-chloro-2-formyl-phenoxy)-2-ethyl-butyric acid methyl ester (13 g, 45.8 mmol) prepared in Example 62d in methanol (200 mL) was added pyrrolidine (4.1 mL, 49.7 mmol) dropwise. The mixture was then heated at 70° C. for 2 h. After cooled to room temperature, the mixture was filtered and the precipitate was collected, dried to give the title compound as a yellow solid (16 g).

Example 81b

Preparation of Intermediate E/Z-6-bromo-3-[1-[5-chloro-2-(1-ethyl-1-methoxycarbonyl-propoxy)-phenyl]-meth-(E)-ylidene]-2-oxo-2,3-dihydro-indole-1-carboxylic acid tert-butylester

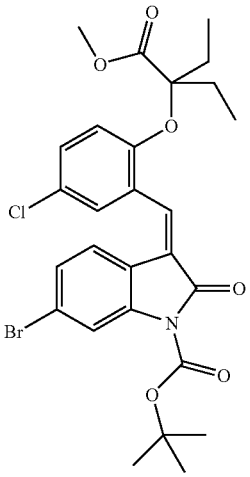

M.W. 578.89
$C_{27}H_{29}BrClNO_6$

To a solution of E/Z-2-{2-[6-bromo-2-oxo-1,2-dihydro-indol-(3E)-ylidenemethyl]-4-chloro-phenoxy}-2-ethyl-butyric acid methyl ester (16 g, 33.5 mmol) in dichloromethane (200 mL) at room temperature was added di-tert-butyl-dicarbonate (8.6 g, 39 mmol), followed by the addition of 4-dimethylaminopyridine (0.4 g, 3.3 mmol). After the reaction mixture was stirred at room temperature for 1 h, the solution was washed with 1 M HC and brine twice, dried over anhydrous $Na_2SO_4$ and concentrated to give the title compound as a yellow solid (16 g).

Example 81c

Preparation of Intermediate racemic (2'S,3S,4'R)-6-bromo-4'-[5-chloro-2-(1-ethyl-1-methoxycarbonyl-propoxy)-phenyl]-2'-(5-fluoro-2-methyl-phenyl)spiro[3H-indole-3,3'-piperidine]-2,6'(1H)-dione

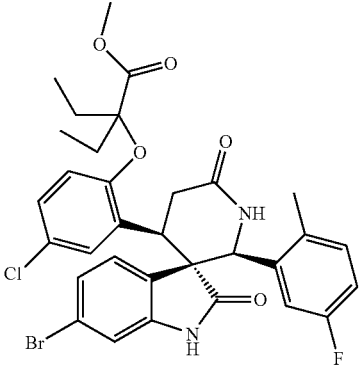

M.W. 657.97
$C_{32}H_{31}BrClFN_2O_5$

In a manner similar to the method described in Example 10d, E/Z-6-bromo-3-[1-[5-chloro-2-(1-ethyl-1-methoxycarbonyl-propoxy)-phenyl]-meth-(E)-ylidene]-2-oxo-2,3-dihydro-indole-1-carboxylic acid tert-butylester (6 g, 10 mmol) was reacted with 1-(5-fluoro-2-methyl-phenyl)-3-trimethylsilyoxy-2-aza-1,3-butadiene (40 mmol) in toluene to give the title compound as a white solid (1.2 g).

m/z (M+H)$^+$: 657

Example 81d

Preparation of Intermediate racemic (2'S,3S,4'R)-6-bromo-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione

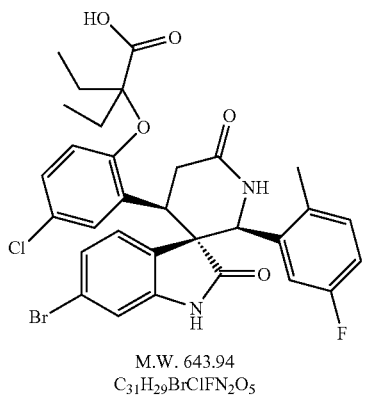

M.W. 643.94
C₃₁H₂₉BrClFN₂O₅

A mixture of racemic (2'S,3S,4'R)-6-bromo-4'-[5-chloro-2-(1-ethyl-1-methoxycarbonyl-propoxy)-phenyl]-2'-(5-fluoro-2-methyl-phenyl)spiro[3H-indole-3,3'-piperidine]-2,6'(1H)-dione (1.2 g, 1.8 mmol), LiOH.H₂O (1.5 g, 36 mmol), H₂O (3 mL) and methanol (10 mL) was refluxed for 2 h. After cooled to room temperature, the solution was concentrated. The water phase was acidified to "pH" 2-3 by addition of concentrated HCl solution and extracted with EtOAc. The combined organic phases were washed with water and brine, dried over anhydrous Na₂SO₄ and concentrated. The residue was washed with methanol to give the title compound (660 mg).

m/z (M+H)⁺: 643

Example 81e

Preparation of Racemic (2'S,3S,4'R)-6-bromo-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione

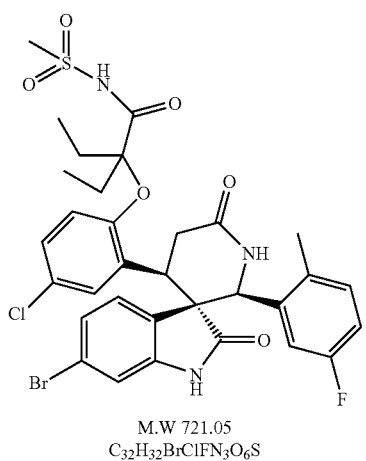

M.W 721.05
C₃₂H₃₂BrClFN₃O₆S

A solution of racemic (2'S,3S,4'R)-6-bromo-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione (480 mg, 0.75 mmol) and CDI (242 mg, 1.5 mmol) in DMF (5 mL) was heated at 60° C. for 2 h. Then to this solution was added a mixture of methanesulfonamide (712 mg, 7.5 mmol) and NaH (300 mg, 60%, 7.5 mmol) in DMF (5 mL), which had been stirred at room temperature for 2 h. After the resulting mixture was stirred at room temperature for 1 h, it was poured into water and the aqueous solution was acidified by concentrated HCl solution. After the aqueous phase was extracted with EtOAc twice, the combined organic layers were dried over anhydrous Na₂SO₄, concentrated and the residue was purified by flash column to give the title compound as a white solid (300 mg).

m/z (M+H)⁺: 720

Example 82a

Preparation of Intermediate 5-chloro-2-methylsulfanylmethoxy-benzaldehyde

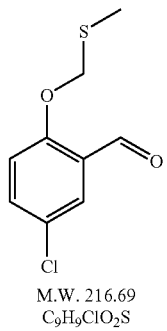

M.W. 216.69
C₉H₉ClO₂S

A mixture of 5-chloro-2-hydroxy-benzaldehyde (15.6 g, 0.1 mol), chloro-methylsulfanyl-methane (9.6 g, 0.1 mol), K₂CO₃ (14 g, 0.1 mol) and KI (1 g, 0.006 mol) in DMF (70 mL) was heated at 70° C. for 2 h. After cooled to the room temperature, the mixture was poured into ice water. The aqueous phase was extracted with diethyl ether. The combined organic layers were washed with NaOH solution (1 N), dried over anhydrous Na₂SO₄ and concentrated to give the title compound as a yellow oil (14.2 g).

Example 82b

Preparation of Intermediate 5-chloro-2-methanesulfonylmethoxy-benzaldehyde

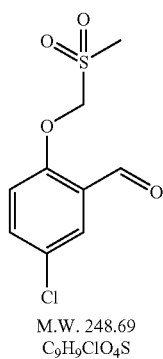

M.W. 248.69
C₉H₉ClO₄S

At 0° C., to a solution of 5-Chloro-2-methylsulfanyl-methoxy-benzaldehyde (4.32 g, 20 mmol) in DCM (100 mL) was added m-CPBA (10 g, 77%, 40 mmol) slowly. The solution was stirred at room temperature for 1 h. Then the solution was washed with saturated K₂CO₃ solution, 1N NaOH solution, dried over anhydrous Na₂SO₄ and concentrated. The residue was purified by flash column to give 5-chloro-2-methanesulfonylmethoxy-benzaldehyde as a white solid (2.78 g).

Example 82c

Preparation of Intermediate E/Z-6-chloro-3-(5-chloro-2-methanesulfonylmethoxy-benzylidene)-1,3-dihydro-indol-2-one

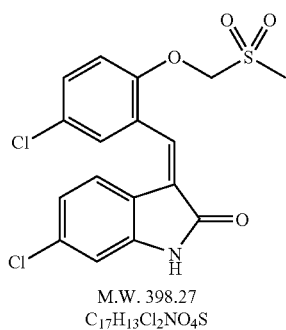

M.W. 398.27
C₁₇H₁₃Cl₂NO₄S

In a manner similar to the method described in Example 9b, 5-chloro-2-methanesulfinylmethoxy-benzaldehyde (1.25 g, 5 mmol) was reacted with 6-chlorooxindole (0.9 g, 5.4 mmol) and pyrrolidine (0.5 mL, 6.1 mmol) in methanol (50 mL) to give the title compound as a yellow solid (1.8 g).

Example 82d

Preparation of Intermediate E/Z-6-chloro-3-(5-chloro-2-methanesulfonylmethoxy-benzylidene)-2-oxo-2,3-dihydro-indole-1-carboxylic acid tert-butyl ester

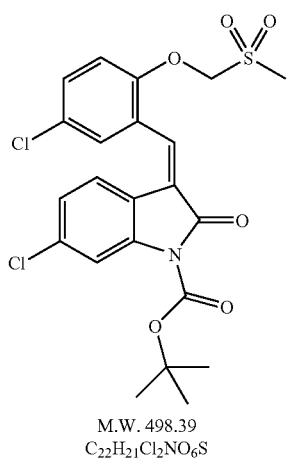

M.W. 498.39
C₂₂H₂₁Cl₂NO₆S

In a manner similar to the method described in Example 9c, E/Z-6-chloro-3-(5-chloro-2-methanesulfonylmethoxy-benzylidene)-1,3-dihydro-indol-2-one (1.0 g, 2.5 mmol) was reacted with Di-tert-butyl-dicarbonate (0.6 g, 2.8 mmol) and 4-dimethylaminopyridine (0.1 g, 0.8 mmol) in CH₂Cl₂ to give the title compound as a yellow solid (1.2 g).

Example 82e

Preparation of Intermediate racemic (2'S,3S,4'R)-6-chloro-4'-(5-chloro-2methanesulfonylmethoxy-phenyl)-2'-(5-fluoro-2-methyl-phenyl)spiro[3H-indole-3,3'-piperidine]-2,6'(1H)-dione

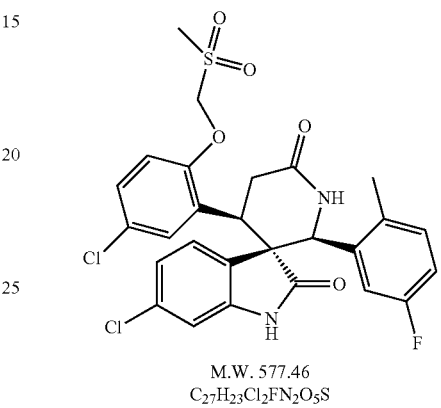

M.W. 577.46
C₂₇H₂₃Cl₂FN₂O₅S

In a manner similar to the method described in Example 10d, E/Z-6-chloro-3-(5-chloro-2-methanesulfonylmethoxy-benzylidene)-2-oxo-2,3-dihydro-indole-1-carboxylic acid tert-butyl ester (600 mg, 1.2 mmol) was reacted with 1-(5-fluoro-2-methyl-phenyl)-3-trimethylsilyoxy-2-aza-1,3-butadiene (5 mmol) in toluene to give the title compound as a white solid (40 mg).

m/z (M+H)⁺: 577

Example 83a

Preparation of Intermediate 5-chloro-2-methanesulfinylmethoxy-benzaldehyde

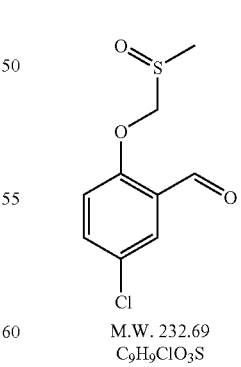

M.W. 232.69
C₉H₉ClO₃S

In the preparation of 5-chloro-2-methanesulfonyl-methoxy-benzaldehyde as described in Example 82b, a second product 5-chloro-2-methanesulfinylmethoxy-benzaldehyde was obtained as a light yellow solid (0.62 g).

Example 83b

Preparation of Intermediate E/Z-6-chloro-3-(5-chloro-2-methanesulfinylmethoxy-benzylidene)-1,3-dihydro-indol-2-one

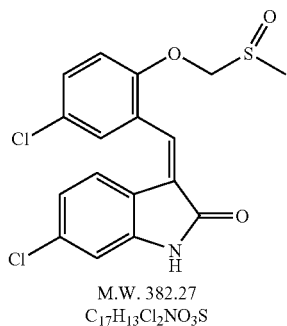

M.W. 382.27
$C_{17}H_{13}Cl_2NO_3S$

In a manner similar to the method described in Example 9b, 5-chloro-2-methanesulfinylmethoxy-benzaldehyde (0.4 g, 1.72 mmol) was reacted with 6-chlorooxindole (0.31 g, 1.86 mmol) and pyrrolidine (0.13 g, 1.86 mmol) in methanol (10 mL) to give the title compound as a yellow solid (0.6 g).

Example 83c

Preparation of Intermediate E/Z-6-chloro-3-(5-chloro-2-methanesulfinylmethoxy-benzylidene)-2-oxo-2,3-dihydro-indole-1-carboxylic acid tert-butyl ester

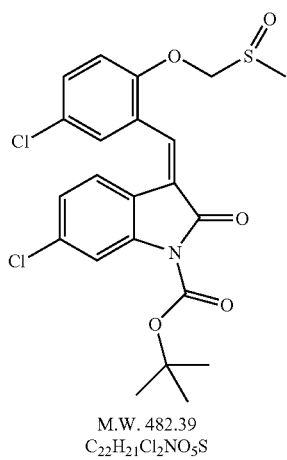

M.W. 482.39
$C_{22}H_{21}Cl_2NO_5S$

In a manner similar to the method described in Example 9c, E/Z-6-chloro-3-(5-chloro-2-methanesulfinylmethoxy-benzylidene)-1,3-dihydro-indol-2-one (400 mg, 1.05 mmol) was reacted with di-tert-butyl-dicarbonate (300 mg, 1.39 mmol) and 4-dimethylaminopyridine (50 mg, 0.41 mmol) in $CH_2Cl_2$ to give the title compound as a yellow solid (500 mg).

Example 83d

Preparation of Racemic (2'S,3S,4'R)-6-chloro-4'-(5-chloro-2-methanesulfinylmethoxy-phenyl)-2'-(5-fluoro-2-methyl-phenyl)spiro[3H-indole-3,3'-piperidine]-2,6'(1H)-dione

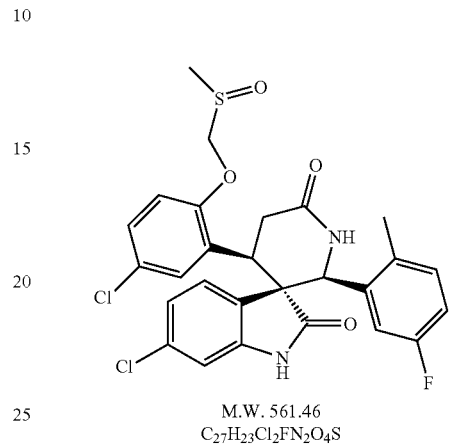

M.W. 561.46
$C_{27}H_{23}Cl_2FN_2O_4S$

In a manner similar to the method described in Example 10d, E/Z-6-chloro-3-(5-chloro-2-methanesulfinylmethoxy-benzylidene)-2-oxo-2,3-dihydro-indole-1-carboxylic acid tert-butyl ester (400 mg, 0.83 mmol) was reacted with 1-(5-fluoro-2-methyl-phenyl)-3-trimethylsilyoxy-2-aza-1,3-butadiene (5 mmol) in toluene to give the title compound as a white solid (45 mg).

m/z (M+H)$^+$: 561

Example 84a

Preparation of Intermediate N-tert-butyl-C-chloro-methanesulfonamide

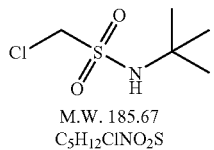

M.W. 185.67
$C_5H_{12}ClNO_2S$

At 0° C., to a mixture of tert-butylamine (10.3 g, 141 mmol) and N-methylmorpholine (14.9 g, 147 mmol) in diethyl ether (200 mL) was added dropwise a solution of chloromethanesulfonyl chloride (20 g, 134 mmol) in diethyl ether (400 mL). After stirred for 5 h, the solution was diluted with ethyl acetate (200 mL). The organic phase was washed with HCl solution (1 N), water and brine, dried over anhydrous $Na_2SO_4$ and concentrated to give the title compound as a colorless oil (16 g).

Example 84b

Preparation of Intermediate N-tert-butyl-C-(4-chloro-2-formyl-phenoxy)-methanesulfonamide

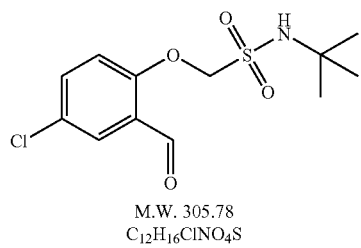

M.W. 305.78
C$_{12}$H$_{16}$ClNO$_4$S

A mixture of 5-chloro-2-hydroxy-benzaldehyde (13.9 g, 89.2 mmol), K$_2$CO$_3$ (24.6 g, 178.3 mmol) and N-tert-butyl-C-chloro-methanesulfonamide (16.5 g, 89.2 mmol) in DMF (20 mL) was heated at 60° C. overnight. After cooled to room temperature, the mixture was neutralized by addition of aqueous HCl solution and extracted with ethyl acetate. The organic phase was washed with water, brine, dried over anhydrous Na$_2$SO$_4$ and concentrated to give the crude product. The crude product was washed with diethyl ether to give the title compound (13.5 g).

Example 84c

Preparation of Intermediate E/Z—N-tert-butyl-C-[4-chloro-2-(6-chloro-2-oxo-1,2-dihydro-indol-3-ylidenemethyl)-phenoxy]-methanesulfonamide

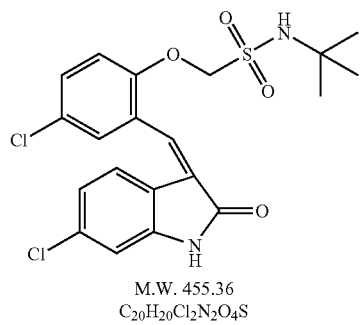

M.W. 455.36
C$_{20}$H$_{20}$Cl$_2$N$_2$O$_4$S

To the mixture of 6-chlorooxindole (3.05 g, 10 mmol) and N-tert-butyl-C-(4-chloro-2-formyl-phenoxy)-methanesulfonamide (1.65 g, 10 mmol)) in methanol (20 mL) was added pyrrolidine (1.41 g, 20 mmol) dropwise. The mixture was then heated at 70° C. for 1 h. After cooled to 4° C., the mixture was filtered and the precipitate was collected, dried to give the title compound (4 g).

Example 84d

Preparation of Intermediate E/Z-3-[2-(tert-butylsulfamoyl-methoxy)-5-chloro-benzylidene]-6-chloro-2-oxo-2,3-dihydro-indole-1-carboxylic acid tert-butyl ester

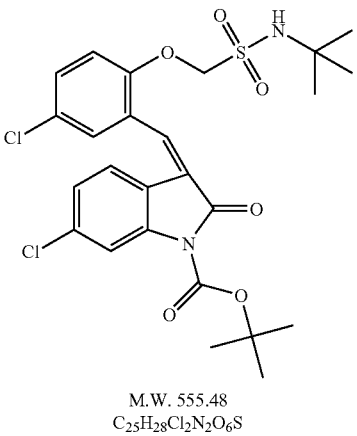

M.W. 555.48
C$_{25}$H$_{28}$Cl$_2$N$_2$O$_6$S

To a solution of N-tert-butyl-C-[4-chloro-2-(6-chloro-2-oxo-1,2-dihydro-indol-3-ylidenemethyl)-phenoxy]-methanesulfonamide (4 g, 8.79 mmol) in dichloromethane (50 mL) at r.t was added di-tert-butyl-dicarbonate (6.54 g, 30 mmol), followed by the addition of 4-dimethylaminopyridine (3.66 g, 30 mmol). After stirred at room temperature overnight, the mixture was concentrated. The residue was purified by column chromatography to give the title compound as a yellow solid (3.8 g).

Example 84e

Preparation of Intermediate racemic (2'S,3S,4'R)-[2-(tert-butylsulfamoyl-methoxy)-5-chloro-phenyl]-6-chloro-2'-(5-fluoro-2-methyl-phenyl)-2,3-dihydro-4'-2,6'-dioxo spiro[indole-3,3'-piperidine]-1-carboxylic acid tert-butyl ester

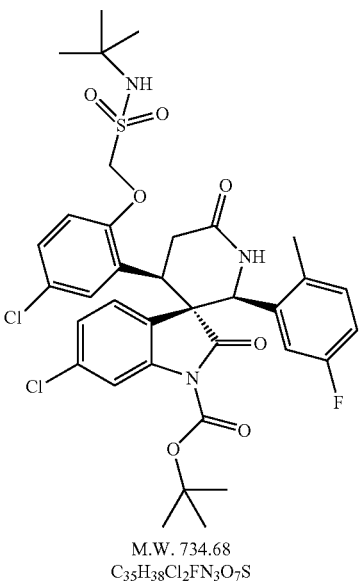

M.W. 734.68
C$_{35}$H$_{38}$Cl$_2$FN$_3$O$_7$S

To a toluene solution of 1-(5-fluoro-2-methylphenyl)-3-trimethylsilyoxy-2-aza-1,3-butadiene (10.8 mmol) prepared in Example 1d was added E/Z-3-[2-(tert-butylsufamoyl-methoxy)-5-chloro-benzylidene]-6-chloro-2-oxo-2,3-dihydro-indole-1-carboxylic acid tert-butyl ester (2 g, 3.61 mmol). After stirred at room temperature for 4 h, methanol was added. The stirring was continued for 1 h and the white solid was precipitated from the solvent. The precipitate was filtered and washed with diethyl ether to give the title compound (1.3 g).

Example 84f

Preparation of Racemic (2'S,3S,4'R)-[2-(tert-butyl-sulfamoyl-methoxy)-5-chloro-phenyl]-6-chloro-2'-(5-fluoro-2-methyl-phenyl)spiro[3H-indole-3,3'-piperidine]-2,6'(1H)-dione

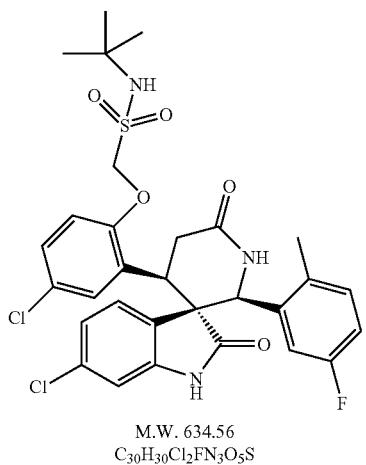

M.W. 634.56
C$_{30}$H$_{30}$Cl$_2$FN$_3$O$_5$S

At room temperature, TFA (114 mg, 1 mmol) was added a solution of racemic (2'S,3S,4'R)-[2-(tert-butylsulfamoyl-methoxy)-5-chloro-phenyl]-6-chloro-2'-(5-fluoro-2-methyl-phenyl)-2,6'-dioxo spiro[indole-3,3'-piperidine]-1-carboxylic acid tert-butyl ester in DCM (2 mL). Then the mixture was heated at 40° C. for 3 h. After cooled to room temperature, the mixture was concentrated and EtOAc was added. The precipitate was collected and dried to give the title compound (65 mg).

Example 85a

Preparation of Intermediate (tetrahydro-pyran-4-yl)-methanol

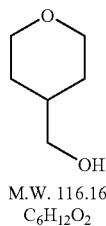

M.W. 116.16
C$_6$H$_{12}$O$_2$

At 0° C., to a solution of 4-tetrahydropyran carboxylic acid methyl ester (28.83 g, 0.2 mol) in THF (200 mL) was added LiAlH$_4$ (7.6 g, 0.2 mol) in several portions. After stirred for 2 h, the reaction was quenched with water slowly. Then diethyl ether (300 mL) was added and the mixture was filtered. The filtrate was washed with 2 N HCl and brine, dried and concentrated to give the title compound as a yellow oil (12.8 g).

Example 85b

Preparation of Intermediate toluene-4-sulfonic acid tetrahydro-pyran-4-ylmethyl ester

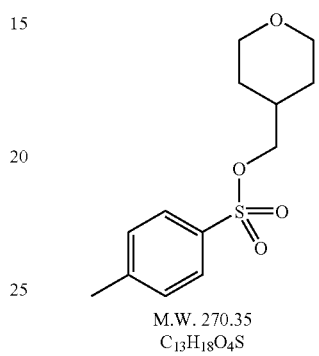

M.W. 270.35
C$_{13}$H$_{18}$O$_4$S

At room temperature, a mixture of (tetrahydro-pyran-4-yl)-methanol (2.4 g, 20.7 mmol), p-toluenesulfonyl chloride (6.73 g, 35.4 mmol), triethylamine (6.6 mL, 47.6 mmol) and DMAP (0.288 g, 2.36 mmol) in DCM (50 mL) was stirred overnight. The solution was washed with water and brine, dried over anhydrous Na$_2$SO$_4$ and concentrated. The residue was purified by column chromatography to give the title compound as an oil (4.2 g).

Example 85c

Preparation of Intermediate 5-chloro-2-(tetrahydro-pyran-4-yl-methoxy)-benzaldehyde

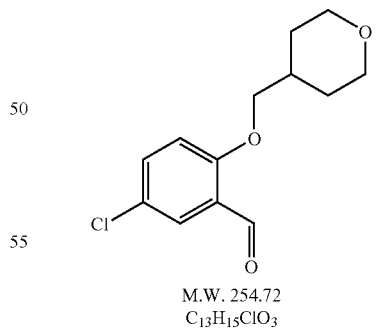

M.W. 254.72
C$_{13}$H$_{15}$ClO$_3$

A mixture of 5-chlorosalicylaldehyde (5.0 g, 32 mmol), toluene-4-sulfonic acid tetrahydro-pyran-4-ylmethyl ester (8.6 g, 32 mmol) and K$_2$CO$_3$ (9.5 g, 68.8 mmol) in DMF (50 mL) was heated at 75° C. overnight. After cooled to room temperature, the mixture was poured into water. The aqueous phase was extracted with EtOAc twice. The combined organic phases were washed with water and brine, dried and concentrated. The residue was purified by column chromatography to give the title compound (7.0 g).

Example 85d

Preparation of Intermediate E/Z-6-chloro-3-[5-chloro-2-(tetrahydro-pyran-4-ylmethoxy)benzylidene]-1,3-dihydro-indol-2-one

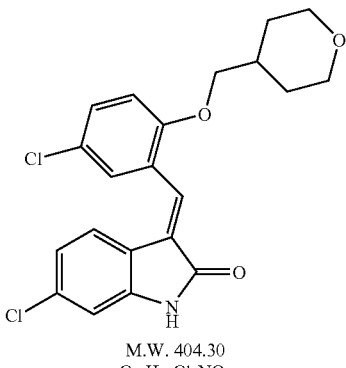

M.W. 404.30
C$_{21}$H$_{19}$Cl$_2$NO$_3$

To the mixture of 6-xhlorooxindole (0.96 g, 5.7 mmol) and 5-chloro-2-(tetrahydro-pyran-4-yl-methoxy)-benzaldehyde (2.03 g, 8.0 mmol) in methanol (90 mL) was added pyrrolidine (0.67 mL, 8.0 mmol) dropwise. Then the mixture was heated at 100° C. for 2 h. After cooled to room temperature, the mixture was filtered and the precipitate was collected, dried to give the title compound as a yellow solid (1.81 g).

Example 85e

Preparation of Intermediate E/Z-1-(1-tert-butoxy-vinyl)-6-chloro-3-[5-chloro-2-(tetrahydro-pyran-4-ylmethoxy)-benzylidene]-1,3-dihydro-indol-2-one

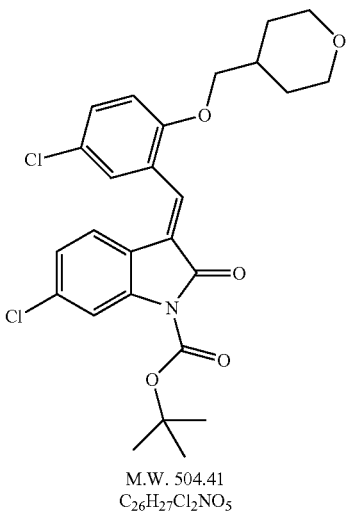

M.W. 504.41
C$_{26}$H$_{27}$Cl$_2$NO$_5$

To a solution of E/Z-6-chloro-3-[5-chloro-2-(tetrahydro-pyran-4-ylmethoxy)-benzylidene]-1,3-dihydro-indol-2-one (1.69 g, 4.2 mmol) in dichloromethane (25 mL) at room temperature was added di-tert-butyl-dicarbonate (1.83 g, 8.4 mmol), followed by the addition of 4-dimethylaminopyridine (1.23 g, 10.1 mmol). After the reaction mixture was stirred at room temperature for 1 h, the solution concentrated. The residue was purified by column chromatography to give the title compound as a brown solid (2.02 g).

Example 85f

Preparation of Intermediate racemic (2'S,3S,4'R)-6-chloro-4'-[5-chloro-2-(tetrahydro-pyran-4-ylmethoxy)-phenyl]-2'-(5-fluoro-2-methyl-phenyl)spiro[3H-indole-3,3'-piperidine]-2,6'(1H)-dione

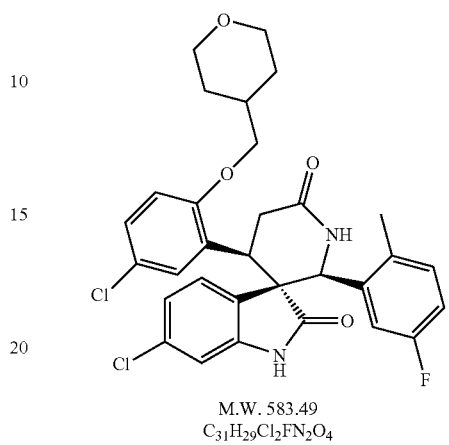

M.W. 583.49
C$_{31}$H$_{29}$Cl$_2$FN$_2$O$_4$

In a manner similar to the method described in Example 10d, E/Z-1-(1-tert-butoxy-vinyl)-6-chloro-3-[5-chloro-2-(tetrahydro-pyran-4-ylmethoxy)-benzylidene]-1,3-dihydro-indol-2-one (2 g, 3.97 mmol) was reacted with 1-(5-fluoro-2-methyl-phenyl)-3-trimethylsilyoxy-2-aza-1,3-butadiene (20 mmol) in toluene to give the title compound as a white solid (770 mg).

m/z (M+H)$^+$: 583

Example 86a

Preparation of Intermediate of E/Z-2-[4-chloro-2-(6-chloro-5-fluoro-2-oxo-1,2-dihydro-indol-3-ylidenemethyl)-phenoxy]-2-ethyl-butyric acid methyl ester

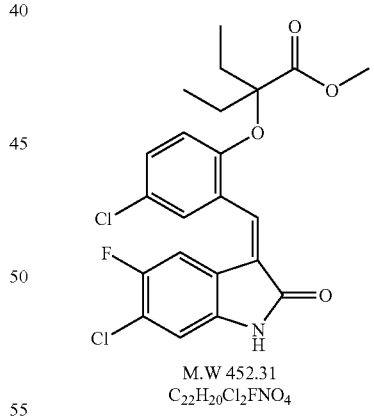

M.W 452.31
C$_{22}$H$_{20}$Cl$_2$FNO$_4$

To the mixture of 6-chloro-5-fluoro-1,3-dihydro-indol-2-one (500 mg, 2.7 mmol) and 2-(4-chloro-2-formyl-phenoxy)-2-ethyl-butyric acid methyl ester (844 mg, 2.97 mmol) in methanol (5 mL) was added pyrrolidine (95 mg, 1.35 mmol) dropwise. The mixture was then heated at 70° C. for 1 h. After cooled to room temperature, the mixture was partitioned between EtOAc and diluted HCl solution. The organic phase was washed with water, brine, dried over anhydrous Na$_2$SO$_4$ and concentrated to give the crude product as a red-yellow solid, which was used for the next step reaction without further purification.

Example 86b

Preparation of Intermediate E/Z-6-chloro-3-[5-chloro-2-(1-ethyl-1-methoxycarbonylpropoxy)-benzylidene]-5-fluoro-2-oxo-2,3-dihydro-indole-1-carboxylic acid tert-butyl ester

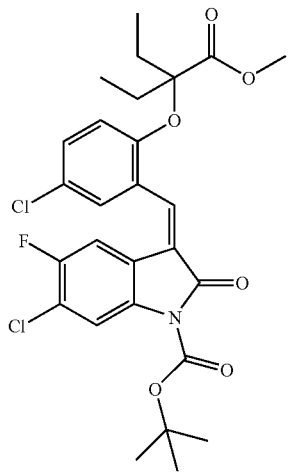

M.W. 552.43
$C_{27}H_{28}Cl_2FNO_6$

To a solution of E/Z-2-[4-chloro-2-(6-chloro-5-fluoro-2-oxo-1,2-dihydro-indol-3-ylidenemethyl)-phenoxy]-2-ethyl-butyric acid methyl ester (1.22 g, 2.7 mmol) in dichloromethane (10 mL) at room temperature was added di-tert-butyl-dicarbonate (0.7 g, 3.24 mmol), followed by the addition of 4-dimethylaminopyridine (0.05 g, 0.41 mmol). After the reaction mixture was stirred at room temperature for 1 h, the solution was concentrated. The residue was purified by flash column to give the title compound as a yellow solid (1.4 g).

Example 86c

Preparation of Intermediate racemic (2'S,3S,4'R)-6-chloro-4'-[5-chloro-2-(1-methoxycarbonyl-1-ethyl-propoxy)-phenyl]-5-fluoro-2'-(5-fluoro-2-methyl-phenyl)spiro[3H-indole-3,3'-piperidine]-2,6'(1H)-dione

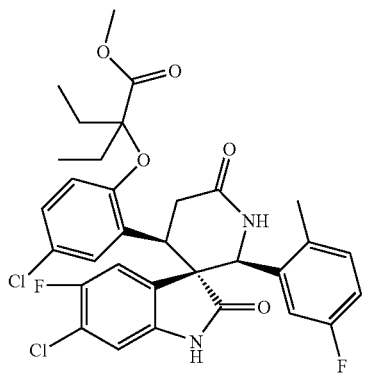

M.W. 631.51
$C_{32}H_{30}Cl_2F_2N_2O_5$

In a manner similar to the method described in Example 10d, E/Z-6-chloro-3-[5-chloro-2-(1-ethyl-1-methoxycarbonyl-propoxy)-benzylidene]-5-fluoro-2-oxo-2,3-dihydro-indole-1-carboxylic acid tert-butyl ester (1.4 g, 2.5 mmol) was reacted with 1-(5-fluoro-2-methyl-phenyl)-3-trimethylsilyloxy-2-aza-1,3-butadiene (8 mmol) in toluene (8 mL) to give the title compound (300 mg).

m/z (M+H)+: 631

Example 86d

Preparation of Intermediate racemic (2'S,3S,4'R)-6-chloro-5-fluoro-4'-[5-chloro-2-(1-hydroxycarbonyl-1-ethyl-propoxy)-phenyl]-2'-(5-fluoro-2-methyl-phenyl)spiro[3H-indole-3,3'-piperidine]-2,6'(1H)-dione

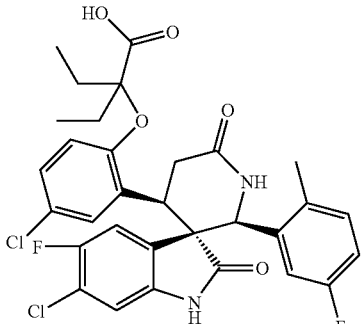

M.W. 617.48
$C_{31}H_{28}Cl_2F_2N_2O_5$

A mixture of racemic (2'S,3S,4'R)-6-chloro-4'-[5-chloro-2-(1-methoxycarbonyl-1-ethyl-propoxy)-phenyl]-5-fluoro-2'-(5-fluoro-2-methyl-phenyl)spiro[3H-indole-3,3'-piperidine]-2,6'(1H)-dione (120 mg, 0.19 mmol), LiOH.H₂O (140 mg, 3.3 mmol), H₂O (1.25 mL) and methanol (3.75 mL) was heated at 80° C. for 1 h. After cooled to room temperature, the mixture was acidified by addition of 0.5 N HCl and partitioned between EtOAc and water. The organic phase was washed with brine, dried over anhydrous Na₂SO₄ and concentrated to give the crude product, which was used for the next step reaction without further purification.

m/z (M+H)+: 617

Example 86e

Preparation of Racemic (2'S,3S,4'R)-6-chloro-4'-[5-chloro-2-(2-methanesulfonylamino-1,1-diethyl-2-oxo-ethoxy)-phenyl]-5-fluoro-2'-(5-fluoro-2-methyl-phenyl)-spiro[3H-indole-3,3'-piperidine]-2,6'(1H)-dione

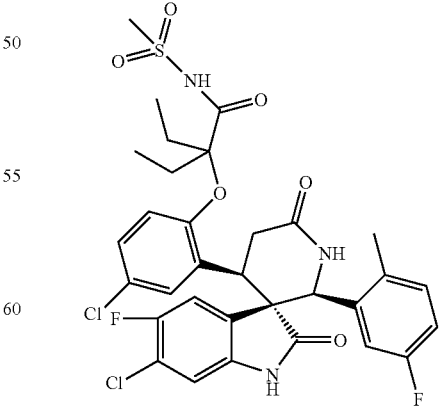

M.W 694.59
$C_{32}H_{31}Cl_2F_2N_3O_6S$

A solution of racemic (2'S,3S,4'R)-6-chloro-5-fluoro-4'-[5-chloro-2-(1-hydroxycarbonyl-1-ethyl-propoxy)-phenyl]-2'-(5-fluoro-2-methyl-phenyl)spiro[3H-indole-3,3'-piperidine]-2,6'(1H)-dione (100 mg, 0.16 mmol) and CDI (123 mg, 0.64 mmol) in DMF (3 mL) was heated at 75° C. for 3 h. Then to this solution was added a mixture of methanesulfonamide (144 mg, 1.5 mmol) and NaH (53 mg, 60%,1.3 mmol) in DMF (1.5 mL), which had been previously stirred at room temperature for 2 h. After the resulting mixture was stirred at room temperature for 20 mins, it was poured into water and the aqueous solution was acidified by diluted HCl solution. After the aqueous phase was extracted with EtOAc twice, the combined organic phases were dried over anhydrous $Na_2SO_4$, concentrated and the residue was purified by flash column to give the title compound (50 mg).

m/z (M+H)⁺: 694

Example 87

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$'s showing the biological activity of this invention exhibit activities less than about 10 μM.

Representative values are, for example:

| Example | IC₅₀ (μM, 0.02% BSA) |
|---|---|
| 1g | 0.278 |
| 8 | 0.327 |
| 11 | 0.065 |
| 29b | 0.054 |
| 34d | 0.155 |

What is claimed:

1. A compound of the formula

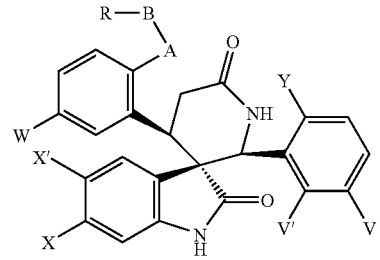

wherein
X is Cl, F or Br,
X' is hydrogen or F,
V is F, Cl or Br,
V' is hydrogen or F,
Y is hydrogen, methyl, methoxy, F or Cl,
W is F, Cl, Br, I, ethynyl or isopropenyl,
A is O, NH, $CH_2$, C(=O), C(=O)NH, NHC(=O) or $NHS(=O)_2$,
B is a bond or $(CH_2)_m CR_1 R_2 (CH_2)_n$,
m=0 or 1,
n=0 or 1,
$R_1$, $R_2$ are hydrogen or lower alkyl,
and in the case of $R_1$ and $R_2$ they may independently link to form a cyclic structure selected from a substituted or unsubstituted cycloalkyl,
provided that
if B is a bond, then R is selected from heterocycle, substituted heterocyle, heteroaryl, substituted heteroaryl, aryl or substituted aryl,
if B is not a bond, then R is selected from OR", NR'R", C(=O)NR'R", NHC(=O)R", NHS(=O)₂R", NHC(=O)NR'R" or C(=O)NR'S(=O)₂R",
R', R" is independently selected from the group consisting of hydrogen, lower alkyl, aryl, lower alkenyl, substituted aryl, heteroaryl, substituted heteroaryl, heterocycle, substituted heterocycle, cycloalkyl and substituted cycloalkyl with the proviso that R" is not a hydrogen,
and in the case of R' and R" they may independently link to form a cyclic structure selected from substituted or unsubstituted heteroaryl, substituted or unsubstituted cycloalkyl, substituted or unsubstituted cycloalkenyl or substituted or unsubstituted heterocycle
and the pharmaceutically acceptable salts and enantiomers thereof.

2. The compound of claim 1 wherein X is Cl, X' is hydrogen or F, A is O, V is F or Cl, V' is hydrogen or F, Y is methyl, methoxyl, Cl or F, W is Cl, F or Br.

3. A compound of claim 1 selected from the group consisting of
racemic (2'S,3S,4'R)-6-chloro-4'-{5-chloro-2-[1-methyl-1-(1-methyl-piperidin-4-ylcarbamoyl)-ethoxy]-phenyl}-2'-(5-fluoro-2-methyl-phenyl)spiro[3H-indole-3,3'-piperidine]-2,6'(1H)-dione,
racemic (2'S,3S,4'R)-6-chloro-4'-[5-chloro-2-(1-cyclobutylcarbamoyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-(2-hydroxy-ethylcarbamoyl)-1-methyl-ethoxy]-phenyl}-2'-(5-fluoro-2-methyl-phenyl)-spiro[3H-indole-3,3'-piperidine]-2,6'(1H)-dione, racemic (2'S,3S,4'R)-4'-{2-[1-(2-acetylamino-ethylcarbamoyl)-1-methyl-ethoxy]-5-chloro-phenyl}-6-chloro-2'-(5-fluoro-2-methyl-phenyl)spiro[3H-indole-3,3'-piperidine]-2,6'(1H)-dione, (2'S,3S,4'R)-6-chloro-4'-{5-chloro-2-[1-(S-2,3-dihydroxy-propylcarbamoyl)-1-methyl-ethoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-(2-methoxy-ethylcarbamoyl)-1-methyl-ethoxy]-phenyl}-2'-(5-fluoro-2-methyl-phenyl)-spiro[3H-indole-3,3'-piperidine]-2,6'(1H)-dione, racemic (2'S,3S,4'R)-6-chloro-4'-{5-chloro-2-[1-(3-dimethylamino-propylcarbamoyl)-1-methyl-ethoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-methyl-1-(2-piperidin-1-yl-ethylcarbamoyl)-ethoxy]-phenyl}-2'-(5-fluoro-2-methyl-phenyl)-spiro[3H-indole-3,3'-piperidine]-2,6'(1H)-dione, racemic (2'S,3S,4'R)-4'-[5-bromo-2-(2-methanesulfonylamino-1,1-dimethyl-2-oxo-ethoxy)-phenyl]-6-chloro-2'-(5-fluoro-2-methyl-phenyl)-spiro[3H-indole-3,3'-piperidine]-2,6'(1H)-dione, racemic (2'S,3S,4'R)-6-chloro-4'-[5-chloro-2-(1-methanesulfonylaminocarbonyl-cyclobutoxy)-phenyl]-2'-(5-fluoro-2-methyl-phenyl)-spiro[3H-indole-3,3'-piperidine]-2,6'(1H)-dione and racemic (2'S,3S,4'R)-6-chloro-4'-{5-chloro-2-[1-(4-fluoro-benzenesulfonylaminocarbonyl)-cyclobutoxy]-phenyl}-2'-(5-fluoro-2-methyl-phenyl)-spiro[3H-indole-3,3'-piperidine]-2,6'(1H)-dione.

4. A pharmaceutical composition comprising a compound of the formula

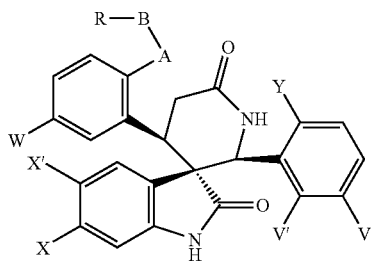

I wherein

X is Cl, F or Br,

X' is hydrogen or F,

V is F, Cl or Br,

V' is hydrogen or F,

Y is hydrogen, methyl, methoxy, F or Cl,

W is F, Cl, Br, I, ethynyl or isopropenyl,

A is O, NH, $CH_2$, C(=O), C(=O)NH, NHC(=O) or $NHS(=O)_2$,

B is a bond or $(CH_2)_m CR_1R_2(CH_2)_n$, m=0 or 1, n=0 or 1, $R_1$, $R_2$ are hydrogen or lower alkyl, and in the case of $R_1$ and $R_2$ they may independently link to form a cyclic structure selected from a substituted or unsubstituted cycloalkyl, provided that if B is a bond, then R is selected from heterocycle, substituted heterocyle, heteroaryl, substituted heteroaryl, aryl or substituted aryl, if B is not a bond, then R is selected from OR", NR'R", C(=O)NR'R", NHC(=O)R", NHS(=O)$_2$R", NHC(=O)NR'R" or C(=O)NR'S(=O)$_2$R", R', R" is independently selected from the group consisting of hydrogen, lower alkyl, aryl, lower alkenyl, substituted aryl, heteroaryl, substituted heteroaryl, heterocycle, substituted heterocycle, cycloalkyl and substituted cycloalkyl with the proviso that R" is not a hydrogen, and in the case of R' and R" they may independently link to form a cyclic structure selected from substituted or unsubstituted heteroaryl, substituted or unsubstituted cycloalkyl, substituted or unsubstituted cycloalkenyl or substituted or unsubstituted heterocycle and the pharmaceutically acceptable salts and enantiomers thereof together with a pharmaceutically acceptable carrier or excipient.

5. A compound of claim 1 selected from the group consisting of chiral (2'S,3S,4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione, racemic (2'S,3S,4'R)-4'-[5-bromo-2-(3-methyl-oxetan-3-ylmethoxy)-phenyl]-6-chloro-2'-(5-chloro-2-methyl-phenyl)-spiro[3H-indole-3,3'-piperidine]-2,6'(1H)-dione, racemic (2'S,3S,4'R)-6-chloro-4'-[5-isopropenyl-2-(3-methyl-oxetan-3-ylmethoxy)-phenyl]-2'-(5-chloro-2-methyl-phenyl)-spiro[3H-indole-3,3'-piperidine]-2,6'(1H)-dione, racemic (2'S,3S,4'R)-6-chloro-2'-(5-chloro-2-methyl-phenyl)-4'-[5-ethynyl-2-(3-methyl-oxetan-3-ylmethoxy)-phenyl]-spiro[3H-indole-3,3'-piperidine]-2,6'(1H)-dione, racemic (2'S,3S,4'R)-4'-[2-(1-tert-butoxycarbonyl-piperidin-4-yloxy)-5-chloro-phenyl]-6-chloro-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(4-piperidinyloxy)-phenyl]-2'-(5-fluoro-2-methyl-phenyl)spiro[3H-indole-3,3'-piperidine]-2,6'(1H)-dione, racemic (2'S,3S,4'R)-4'-[2-(1-acetyl-4-piperidinyloxy)-5-chloro-phenyl]-6-chloro-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-methanesulfonyl-4-piperidinyloxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(pyrimidin-2-yloxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(2,2-dimethyl-3-oxo-3-pyrrolidin-1-yl-propoxy)-phenyl]-2'-(5-fluoro-2-methylphenyl)spiro[3H-indole-3,3'-piperidine]-2,6'(1H)-dione, racemic (2'S,3S,4'R)-6-chloro-4'-[5-chloro-2-(2-dimethylcarbamoyl-2-methyl-propoxy)-phenyl]-2'-(5-fluoro-2-methylphenyl)-spiro[3H-indole-3,3'-piperidine]-2,6'(1H)-dione and racemic (2'R,3S,4'R)-6-chloro-4'-[5-chloro-2-{[(2-hydroxy-ethyl)-methyl-carbamoyl]-methoxy}-phenyl]-2'-[2,5-difluorophenyl]spiro[3H-indole-3,3'-piperidine]-2,6'(1H)-dione.

6. A compound of claim 1 selected from the group consisting of racemic (2'R,3S,4'R)-6-chloro-4'-[5-chloro-2-dimethylcarbamoylmethoxy-phenyl]-2'-(2,5-difluorophenyl)spiro[3H-indole-3,3'-piperidine]-2,6'(1H)-dione, racemic (2'R,3S,4'R)-6-chloro-4'-[5-chloro-2-(2-oxo-2-pyrrolidin-1-yl-ethoxy)-phenyl]-2'-(2,5-difluorophenyl)spiro[3H-indole-3,3'-piperidine]-2,6'(1H)-dione, racemic (2'S,3S,4'R)-6-chloro-4'-[5-bromo-2-(1-dimethylcarbamoyl-1-methyl-ethoxy)-phenyl]-2'-(5-chloro-2-methyl phenyl)spiro[3H-indole-3,3'-piperidine]-2,6'(1H)-dione, racemic (2'S,3S,4'R)-6-chloro-4'-[5-chloro-2-(1-dimethylcarbamoyl-1-methyl-ethoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(1-dimethylcarbamoyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-4'-{2-[2-(4-acetyl-piperazin-1-yl)-1,1-dimethyl-2-oxo-ethoxy]-5-chloro-phenyl}-6-chloro-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-methyl-1-(2,2,2-trifluoro-ethylcarbamoyl)-ethoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[2-(4,4-difluoro-piperidin-1-yl)-1,1-dimethyl-2-oxo-ethoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(3-methyloxetan-3-ylmethoxy)-phenyl]-2'-(5-fluoro-2-methyl-phenyl)-spiro[3H-indole-3,3'-piperidine]-2,6'(1H)-dione, racemic (2'R,3S,4'R)-6-chloro-4'-[5-chloro-2-(1-dimethylcarbamoyl-1-methyl-ethoxy)-phenyl]-2'-(2,5-difluoro-phenyl)spiro[3H-indole-3,3'-piperidine]-2,6'(1H)-dione and racemic (2'S,3S,4'R)-4'-[2-(2-amino-ethoxy)5-chloro-phenyl]-6-chloro-2'-(5-fluoro-2-methyl phenyl)spiro[3H-indole-3,3'-piperidine]-2,6'(1H)-dione.

7. A compound of claim 1 selected from the group consisting of racemic (2'S,3S,4'R)-6-chloro-4'-[5-chloro-2-(2-methanesulfonylamino-ethoxy)-phenyl]-2'-(5-fluoro-2-methyl phenyl)spiro[3H-indole-3,3'-piperidine]-2,6'(1H)-dione, racemic (2'S,3S,4'R)-6-chloro-4'-[5-chloro-2-[2-(3,3-dimethyl-ureido)-ethoxy]-phenyl]-2'-(5-fluoro-2-methyl phenyl)spiro[3H-indole-3,3'-piperidine]-2,6'(1H)-dione, racemic (2'R,3S,4'R)-6-chloro-4'-[5-chloro-2-(1-dimethylcarbamoyl-1-methyl-ethoxy)-phenyl]-2'-(2-fluoro-5chloro-phenyl)spiro[3H-indole-3,3'-piperidine]-2,6'(1H)-dione, racemic (2'S,3S,4'R)-2'-[5-bromo-2-(4-methoxycarbonyl-phenoxy)-phenyl]-6-chloro-4'-(3-chlorophenyl)spiro[3H-indole-3,3'-piperidine]-2,6'(1H)-dione, racemic (2'S,3S,4'R)-2'-[5-bromo-2-(4-methoxycarbonyl-phenoxy)-phenyl]-6-chloro-4'-(3-fluorophenyl)spiro[3H-indole-3,3'-piperidine]-2,6'(1H)-dione, racemic (2'S,3S,4'R)-4'-[5-bromo-2-(1-tert-butoxycarbonyl-piperidin-4-yloxy)-phenyl]-6-chloro-2'-(3-fluorophenyl)spiro[3H-indole-3,3'-piperidine]-2,6'(1H)-dione, racemic (2'S,3S,4'R)-4'-[5-bromo-2-(4-piperidinyloxy)-phenyl]-6-chloro-2'-(5-fluorophenyl)spiro[3H-indole-3,3'-piperidine]-2,6'(1H)-dione, racemic (2'S,3S,4'R)-4'-[2-(1-acetyl-4-piperidinyloxy)-5-bromo-phenyl]-6-chloro-2'-(3-fluorophenyl)spiro[3H-indole-3,3'-piperidine]-2,6'(1H)-dione, racemic (2'S,3S,4'R)-4'-[5-bromo-2-(1-methyl-4-piperidinyloxy)-phenyl]-6-chloro-2'-(3-fluorophenyl)spiro[3H-indole-3,3'-piperidine]-2,6'(1H)-dione, racemic (2'S,3S,4'R)-4'-[5-bromo-2-(1-tert-butoxycarbonyl-piperidin-4-yloxy)-phenyl]-6-chloro-2'-(3-chlorophenyl)spiro[3H-indole-3,3'-piperidine]-2,6'(1H)-dione, racemic (2'S,3S,4'R)-4'-[5-bromo-2-(4-piperidinyloxy)-phenyl]-6-chloro-2'-(5-chlorophenyl)spiro[3H-indole-3,3'-piperidine]-2,6'(1H)-dione and racemic (2'S,3S,4'R)-4'-[2-(1-acetyl-4-piperidinyloxy)-5-bromo-phenyl]-6-chloro-2'-(3-chlorophenyl)spiro[3H-indole-3,3'-piperidine]-2,6'(1H)-dione.

8. A compound of claim 1 selected from the group consisting of racemic (2'S,3S,4'R)-4'-[5-bromo-2-(1-methyl-4-piperidinyloxy)-phenyl]-6-chloro-2'-(3-chlorophenyl)spiro[3H-indole-3,3'-piperidine]-2,6'(1H)-dione, chiral (2'S,3S,4'R)-6-chloro-4'-[5-chloro-2-(2-methanesulfonylamino-ethoxy)-phenyl]-2'-(5-fluoro-2-methyl-phenyl)spiro[3H-indole-3,3'-piperidine]-2,6'(1H)-dione, racemic (2'R,3S,4'R)-6-chloro-2'-(2-chloro-5-fluoro-phenyl)-4'-[5-chloro-2-(2-methanesulfonylamino-1,1-dimethyl-2-oxo-ethoxy)-phenyl]spiro[3H-indole-3,3'-piperidine]-2,6'(1H)-dione, chiral (2'S,3S,4'R)-6-chloro-4'-[5-chloro-2-(2-methanesulfonylamino-1,1-dimethyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-methoxylcarbamoyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-cyanocarbamoyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-hydroxycarbamoyl-1-methyl-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-fluoro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(4-methoxy-phenoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(2-tert-butoxycarbonylamino-ethoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(2-tert-butoxycarbonylamino-ethoxy)-phenyl]-2'-(5-fluoro-2-methyl phenyl)spiro[3H-indole-3,3'-piperidine]-2,6'(1H)-dione and racemic (2'S,3S,4'R)-6-chloro-4'-{5-chloro-2-[(2-cyclobutanecarbonyl-amino)-ethoxy]-phenyl}-2'-(5-fluoro-2-methyl-phenyl)spiro[3H-indole-3,3'-piperidine]-2,6'(1H)-dione.

9. A compound of claim 1 selected from the group consisting of chiral (2'S,3S,4'R)-6-chloro-4'-[5-chloro-2-(2-cyano-2-cyclopropyl-methoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-cyano-cyclopentyl-methoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-cyanomethoxy-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-cyanomethoxy-phenyl]-2'-(5-fluoro-2-methyl-phenyl)spiro[3H-indole-3,3'-piperidine]-2,6'(1H)-dione, racemic (2'S,3S,4'R)-4'-[2-(4-tert-butoxycarbonyl-piperazin-1-yl)-5-chloro-phenyl]-6-chloro-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(piperazin-1-yl)-phenyl]-2'-(5-fluoro-2-methyl phenyl)spiro[3H-indole-3,3'-piperidine]-2,6'(1H)-dione, racemic (2'S,3S,4'R)-4'-[2-(4-acetyl-piperazin-1-yl)-5-chloro-phenyl]-6-chloro-2'-(5-fluoro-2-methyl phenyl)spiro[3H-indole-3,3'-piperidine]-2,6'(1H)-dione, racemic (2'S,3S,4'R)-6-chloro-4'-{5-chloro-2-[4-(2-hydroxy-ethyl)-piperazin-1-yl]-phenyl}-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(2-cyclopropanesulfonylamino-1,1-dimethyl-2-oxo-ethoxy)-phenyl]-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(2-trifluoromethanesulfonylamino-1,1-dimethyl-2-oxo-ethoxy)-phenyl]-2'-(5-fluoro-2-methyl-phenyl)-spiro[3H-indole-3,3'-piperidine]-2,6'(1H)-dione, racemic (2'R,3S,4'R)-4'-[5-chloro-2-(2-methanesulfonylamino-1,1-dimethyl-2-oxo-ethoxy)-phenyl]-6-chloro-2'-(2,3-difluoro-6-methyl-phenyl)spiro[3H-indole-3,3'-piperidine]-2,6'(1H)-dione and racemic (2'S,3S,4'R)-6-chloro-4'-[5-chloro-2-(2-methanesulfonylamino-2-oxo-ethoxy)-phenyl]-2'-(5-fluoro-2-methyl-phenyl)spiro[3H-indole-3,3'-piperidine]-2,6'(1H)-dione.

10. A compound of claim 1 selected from the group consisting of racemic (2'S,3S,4'R)-4'-[5-chloro-2-(2-methanesulfonylamino-1,1-dimethyl-2-oxo-ethoxy)-phenyl]-6-chloro-2'-(5-chloro-2-methoxy-phenyl)-spiro[3H-indole-3,3'-piperidine]-2,6'(1H)-dione, racemic (2'S,3S,4'R)-6-chloro-4'-[5-chloro-2-(1-ethyl-1-hydroxycarbonyl-propoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(1-ethyl-1-dimethylcarbamoyl-propoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-{5-chloro-2-[1-ethyl-1-(2-hydroxy-ethylcarbamoyl)-propoxy]-phenyl}-2'-(5-fluoro-2-methyl-phenyl)spiro[3H-indole-3,3-piperidine]-2,6'(1H)-dione, racemic (2'S,3S,4R)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[1-ethyl-1-((S)-2,3-dihydroxy-propylcarbamoyl)-propoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[1-ethyl-1-(pyrrolidine-1-carbonyl)-propoxy]-phenyl}-2'-(5-fluoro-2-methyl-phenyl)spiro[3H-indole-3,3'-piperidine]-2,6'(1H)-dione and racemic (2'S,3S,4'R)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione.

11. A compound of claim 1 selected from the group consisting of chiral (2'S,3S,4'R)-6-chloro-4'-{5-chloro-2-[1-ethyl-1-((S)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione, chiral (2'S,3S,4'R)-6-chloro-4'-{5-chloro-2-[1-ethyl-1-((R)-3-hydroxy-pyrrolidine-1-carbonyl)-propoxy]-phenyl}-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione, chiral (2'S,3S,4'R)-6-chloro-4'-[5-chloro-2-(1-carbamoyl-1-ethyl-propoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione, chiral (2'S,3S,4'R)-1-acetyl-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione, chiral (2'R,3R,4'S)-6-chloro-4'-[5-chloro-2-(1-ethyl-1-methanesulfonylaminocarbonyl-propoxy)-phenyl]-2'-(5-chloro-2-methyl-phenyl)-spiro[3H-indole-3,3'-piperidine]-2,6'(1H)-dione, chiral (2'S,3S,4'R)-4'-[5-chloro-2-(2-ethanesulfonylamino-1,1-dimethyl-2-oxo-ethoxy)-phenyl]-6-chloro-2'-(5-fluoro-2-methyl-phenyl)spiro[3H-indole-3,3'-piperidine]-2,6'(1H)-dione, racemic (2'S,3S,4'R)-4'-[5-chloro-2-(2-methanesulfonylamino-1,1-dimethyl-2-oxo-ethoxy)-phenyl]-6-chloro-2'-(5-methyl-2-methoxy-phenyl)-spiro[3H-indole-3,3'-piperidine]-2,6'(1H)-dione, racemic (2'S,3S,4'R)-6-chloro-4'-[5-chloro-2-(3-methanesulfonylamino-2,2-dimethyl-3-oxo-propoxy)-phenyl]-2'-(5-fluoro-2-methyl-phenyl)spiro[3H-indole-3,3'-piperidine]-2,6'(1H)-dione and racemic (2'S,3S,4'R)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione.

12. A compound of claim 1 selected from the group consisting of chiral (2'R,3R,4'S)-6-chloro-4'-[5-chloro-2-(2-methanesulfonylamino-1,1-dimethyl-2-oxo-ethoxy)-phenyl]-2'-(5-fluoro-2-methyl-phenyl)spiro[3H-indole-3,3'-piperidine]-2,6'(1H)-dione, racemic (2'S,3S,4'R)-6-chloro-4'-[5-chloro-2-(2-methanesulfonylamino-1,1-dimethyl-2-oxo-ethoxy)-phenyl]-2'-(5-chloro-2-methyl-phenyl)-spiro[3H-indole-3,3'-piperidine]-2,6'(1H)-dione, chiral (2'S,3S,4'R)-6-chloro-4'-[5-chloro-2-(2-methanesulfonylamino-1,1-dimethyl-2-oxo-ethoxy)-phenyl]-2'-(5-chloro-2-methyl-phenyl)-spiro[3H-indole-3,3'-piperidine]-2,6'(1H)-dione, chiral (2'S,3S,4'R)-6-chloro-4'-{5-chloro-2-[2-(2-methoxy-ethanesulfonylamino)-1,1-dimethyl-2-oxo-ethoxy]-phenyl}-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(1-methanesulfonylaminocarbonyl-1-propyl-butoxy)-phenyl]-2'-(5-chloro-2-methyl-phenyl)-spiro[3H-indole-3,3'-piperidine]-2,6'(1H)-dione, racemic (2'S,3S,4'R)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione, chiral (2'S,3S,4'R)-6-chloro-4'-[5-chloro-2-(1-methanesulfonylaminocarbonyl-1-propyl-butoxy)-phenyl]-2'-(5-fluoro-2-methyl-phenyl)-spiro[3H-indole-3,3'-piperidine]-2,6'(1H)-dione, racemic (2'S,3S,4'R)-6-bromo-4'-[5-chloro-2-(1-ethyl-1-methanesulfonylaminocarbonyl-propoxy)-phenyl]-2'-(5-fluoro-2-methyl-phenyl)-spiro[3H-indole-3,3'-piperidine]-2,6'(1H)-dione, racemic (2'S,3S,4'R)-6-chloro-4'-(5-chloro-2-methanesulfinylmethoxy-phenyl)-2'-(5-fluoro-2-methyl-phenyl)spiro[3H-indole-3,3'-piperidine]-2,6'(1H)-dione, racemic (2'S,3S,4'R)-[2-(tert-butylsulfamoyl-methoxy)-5-chloro-phenyl]-6-chloro-2'-(5-fluoro-2-methyl-phenyl)spiro[3H-indole-3,3'-piperidine]-2,6'(1H)-dione and racemic (2'S,3S,4'R)-6-chloro-4'-[5-chloro-2-(2-methanesulfonylamino-1,1-diethyl-2-oxo-ethoxy)-phenyl]-5-fluoro-2'-(5-fluoro-2-methyl-phenyl)-spiro[3H-indole-3,3'-piperidine]-2,6'(1H)-dione.

* * * * *